(12) United States Patent
Dengl et al.

(10) Patent No.: US 10,434,184 B2
(45) Date of Patent: Oct. 8, 2019

(54) ANTI-TPBG ANTIBODIES AND METHODS OF USE

(71) Applicant: Hoffmann-La Roche Inc., Little Falls, NJ (US)

(72) Inventors: Stefan Dengl, Munich (DE); Sebastian Fenn, Achmuhle/Eurasburg (GB); Jens Fischer, Weilheim (GB); Thomas Friess, Diessen-Dettenhofen (GB); Sabine Imhof-Jung, Planegg (GB); Ben-Fillippo Krippendorff, Loerrach (GB); Christian Schantz, Penzberg (GB); Tilman Schlothauer, Penzberg (GB); Claudio Sustmann, Munich (DE); Barbara Weiser, Penzberg (GB); Adrian Zwick, Penzberg (GB)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/965,517

(22) Filed: Apr. 27, 2018

(65) Prior Publication Data

US 2018/0311371 A1    Nov. 1, 2018

Related U.S. Application Data

(63) Continuation of application No. PCT/EP2016/075881, filed on Oct. 27, 2016.

(30) Foreign Application Priority Data

Oct. 29, 2015 (EP) .................................. 15192002

(51) Int. Cl.
*C07K 16/30* (2006.01)
*A61K 47/68* (2017.01)
*A61K 49/00* (2006.01)
*A61P 35/00* (2006.01)
*C07K 16/46* (2006.01)
*C07K 19/00* (2006.01)
*A61K 39/00* (2006.01)

(52) U.S. Cl.
CPC .......... *A61K 47/68* (2017.08); *A61K 49/0058* (2013.01); *A61P 35/00* (2018.01); *C07K 16/30* (2013.01); *C07K 16/462* (2013.01); *C07K 16/465* (2013.01); *C07K 19/00* (2013.01); *A61K 2039/505* (2013.01); *C07K 2317/33* (2013.01); *C07K 2317/55* (2013.01); *C07K 2317/77* (2013.01); *C07K 2317/92* (2013.01); *C07K 2317/94* (2013.01)

(58) Field of Classification Search
None
See application file for complete search history.

(56) References Cited

U.S. PATENT DOCUMENTS 5,869,053 A       2/1999  Stern et al.
2003/0018004 A1   1/2003  Kingsman et al.

FOREIGN PATENT DOCUMENTS

| WO | 98/55607 A2    |   | 12/1998 |
| WO | 98/55607 A3    |   | 12/1998 |
| WO | 2006/031653 A2 |   | 3/2006  |
| WO | 2006/031653 A3 |   | 3/2006  |
| WO | WO2006/031653  | * | 3/2006  |
| WO | 2007/106744 A2 |   | 9/2007  |
| WO | 2007/106744 A3 |   | 9/2007  |

OTHER PUBLICATIONS

Cheng et al., "Individualized patient dosing in phase I clinical trials: The role of escalation with overdose control in PNU-214936" J Clin Oncol 22(4):602-609 (Feb. 15, 2004).
International Search Report and Written Opinion of the International Searching Authority on patentability for International Application No. PCT/EP2016/075881 completed on Jan. 25, 2017.
Eisen et al., "Naptumomab Estafenatox: Targeted immunotherapy with a novel immunotoxin" Curr Oncol Rep 16:370 ( 2014).
Myers et al., "Targeting immune effector molecules to human tumor cells through genetic delivery of 5T4-specific scFv fusion proteins" Cancer Gene Therapy 9:884-896 ( 2002).
Shaw et al., "Glycosylation and epitope mapping of the 5T4 glycoprotein oncofoetal antigen" Biochem J 363(Pt 1):137-45 (Apr. 1, 2002).
Shaw et al., "Isolation of a high affinity scFv from a monoclonal antibody recognising the oncofoetal antigen 5T4" Biochim Biophys ACTA 1524:238-246 ( 2000).
Woods et al., "Characterization of the murine 5T4 oncofoetal antigen: a target for immunotherapy in cancer" Biochem J 366:353-365 ( 2002).

* cited by examiner

*Primary Examiner* — Meera Natarajan

(57) ABSTRACT

The invention provides anti-TPBG antibodies and methods of using the same.

22 Claims, 18 Drawing Sheets

Specification includes a Sequence Listing.

SEQUENCE LISTING

<160> NUMBER OF SEQ ID NOS: 87

<210> SEQ ID NO 1
<211> LENGTH: 389
<212> TYPE: PRT
<213> ORGANISM: Homo sapiens

<400> SEQUENCE: 1

```
Ser Ser Pro Thr Ser Ser Ala Ser Ser Phe Ser Ser Ser Ala Pro Phe
1               5                   10                  15

Leu Ala Ser Ala Val Ser Ala Gln Pro Pro Leu Pro Asp Gln Cys Pro
            20                  25                  30

Ala Leu Cys Glu Cys Ser Glu Ala Ala Arg Thr Val Lys Cys Val Asn
        35                  40                  45

Arg Asn Leu Thr Glu Val Pro Thr Asp Leu Pro Ala Tyr Val Arg Asn
50                  55                  60

Leu Phe Leu Thr Gly Asn Gln Leu Ala Val Leu Pro Ala Gly Ala Phe
65                  70                  75                  80

Ala Arg Arg Pro Pro Leu Ala Glu Leu Ala Ala Leu Asn Leu Ser Gly
                85                  90                  95

Ser Arg Leu Asp Glu Val Arg Ala Gly Ala Phe Glu His Leu Pro Ser
            100                 105                 110

Leu Arg Gln Leu Asp Leu Ser His Asn Pro Leu Ala Asp Leu Ser Pro
        115                 120                 125

Phe Ala Phe Ser Gly Ser Asn Ala Ser Val Ser Ala Pro Ser Pro Leu
130                 135                 140

Val Glu Leu Ile Leu Asn His Ile Val Pro Pro Glu Asp Glu Arg Gln
145                 150                 155                 160

Asn Arg Ser Phe Glu Gly Met Val Val Ala Ala Leu Leu Ala Gly Arg
                165                 170                 175

Ala Leu Gln Gly Leu Arg Arg Leu Glu Leu Ala Ser Asn His Phe Leu
            180                 185                 190

Tyr Leu Pro Arg Asp Val Leu Ala Gln Leu Pro Ser Leu Arg His Leu
        195                 200                 205

Asp Leu Ser Asn Asn Ser Leu Val Ser Leu Thr Tyr Val Ser Phe Arg
210                 215                 220
```

-continued

Asn Leu Thr His Leu Glu Ser Leu His Leu Glu Asp Asn Ala Leu Lys
225                 230                 235                 240

Val Leu His Asn Gly Thr Leu Ala Glu Leu Gln Gly Leu Pro His Ile
            245                 250                 255

Arg Val Phe Leu Asp Asn Asn Pro Trp Val Cys Asp Cys His Met Ala
        260                 265                 270

Asp Met Val Thr Trp Leu Lys Glu Thr Glu Val Val Gln Gly Lys Asp
    275                 280                 285

Arg Leu Thr Cys Ala Tyr Pro Glu Lys Met Arg Asn Arg Val Leu Leu
290                 295                 300

Glu Leu Asn Ser Ala Asp Leu Asp Cys Asp Pro Ile Leu Pro Pro Ser
305                 310                 315                 320

Leu Gln Thr Ser Tyr Val Phe Leu Gly Ile Val Leu Ala Leu Ile Gly
            325                 330                 335

Ala Ile Phe Leu Leu Val Leu Tyr Leu Asn Arg Lys Gly Ile Lys Lys
        340                 345                 350

Trp Met His Asn Ile Arg Asp Ala Cys Arg Asp His Met Glu Gly Tyr
    355                 360                 365

His Tyr Arg Tyr Glu Ile Asn Ala Asp Pro Arg Leu Thr Asn Leu Ser
370                 375                 380

Ser Asn Ser Asp Val
385

<210> SEQ ID NO 2
<211> LENGTH: 388
<212> TYPE: PRT
<213> ORGANISM: Sus scrofa

<400> SEQUENCE: 2

Ser Ser Leu Thr Ser Ser Ala Ser Ser Thr Ser Ser Ala Ser Phe Pro
1               5                   10                  15

Ala Ser Ala Ala Ser Ala Leu Pro Pro Leu Pro Gly Arg Cys Pro Gln
            20                  25                  30

Pro Cys Glu Cys Ser Glu Ala Ala Arg Thr Val Lys Cys Val Gly Arg
        35                  40                  45

Asn Leu Thr Glu Val Pro Ala Asp Leu Pro Pro Tyr Val Arg Thr Leu
50                  55                  60

Phe Leu Thr Gly Asn Gln Leu Ala Val Leu Pro Thr Gly Ala Phe Ala
65                  70                  75                  80

Arg Arg Pro Pro Leu Ala Glu Leu Ser Ala Leu Asn Leu Ser Gly Ser
            85                  90                  95

Arg Leu Thr Glu Val Gln Ala Gly Ala Phe Glu His Leu Pro Ser Leu
            100                 105                 110

Arg Leu Leu Asp Leu Ser His Asn Pro Leu Ala Asn Leu Ser Ala Phe
        115                 120                 125

Ala Phe Ser Gly Ser Asn Ala Ser Val Ala Ala Pro Ser Pro Leu Val
    130                 135                 140

Asp Leu Ile Leu Asn His Ile Val Thr Ser Ala Ala Gln Arg Gln Asn
145                 150                 155                 160

Arg Ser Phe Glu Gly Met Val Ala Ala Leu Arg Ala Gly His Ala
            165                 170                 175

Leu Arg Gly Leu Arg Arg Leu Glu Leu Ala Ser Asn His Leu Leu Tyr
        180                 185                 190

Leu Pro Leu Asp Val Leu Ala Gln Leu Pro Asp Leu Arg His Leu Asp

-continued

```
                195                 200                 205
Leu Arg Asn Asn Ser Leu Val Ser Leu Thr Tyr Val Phe Phe Arg Asn
            210                 215                 220
Leu Thr His Leu Glu Ser Phe His Leu Glu Asp Asn Ala Leu Lys Val
225                 230                 235                 240
Leu His Asn Gly Thr Leu Ala Glu Leu Gln Ser Leu Pro His Val Arg
                245                 250                 255
Val Phe Leu Asp Asp Asn Pro Trp Val Cys Asp Cys His Leu Ala Asp
            260                 265                 270
Met Val Ala Trp Leu Lys Glu Thr Glu Val Val Gln Asp Lys Ala Arg
                275                 280                 285
Leu Thr Cys Ala Phe Pro Glu Lys Met Arg His Arg Val Leu Leu Glu
            290                 295                 300
Leu Asn Ser Ser Asp Leu Asp Cys Asp Pro Asp Leu Pro Pro Ser Leu
305                 310                 315                 320
Gln Thr Ser Tyr Val Phe Leu Gly Ile Val Leu Ala Leu Ile Gly Ala
                325                 330                 335
Ile Phe Leu Leu Val Leu Tyr Leu Asn Arg Lys Gly Ile Lys Lys Trp
            340                 345                 350
Met His Asn Ile Arg Asp Ala Cys Arg Asp His Met Glu Gly Tyr His
                355                 360                 365
Tyr Arg Tyr Glu Ile Asn Ala Asp Pro Arg Leu Thr Asn Leu Ser Ser
            370                 375                 380
Asn Ser Asp Val
385

<210> SEQ ID NO 3
<211> LENGTH: 5
<212> TYPE: PRT
<213> ORGANISM: Artificial Sequence
<220> FEATURE:
<223> OTHER INFORMATION: heavy chain CDR1 of antibody 051

<400> SEQUENCE: 3

Ile Tyr Trp Met Thr
1               5

<210> SEQ ID NO 4
<211> LENGTH: 17
<212> TYPE: PRT
<213> ORGANISM: Artificial Sequence
<220> FEATURE:
<223> OTHER INFORMATION: heavy chain CDR2 of antibody 051

<400> SEQUENCE: 4

Ala Ile Ser Gly Ser Gly Gly Ser Thr Tyr Tyr Ala Asp Ser Val Lys
1               5                   10                  15
Gly

<210> SEQ ID NO 5
<211> LENGTH: 7
<212> TYPE: PRT
<213> ORGANISM: Artificial Sequence
<220> FEATURE:
<223> OTHER INFORMATION: heavy chain CDR3 of antibody 051

<400> SEQUENCE: 5

Asp Tyr Tyr Ser Asn Val Tyr
1               5
```

```
<210> SEQ ID NO 6
<211> LENGTH: 11
<212> TYPE: PRT
<213> ORGANISM: Artificial Sequence
<220> FEATURE:
<223> OTHER INFORMATION: light chain CDR1 of antibody 051

<400> SEQUENCE: 6

Arg Ala Ser Gln Gly Ile Tyr Ser Trp Leu Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: light chain CDR2 of antibody 051

<400> SEQUENCE: 7

Ala Ala Ser Ser Leu Gln Ser
1               5

<210> SEQ ID NO 8
<211> LENGTH: 9
<212> TYPE: PRT
<213> ORGANISM: Artificial Sequence
<220> FEATURE:
<223> OTHER INFORMATION: light chain CDR3 of antibody 051

<400> SEQUENCE: 8

Gln Gln Ser Asp Ser Pro Pro Tyr Thr
1               5

<210> SEQ ID NO 9
<211> LENGTH: 116
<212> TYPE: PRT
<213> ORGANISM: Artificial Sequence
<220> FEATURE:
<223> OTHER INFORMATION: variable heavy chain domain VH of antibody 051

<400> SEQUENCE: 9

Glu Val Gln Leu Leu Glu Ser Gly Gly Gly Leu Leu Gln Pro Gly Gly
1               5                   10                  15

Ser Leu Arg Leu Ser Cys Ala Ala Ser Gly Phe Thr Phe Ser Ile Tyr
            20                  25                  30

Trp Met Thr Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Tyr Tyr Ser Asn Val Tyr Trp Gly Gln Gly Thr Leu Val
            100                 105                 110

Thr Val Ser Ser
        115

<210> SEQ ID NO 10
<211> LENGTH: 107
<212> TYPE: PRT
<213> ORGANISM: Artificial Sequence
<220> FEATURE:
```

<223> OTHER INFORMATION: variable light chain domain VL of antibody 051

<400> SEQUENCE: 10

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Tyr Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ser Pro Pro Tyr
                85                  90                  95

Thr Phe Gly Gln Gly Thr Lys Leu Glu Ile Lys
            100                 105

<210> SEQ ID NO 11
<211> LENGTH: 5
<212> TYPE: PRT
<213> ORGANISM: Artificial Sequence
<220> FEATURE:
<223> OTHER INFORMATION: heavy chain CDR1 of antibody 091

<400> SEQUENCE: 11

Ser Asp Ala Met His
1               5

<210> SEQ ID NO 12
<211> LENGTH: 17
<212> TYPE: PRT
<213> ORGANISM: Artificial Sequence
<220> FEATURE:
<223> OTHER INFORMATION: heavy chain CDR2 of antibody 091

<400> SEQUENCE: 12

Gly Val Ser Gly Ser Gly Gly Ser Pro Tyr Tyr Ala Asp Ser Val Lys
1               5                   10                  15

Gly

<210> SEQ ID NO 13
<211> LENGTH: 15
<212> TYPE: PRT
<213> ORGANISM: Artificial Sequence
<220> FEATURE:
<223> OTHER INFORMATION: heavy chain CDR3 of antibody 091

<400> SEQUENCE: 13

Gly Gly Ser Ile Ala Gly Ser Tyr Tyr Tyr Tyr Pro Met Asp Val
1               5                   10                  15

<210> SEQ ID NO 14
<211> LENGTH: 11
<212> TYPE: PRT
<213> ORGANISM: Artificial Sequence
<220> FEATURE:
<223> OTHER INFORMATION: light chain CDR1 of antibody 091

<400> SEQUENCE: 14

Gln Ala Ser Gln Asp Ile Ser Asn Tyr Leu Asn
1               5                   10

```
<210> SEQ ID NO 15
<211> LENGTH: 7
<212> TYPE: PRT
<213> ORGANISM: Artificial Sequence
<220> FEATURE:
<223> OTHER INFORMATION: light chain CDR2 of antibody 091

<400> SEQUENCE: 15

Ala Ala Ser Thr Leu Gln Ile
1               5

<210> SEQ ID NO 16
<211> LENGTH: 9
<212> TYPE: PRT
<213> ORGANISM: Artificial Sequence
<220> FEATURE:
<223> OTHER INFORMATION: light chain CDR3 of antibody 091

<400> SEQUENCE: 16

Gln Gln Ala Asn Ser Phe Pro Leu Thr
1               5

<210> SEQ ID NO 17
<211> LENGTH: 124
<212> TYPE: PRT
<213> ORGANISM: Artificial Sequence
<220> FEATURE:
<223> OTHER INFORMATION: variable heavy chain domain VH of antibody 091

<400> SEQUENCE: 17

Glu Val His Leu Leu Glu Ser Gly Gly Gly Leu Val His Pro Gly Gly
1               5                   10                  15

Ser Leu Arg Leu Ser Cys Ala Ala Ser Gly Phe Thr Phe Arg Ser Asp
            20                  25                  30

Ala Met His Trp Val Arg Gln Ala Pro Gly Lys Gly Leu Glu Trp Val
        35                  40                  45

Ser Gly Val Ser Gly Ser Gly Ser Pro Tyr Tyr Ala Asp Ser Val
    50                  55                  60

Lys Gly Arg Phe Thr Ile Ser Arg Asp Asp Ser Lys Thr Thr Leu Tyr
65                  70                  75                  80

Leu Gln Met Asn Ser Leu Arg Ala Glu Asp Thr Ala Val Tyr Tyr Cys
                85                  90                  95

Ala Thr Gly Gly Ser Ile Ala Gly Ser Tyr Tyr Tyr Pro Met Asp
            100                 105                 110

Val Trp Gly Gln Gly Thr Thr Val Thr Val Ser Ser
        115                 120

<210> SEQ ID NO 18
<211> LENGTH: 107
<212> TYPE: PRT
<213> ORGANISM: Artificial Sequence
<220> FEATURE:
<223> OTHER INFORMATION: variable light chain domain VL of antibody 091

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45
```

```
Tyr Ala Ala Ser Thr Leu Gln Ile Gly Val Pro Ser Arg Phe Ser Gly
            50                  55                  60

Ser Gly Ser Gly Thr Asp Phe Thr Phe Thr Ile Ser Ser Leu Gln Pro
 65                  70                  75                  80

Glu Asp Phe Ala Thr Tyr Tyr Cys Gln Gln Ala Asn Ser Phe Pro Leu
                 85                  90                  95

Thr Phe Gly Gly Gly Thr Lys Val Glu Ile Lys
                100                 105

<210> SEQ ID NO 19
<211> LENGTH: 5
<212> TYPE: PRT
<213> ORGANISM: Artificial Sequence
<220> FEATURE:
<223> OTHER INFORMATION: heavy chain CDR1 of antibody 097

<400> SEQUENCE: 19

Asn Asp Ala Met Thr
1               5

<210> SEQ ID NO 20
<211> LENGTH: 17
<212> TYPE: PRT
<213> ORGANISM: Artificial Sequence
<220> FEATURE:
<223> OTHER INFORMATION: heavy chain CDR2 of antibody 097

<400> SEQUENCE: 20

Ala Ile Ser Gly Ser Gly Gly Ser Thr Tyr Tyr Ala Asp Ser Val Lys
1               5                  10                  15

Gly

<210> SEQ ID NO 21
<211> LENGTH: 16
<212> TYPE: PRT
<213> ORGANISM: Artificial Sequence
<220> FEATURE:
<223> OTHER INFORMATION: heavy chain CDR3 of antibody 097

<400> SEQUENCE: 21

Gly Gly Ser Trp Gly Asp Trp Tyr Tyr Tyr Phe Tyr Pro Met Asp Val
1               5                  10                  15

<210> SEQ ID NO 22
<211> LENGTH: 11
<212> TYPE: PRT
<213> ORGANISM: Artificial Sequence
<220> FEATURE:
<223> OTHER INFORMATION: light chain CDR1 of antibody 097

<400> SEQUENCE: 22

Arg Ala Ser Gln Ser Ile Ser Ser Tyr Leu Asn
1               5                  10

<210> SEQ ID NO 23
<211> LENGTH: 7
<212> TYPE: PRT
<213> ORGANISM: Artificial Sequence
<220> FEATURE:
<223> OTHER INFORMATION: light chain CDR2 of antibody 097

<400> SEQUENCE: 23

Ala Ala Ser Ser Leu Gln Ser
1               5
```

```
<210> SEQ ID NO 24
<211> LENGTH: 9
<212> TYPE: PRT
<213> ORGANISM: Artificial Sequence
<220> FEATURE:
<223> OTHER INFORMATION: light chain CDR3 of antibody 097

<400> SEQUENCE: 24

Gln Gln Ser Asp Ser Phe Pro Leu Thr
1               5

<210> SEQ ID NO 25
<211> LENGTH: 125
<212> TYPE: PRT
<213> ORGANISM: Artificial Sequence
<220> FEATURE:
<223> OTHER INFORMATION: variable heavy chain domain VH of antibody 097

<400> SEQUENCE: 25

Glu Val Gln Leu Leu Glu Ser Gly Gly Gly Leu Ala Gln Pro Gly Gly
1               5                   10                  15

Ser Leu Arg Leu Ser Cys Ala Ala Ser Gly Phe Thr Phe Asn Asn Asp
            20                  25                  30

Ala Met Thr Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Ser Trp Gly Asp Trp Tyr Tyr Tyr Phe Tyr Pro Met
            100                 105                 110

Asp Val Trp Gly Gln Gly Thr Thr Val Thr Val Ser Ser
        115                 120                 125

<210> SEQ ID NO 26
<211> LENGTH: 107
<212> TYPE: PRT
<213> ORGANISM: Artificial Sequence
<220> FEATURE:
<223> OTHER INFORMATION: variable light chain domain VL of antibody 097

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ser Phe Pro Leu
                85                  90                  95

Thr Phe Gly Gly Gly Thr Lys Val Glu Ile Lys
            100                 105
```

```
<210> SEQ ID NO 27
<211> LENGTH: 394
<212> TYPE: PRT
<213> ORGANISM: Artificial Sequence
<220> FEATURE:
<223> OTHER INFORMATION: human TPBG extracellular domain, aa 1-355,
      His6Avi

<400> SEQUENCE: 27

Met Pro Gly Gly Cys Ser Arg Gly Pro Ala Ala Gly Asp Gly Arg Leu
1               5                   10                  15

Arg Leu Ala Arg Leu Ala Leu Val Leu Leu Gly Trp Val Ser Ser Ser
                20                  25                  30

Ser Pro Thr Ser Ser Ala Ser Ser Phe Ser Ser Ser Ala Pro Phe Leu
            35                  40                  45

Ala Ser Ala Val Ser Ala Gln Pro Pro Leu Pro Asp Gln Cys Pro Ala
        50                  55                  60

Leu Cys Glu Cys Ser Glu Ala Ala Arg Thr Val Lys Cys Val Asn Arg
65                  70                  75                  80

Asn Leu Thr Glu Val Pro Thr Asp Leu Pro Ala Tyr Val Arg Asn Leu
                85                  90                  95

Phe Leu Thr Gly Asn Gln Leu Ala Val Leu Pro Ala Gly Ala Phe Ala
            100                 105                 110

Arg Arg Pro Pro Leu Ala Glu Leu Ala Ala Leu Asn Leu Ser Gly Ser
        115                 120                 125

Arg Leu Asp Glu Val Arg Ala Gly Ala Phe Glu His Leu Pro Ser Leu
130                 135                 140

Arg Gln Leu Asp Leu Ser His Asn Pro Leu Ala Asp Leu Ser Pro Phe
145                 150                 155                 160

Ala Phe Ser Gly Ser Asn Ala Ser Val Ser Ala Pro Ser Pro Leu Val
                165                 170                 175

Glu Leu Ile Leu Asn His Ile Val Pro Pro Glu Asp Glu Arg Gln Asn
            180                 185                 190

Arg Ser Phe Glu Gly Met Val Val Ala Ala Leu Leu Ala Gly Arg Ala
        195                 200                 205

Leu Gln Gly Leu Arg Arg Leu Glu Leu Ala Ser Asn His Phe Leu Tyr
210                 215                 220

Leu Pro Arg Asp Val Leu Ala Gln Leu Pro Ser Leu Arg His Leu Asp
225                 230                 235                 240

Leu Ser Asn Asn Ser Leu Val Ser Leu Thr Tyr Val Ser Phe Arg Asn
                245                 250                 255

Leu Thr His Leu Glu Ser Leu His Leu Glu Asp Asn Ala Leu Lys Val
            260                 265                 270

Leu His Asn Gly Thr Leu Ala Glu Leu Gln Gly Leu Pro His Ile Arg
        275                 280                 285

Val Phe Leu Asp Asn Asn Pro Trp Val Cys Asp Cys His Met Ala Asp
290                 295                 300

Met Val Thr Trp Leu Lys Glu Thr Glu Val Val Gln Gly Lys Asp Arg
305                 310                 315                 320

Leu Thr Cys Ala Tyr Pro Glu Lys Met Arg Asn Arg Val Leu Leu Glu
                325                 330                 335

Leu Asn Ser Ala Asp Leu Asp Cys Asp Pro Ile Leu Pro Pro Ser Leu
            340                 345                 350

Gln Thr Ser Ala Ala Ala Leu Glu Val Leu Phe Gln Gly Pro Gly Thr
        355                 360                 365
```

```
His His His His His His His His Ile Gly Leu Asn Asp Ile
    370                 375                 380

Phe Glu Ala Gln Lys Ile Glu Trp His Glu
385                 390

<210> SEQ ID NO 28
<211> LENGTH: 613
<212> TYPE: PRT
<213> ORGANISM: Artificial Sequence
<220> FEATURE:
<223> OTHER INFORMATION: human TPBG extracellular domain, aa 1-355
      huIgG1-Fc-His6

<400> SEQUENCE: 28

Met Pro Gly Gly Cys Ser Arg Gly Pro Ala Ala Gly Asp Gly Arg Leu
1               5                   10                  15

Arg Leu Ala Arg Leu Ala Leu Val Leu Leu Gly Trp Val Ser Ser Ser
                20                  25                  30

Ser Pro Thr Ser Ser Ala Ser Ser Phe Ser Ser Ser Ala Pro Phe Leu
            35                  40                  45

Ala Ser Ala Val Ser Ala Gln Pro Pro Leu Pro Asp Gln Cys Pro Ala
        50                  55                  60

Leu Cys Glu Cys Ser Glu Ala Ala Arg Thr Val Lys Cys Val Asn Arg
65                  70                  75                  80

Asn Leu Thr Glu Val Pro Thr Asp Leu Pro Ala Tyr Val Arg Asn Leu
                85                  90                  95

Phe Leu Thr Gly Asn Gln Leu Ala Val Leu Pro Ala Gly Ala Phe Ala
            100                 105                 110

Arg Arg Pro Pro Leu Ala Glu Leu Ala Ala Leu Asn Leu Ser Gly Ser
        115                 120                 125

Arg Leu Asp Glu Val Arg Ala Gly Ala Phe Glu His Leu Pro Ser Leu
130                 135                 140

Arg Gln Leu Asp Leu Ser His Asn Pro Leu Ala Asp Leu Ser Pro Phe
145                 150                 155                 160

Ala Phe Ser Gly Ser Asn Ala Ser Val Ser Ala Pro Ser Pro Leu Val
                165                 170                 175

Glu Leu Ile Leu Asn His Ile Val Pro Pro Glu Asp Glu Arg Gln Asn
            180                 185                 190

Arg Ser Phe Glu Gly Met Val Val Ala Ala Leu Leu Ala Gly Arg Ala
        195                 200                 205

Leu Gln Gly Leu Arg Arg Leu Glu Leu Ala Ser Asn His Phe Leu Tyr
210                 215                 220

Leu Pro Arg Asp Val Leu Ala Gln Leu Pro Ser Leu Arg His Leu Asp
225                 230                 235                 240

Leu Ser Asn Asn Ser Leu Val Ser Leu Thr Tyr Val Ser Phe Arg Asn
                245                 250                 255

Leu Thr His Leu Glu Ser Leu His Leu Glu Asp Asn Ala Leu Lys Val
            260                 265                 270

Leu His Asn Gly Thr Leu Ala Glu Leu Gln Gly Leu Pro His Ile Arg
        275                 280                 285

Val Phe Leu Asp Asn Asn Pro Trp Val Cys Asp Cys His Met Ala Asp
290                 295                 300

Met Val Thr Trp Leu Lys Glu Thr Glu Val Val Gln Gly Lys Asp Arg
305                 310                 315                 320

Leu Thr Cys Ala Tyr Pro Glu Lys Met Arg Asn Arg Val Leu Leu Glu
                325                 330                 335
```

Leu Asn Ser Ala Asp Leu Asp Cys Asp Pro Ile Leu Pro Ser Leu
            340                 345                 350

Gln Thr Ser Ala Ala Leu Glu Val Leu Phe Gln Gly Pro Gly Thr
            355                 360                 365

Ile Glu Gly Arg Met Asp Pro Lys Ser Cys Asp Lys Thr His Thr Cys
370                 375                 380

Pro Pro Cys Pro Ala Pro Glu Leu Leu Gly Gly Pro Ser Val Phe Leu
385                 390                 395                 400

Phe Pro Pro Lys Pro Lys Asp Thr Leu Met Ile Ser Arg Thr Pro Glu
                405                 410                 415

Val Thr Cys Val Val Val Asp Val Ser His Glu Asp Pro Glu Val Lys
                420                 425                 430

Phe Asn Trp Tyr Val Asp Gly Val Glu Val His Asn Ala Lys Thr Lys
            435                 440                 445

Pro Arg Glu Glu Gln Tyr Asn Ser Thr Tyr Arg Val Val Ser Val Leu
    450                 455                 460

Thr Val Leu His Gln Asp Trp Leu Asn Gly Lys Glu Tyr Lys Cys Lys
465                 470                 475                 480

Val Ser Asn Lys Ala Leu Pro Ala Pro Ile Glu Lys Thr Ile Ser Lys
                485                 490                 495

Ala Lys Gly Gln Pro Arg Glu Pro Gln Val Tyr Thr Leu Pro Pro Ser
            500                 505                 510

Arg Glu Glu Met Thr Lys Asn Gln Val Ser Leu Thr Cys Leu Val Lys
        515                 520                 525

Gly Phe Tyr Pro Ser Asp Ile Ala Val Glu Trp Glu Ser Asn Gly Gln
    530                 535                 540

Pro Glu Asn Asn Tyr Lys Thr Thr Pro Pro Val Leu Asp Ser Asp Gly
545                 550                 555                 560

Ser Phe Phe Leu Tyr Ser Lys Leu Thr Val Asp Lys Ser Arg Trp Gln
                565                 570                 575

Gln Gly Asn Val Phe Ser Cys Ser Val Met His Glu Ala Leu His Asn
            580                 585                 590

His Tyr Thr Gln Lys Ser Leu Ser Leu Ser Pro Gly Lys Ser Gly His
        595                 600                 605

His His His His His
    610

<210> SEQ ID NO 29
<211> LENGTH: 393
<212> TYPE: PRT
<213> ORGANISM: Artificial Sequence
<220> FEATURE:
<223> OTHER INFORMATION: minipig TPBG extracellular domain, aa 1-368
      His6Avi

<400> SEQUENCE: 29

Met Pro Gly Gly Cys Ser Arg Gly Pro Ala Ala Gly Asp Gly Arg Leu
1               5                   10                  15

Arg Leu Ala Arg Leu Ala Leu Val Leu Leu Gly Trp Val Ser Ser Ser
            20                  25                  30

Ser Leu Thr Ser Ser Ala Ser Ser Thr Ser Ala Ser Phe Pro Ala
            35                  40                  45

Ser Ala Ala Ser Ala Leu Pro Pro Leu Pro Gly Arg Cys Pro Gln Pro
50                  55                  60

Cys Glu Cys Ser Glu Ala Ala Arg Thr Val Lys Cys Val Gly Arg Asn

```
                    65                  70                  75                  80
Leu Thr Glu Val Pro Ala Asp Leu Pro Pro Tyr Val Arg Thr Leu Phe
                    85                  90                  95
Leu Thr Gly Asn Gln Leu Ala Val Leu Pro Thr Gly Ala Phe Ala Arg
                   100                 105                 110
Arg Pro Pro Leu Ala Glu Leu Ser Ala Leu Asn Leu Ser Gly Ser Arg
               115                 120                 125
Leu Thr Glu Val Gln Ala Gly Ala Phe Glu His Leu Pro Ser Leu Arg
           130                 135                 140
Leu Leu Asp Leu Ser His Asn Pro Leu Ala Asn Leu Ser Ala Phe Ala
145                 150                 155                 160
Phe Ser Gly Ser Asn Ala Ser Val Ala Pro Ser Pro Leu Val Asp
                   165                 170                 175
Leu Ile Leu Asn His Ile Val Thr Ser Ala Ala Gln Arg Gln Asn Arg
               180                 185                 190
Ser Phe Glu Gly Met Val Ala Ala Leu Arg Ala Gly His Ala Leu
           195                 200                 205
Arg Gly Leu Arg Arg Leu Glu Leu Ala Ser Asn His Leu Leu Tyr Leu
       210                 215                 220
Pro Leu Asp Val Leu Ala Gln Leu Pro Asp Leu Arg His Leu Asp Leu
225                 230                 235                 240
Arg Asn Asn Ser Leu Val Ser Leu Thr Tyr Val Phe Phe Arg Asn Leu
                   245                 250                 255
Thr His Leu Glu Ser Phe His Leu Glu Asp Asn Ala Leu Lys Val Leu
               260                 265                 270
His Asn Gly Thr Leu Ala Glu Leu Gln Ser Leu Pro His Val Arg Val
           275                 280                 285
Phe Leu Asp Asp Asn Pro Trp Val Cys Asp Cys His Leu Ala Asp Met
       290                 295                 300
Val Ala Trp Leu Lys Glu Thr Glu Val Val Gln Asp Lys Ala Arg Leu
305                 310                 315                 320
Thr Cys Ala Phe Pro Glu Lys Met Arg His Arg Val Leu Leu Glu Leu
                   325                 330                 335
Asn Ser Ser Asp Leu Asp Cys Asp Pro Asp Leu Pro Pro Ser Leu Gln
               340                 345                 350
Thr Ser Ala Ala Ala Leu Glu Val Leu Phe Gln Gly Pro Gly Thr His
           355                 360                 365
His His His His His His His His Ile Gly Leu Asn Asp Ile Phe
       370                 375                 380
Glu Ala Gln Lys Ile Glu Trp His Glu
385                 390

<210> SEQ ID NO 30
<211> LENGTH: 612
<212> TYPE: PRT
<213> ORGANISM: Artificial Sequence
<220> FEATURE:
<223> OTHER INFORMATION: minipig TPBG extracellular domain, aa 1-368
      huIgG1-Fc-His

<400> SEQUENCE: 30

Met Pro Gly Gly Cys Ser Arg Gly Pro Ala Ala Gly Asp Gly Arg Leu
1               5                   10                  15
Arg Leu Ala Arg Leu Ala Leu Val Leu Leu Gly Trp Val Ser Ser Ser
            20                  25                  30
```

```
Ser Leu Thr Ser Ser Ala Ser Ser Thr Ser Ser Ala Ser Phe Pro Ala
         35              40              45

Ser Ala Ala Ser Ala Leu Pro Pro Leu Pro Gly Arg Cys Pro Gln Pro
 50              55              60

Cys Glu Cys Ser Glu Ala Ala Arg Thr Val Lys Cys Val Gly Arg Asn
 65              70              75              80

Leu Thr Glu Val Pro Ala Asp Leu Pro Pro Tyr Val Arg Thr Leu Phe
             85              90              95

Leu Thr Gly Asn Gln Leu Ala Val Leu Pro Thr Gly Ala Phe Ala Arg
         100             105             110

Arg Pro Pro Leu Ala Glu Leu Ser Ala Leu Asn Leu Ser Gly Ser Arg
         115             120             125

Leu Thr Glu Val Gln Ala Gly Ala Phe Glu His Leu Pro Ser Leu Arg
         130             135             140

Leu Leu Asp Leu Ser His Asn Pro Leu Ala Asn Leu Ser Ala Phe Ala
145             150             155             160

Phe Ser Gly Ser Asn Ala Ser Val Ala Ala Pro Ser Pro Leu Val Asp
                 165             170             175

Leu Ile Leu Asn His Ile Val Thr Ser Ala Ala Gln Arg Gln Asn Arg
             180             185             190

Ser Phe Glu Gly Met Val Ala Ala Leu Arg Ala Gly His Ala Leu
         195             200             205

Arg Gly Leu Arg Arg Leu Glu Leu Ala Ser Asn His Leu Leu Tyr Leu
     210             215             220

Pro Leu Asp Val Leu Ala Gln Leu Pro Asp Leu Arg His Leu Asp Leu
225             230             235             240

Arg Asn Asn Ser Leu Val Ser Leu Thr Tyr Val Phe Phe Arg Asn Leu
             245             250             255

Thr His Leu Glu Ser Phe His Leu Glu Asp Asn Ala Leu Lys Val Leu
         260             265             270

His Asn Gly Thr Leu Ala Glu Leu Gln Ser Leu Pro His Val Arg Val
         275             280             285

Phe Leu Asp Asp Asn Pro Trp Val Cys Asp Cys His Leu Ala Asp Met
290             295             300

Val Ala Trp Leu Lys Glu Thr Glu Val Val Gln Asp Lys Ala Arg Leu
305             310             315             320

Thr Cys Ala Phe Pro Glu Lys Met Arg His Arg Val Leu Leu Glu Leu
                 325             330             335

Asn Ser Asp Leu Asp Cys Asp Pro Asp Leu Pro Pro Ser Leu Gln
             340             345             350

Thr Ser Ala Ala Ala Leu Glu Val Leu Phe Gln Gly Pro Gly Thr Ile
         355             360             365

Glu Gly Arg Met Asp Pro Lys Ser Cys Asp Lys Thr His Thr Cys Pro
     370             375             380

Pro Cys Pro Ala Pro Glu Leu Leu Gly Gly Pro Ser Val Phe Leu Phe
385             390             395             400

Pro Pro Lys Pro Lys Asp Thr Leu Met Ile Ser Arg Thr Pro Glu Val
             405             410             415

Thr Cys Val Val Val Asp Val Ser His Glu Asp Pro Glu Val Lys Phe
             420             425             430

Asn Trp Tyr Val Asp Gly Val Glu Val His Asn Ala Lys Thr Lys Pro
         435             440             445

Arg Glu Glu Gln Tyr Asn Ser Thr Tyr Arg Val Val Ser Val Leu Thr
```

```
              450                 455                 460
Val Leu His Gln Asp Trp Leu Asn Gly Lys Glu Tyr Lys Cys Lys Val
465                 470                 475                 480

Ser Asn Lys Ala Leu Pro Ala Pro Ile Glu Lys Thr Ile Ser Lys Ala
                485                 490                 495

Lys Gly Gln Pro Arg Glu Pro Gln Val Tyr Thr Leu Pro Pro Ser Arg
                500                 505                 510

Glu Glu Met Thr Lys Asn Gln Val Ser Leu Thr Cys Leu Val Lys Gly
            515                 520                 525

Phe Tyr Pro Ser Asp Ile Ala Val Glu Trp Glu Ser Asn Gly Gln Pro
        530                 535                 540

Glu Asn Asn Tyr Lys Thr Thr Pro Pro Val Leu Asp Ser Asp Gly Ser
545                 550                 555                 560

Phe Phe Leu Tyr Ser Lys Leu Thr Val Asp Lys Ser Arg Trp Gln Gln
                565                 570                 575

Gly Asn Val Phe Ser Cys Ser Val Met His Glu Ala Leu His Asn His
                580                 585                 590

Tyr Thr Gln Lys Ser Leu Ser Leu Ser Pro Gly Lys Ser Gly His His
            595                 600                 605

His His His His
        610

<210> SEQ ID NO 31
<211> LENGTH: 394
<212> TYPE: PRT
<213> ORGANISM: Artificial Sequence
<220> FEATURE:
<223> OTHER INFORMATION: cynomolgus TPBG extracellular domain, aa 1-368
      His6Avi

<400> SEQUENCE: 31

Met Pro Gly Gly Cys Ser Arg Gly Pro Ala Ala Gly Asp Gly Arg Leu
1               5                   10                  15

Arg Leu Ala Arg Leu Ala Leu Val Leu Leu Gly Trp Val Ser Ser Ser
                20                  25                  30

Ser Pro Thr Ser Ser Ala Ser Ser Phe Ser Ser Ser Ala Pro Phe Leu
            35                  40                  45

Ala Ser Ala Ala Ser Ala Gln Pro Pro Leu Pro Asp Gln Cys Pro Ala
        50                  55                  60

Leu Cys Glu Cys Ser Glu Ala Ala Arg Thr Val Lys Cys Val Asn Arg
65                  70                  75                  80

Asn Leu Thr Glu Val Pro Thr Asp Leu Pro Leu Tyr Val Arg Asn Leu
                85                  90                  95

Phe Leu Thr Gly Asn Gln Leu Ala Val Leu Pro Ala Gly Ala Phe Ala
            100                 105                 110

Arg Arg Pro Pro Leu Ala Glu Leu Ala Ala Leu Asn Leu Ser Gly Ser
        115                 120                 125

Arg Leu Asp Glu Val Arg Ala Gly Ala Phe Glu His Leu Pro Ser Leu
    130                 135                 140

Arg Gln Leu Asp Leu Ser His Asn Pro Leu Ala Tyr Leu Ser Pro Phe
145                 150                 155                 160

Ala Phe Ser Gly Ser Asn Ala Ser Ile Ser Ala Pro Ser Pro Leu Val
                165                 170                 175

Glu Leu Ile Leu Asn His Ile Val Pro Pro Asp Asp Lys Arg Gln Asn
            180                 185                 190
```

-continued

```
Arg Ser Phe Glu Gly Met Val Ala Ala Leu Val Ala Gly Arg Ala
            195                 200                 205

Leu Gln Gly Leu His Leu Leu Glu Leu Ala Ser Asn His Phe Leu Tyr
    210                 215                 220

Leu Pro Arg Asp Val Leu Ala Gln Leu Pro Ser Leu Arg Tyr Leu Asp
225                 230                 235                 240

Leu Ser Asn Asn Ser Leu Val Ser Leu Thr Tyr Val Ser Phe Arg Asn
                245                 250                 255

Leu Thr His Leu Glu Ser Leu His Leu Glu Asp Asn Ala Leu Lys Val
            260                 265                 270

Leu His Asn Gly Thr Leu Ala Glu Leu Gln Gly Leu Pro His Val Arg
        275                 280                 285

Val Phe Leu Asp Asn Asn Pro Trp Val Cys Asp Cys His Met Ala Asp
    290                 295                 300

Met Val Thr Trp Leu Lys Gln Thr Glu Val Val Gln Gly Lys Asp Arg
305                 310                 315                 320

Leu Thr Cys Ala Phe Pro Glu Lys Met Arg Asn Arg Val Leu Leu Glu
                325                 330                 335

Leu Asn Ser Ala Asp Leu Asp Cys Asp Pro Ile Leu Pro Pro Ser Leu
            340                 345                 350

Gln Thr Ser Ala Ala Ala Leu Glu Val Leu Phe Gln Gly Pro Gly Thr
        355                 360                 365

His His His His His His His His Ile Gly Leu Asn Asp Ile
    370                 375                 380

Phe Glu Ala Gln Lys Ile Glu Trp His Glu
385                 390
```

<210> SEQ ID NO 32
<211> LENGTH: 613
<212> TYPE: PRT
<213> ORGANISM: Artificial Sequence
<220> FEATURE:
<223> OTHER INFORMATION: cynomolgus TPBG extracellular domain, aa 1-368
      huIgG1-Fc-His6

<400> SEQUENCE: 32

```
Met Pro Gly Gly Cys Ser Arg Gly Pro Ala Ala Gly Asp Gly Arg Leu
1               5                   10                  15

Arg Leu Ala Arg Leu Ala Leu Val Leu Leu Gly Trp Val Ser Ser Ser
            20                  25                  30

Ser Pro Thr Ser Ser Ala Ser Ser Phe Ser Ser Ser Ala Pro Phe Leu
        35                  40                  45

Ala Ser Ala Ala Ser Ala Gln Pro Pro Leu Pro Asp Gln Cys Pro Ala
    50                  55                  60

Leu Cys Glu Cys Ser Glu Ala Ala Arg Thr Val Lys Cys Val Asn Arg
65                  70                  75                  80

Asn Leu Thr Glu Val Pro Thr Asp Leu Pro Leu Tyr Val Arg Asn Leu
                85                  90                  95

Phe Leu Thr Gly Asn Gln Leu Ala Val Leu Pro Ala Gly Ala Phe Ala
            100                 105                 110

Arg Arg Pro Pro Leu Ala Glu Leu Ala Ala Leu Asn Leu Ser Gly Ser
        115                 120                 125

Arg Leu Asp Glu Val Arg Ala Gly Ala Phe Glu His Leu Pro Ser Leu
    130                 135                 140

Arg Gln Leu Asp Leu Ser His Asn Pro Leu Ala Tyr Leu Ser Pro Phe
145                 150                 155                 160
```

-continued

```
Ala Phe Ser Gly Ser Asn Ala Ser Ile Ser Ala Pro Ser Pro Leu Val
                165                 170                 175

Glu Leu Ile Leu Asn His Ile Val Pro Pro Asp Asp Lys Arg Gln Asn
            180                 185                 190

Arg Ser Phe Glu Gly Met Val Ala Ala Leu Val Ala Gly Arg Ala
        195                 200                 205

Leu Gln Gly Leu His Leu Leu Glu Leu Ala Ser Asn His Phe Leu Tyr
    210                 215                 220

Leu Pro Arg Asp Val Leu Ala Gln Leu Pro Ser Leu Arg Tyr Leu Asp
225                 230                 235                 240

Leu Ser Asn Asn Ser Leu Val Ser Leu Thr Tyr Val Ser Phe Arg Asn
                245                 250                 255

Leu Thr His Leu Glu Ser Leu His Leu Glu Asp Asn Ala Leu Lys Val
            260                 265                 270

Leu His Asn Gly Thr Leu Ala Glu Leu Gln Gly Leu Pro His Val Arg
        275                 280                 285

Val Phe Leu Asp Asn Asn Pro Trp Val Cys Asp Cys His Met Ala Asp
    290                 295                 300

Met Val Thr Trp Leu Lys Gln Thr Glu Val Val Gln Gly Lys Asp Arg
305                 310                 315                 320

Leu Thr Cys Ala Phe Pro Glu Lys Met Arg Asn Arg Val Leu Leu Glu
                325                 330                 335

Leu Asn Ser Ala Asp Leu Asp Cys Asp Pro Ile Leu Pro Pro Ser Leu
            340                 345                 350

Gln Thr Ser Ala Ala Ala Leu Glu Val Leu Phe Gln Gly Pro Gly Thr
        355                 360                 365

Ile Glu Gly Arg Met Asp Pro Lys Ser Cys Asp Lys Thr His Thr Cys
    370                 375                 380

Pro Pro Cys Pro Ala Pro Glu Leu Leu Gly Gly Pro Ser Val Phe Leu
385                 390                 395                 400

Phe Pro Pro Lys Pro Lys Asp Thr Leu Met Ile Ser Arg Thr Pro Glu
                405                 410                 415

Val Thr Cys Val Val Val Asp Val Ser His Glu Asp Pro Glu Val Lys
            420                 425                 430

Phe Asn Trp Tyr Val Asp Gly Val Glu Val His Asn Ala Lys Thr Lys
        435                 440                 445

Pro Arg Glu Glu Gln Tyr Asn Ser Thr Tyr Arg Val Val Ser Val Leu
    450                 455                 460

Thr Val Leu His Gln Asp Trp Leu Asn Gly Lys Glu Tyr Lys Cys Lys
465                 470                 475                 480

Val Ser Asn Lys Ala Leu Pro Ala Pro Ile Glu Lys Thr Ile Ser Lys
                485                 490                 495

Ala Lys Gly Gln Pro Arg Glu Pro Gln Val Tyr Thr Leu Pro Pro Ser
            500                 505                 510

Arg Glu Glu Met Thr Lys Asn Gln Val Ser Leu Thr Cys Leu Val Lys
        515                 520                 525

Gly Phe Tyr Pro Ser Asp Ile Ala Val Glu Trp Glu Ser Asn Gly Gln
    530                 535                 540

Pro Glu Asn Asn Tyr Lys Thr Thr Pro Pro Val Leu Asp Ser Asp Gly
545                 550                 555                 560

Ser Phe Phe Leu Tyr Ser Lys Leu Thr Val Asp Lys Ser Arg Trp Gln
                565                 570                 575
```

```
Gln Gly Asn Val Phe Ser Cys Ser Val Met His Glu Ala Leu His Asn
                580                 585                 590

His Tyr Thr Gln Lys Ser Leu Ser Leu Ser Pro Gly Lys Ser Gly His
        595                 600                 605

His His His His His
    610

<210> SEQ ID NO 33
<211> LENGTH: 400
<212> TYPE: PRT
<213> ORGANISM: Artificial Sequence
<220> FEATURE:
<223> OTHER INFORMATION: murine TPBG extracellular domain, aa 1-374
      His6Avi

<400> SEQUENCE: 33

Met Pro Gly Ala Gly Ser Arg Gly Pro Ser Ala Gly Asp Gly Arg Leu
1               5                   10                  15

Arg Leu Ala Arg Leu Ala Leu Val Leu Leu Gly Trp Val Ser Ala Ser
            20                  25                  30

Ala Pro Ser Ser Ser Val Pro Ser Ser Thr Ser Pro Ala Ala Phe
        35                  40                  45

Leu Ala Ser Gly Ser Ala Gln Pro Pro Ala Glu Arg Cys Pro Ala
    50                  55                  60

Ala Cys Glu Cys Ser Glu Ala Ala Arg Thr Val Lys Cys Val Asn Arg
65                  70                  75                  80

Asn Leu Leu Glu Val Pro Ala Asp Leu Pro Pro Tyr Val Arg Asn Leu
                85                  90                  95

Phe Leu Thr Gly Asn Gln Met Thr Val Leu Pro Ala Gly Ala Phe Ala
            100                 105                 110

Arg Gln Pro Pro Leu Ala Asp Leu Glu Ala Leu Asn Leu Ser Gly Asn
        115                 120                 125

His Leu Lys Glu Val Cys Ala Gly Ala Phe Glu His Leu Pro Gly Leu
    130                 135                 140

Arg Arg Leu Asp Leu Ser His Asn Pro Leu Thr Asn Leu Ser Ala Phe
145                 150                 155                 160

Ala Phe Ala Gly Ser Asn Ala Ser Val Ser Ala Pro Ser Pro Leu Glu
                165                 170                 175

Glu Leu Ile Leu Asn His Ile Val Pro Pro Glu Asp Gln Arg Gln Asn
            180                 185                 190

Gly Ser Phe Glu Gly Met Val Ala Phe Glu Gly Met Val Ala Ala Ala
        195                 200                 205

Leu Arg Ser Gly Leu Ala Leu Arg Gly Leu Thr Arg Leu Glu Leu Ala
    210                 215                 220

Ser Asn His Phe Leu Phe Leu Pro Arg Asp Leu Leu Ala Gln Leu Pro
225                 230                 235                 240

Ser Leu Arg Tyr Leu Asp Leu Arg Asn Asn Ser Leu Val Ser Leu Thr
                245                 250                 255

Tyr Ala Ser Phe Arg Asn Leu Thr His Leu Glu Ser Leu His Leu Glu
            260                 265                 270

Asp Asn Ala Leu Lys Val Leu His Asn Ser Thr Leu Ala Glu Trp His
        275                 280                 285

Gly Leu Ala His Val Lys Val Phe Leu Asp Asn Asn Pro Trp Val Cys
    290                 295                 300

Asp Cys Tyr Met Ala Asp Met Val Ala Trp Leu Lys Glu Thr Glu Val
305                 310                 315                 320
```

```
Val Pro Asp Lys Ala Arg Leu Thr Cys Ala Phe Pro Glu Lys Met Arg
            325                 330                 335

Asn Arg Gly Leu Leu Asp Leu Asn Ser Ser Asp Leu Asp Cys Asp Ala
            340                 345                 350

Val Leu Pro Gln Ser Leu Gln Thr Ser Ala Ala Leu Glu Val Leu
        355                 360                 365

Phe Gln Gly Pro Gly Thr His His His His His His His His
    370                 375                 380

Ile Gly Leu Asn Asp Ile Phe Glu Ala Gln Lys Ile Glu Trp His Glu
385                 390                 395                 400

<210> SEQ ID NO 34
<211> LENGTH: 619
<212> TYPE: PRT
<213> ORGANISM: Artificial Sequence
<220> FEATURE:
<223> OTHER INFORMATION: murine TPBG extracellular domain, aa 1-374
      huIgG1-Fc-His6

<400> SEQUENCE: 34

Met Pro Gly Ala Gly Ser Arg Gly Pro Ser Ala Gly Asp Gly Arg Leu
1               5                   10                  15

Arg Leu Ala Arg Leu Ala Leu Val Leu Leu Gly Trp Val Ser Ala Ser
            20                  25                  30

Ala Pro Ser Ser Ser Val Pro Ser Ser Thr Ser Pro Ala Ala Phe
        35                  40                  45

Leu Ala Ser Gly Ser Ala Gln Pro Pro Ala Glu Arg Cys Pro Ala
50                  55                  60

Ala Cys Glu Cys Ser Glu Ala Ala Arg Thr Val Lys Cys Val Asn Arg
65                  70                  75                  80

Asn Leu Leu Glu Val Pro Ala Asp Leu Pro Pro Tyr Val Arg Asn Leu
            85                  90                  95

Phe Leu Thr Gly Asn Gln Met Thr Val Leu Pro Ala Gly Ala Phe Ala
            100                 105                 110

Arg Gln Pro Pro Leu Ala Asp Leu Glu Ala Leu Asn Leu Ser Gly Asn
            115                 120                 125

His Leu Lys Glu Val Cys Ala Gly Ala Phe Glu His Leu Pro Gly Leu
    130                 135                 140

Arg Arg Leu Asp Leu Ser His Asn Pro Leu Thr Asn Leu Ser Ala Phe
145                 150                 155                 160

Ala Phe Ala Gly Ser Asn Ala Ser Val Ser Ala Pro Ser Pro Leu Glu
            165                 170                 175

Glu Leu Ile Leu Asn His Ile Val Pro Pro Glu Asp Gln Arg Gln Asn
            180                 185                 190

Gly Ser Phe Glu Gly Met Val Ala Phe Glu Gly Met Val Ala Ala Ala
        195                 200                 205

Leu Arg Ser Gly Leu Ala Leu Arg Gly Leu Thr Arg Leu Glu Leu Ala
    210                 215                 220

Ser Asn His Phe Leu Phe Leu Pro Arg Asp Leu Leu Ala Gln Leu Pro
225                 230                 235                 240

Ser Leu Arg Tyr Leu Asp Leu Arg Asn Asn Ser Leu Val Ser Leu Thr
            245                 250                 255

Tyr Ala Ser Phe Arg Asn Leu Thr His Leu Glu Ser Leu His Leu Glu
            260                 265                 270

Asp Asn Ala Leu Lys Val Leu His Asn Ser Thr Leu Ala Glu Trp His
```

```
                275                 280                 285
Gly Leu Ala His Val Lys Val Phe Leu Asp Asn Pro Trp Val Cys
        290                 295                 300

Asp Cys Tyr Met Ala Asp Met Val Ala Trp Leu Lys Glu Thr Glu Val
305                 310                 315                 320

Val Pro Asp Lys Ala Arg Leu Thr Cys Ala Phe Pro Glu Lys Met Arg
                325                 330                 335

Asn Arg Gly Leu Leu Asp Leu Asn Ser Ser Asp Leu Asp Cys Asp Ala
            340                 345                 350

Val Leu Pro Gln Ser Leu Gln Thr Ser Ala Ala Leu Glu Val Leu
        355                 360                 365

Phe Gln Gly Pro Gly Thr Ile Glu Gly Arg Met Asp Pro Lys Ser Cys
370                 375                 380

Asp Lys Thr His Thr Cys Pro Pro Cys Pro Ala Pro Glu Leu Leu Gly
385                 390                 395                 400

Gly Pro Ser Val Phe Leu Phe Pro Pro Lys Pro Lys Asp Thr Leu Met
                405                 410                 415

Ile Ser Arg Thr Pro Glu Val Thr Cys Val Val Val Asp Val Ser His
            420                 425                 430

Glu Asp Pro Glu Val Lys Phe Asn Trp Tyr Val Asp Gly Val Glu Val
        435                 440                 445

His Asn Ala Lys Thr Lys Pro Arg Glu Glu Gln Tyr Asn Ser Thr Tyr
    450                 455                 460

Arg Val Val Ser Val Leu Thr Val Leu His Gln Asp Trp Leu Asn Gly
465                 470                 475                 480

Lys Glu Tyr Lys Cys Lys Val Ser Asn Lys Ala Leu Pro Ala Pro Ile
                485                 490                 495

Glu Lys Thr Ile Ser Lys Ala Lys Gly Gln Pro Arg Glu Pro Gln Val
            500                 505                 510

Tyr Thr Leu Pro Pro Ser Arg Glu Glu Met Thr Lys Asn Gln Val Ser
        515                 520                 525

Leu Thr Cys Leu Val Lys Gly Phe Tyr Pro Ser Asp Ile Ala Val Glu
    530                 535                 540

Trp Glu Ser Asn Gly Gln Pro Glu Asn Asn Tyr Lys Thr Thr Pro Pro
545                 550                 555                 560

Val Leu Asp Ser Asp Gly Ser Phe Phe Leu Tyr Ser Lys Leu Thr Val
                565                 570                 575

Asp Lys Ser Arg Trp Gln Gln Gly Asn Val Phe Ser Cys Ser Val Met
            580                 585                 590

His Glu Ala Leu His Asn His Tyr Thr Gln Lys Ser Leu Ser Leu Ser
        595                 600                 605

Pro Gly Lys Ser Gly His His His His His His
    610                 615

<210> SEQ ID NO 35
<211> LENGTH: 400
<212> TYPE: PRT
<213> ORGANISM: Artificial Sequence
<220> FEATURE:
<223> OTHER INFORMATION: rat TPBG extracellular domain, aa 1-374 His6Avi

<400> SEQUENCE: 35

Met Pro Gly Ala Gly Ser Arg Gly Pro Ser Ala Gly Asp Gly Arg Leu
1               5                   10                  15

Arg Leu Ala Arg Leu Ala Leu Val Leu Leu Gly Trp Val Ser Ala Ser
```

```
            20                  25                  30
Ala Pro Ser Ser Leu Pro Ser Ser Thr Ser Pro Ala Ala Phe
        35                  40                  45
Leu Ala Ser Gly Ser Ala Gln Pro Pro Ala Glu Arg Cys Pro Ala
50                  55                  60
Ala Cys Glu Cys Ser Glu Ala Ala Arg Thr Val Lys Cys Val Asn Arg
65                  70                  75                  80
Asn Leu Leu Glu Val Pro Ala Asp Leu Pro Pro Tyr Val Arg Asn Leu
                85                  90                  95
Phe Leu Thr Gly Asn Gln Met Thr Val Leu Pro Ala Gly Ala Phe Ala
            100                 105                 110
Arg Gln Pro Pro Leu Ala Asp Leu Ala Val Leu Asn Leu Ser Gly Asn
        115                 120                 125
His Leu Lys Glu Val Gly Ala Gly Ala Phe Glu His Leu Pro Gly Leu
    130                 135                 140
Arg Arg Leu Asp Leu Ser His Asn Pro Leu Thr Asn Leu Ser Ala Phe
145                 150                 155                 160
Thr Phe Ala Gly Ser Asn Val Ser Val Ser Thr Pro Ser Pro Leu Leu
                165                 170                 175
Glu Leu Ile Leu Asn His Ile Val Pro Pro Glu Asp Gln Arg Gln Asn
            180                 185                 190
Gly Ser Phe Glu Gly Met Val Ala Phe Glu Gly Met Val Ala Ala Ala
        195                 200                 205
Leu Arg Ser Gly Leu Ala Leu Arg Gly Leu His His Leu Glu Leu Ala
    210                 215                 220
Ser Asn His Phe Leu Tyr Leu Pro Arg Asp Leu Leu Asp Gln Leu Pro
225                 230                 235                 240
Ser Leu Lys His Leu Asp Leu Arg Asn Asn Ser Leu Val Ser Leu Thr
                245                 250                 255
Tyr Ala Ser Phe Arg Asn Leu Thr His Leu Glu Ser Leu His Leu Glu
            260                 265                 270
Asp Asn Ala Leu Lys Val Leu His Asn Ser Thr Leu Ala Glu Trp Gln
        275                 280                 285
Gly Leu Ala His Val Arg Val Phe Leu Asp Asn Asn Pro Trp Val Cys
    290                 295                 300
Asp Cys Tyr Met Ala Asp Met Val Ser Trp Leu Lys Glu Thr Glu Val
305                 310                 315                 320
Val Pro Asp Lys Ala Arg Leu Thr Cys Ala Phe Pro Glu Lys Met Arg
                325                 330                 335
Asn Arg Gly Leu Leu Asp Leu Thr Ser Ser Asp Leu Asp Cys Asp Ala
            340                 345                 350
Thr Leu Pro Gln Ser Leu Gln Thr Ser Ala Ala Leu Glu Val Leu
        355                 360                 365
Phe Gln Gly Pro Gly Thr His His His His His His His His
    370                 375                 380
Ile Gly Leu Asn Asp Ile Phe Glu Ala Gln Lys Ile Glu Trp His Glu
385                 390                 395                 400
```

<210> SEQ ID NO 36
<211> LENGTH: 619
<212> TYPE: PRT
<213> ORGANISM: Artificial Sequence
<220> FEATURE:
<223> OTHER INFORMATION: rat TPBG extracellular domain, aa 1-374
    huIgG1-Fc-His6

<400> SEQUENCE: 36

```
Met Pro Gly Ala Gly Ser Arg Gly Pro Ser Ala Gly Asp Gly Arg Leu
1               5                   10                  15

Arg Leu Ala Arg Leu Ala Leu Val Leu Leu Gly Trp Val Ser Ala Ser
            20                  25                  30

Ala Pro Ser Ser Ser Leu Pro Ser Ser Ser Thr Ser Pro Ala Ala Phe
        35                  40                  45

Leu Ala Ser Gly Ser Ala Gln Pro Pro Ala Glu Arg Cys Pro Ala
    50                  55                  60

Ala Cys Glu Cys Ser Glu Ala Ala Arg Thr Val Lys Cys Val Asn Arg
65                  70                  75                  80

Asn Leu Leu Glu Val Pro Ala Asp Leu Pro Pro Tyr Val Arg Asn Leu
                85                  90                  95

Phe Leu Thr Gly Asn Gln Met Thr Val Leu Pro Ala Gly Ala Phe Ala
            100                 105                 110

Arg Gln Pro Pro Leu Ala Asp Leu Ala Val Leu Asn Leu Ser Gly Asn
        115                 120                 125

His Leu Lys Glu Val Gly Ala Gly Ala Phe Glu His Leu Pro Gly Leu
    130                 135                 140

Arg Arg Leu Asp Leu Ser His Asn Pro Leu Thr Asn Leu Ser Ala Phe
145                 150                 155                 160

Thr Phe Ala Gly Ser Asn Val Ser Val Ser Thr Pro Ser Pro Leu Leu
                165                 170                 175

Glu Leu Ile Leu Asn His Ile Val Pro Pro Glu Asp Gln Arg Gln Asn
            180                 185                 190

Gly Ser Phe Glu Gly Met Val Ala Phe Glu Gly Met Val Ala Ala Ala
        195                 200                 205

Leu Arg Ser Gly Leu Ala Leu Arg Gly Leu His His Leu Glu Leu Ala
    210                 215                 220

Ser Asn His Phe Leu Tyr Leu Pro Arg Asp Leu Leu Asp Gln Leu Pro
225                 230                 235                 240

Ser Leu Lys His Leu Asp Leu Arg Asn Asn Ser Leu Val Ser Leu Thr
                245                 250                 255

Tyr Ala Ser Phe Arg Asn Leu Thr His Leu Glu Ser Leu His Leu Glu
            260                 265                 270

Asp Asn Ala Leu Lys Val Leu His Asn Ser Thr Leu Ala Glu Trp Gln
        275                 280                 285

Gly Leu Ala His Val Arg Val Phe Leu Asp Asn Asn Pro Trp Val Cys
    290                 295                 300

Asp Cys Tyr Met Ala Asp Met Val Ser Trp Leu Lys Glu Thr Glu Val
305                 310                 315                 320

Val Pro Asp Lys Ala Arg Leu Thr Cys Ala Phe Pro Glu Lys Met Arg
                325                 330                 335

Asn Arg Gly Leu Leu Asp Leu Ser Ser Asp Leu Asp Cys Asp Ala
            340                 345                 350

Thr Leu Pro Gln Ser Leu Gln Thr Ser Ala Ala Leu Glu Val Leu
        355                 360                 365

Phe Gln Gly Pro Gly Thr Ile Glu Gly Arg Met Asp Pro Lys Ser Cys
    370                 375                 380

Asp Lys Thr His Thr Cys Pro Pro Cys Pro Ala Pro Glu Leu Leu Gly
385                 390                 395                 400

Gly Pro Ser Val Phe Leu Phe Pro Pro Lys Pro Lys Asp Thr Leu Met
```

```
                    405                 410                 415
Ile Ser Arg Thr Pro Glu Val Thr Cys Val Val Val Asp Val Ser His
            420                 425                 430

Glu Asp Pro Glu Val Lys Phe Asn Trp Tyr Val Asp Gly Val Glu Val
        435                 440                 445

His Asn Ala Lys Thr Lys Pro Arg Glu Glu Gln Tyr Asn Ser Thr Tyr
    450                 455                 460

Arg Val Val Ser Val Leu Thr Val Leu His Gln Asp Trp Leu Asn Gly
465                 470                 475                 480

Lys Glu Tyr Lys Cys Lys Val Ser Asn Lys Ala Leu Pro Ala Pro Ile
                485                 490                 495

Glu Lys Thr Ile Ser Lys Ala Lys Gly Gln Pro Arg Glu Pro Gln Val
            500                 505                 510

Tyr Thr Leu Pro Pro Ser Arg Glu Glu Met Thr Lys Asn Gln Val Ser
        515                 520                 525

Leu Thr Cys Leu Val Lys Gly Phe Tyr Pro Ser Asp Ile Ala Val Glu
    530                 535                 540

Trp Glu Ser Asn Gly Gln Pro Glu Asn Asn Tyr Lys Thr Thr Pro Pro
545                 550                 555                 560

Val Leu Asp Ser Asp Gly Ser Phe Phe Leu Tyr Ser Lys Leu Thr Val
                565                 570                 575

Asp Lys Ser Arg Trp Gln Gln Gly Asn Val Phe Ser Cys Ser Val Met
            580                 585                 590

His Glu Ala Leu His Asn His Tyr Thr Gln Lys Ser Leu Ser Leu Ser
        595                 600                 605

Pro Gly Lys Ser Gly His His His His His
    610                 615

<210> SEQ ID NO 37
<211> LENGTH: 242
<212> TYPE: PRT
<213> ORGANISM: Artificial Sequence
<220> FEATURE:
<223> OTHER INFORMATION: H8 heavy chain for sortase coupling without
      signal peptide

<400> SEQUENCE: 37

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Met His Trp Val Lys Gln Ser His Gly Lys Ser Leu Glu Trp Ile
        35                  40                  45

Gly Arg Ile Asn Pro Asn Asn Gly Val Thr Leu Tyr Asn Gln Lys Phe
    50                  55                  60

Lys Asp Lys Ala Ile Leu Thr Val Asp Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ala Arg Ser Thr Met Ile Thr Asn Tyr Val Met Asp Tyr Trp Gly Gln
            100                 105                 110

Val Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140
```

-continued

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Gly
    210                 215                 220

Gly Gly Ser Leu Pro Glu Thr Gly Gly Ser Gly Ser His His His His
225                 230                 235                 240

His His
```

<210> SEQ ID NO 38
<211> LENGTH: 214
<212> TYPE: PRT
<213> ORGANISM: Artificial Sequence
<220> FEATURE:
<223> OTHER INFORMATION: H8 light chain for sortase coupling without
      signal peptide

<400> SEQUENCE: 38

```
Ser Ile Val Met Thr Gln Thr Pro Thr Phe Leu Leu Val Ser Ala Gly
1               5                   10                  15

Asp Arg Val Thr Ile Thr Cys Lys Ala Ser Gln Ser Val Ser Asn Asp
                20                  25                  30

Val Ala Trp Tyr Gln Gln Lys Pro Gly Gln Ser Pro Thr Leu Leu Ile
            35                  40                  45

Ser Tyr Thr Ser Ser Arg Tyr Ala Gly Val Pro Asp Arg Phe Ile Gly
        50                  55                  60

Ser Gly Tyr Gly Thr Asp Phe Thr Phe Thr Ile Ser Thr Leu Gln Ala
65                  70                  75                  80

Glu Asp Leu Ala Val Tyr Phe Cys Gln Gln Asp Tyr Asn Ser Pro Pro
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 39
<211> LENGTH: 255
<212> TYPE: PRT
<213> ORGANISM: Artificial Sequence
<220> FEATURE:

<223> OTHER INFORMATION: 051 heavy chain for sortase coupling without
     signal peptide

<400> SEQUENCE: 39

Glu Val Gln Leu Leu Glu Ser Gly Gly Gly Leu Leu Gln Pro Gly Gly
1               5                   10                  15

Ser Leu Arg Leu Ser Cys Ala Ala Ser Gly Phe Thr Phe Ser Ile Tyr
            20                  25                  30

Trp Met Thr Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Tyr Tyr Ser Asn Val Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Gly Gly Gly Ser Leu
    210                 215                 220

Pro Glu Thr Gly Gly Ser Gly Ser Glu Gln Lys Leu Ile Ser Glu Glu
225                 230                 235                 240

Asp Leu His His His His His His Gly Ala Ala Glu Pro Glu Ala
                245                 250                 255

<210> SEQ ID NO 40
<211> LENGTH: 214
<212> TYPE: PRT
<213> ORGANISM: Artificial Sequence
<220> FEATURE:
<223> OTHER INFORMATION: 051 light chain for sortase coupling without
     signal peptide

<400> SEQUENCE: 40

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Tyr Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Gln Ser Asp Ser Pro Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 41
<211> LENGTH: 263
<212> TYPE: PRT
<213> ORGANISM: Artificial Sequence
<220> FEATURE:
<223> OTHER INFORMATION: 091 heavy chain for sortase coupling without
      signal peptide

<400> SEQUENCE: 41

Glu Val His Leu Leu Glu Ser Gly Gly Gly Leu Val His Pro Gly Gly
1               5                   10                  15

Ser Leu Arg Leu Ser Cys Ala Ala Ser Gly Phe Thr Phe Arg Ser Asp
            20                  25                  30

Ala Met His Trp Val Arg Gln Ala Pro Gly Lys Gly Leu Glu Trp Val
        35                  40                  45

Ser Gly Val Ser Gly Ser Gly Gly Ser Pro Tyr Tyr Ala Asp Ser Val
    50                  55                  60

Lys Gly Arg Phe Thr Ile Ser Arg Asp Asp Ser Lys Thr Thr Leu Tyr
65                  70                  75                  80

Leu Gln Met Asn Ser Leu Arg Ala Glu Asp Thr Ala Val Tyr Tyr Cys
                85                  90                  95

Ala Thr Gly Gly Ser Ile Ala Gly Ser Tyr Tyr Tyr Pro Met Asp
            100                 105                 110

Val Trp Gly Gln Gly Thr Thr Val Thr Val Ser Ser Ala Ser Thr Lys
            115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Lys Val Glu Pro
210                 215                 220
```

```
Lys Ser Cys Gly Gly Gly Ser Leu Pro Glu Thr Gly Gly Ser Gly Ser
225                 230                 235                 240

Glu Gln Lys Leu Ile Ser Glu Glu Asp Leu His His His His His His
            245                 250                 255

Gly Ala Ala Glu Pro Glu Ala
            260

<210> SEQ ID NO 42
<211> LENGTH: 214
<212> TYPE: PRT
<213> ORGANISM: Artificial Sequence
<220> FEATURE:
<223> OTHER INFORMATION: 091 light chain for sortase coupling without
      signal peptide

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ile Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 43
<211> LENGTH: 264
<212> TYPE: PRT
<213> ORGANISM: Artificial Sequence
<220> FEATURE:
<223> OTHER INFORMATION: 097 heavy chain for sortase coupling without
      signal peptide

<400> SEQUENCE: 43

Glu Val Gln Leu Leu Glu Ser Gly Gly Gly Leu Ala Gln Pro Gly Gly
1               5                   10                  15

Ser Leu Arg Leu Ser Cys Ala Ala Ser Gly Phe Thr Phe Asn Asn Asp
            20                  25                  30
```

Ala Met Thr Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Ser Trp Gly Asp Trp Tyr Tyr Tyr Phe Tyr Pro Met
            100                 105                 110

Asp Val Trp Gly Gln Gly Thr Thr Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
            195                 200                 205

Asn Val Asn His Lys Pro Ser Asn Thr Lys Val Asp Lys Lys Val Glu
210                 215                 220

Pro Lys Ser Cys Gly Gly Gly Ser Leu Pro Thr Gly Gly Ser Gly
225                 230                 235                 240

Ser Glu Gln Lys Leu Ile Ser Glu Glu Asp Leu His His His His
                245                 250                 255

His Gly Ala Ala Glu Pro Glu Ala
            260

<210> SEQ ID NO 44
<211> LENGTH: 214
<212> TYPE: PRT
<213> ORGANISM: Artificial Sequence
<220> FEATURE:
<223> OTHER INFORMATION: 097 light chain for sortase coupling without
      signal peptide

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ser Phe Pro Leu
                85                  90                  95

Thr Phe Gly Gly Gly Thr Lys Val Glu Ile Lys Gly Thr Val Ala Ala
            100                 105                 110

Pro Ser Val Phe Ile Phe Pro Pro Ser Asp Glu Gln Leu Lys Ser Gly

```
              115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
                195                 200                 205
Phe Asn Arg Gly Glu Cys
    210

<210> SEQ ID NO 45
<211> LENGTH: 233
<212> TYPE: PRT
<213> ORGANISM: Artificial Sequence
<220> FEATURE:
<223> OTHER INFORMATION: Pseudomonas exotoxin for sortase coupling

<400> SEQUENCE: 45

Gly Gly Gly Arg His Arg Gln Pro Arg Gly Trp Glu Gln Leu Tyr Pro
1               5                  10                  15
Thr Gly Ala Glu Phe Leu Gly Asp Gly Gly Ala Val Ser Phe Ser Thr
            20                  25                  30
Arg Gly Thr Gln Asn Trp Thr Val Glu Arg Leu Leu Gln Ala His Arg
        35                  40                  45
Gln Leu Glu Glu Gly Gly Tyr Val Phe Val Gly Tyr His Gly Thr Phe
    50                  55                  60
Leu Glu Ala Ala Gln Ser Ile Val Phe Gly Gly Val Arg Ala Arg Ser
65                  70                  75                  80
Gln Asp Leu Asp Ala Ile Trp Ala Gly Phe Tyr Ile Ala Gly Asp Pro
                85                  90                  95
Ala Leu Ala Tyr Gly Tyr Ala Gln Asp Gln Glu Pro Asp Ala Ala Gly
            100                 105                 110
Arg Ile Arg Asn Gly Ala Leu Leu Arg Val Tyr Val Pro Arg Ser Ser
        115                 120                 125
Leu Pro Gly Phe Tyr Ala Thr Ser Leu Thr Leu Ala Ala Pro Glu Ala
    130                 135                 140
Ala Gly Glu Val Glu Arg Leu Ile Gly His Pro Leu Pro Leu Arg Leu
145                 150                 155                 160
Asp Ala Ile Thr Gly Pro Glu Glu Ser Gly Gly Arg Leu Glu Thr Ile
                165                 170                 175
Leu Gly Trp Pro Leu Ala Glu Arg Thr Val Val Ile Pro Ser Ala Ile
            180                 185                 190
Pro Thr Asp Pro Arg Asn Val Gly Gly Asp Leu Asp Pro Ser Ser Ile
        195                 200                 205
Pro Asp Ser Glu Ala Ala Ile Ser Ala Leu Pro Asp Tyr Ala Ser Gln
    210                 215                 220
Pro Gly Lys Pro Pro Arg Glu Asp Leu
225                 230

<210> SEQ ID NO 46
<211> LENGTH: 465
<212> TYPE: PRT
```

<213> ORGANISM: Artificial Sequence
<220> FEATURE:
<223> OTHER INFORMATION: heavy chain of anti-TPBG 051 Fab-PE fusion protein

<400> SEQUENCE: 46

```
Met Glu Val Gln Leu Leu Glu Ser Gly Gly Gly Leu Leu Gln Pro Gly
1               5                   10                  15

Gly Ser Leu Arg Leu Ser Cys Ala Ala Ser Gly Phe Thr Phe Ser Ile
            20                  25                  30

Tyr Trp Met Thr Trp Val Arg Gln Ala Pro Gly Lys Gly Leu Glu Trp
        35                  40                  45

Val Ser Ala Ile Ser Gly Ser Gly Gly Ser Thr Tyr Tyr Ala Asp Ser
50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Asp Tyr Tyr Ser Asn Val Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Lys Ala Ser Gly Gly Arg His Arg Gln Pro Arg Gly Trp Glu Gln Leu
225                 230                 235                 240

Gly Gly Gly Gly Gly Ser Pro Thr Gly Ala Glu Phe Leu Gly Asp Gly
                245                 250                 255

Gly Asp Val Ser Phe Ser Thr Arg Gly Thr Gln Asn Trp Thr Val Glu
            260                 265                 270

Arg Leu Leu Gln Ala His Ala Gln Leu Glu Glu Arg Gly Tyr Val Phe
        275                 280                 285

Val Gly Tyr His Gly Thr Phe Leu Glu Ala Ala Gln Ser Ile Val Phe
290                 295                 300

Gly Gly Val Ala Ala Arg Ser Gln Asp Leu Ala Ala Ile Trp Ala Gly
305                 310                 315                 320

Phe Tyr Ile Ala Gly Asp Pro Ala Leu Ala Tyr Gly Tyr Ala Gln Asp
                325                 330                 335

Gln Glu Pro Asp Ala Ala Gly Arg Ile Arg Asn Gly Ala Leu Leu Arg
            340                 345                 350

Val Tyr Val Pro Ala Ser Ser Leu Pro Gly Phe Tyr Arg Thr Ser Leu
        355                 360                 365

Thr Leu Ala Ala Pro Glu Ala Ala Gly Glu Val Glu Arg Leu Ile Gly
370                 375                 380
```

His Pro Leu Pro Leu Ala Leu Asp Ala Ile Thr Gly Pro Glu Glu
385                 390                 395                 400

Gly Gly Arg Leu Glu Thr Ile Leu Gly Trp Pro Leu Ala Glu Arg Thr
            405                 410                 415

Val Val Ile Pro Ser Ala Ile Pro Thr Asp Pro Arg Asn Val Gly Gly
                420                 425                 430

Asp Leu Asp Pro Ser Ser Ile Pro Asp Lys Glu Gln Ala Ile Ser Ala
            435                 440                 445

Leu Pro Asp Tyr Ala Ser Gln Pro Gly Lys Pro Pro Arg Glu Asp Leu
        450                 455                 460

Lys
465

<210> SEQ ID NO 47
<211> LENGTH: 215
<212> TYPE: PRT
<213> ORGANISM: Artificial Sequence
<220> FEATURE:
<223> OTHER INFORMATION: light chain of anti-TPBG 051 Fab-PE
      fusion protein

<400> SEQUENCE: 47

Met Asp Ile Gln Met Thr Gln Ser Pro Ser Ser Val Ser Ala Ser Val
1               5                   10                  15

Gly Asp Arg Val Thr Ile Thr Cys Arg Ala Ser Gln Gly Ile Tyr Ser
            20                  25                  30

Trp Leu Ala Trp Tyr Gln Gln Lys Pro Gly Lys Ala Pro Lys Leu Leu
        35                  40                  45

Ile Tyr Ala Ala Ser Ser Leu Gln Ser Gly Val Pro Ser Arg Phe Ser
50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Asp Ser Pro Pro
                85                  90                  95

Tyr Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
210                 215

<210> SEQ ID NO 48
<211> LENGTH: 473
<212> TYPE: PRT
<213> ORGANISM: Artificial Sequence
<220> FEATURE:
<223> OTHER INFORMATION: heavy chain of anti-TPBG 091 Fab-PE
      fusion protein

<400> SEQUENCE: 48

```
Met Glu Val His Leu Leu Glu Ser Gly Gly Leu Val His Pro Gly
1               5                   10                  15

Gly Ser Leu Arg Leu Ser Cys Ala Ala Ser Gly Phe Thr Phe Arg Ser
            20                  25                  30

Asp Ala Met His Trp Val Arg Gln Ala Pro Gly Lys Gly Leu Glu Trp
            35                  40                  45

Val Ser Gly Val Ser Gly Ser Gly Gly Ser Pro Tyr Tyr Ala Asp Ser
50                  55                  60

Val Lys Gly Arg Phe Thr Ile Ser Arg Asp Asp Ser Lys Thr Thr Leu
65                  70                  75                  80

Tyr Leu Gln Met Asn Ser Leu Arg Ala Glu Asp Thr Ala Val Tyr Tyr
                85                  90                  95

Cys Ala Thr Gly Gly Ser Ile Ala Gly Ser Tyr Tyr Tyr Pro Met
            100                 105                 110

Asp Val Trp Gly Gln Gly Thr Thr Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
210                 215                 220

Pro Lys Ser Cys Asp Lys Thr His Lys Ala Ser Gly Gly Arg His Arg
225                 230                 235                 240

Gln Pro Arg Gly Trp Glu Gln Leu Gly Gly Gly Gly Ser Pro Thr
                245                 250                 255

Gly Ala Glu Phe Leu Gly Asp Gly Asp Val Ser Phe Ser Thr Arg
            260                 265                 270

Gly Thr Gln Asn Trp Thr Val Glu Arg Leu Leu Gln Ala His Ala Gln
            275                 280                 285

Leu Glu Glu Arg Gly Tyr Val Phe Val Gly Tyr His Gly Thr Phe Leu
290                 295                 300

Glu Ala Ala Gln Ser Ile Val Phe Gly Gly Val Ala Ala Arg Ser Gln
305                 310                 315                 320

Asp Leu Ala Ala Ile Trp Ala Gly Phe Tyr Ile Ala Gly Asp Pro Ala
                325                 330                 335

Leu Ala Tyr Gly Tyr Ala Gln Asp Gln Glu Pro Asp Ala Ala Gly Arg
            340                 345                 350

Ile Arg Asn Gly Ala Leu Leu Arg Val Tyr Val Pro Ala Ser Ser Leu
            355                 360                 365

Pro Gly Phe Tyr Arg Thr Ser Leu Thr Leu Ala Ala Pro Glu Ala Ala
            370                 375                 380

Gly Glu Val Glu Arg Leu Ile Gly His Pro Leu Pro Leu Ala Leu Asp
385                 390                 395                 400

Ala Ile Thr Gly Pro Glu Glu Glu Gly Gly Arg Leu Glu Thr Ile Leu
```

```
                    405                 410                 415
Gly Trp Pro Leu Ala Glu Arg Thr Val Val Ile Pro Ser Ala Ile Pro
            420                 425                 430

Thr Asp Pro Arg Asn Val Gly Gly Asp Leu Asp Pro Ser Ser Ile Pro
        435                 440                 445

Asp Lys Glu Gln Ala Ile Ser Ala Leu Pro Asp Tyr Ala Ser Gln Pro
    450                 455                 460

Gly Lys Pro Pro Arg Glu Asp Leu Lys
465                 470

<210> SEQ ID NO 49
<211> LENGTH: 215
<212> TYPE: PRT
<213> ORGANISM: Artificial Sequence
<220> FEATURE:
<223> OTHER INFORMATION: light chain of anti-TPBG 091 Fab-PE
      fusion protein

<400> SEQUENCE: 49

Met Asp Ile Gln Met Thr Gln Ser Pro Ser Ser Leu Ser Ala Ser Val
1               5                   10                  15

Gly Asp Arg Val Thr Ile Thr Cys Gln Ala Ser Gln Asp Ile Ser Asn
            20                  25                  30

Tyr Leu Asn Trp Tyr Gln Gln Lys Pro Gly Lys Ala Pro Lys Leu Leu
        35                  40                  45

Ile Tyr Ala Ala Ser Thr Leu Gln Ile Gly Val Pro Ser Arg Phe Ser
    50                  55                  60

Gly Ser Gly Ser Gly Thr Asp Phe Thr Phe Thr Ile Ser Ser Leu Gln
65                  70                  75                  80

Pro Glu Asp Phe Ala Thr Tyr Tyr Cys Gln Gln Ala Asn Ser Phe Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 50
<211> LENGTH: 474
<212> TYPE: PRT
<213> ORGANISM: Artificial Sequence
<220> FEATURE:
<223> OTHER INFORMATION: heavy chain of anti-TPBG 097 Fab-PE
      fusion protein

<400> SEQUENCE: 50

Met Glu Val Gln Leu Leu Glu Ser Gly Gly Gly Leu Ala Gln Pro Gly
```

-continued

```
1               5                   10                  15
Gly Ser Leu Arg Leu Ser Cys Ala Ala Ser Gly Phe Thr Phe Asn Asn
        20                  25                  30

Asp Ala Met Thr Trp Val Arg Gln Ala Pro Gly Lys Gly Leu Glu Trp
        35                  40                  45

Val Ser Ala Ile Ser Gly Ser Gly Gly Ser Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Gly Ser Trp Gly Asp Trp Tyr Tyr Phe Tyr Pro
                100                 105                 110

Met Asp Val Trp Gly Gln Gly Thr Thr Val Thr Val Ser Ser Ala Ser
            115                 120                 125

Thr Lys Gly Pro Ser Val Phe Pro Leu Ala Pro Ser Ser Lys Ser Thr
        130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Lys Ala Ser Gly Gly Arg His
225                 230                 235                 240

Arg Gln Pro Arg Gly Trp Glu Gln Leu Gly Gly Gly Gly Ser Pro
                245                 250                 255

Thr Gly Ala Glu Phe Leu Gly Asp Gly Asp Val Ser Phe Ser Thr
            260                 265                 270

Arg Gly Thr Gln Asn Trp Thr Val Glu Arg Leu Leu Gln Ala His Ala
        275                 280                 285

Gln Leu Glu Glu Arg Gly Tyr Val Phe Val Gly Tyr His Gly Thr Phe
290                 295                 300

Leu Glu Ala Ala Gln Ser Ile Val Phe Gly Gly Val Ala Ala Arg Ser
305                 310                 315                 320

Gln Asp Leu Ala Ala Ile Trp Ala Gly Phe Tyr Ile Ala Gly Asp Pro
                325                 330                 335

Ala Leu Ala Tyr Gly Tyr Ala Gln Asp Gln Glu Pro Asp Ala Ala Gly
            340                 345                 350

Arg Ile Arg Asn Gly Ala Leu Leu Arg Val Tyr Val Pro Ala Ser Ser
        355                 360                 365

Leu Pro Gly Phe Tyr Arg Thr Ser Leu Thr Leu Ala Ala Pro Glu Ala
    370                 375                 380

Ala Gly Glu Val Glu Arg Leu Ile Gly His Pro Leu Pro Leu Ala Leu
385                 390                 395                 400

Asp Ala Ile Thr Gly Pro Glu Glu Gly Gly Arg Leu Glu Thr Ile
                405                 410                 415

Leu Gly Trp Pro Leu Ala Glu Arg Thr Val Val Ile Pro Ser Ala Ile
            420                 425                 430
```

```
Pro Thr Asp Pro Arg Asn Val Gly Gly Asp Leu Asp Pro Ser Ser Ile
        435                 440                 445

Pro Asp Lys Glu Gln Ala Ile Ser Ala Leu Pro Asp Tyr Ala Ser Gln
    450                 455                 460

Pro Gly Lys Pro Pro Arg Glu Asp Leu Lys
465                 470

<210> SEQ ID NO 51
<211> LENGTH: 215
<212> TYPE: PRT
<213> ORGANISM: Artificial Sequence
<220> FEATURE:
<223> OTHER INFORMATION: light chain of anti-TPBG 097 Fab-PE
      fusion protein

<400> SEQUENCE: 51

Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
        35                  40                  45

Ile Tyr Ala Ala Ser Ser Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Asp Ser Phe Pro
                85                  90                  95

Leu Thr Phe Gly Gly Gly Thr Lys Val Glu Ile Lys Gly Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 52
<211> LENGTH: 613
<212> TYPE: PRT
<213> ORGANISM: Pseudomonas aeruginosa

<400> SEQUENCE: 52

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45
```

```
Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
                100                 105                 110

Ile Lys Val Phe Ile His Glu Leu Asn Ala Gly Asn Gln Leu Ser His
                115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
                180                 185                 190

Gly Lys Val Leu Cys Leu Leu Asp Pro Leu Asp Gly Val Tyr Asn Tyr
                195                 200                 205

Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
                260                 265                 270

Thr Arg His Arg Gln Pro Arg Gly Trp Glu Gln Leu Glu Gln Cys Gly
    275                 280                 285

Tyr Pro Val Gln Arg Leu Val Ala Leu Tyr Leu Ala Ala Arg Leu Ser
290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Ala Glu Ser Glu Arg Phe Val Arg
                340                 345                 350

Gln Gly Thr Gly Asn Asp Glu Ala Gly Ala Ala Asn Ala Asp Val Val
                355                 360                 365

Ser Leu Thr Cys Pro Val Ala Ala Gly Glu Cys Ala Gly Pro Ala Asp
    370                 375                 380

Ser Gly Asp Ala Leu Leu Glu Arg Asn Tyr Pro Thr Gly Ala Glu Phe
385                 390                 395                 400

Leu Gly Asp Gly Gly Asp Val Ser Phe Ser Thr Arg Gly Thr Gln Asn
                405                 410                 415

Trp Thr Val Glu Arg Leu Leu Gln Ala His Arg Gln Leu Glu Glu Arg
                420                 425                 430

Gly Tyr Val Phe Val Gly Tyr His Gly Thr Phe Leu Glu Ala Ala Gln
    435                 440                 445

Ser Ile Val Phe Gly Gly Val Arg Ala Arg Ser Gln Asp Leu Asp Ala
    450                 455                 460
```

-continued

```
Ile Trp Arg Gly Phe Tyr Ile Ala Gly Asp Pro Ala Leu Ala Tyr Gly
465                 470                 475                 480

Tyr Ala Gln Asp Gln Glu Pro Asp Ala Arg Gly Arg Ile Arg Asn Gly
                485                 490                 495

Ala Leu Leu Arg Val Tyr Val Pro Arg Ser Ser Leu Pro Gly Phe Tyr
            500                 505                 510

Arg Thr Ser Leu Thr Leu Ala Ala Pro Glu Ala Ala Gly Glu Val Glu
        515                 520                 525

Arg Leu Ile Gly His Pro Leu Pro Leu Arg Leu Asp Ala Ile Thr Gly
    530                 535                 540

Pro Glu Glu Gly Gly Arg Leu Glu Thr Ile Leu Gly Trp Pro Leu
545                 550                 555                 560

Ala Glu Arg Thr Val Val Ile Pro Ser Ala Ile Pro Thr Asp Pro Arg
                565                 570                 575

Asn Val Gly Gly Asp Leu Asp Pro Ser Ser Ile Pro Asp Lys Glu Gln
                580                 585                 590

Ala Ile Ser Ala Leu Pro Asp Tyr Ala Ser Gln Pro Gly Lys Pro Pro
            595                 600                 605

Arg Glu Asp Leu Lys
    610

<210> SEQ ID NO 53
<211> LENGTH: 345
<212> TYPE: PRT
<213> ORGANISM: Artificial Sequence
<220> FEATURE:
<223> OTHER INFORMATION: Pseudomonas exotoxin A synthetic variant PE38

<400> SEQUENCE: 53

Gly Gly Ser Leu Ala Ala Leu Thr Ala His Gln Ala Cys His Leu Pro
1               5                   10                  15

Leu Glu Thr Phe Thr Arg His Arg Gln Pro Arg Gly Trp Glu Gln Leu
                20                  25                  30

Glu Gln Cys Gly Tyr Pro Val Gln Arg Leu Val Ala Leu Tyr Leu Ala
            35                  40                  45

Ala Arg Leu Ser Trp Asn Gln Val Asp Gln Val Ile Arg Asn Ala Leu
    50                  55                  60

Ala Ser Pro Gly Ser Gly Gly Asp Leu Gly Glu Ala Ile Arg Glu Gln
65                  70                  75                  80

Pro Glu Gln Ala Arg Leu Ala Leu Thr Leu Ala Ala Ala Glu Ser Glu
                85                  90                  95

Arg Phe Val Arg Gln Gly Thr Gly Asn Asp Glu Ala Gly Ala Ala Asn
            100                 105                 110

Gly Pro Ala Asp Ser Gly Asp Ala Leu Leu Glu Arg Asn Tyr Pro Thr
        115                 120                 125

Gly Ala Glu Phe Leu Gly Asp Gly Gly Asp Val Ser Phe Ser Thr Arg
    130                 135                 140

Gly Thr Gln Asn Trp Thr Val Glu Arg Leu Leu Gln Ala His Arg Gln
145                 150                 155                 160

Leu Glu Glu Arg Gly Tyr Val Phe Val Gly Tyr His Gly Thr Phe Leu
                165                 170                 175

Glu Ala Ala Gln Ser Ile Val Phe Gly Gly Val Arg Ala Arg Ser Gln
            180                 185                 190

Asp Leu Asp Ala Ile Trp Arg Gly Phe Tyr Ile Ala Gly Asp Pro Ala
        195                 200                 205
```

Leu Ala Tyr Gly Tyr Ala Gln Asp Gln Glu Pro Asp Ala Arg Gly Arg
    210                 215                 220

Ile Arg Asn Gly Ala Leu Leu Arg Val Tyr Val Pro Arg Ser Ser Leu
225                 230                 235                 240

Pro Gly Phe Tyr Arg Thr Ser Leu Thr Leu Ala Ala Pro Glu Ala Ala
                245                 250                 255

Gly Glu Val Glu Arg Leu Ile Gly His Pro Leu Pro Leu Arg Leu Asp
            260                 265                 270

Ala Ile Thr Gly Pro Glu Glu Gly Arg Leu Glu Thr Ile Leu
        275                 280                 285

Gly Trp Pro Leu Ala Glu Arg Thr Val Val Ile Pro Ser Ala Ile Pro
    290                 295                 300

Thr Asp Pro Arg Asn Val Gly Gly Asp Leu Asp Pro Ser Ser Ile Pro
305                 310                 315                 320

Asp Lys Glu Gln Ala Ile Ser Ala Leu Pro Asp Tyr Ala Ser Gln Pro
                325                 330                 335

Gly Lys Pro Pro Arg Glu Asp Leu Lys
            340                 345

<210> SEQ ID NO 54
<211> LENGTH: 11
<212> TYPE: PRT
<213> ORGANISM: Artificial Sequence
<220> FEATURE:
<223> OTHER INFORMATION: Pseudomonas exotoxin A variant PE-LR

<400> SEQUENCE: 54

Arg His Arg Gln Pro Arg Gly Trp Glu Gln Leu
1               5                   10

<210> SEQ ID NO 55
<211> LENGTH: 6
<212> TYPE: PRT
<213> ORGANISM: Artificial Sequence
<220> FEATURE:
<223> OTHER INFORMATION: flexible glycin serine linker

<400> SEQUENCE: 55

Gly Gly Ser Gly Gly Ser
1               5

<210> SEQ ID NO 56
<211> LENGTH: 5
<212> TYPE: PRT
<213> ORGANISM: Pseudomonas aeruginosa

<400> SEQUENCE: 56

Arg Glu Asp Leu Lys
1               5

<210> SEQ ID NO 57
<211> LENGTH: 4
<212> TYPE: PRT
<213> ORGANISM: Artificial Sequence
<220> FEATURE:
<223> OTHER INFORMATION: C-terminal end of the PE functional domain III
      with endoplasmic reticulum localisation sequences

<400> SEQUENCE: 57

Lys Asp Glu Leu
1

```
<210> SEQ ID NO 58
<211> LENGTH: 4
<212> TYPE: PRT
<213> ORGANISM: Artificial Sequence
<220> FEATURE:
<223> OTHER INFORMATION: C-terminal end of the PE functional domain III
      with endoplasmic reticulum localisation sequences

<400> SEQUENCE: 58

Arg Glu Asp Leu
1

<210> SEQ ID NO 59
<211> LENGTH: 4
<212> TYPE: PRT
<213> ORGANISM: Artificial Sequence
<220> FEATURE:
<223> OTHER INFORMATION: C-terminal end of the PE functional domain III
      with endoplasmic reticulum localisation sequences

<400> SEQUENCE: 59

Arg Asp Glu Leu
1

<210> SEQ ID NO 60
<211> LENGTH: 5
<212> TYPE: PRT
<213> ORGANISM: Artificial Sequence
<220> FEATURE:
<223> OTHER INFORMATION: C-terminal end of the PE functional domain III
      with endoplasmic reticulum localisation sequences

<400> SEQUENCE: 60

Lys Glu Asp Leu Lys
1               5

<210> SEQ ID NO 61
<211> LENGTH: 8
<212> TYPE: PRT
<213> ORGANISM: Artificial Sequence
<220> FEATURE:
<223> OTHER INFORMATION: C-terminal end of the PE functional domain III
      with endoplasmic reticulum localisation sequences

<400> SEQUENCE: 61

Lys Asp Glu Leu Lys Asp Glu Leu
1               5

<210> SEQ ID NO 62
<211> LENGTH: 12
<212> TYPE: PRT
<213> ORGANISM: Artificial Sequence
<220> FEATURE:
<223> OTHER INFORMATION: C-terminal end of the PE functional domain III
      with endoplasmic reticulum localisation sequences

<400> SEQUENCE: 62

Lys Asp Glu Leu Lys Asp Glu Leu Lys Asp Glu Leu
1               5                   10

<210> SEQ ID NO 63
<211> LENGTH: 4
<212> TYPE: PRT
<213> ORGANISM: Artificial Sequence
<220> FEATURE:
<223> OTHER INFORMATION: furin cleavage site
<220> FEATURE:
<221> NAME/KEY: misc_feature
<222> LOCATION: (2)..(3)
```

```
<223> OTHER INFORMATION: Xaa can be any naturally occurring amino acid

<400> SEQUENCE: 63

Arg Xaa Xaa Arg
1

<210> SEQ ID NO 64
<211> LENGTH: 4
<212> TYPE: PRT
<213> ORGANISM: Artificial Sequence
<220> FEATURE:
<223> OTHER INFORMATION: furin cleavage site
<220> FEATURE:
<221> NAME/KEY: misc_feature
<222> LOCATION: (2)..(2)
<223> OTHER INFORMATION: Xaa can be any naturally occurring amino acid

<400> SEQUENCE: 64

Arg Xaa Lys Arg
1

<210> SEQ ID NO 65
<211> LENGTH: 4
<212> TYPE: PRT
<213> ORGANISM: Artificial Sequence
<220> FEATURE:
<223> OTHER INFORMATION: furin cleavage site
<220> FEATURE:
<221> NAME/KEY: misc_feature
<222> LOCATION: (2)..(2)
<223> OTHER INFORMATION: Xaa can be any naturally occurring amino acid

<400> SEQUENCE: 65

Arg Xaa Arg Arg
1

<210> SEQ ID NO 66
<211> LENGTH: 11
<212> TYPE: PRT
<213> ORGANISM: Pseudomonas aeruginosa

<400> SEQUENCE: 66

Arg His Arg Gln Pro Arg Gly Trp Glu Gln Leu
1               5                   10

<210> SEQ ID NO 67
<211> LENGTH: 11
<212> TYPE: PRT
<213> ORGANISM: Artificial Sequence
<220> FEATURE:
<223> OTHER INFORMATION: furin-cleavable sequence in domain II of
      modified Pseudomonas exotoxin A

<400> SEQUENCE: 67

Arg His Arg Ser Lys Arg Gly Trp Glu Gln Leu
1               5                   10

<210> SEQ ID NO 68
<211> LENGTH: 4
<212> TYPE: PRT
<213> ORGANISM: Artificial Sequence
<220> FEATURE:
<223> OTHER INFORMATION: furin-cleavable sequence

<400> SEQUENCE: 68

Arg Lys Lys Arg
1
```

<210> SEQ ID NO 69
<211> LENGTH: 4
<212> TYPE: PRT
<213> ORGANISM: Artificial Sequence
<220> FEATURE:
<223> OTHER INFORMATION: furin-cleavable sequence

<400> SEQUENCE: 69

Arg Arg Arg Arg
1

<210> SEQ ID NO 70
<211> LENGTH: 4
<212> TYPE: PRT
<213> ORGANISM: Artificial Sequence
<220> FEATURE:
<223> OTHER INFORMATION: furin-cleavable sequence

<400> SEQUENCE: 70

Arg Lys Ala Arg
1

<210> SEQ ID NO 71
<211> LENGTH: 6
<212> TYPE: PRT
<213> ORGANISM: Artificial Sequence
<220> FEATURE:
<223> OTHER INFORMATION: furin-cleavable sequence

<400> SEQUENCE: 71

Ser Arg Val Ala Arg Ser
1               5

<210> SEQ ID NO 72
<211> LENGTH: 9
<212> TYPE: PRT
<213> ORGANISM: Artificial Sequence
<220> FEATURE:
<223> OTHER INFORMATION: furin-cleavable sequence

<400> SEQUENCE: 72

Thr Ser Ser Arg Lys Arg Arg Phe Trp
1               5

<210> SEQ ID NO 73
<211> LENGTH: 9
<212> TYPE: PRT
<213> ORGANISM: Artificial Sequence
<220> FEATURE:
<223> OTHER INFORMATION: furin-cleavable sequence

<400> SEQUENCE: 73

Ala Ser Arg Arg Lys Ala Arg Ser Trp
1               5

<210> SEQ ID NO 74
<211> LENGTH: 8
<212> TYPE: PRT
<213> ORGANISM: Artificial Sequence
<220> FEATURE:
<223> OTHER INFORMATION: furin-cleavable sequence

<400> SEQUENCE: 74

Arg Arg Val Lys Lys Arg Phe Trp
1               5

```
<210> SEQ ID NO 75
<211> LENGTH: 8
<212> TYPE: PRT
<213> ORGANISM: Artificial Sequence
<220> FEATURE:
<223> OTHER INFORMATION: furin-cleavable sequence

<400> SEQUENCE: 75

Arg Asn Val Val Arg Arg Asp Trp
1               5

<210> SEQ ID NO 76
<211> LENGTH: 9
<212> TYPE: PRT
<213> ORGANISM: Artificial Sequence
<220> FEATURE:
<223> OTHER INFORMATION: furin-cleavable sequence

<400> SEQUENCE: 76

Thr Arg Ala Val Arg Arg Arg Ser Trp
1               5

<210> SEQ ID NO 77
<211> LENGTH: 4
<212> TYPE: PRT
<213> ORGANISM: Pseudomonas aeruginosa

<400> SEQUENCE: 77

Arg Gln Pro Arg
1

<210> SEQ ID NO 78
<211> LENGTH: 8
<212> TYPE: PRT
<213> ORGANISM: Pseudomonas aeruginosa

<400> SEQUENCE: 78

Arg His Arg Gln Pro Arg Gly Trp
1               5

<210> SEQ ID NO 79
<211> LENGTH: 9
<212> TYPE: PRT
<213> ORGANISM: Pseudomonas aeruginosa

<400> SEQUENCE: 79

Arg His Arg Gln Pro Arg Gly Trp Glu
1               5

<210> SEQ ID NO 80
<211> LENGTH: 9
<212> TYPE: PRT
<213> ORGANISM: Pseudomonas aeruginosa

<400> SEQUENCE: 80

His Arg Gln Pro Arg Gly Trp Glu Gln
1               5

<210> SEQ ID NO 81
<211> LENGTH: 7
<212> TYPE: PRT
<213> ORGANISM: Pseudomonas aeruginosa

<400> SEQUENCE: 81

Arg Gln Pro Arg Gly Trp Glu
1               5
```

<210> SEQ ID NO 82
<211> LENGTH: 4
<212> TYPE: PRT
<213> ORGANISM: Artificial Sequence
<220> FEATURE:
<223> OTHER INFORMATION: truncated version of furin-cleavable sequence
      in domain II of modified Pseudomonas exotoxin A

<400> SEQUENCE: 82

Arg Ser Lys Arg
1

<210> SEQ ID NO 83
<211> LENGTH: 8
<212> TYPE: PRT
<213> ORGANISM: Artificial Sequence
<220> FEATURE:
<223> OTHER INFORMATION: truncated version of furin-cleavable sequence
      in domain II of modified Pseudomonas exotoxin A

<400> SEQUENCE: 83

Arg His Arg Ser Lys Arg Gly Trp
1               5

<210> SEQ ID NO 84
<211> LENGTH: 8
<212> TYPE: PRT
<213> ORGANISM: Artificial Sequence
<220> FEATURE:
<223> OTHER INFORMATION: truncated version of furin-cleavable sequence
      in domain II of modified Pseudomonas exotoxin A

<400> SEQUENCE: 84

His Arg Ser Lys Arg Gly Trp Glu
1               5

<210> SEQ ID NO 85
<211> LENGTH: 9
<212> TYPE: PRT
<213> ORGANISM: Artificial Sequence
<220> FEATURE:
<223> OTHER INFORMATION: truncated version of furin-cleavable sequence
      in domain II of modified Pseudomonas exotoxin A

<400> SEQUENCE: 85

Arg Ser Lys Arg Gly Trp Glu Gln Leu
1               5

<210> SEQ ID NO 86
<211> LENGTH: 10
<212> TYPE: PRT
<213> ORGANISM: Artificial Sequence
<220> FEATURE:
<223> OTHER INFORMATION: truncated version of furin-cleavable sequence
      in domain II of modified Pseudomonas exotoxin A

<400> SEQUENCE: 86

His Arg Ser Lys Arg Gly Trp Glu Gln Leu
1               5                   10

<210> SEQ ID NO 87
<211> LENGTH: 6
<212> TYPE: PRT
<213> ORGANISM: Artificial Sequence
<220> FEATURE:
<223> OTHER INFORMATION: truncated version of furin-cleavable sequence
      in domain II of modified Pseudomonas exotoxin A

```
<400> SEQUENCE: 87

Arg His Arg Ser Lys Arg
1               5
```

ANTI-TPBG ANTIBODIES AND METHODS OF USE

CROSS REFERENCE TO RELATED APPLICATIONS

This application is a continuation of International Application No. PCT/EP2016/075881 having an international filing date of Oct. 27, 2016, the entire contents of which are incorporated herein by reference, and which claims benefit under 35 U.S.C. § 119 to European Patent Application No. 15192002.2 filed on Oct. 29, 2015.

SEQUENCE LISTING

The instant application contains a Sequence Listing submitted via EFS-Web and hereby incorporated by reference in its entirety. Said ASCII copy, created on Apr. 17, 2018, is named P33180-US.txt, and is 115,536 bytes in size.

FIELD OF THE INVENTION

The present invention relates to anti-TPBG antibodies and methods of using the same.

BACKGROUND

Trophoblast glycoprotein (TPBG) is a leucine-rich transmembrane glycoprotein involved in cell adhesion. In adults this protein is highly expressed in many tumor cells and is associated with poor clinical outcome in numerous cancers.

Antibodies binding to TPBG (also referred to as "5T4") are, e.g. disclosed in Shaw et al. (2002) Biochem. J. 363: 137-45 and WO98/55607. Those documents disclose antibody "H8", which specifically binds to a conformational epitope of TPBG. Amino acid sequences of original murine H8 antibody and of a humanized version of H8 antibody are disclosed in WO 2006/031653.

Further antibodies binding to TPBG are, e.g. disclosed in Woods et al. (2002) Biochem. J. 366: 353-65 (which discloses a rat monoclonal antibody) and U.S. Pat. No. 5,869,053 (which discloses a mouse monoclonal antibody).

Further antibodies binding to TPGB are, e.g. disclosed and characterized in WO 2007/106744, referred to as antibodies A1, A2 and A3.

Therapeutic use of antibodies binding to TPBG in treatment of cancer is, e.g., disclosed in Myers et al. (2002) Cancer Gene Ther. 9: 884-896, Shaw et al. (2000) Biochim Biophys. Acta. 1524: 238-246; and US 2003/0018004, disclosing that anti-TPBG antibody antibody sequences fused to the human IgG1 constant domain or to the extracellular domain of murine B7.1 induces cytolysis of TPBG-expressing tumor cell lines. A phase I clinical trial using PNU-214936, a murine Fab fragment of a monoclonal anti-TPGB antibody fused to a mutated superantigen staphylococcal enterocytotoxin A (SEA), showed limited toxicity and some anti-tumor response (Cheng et al. (2004) J. Clin. Oncol. 22(4):602-9).

SUMMARY

The invention provides anti-TPBG antibodies, conjugates thereof and methods of using the same. Also provided are isolated anti-TPBG polypeptides and isolated nucleic acids encoding the same.

The invention relates to an isolated antibody that binds to trophoblast glycoprotein (TPBG), wherein the antibody binds to human TPBG (SEQ ID NO: 1) and to minipig TPBG (SEQ ID NO: 2).

In one aspect, the invention relates to an isolated antibody that binds to TPBG, wherein the antibody specifically binds to human and minipig TPBG with a KD of $10^{-8}$ M or less.

In one embodiment the antibody specifically binds to human TPBG with a KD of $10^{-8}$ M or less and the antibody specifically binds to minipig TPBG with a KD of $10^{-8}$ M or less.

In one embodiment the Fab fragment of the antibody specifically binds to human and minipig TPBG with a KD of $10^{-8}$ M or less.

In another aspect the invention relates to an isolated antibody that binds to TPBG, wherein the antibody binds to human TPBG (SEQ ID NO: 1) and to minipig TPBG (SEQ ID NO: 2), and wherein the antibody specifically binds to human TPBG at a pH of 5.5 and a pH of 7.4.

In another aspect the invention relates to an isolated antibody that binds to TPBG, wherein the antibody binds to human TPBG (SEQ ID NO: 1) and to minipig TPBG (SEQ ID NO: 2), and wherein the antibody specifically binds to human TPBG at a pH of 5.5 and a pH of 7.4 with a KD of $10^{-8}$ M or less.

In another aspect, the invention relates to an isolated antibody that binds to TPBG, wherein the antibody binds to human TPBG (SEQ ID NO: 1) and to minipig TPBG (SEQ ID NO: 2), and wherein the antibody specifically binds to human TPBG at a pH of 5.5 and a pH of 7.2.

In one embodiment of the invention, the antibody specifically binds to cell surface expressed human TPBG at a pH of 5.5 and a pH of 7.2.

In one embodiment of the invention, the antibody specifically binds to cell surface expressed TPBG on SW620 cells at a pH of 5.5 and a pH of 7.2.

In one embodiment of the invention, the antibody specifically binds to human TPBG at a pH of 5.5 and a pH of 7.2, wherein binding ratio at pH 7.2 to pH 5.5 is less than 1.5, in one preferred embodiment between 0.8 and 1.5, in another preferred embodiment between 0.9 and 1.2. In one embodiment the binding is detected via flow cytometry and the binding ratio is determined by comparing mean fluorescence intensities as described in Example 18. In one embodiment of the invention, the antibody specifically binds to cell surface expressed human TPBG at a pH of 5.5 and a pH of 7.2, wherein binding ratio at pH 7.2 to pH 5.5 is less than 1.5, in one preferred embodiment between 0.8 and 1.5, in another preferred embodiment between 0.9 and 1.2. In one embodiment the binding is detected via flow cytometry and the binding ratio is determined by comparing mean fluorescence intensities as described in Example 18.

In one embodiment of the invention, the antibody specifically binds to cell surface expressed TPBG on SW620 cells at a pH of 5.5 and a pH of 7.2, wherein binding ratio at pH 7.2 to pH 5.5 is less than 1.5, in one preferred embodiment between 0.8 and 1.5, in another preferred embodiment between 0.9 and 1.2. In one embodiment the binding is detected via flow cytometry and the binding ratio is determined by comparing mean fluorescence intensities as described in Example 18.

In one embodiment of the invention, the antibody binds to cell surface expressed human TPBG and to cell surface expressed minipig TPBG.

In one embodiment of the invention, the antibody is internalized into a human or minipig-TPBG-expressing cell upon binding to cell surface expressed TPBG.

In one embodiment of the invention, the antibody comprises a CDR3 of the heavy chain of SEQ ID NO: 5, a CDR3 of the light chain of SEQ ID NO: 8, and a CDR2 of the heavy chain of SEQ ID NO: 4 (corresponding to the aforementioned CDRs of the antibody "051" as disclosed herein).

In one embodiment of the invention, the antibody comprises a CDR1 of the heavy chain of SEQ ID NO: 3, a CDR2 of the heavy chain of SEQ ID NO: 4, a CDR3 of the heavy chain of SEQ ID NO: 5, a CDR1 of the light chain of SEQ ID NO: 6, a CDR2 of the light chain of SEQ ID NO: 7, and a CDR3 of the light chain of SEQ ID NO: 8 (corresponding to the six CDRs of the antibody "051" as disclosed herein).

In one embodiment of the invention, the antibody comprises a CDR3 of the heavy chain of SEQ ID NO: 13, a CDR3 of the light chain of SEQ ID NO: 16, and a CDR2 of the heavy chain of SEQ ID NO: 12 (corresponding to the aforementioned CDRs of the antibody "091" as disclosed herein).

In one embodiment of the invention, the antibody comprises a CDR1 of the heavy chain of SEQ ID NO: 11, a CDR2 of the heavy chain of SEQ ID NO: 12, and a CDR3 of the heavy chain of SEQ ID NO: 13, a CDR1 of the light chain of SEQ ID NO: 14, a CDR2 of the light chain of SEQ ID NO: 15, and a CDR3 of the light chain of SEQ ID NO: 16 (corresponding to the six CDRs of the antibody "091" as disclosed herein).

In one embodiment of the invention, the antibody comprises a CDR3 of the heavy chain of SEQ ID NO: 21, a CDR3 of the light chain of SEQ ID NO: 24, and a CDR2 of the heavy chain of SEQ ID NO: 20 (corresponding to the aforementioned CDRs of the antibody "097" as disclosed herein).

In one embodiment of the invention, the antibody comprises a CDR1 of the heavy chain of SEQ ID NO: 19, a CDR2 of the heavy chain of SEQ ID NO: 20, and a CDR3 of the heavy chain of SEQ ID NO: 21, a CDR1 of the light chain of SEQ ID NO: 22, a CDR2 of the light chain of SEQ ID NO: 23, and a CDR3 of the light chain of SEQ ID NO: 24 (corresponding to the six CDRs of the antibody "097" as disclosed herein).

In one embodiment of the invention, the antibody is a humanized antibody derived from one of the aforementioned antibodies.

In one embodiment of the invention, the antibody comprises
  (a) a VH sequence having at least 95% sequence identity to the amino acid sequence of SEQ ID NO: 9;
  (b) a VL sequence having at least 95% sequence identity to the amino acid sequence of SEQ ID NO: 10; or
  (c) a VH sequence as in (a) and a VL sequence as in (b).

In one aspect the invention provides an antibody comprising a VH sequence of SEQ ID NO: 9 and a VL sequence of SEQ ID NO: 10 (corresponding to the variable domains of the antibody "051" as disclosed herein).

In one embodiment of the invention, the antibody comprises
  (a) a VH sequence having at least 95% sequence identity to the amino acid sequence of SEQ ID NO: 17;
  (b) a VL sequence having at least 95% sequence identity to the amino acid sequence of SEQ ID NO: 18; or
  (c) a VH sequence as in (a) and a VL sequence as in (b).

In one aspect the invention provides an antibody comprising a VH sequence of SEQ ID NO: 17 and a VL sequence of SEQ ID NO: 18 (corresponding to the variable domains of the antibody "091" as disclosed herein).

In one embodiment of the invention, the antibody comprises
  (a) a VH sequence having at least 95% sequence identity to the amino acid sequence of SEQ ID NO: 25;
  (b) a VL sequence having at least 95% sequence identity to the amino acid sequence of SEQ ID NO: 26; or
  (c) a VH sequence as in (a) and a VL sequence as in (b).

In one aspect the invention provides an antibody comprising a VH sequence of SEQ ID NO: 25 and a VL sequence of SEQ ID NO: 26 (corresponding to the variable domains of the antibody "097" as disclosed herein).

In one embodiment of the invention, the antibody is an antibody fragment that binds TPBG. In one embodiment of the invention, the antibody is a Fab fragment that binds TPBG.

In one aspect the invention provides an isolated nucleic acid encoding the antibody of the invention. In one aspect the invention provides a host cell comprising said nucleic acid.

In one aspect the invention provides a method of producing an antibody comprising culturing said host cell of the invention so that the antibody is produced. In one embodiment of said method the method further comprises recovering the antibody from the host cell.

In one aspect the invention provides an immunoconjugate comprising the antibody of the invention and a cytotoxic agent. In one embodiment the cytotoxic agent is an enzymatically active toxin or fragment thereof. In one embodiment the cytotoxic agent is selected from the group consisting of exotoxin A chain (from *Pseudomonas aeruginosa*), diphtheria toxin, ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. In one embodiment the cytotoxic agent is *Pseudomonas* exotoxin A or a variant thereof.

In one aspect the invention provides a method of producing the immunoconjugate of the invention, including the step of coupling the antibody to the cytotoxic agent. In one embodiment said method further includes the step of providing the antibody before the step of coupling, wherein the antibody is provided by culturing the host cell of the invention, which comprises a nucleic acid encoding the antibody of the invention, so that the antibody is produced. In one embodiment said method further includes the step of recovering the antibody from the host cell before the step of coupling.

In one aspect the invention provides a recombinant fusion protein comprising an antibody of the invention and any other polypeptide. In one embodiment the other polypeptide is fused to at least one of the heavy chains of the antibody. In one embodiment the other polypeptide is fused to the C-terminus of at least one of the heavy chains of the antibody.

In one embodiment the polypeptide is a cytotoxic agent (in consequence, in this embodiment, the recombinant fusion protein is an immunoconjugate). In one embodiment the cytotoxic agent is an enzymatically active toxin or fragment thereof. In one embodiment the cytotoxic agent is selected from the group consisting of exotoxin A chain (from *Pseudomonas aeruginosa*), diphtheria toxin, ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. In one embodiment the cytotoxic agent is *Pseudomonas* exotoxin A or a variant thereof.

In one aspect the invention provides an isolated nucleic acid encoding the recombinant fusion protein of the invention. In one embodiment the nucleic acid encodes the recombinant fusion protein of the invention, wherein the recombinant fusion protein is an immunoconjugate (in this embodiment, the polypeptide comprised in the recombinant fusion protein is a cytotoxic agent). In one aspect the invention provides a host cell comprising said nucleic acid.

In one aspect the invention provides a method of producing a recombinant fusion protein comprising culturing said host cell so that the recombinant fusion protein is produced. In one embodiment the recombinant fusion protein is an immunoconjugate. In one embodiment of said method the method further comprises recovering the recombinant fusion protein from the host cell. In one embodiment of said method the method further comprises isolating inclusion bodies of the host cell and solubilizing the inclusion bodies. In one embodiment of said method the method further comprises the step of renaturation of the material from the solubilized inclusion bodies. In one embodiment of said method host cell is a bacterial cell. In one embodiment of said method host cell is an *Escherichia coli* cell.

In one aspect the invention provides a pharmaceutical formulation comprising the antibody of the invention and a pharmaceutically acceptable carrier. In one embodiment said pharmaceutical composition further comprises an additional therapeutic agent. In one embodiment said additional therapeutic agent is a chemotherapeutic agent.

In one aspect the invention provides a pharmaceutical formulation comprising the recombinant fusion protein of the invention and a pharmaceutically acceptable carrier. In one embodiment said pharmaceutical composition further comprises an additional therapeutic agent. In one embodiment said additional therapeutic agent is a chemotherapeutic agent.

In one aspect the invention provides a pharmaceutical formulation comprising the immunoconjugate of the invention and a pharmaceutically acceptable carrier. In one embodiment said pharmaceutical composition further comprises an additional therapeutic agent. In one embodiment said additional therapeutic agent is a chemotherapeutic agent.

In one aspect the invention provides the antibody of the invention for use as a medicament. In one aspect the invention provides the antibody of the invention for use in the treatment of cancer.

In one aspect the invention provides the use of the antibody of the invention in the manufacture of a medicament.

In one aspect the invention provides a method of treating an individual having cancer comprising administering to the individual an effective amount of the antibody of the invention. In one embodiment said method further comprises administering an additional therapeutic agent to the individual. In one embodiment said additional therapeutic agent is a chemotherapeutic agent.

In one aspect the invention provides the recombinant fusion protein of the invention for use as a medicament. In one aspect the invention provides the recombinant fusion protein of the invention for use in the treatment of cancer.

In one aspect the invention provides the use of the recombinant fusion protein of the invention in the manufacture of a medicament. In one embodiment the medicament is for treatment of cancer In one aspect the invention provides a method of treating an individual having cancer comprising administering to the individual an effective amount of the recombinant fusion protein of the invention. In one embodiment said method further comprises administering an additional therapeutic agent to the individual. In one embodiment said additional therapeutic agent is a chemotherapeutic agent.

In one aspect the invention provides the immunoconjugate of the invention for use as a medicament. In one aspect the invention provides the immunoconjugate of the invention for use in the treatment of cancer.

In one aspect the invention provides the use of the immunoconjugate of the invention in the manufacture of a medicament. In one embodiment the medicament is for treatment of cancer.

In one aspect the invention provides a method of treating an individual having cancer comprising administering to the individual an effective amount of the immunoconjugate of the invention. In one embodiment said method further comprises administering an additional therapeutic agent to the individual. In one embodiment said additional therapeutic agent is a chemotherapeutic agent.

In one aspect the invention provides a method of screening for an antibody that binds to human TPBG and to minipig TPBG, the method comprising the steps of testing the binding of a test antibody to human TPBG and to minipig TPBG, and selecting the antibody that binds to human TPBG and to minipig TPBG.

In one embodiment the method is for the screening of an antibody for therapeutic application.

In one embodiment the method comprises the step of testing the binding of a test antibody in monovalent form.

In one embodiment the method comprises the steps of testing the binding of a test antibody to human TPBG at pH 5.5 and at pH 7.2, and selecting the antibody that binds to human TPBG at both pH (pH 5.5 and pH 7.2).

In one aspect the invention provides an antibody obtained by a method of screening of the invention.

In one aspect the invention provides a method of generating an antibody that binds to human TPBG and to minipig TPBG, the method comprising the steps of (a) immunizing an animal with human TPBG or with human TBPG extracellular domain (ECD), (b) isolating B cells specific for human TPBG from the blood of the animal, (c) identifying the amino acid sequence of the variable domains (VH and VL) of the antibodies produced by the isolated B cells, (d) providing an antibody comprising the variable domains identified, (e) testing the binding of a the provided antibody to human TPBG and to minipig TPBG, and (f) selecting the antibody that binds to human TPBG and to minipig TPBG.

In one embodiment the method is for generating an antibody for therapeutic application. In one embodiment the animal is a rodent. In one embodiment the animal is a rabbit.

In one embodiment the method comprises the step of testing the binding of the provided antibody in monovalent form.

In one embodiment the method comprises the steps of testing the binding of the provided antibody to human TPBG at pH 5.5 and at pH 7.2, and selecting the antibody that binds to human TPBG at both pH (pH 5.5 and pH 7.2).

In one aspect the invention provides an antibody obtained by a method of generating an anti-TPBG antibody of the invention.

The invention provides antibodies that bind to TPBG which are cross-reactive between TPBG of human and minipig species, and thereby are suitable for clinical development as they can be used for studies in minipig species (hence avoiding necessity of monkey studies). In addition the antibodies of the invention that bind to TPBG bind to their target, i.e. human TPBG, both at neutral as well as slightly acidic pH thereby assuring antigen binding in the slightly acidic microenvironment of a tumor, which is advantageous for a therapeutic application of the antibodies in cancer therapy. In addition, antibodies of the invention exhibit superior potency for treatment of several types of cancer, e.g. human non-small cell lung cancer.

BRIEF DESCRIPTION OF THE FIGURES

FIG. 6A: CHO-K1 stably transfected with human TPBG. Figure legend: vertical dash=unspecific control; star=051; open triangle=091; cross=097; plus=H8. FIG. 6B: CHO-K1 stably transfected with human TPBG. Figure legend: plus=H8; open triangle=A1; open diamond=A2; open circle=A3. FIG. 6C: CHO-K1 stably transfected with minipig TPBG. Figure legend: triangle point left=unspecific control; star=051; triangle point down=091; cross=097; plus=H8. FIG. 6D: CHO-K1 stably transfected with minipig TPBG. Figure legend: plus=H8; open triangle=A1; open diamond=A2; open circle=A3.

FIG. 7A: CHO-K1 cells stably transfected with full length human TPBG were incubated with immunoconjugates. FIG. 7B: CHO-K1 cells stably transfected with full length minipig TPBG were incubated with immunoconjugates. FIG. 7C: Parental CHO-K1 cells were incubated with immunoconjugates.

on human TPBG expressing H1975 non-small cell lung cancer cells (Example 28). The human tumor cell line H1975 was incubated with Fab-PE fusion proteins. Viability was determined by ATP-release assay (CellTiter-Glo) after 72 h. Figure legend: star=unspecific control; square=H8; diamond=051; circle=091; triangle=097

Figure 14A:
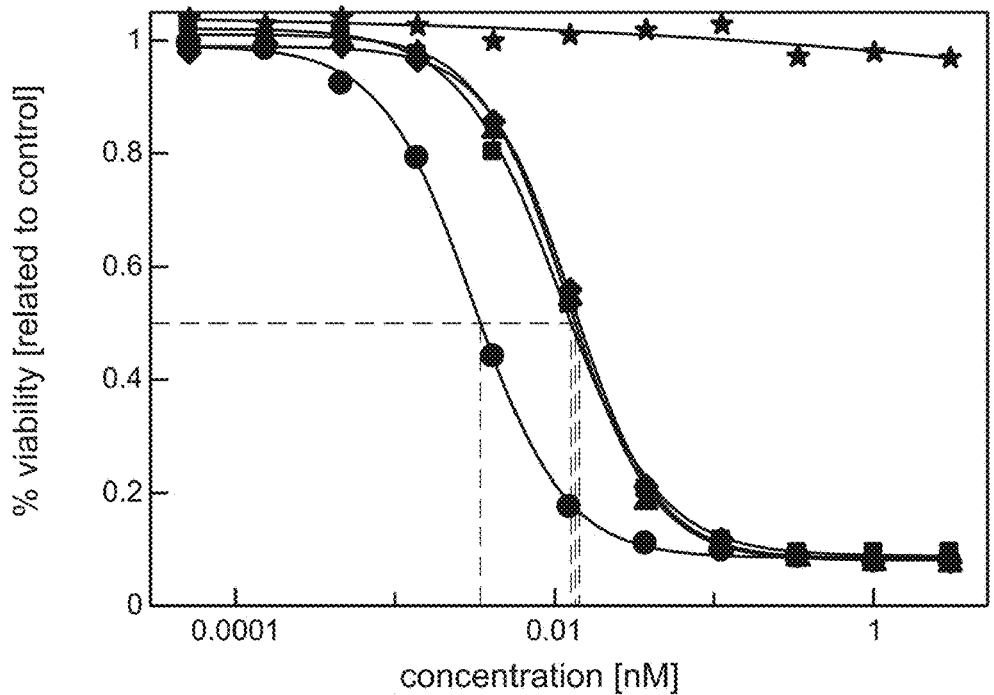
Figure 14B:
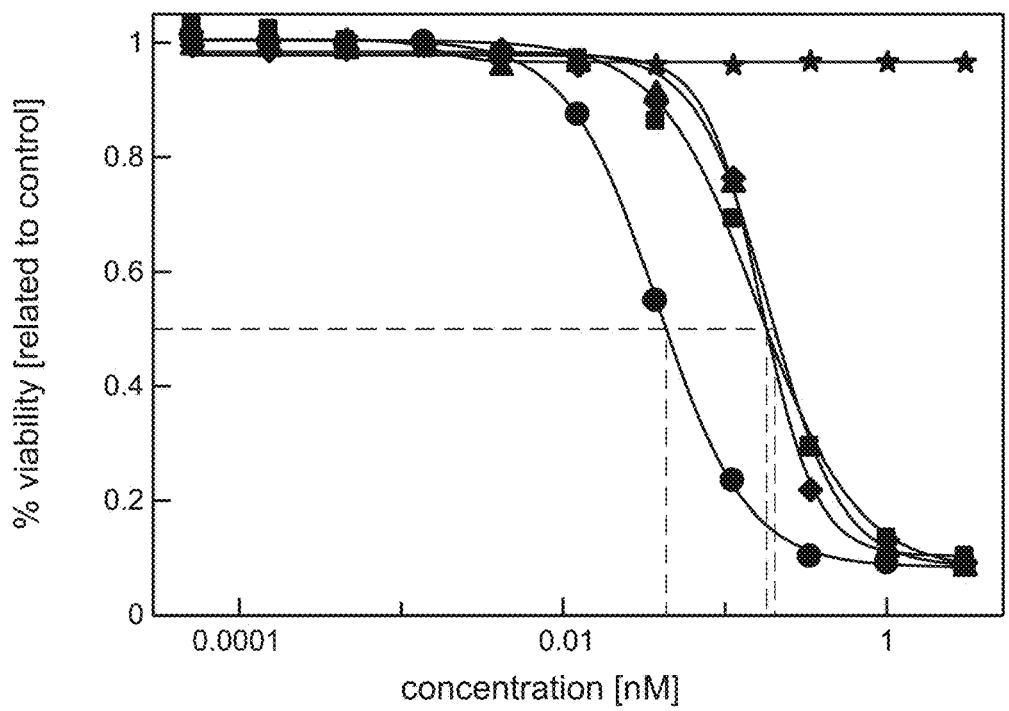
Figure 14C:
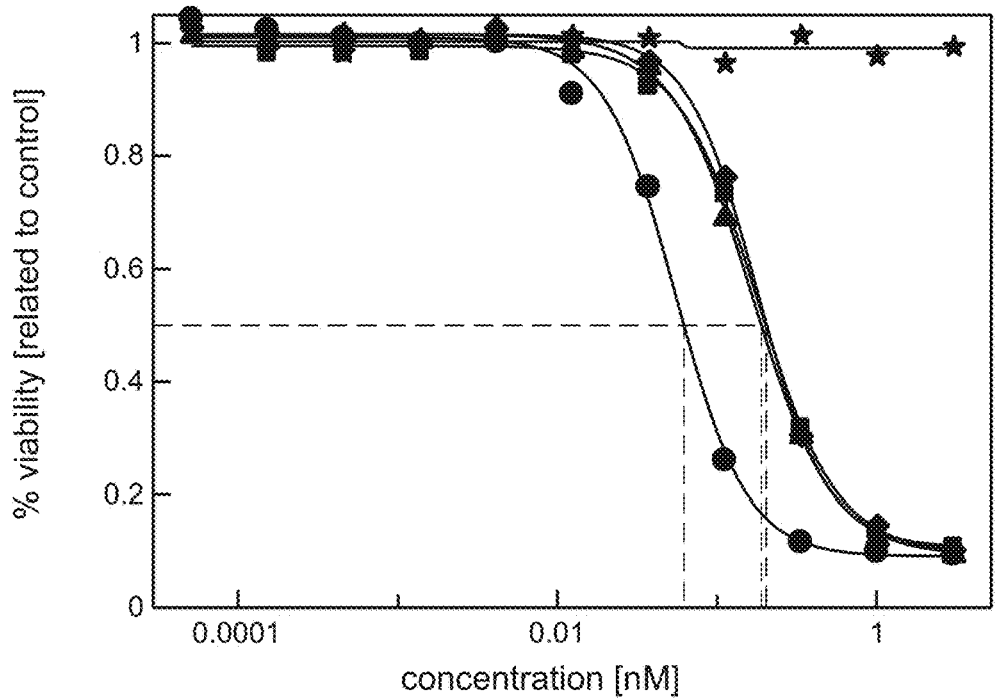
Figure 14D:
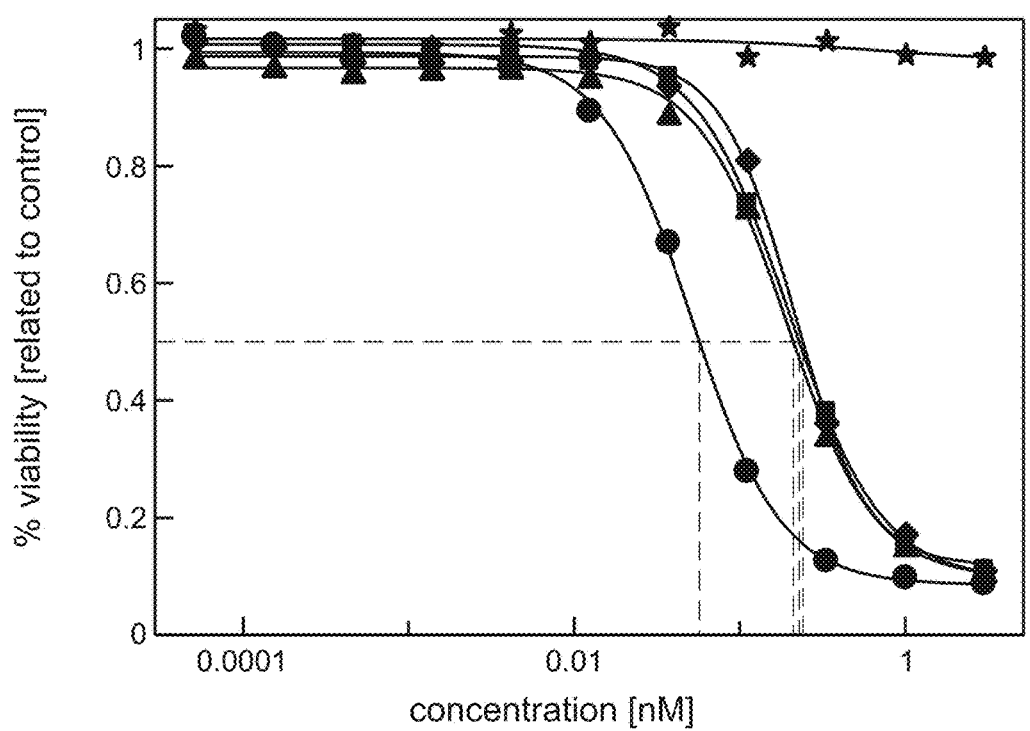

FIG. 14A-D: Time course proliferation assay of immunoconjugates comprising anti-TPBG antibodies (anti-TPBG Fab-PE fusion proteins) applied to human TPBG expressing H1975 non-small cell lung cancer cells (Example 29). The human tumor cell line H1975 was incubated for different periods of time with the respective Fab-PE constructs. Viability was determined by ATP-release assay (CellTiter-Glo) after 72 h. FIG. 14A: Continuos incubation with Fab-PE. FIG. 14B: Incubation with Fab-PE for 60 min FIG. 14C: Incubation with Fab-PE for 30 min FIG. 14D: Incubation with Fab-PE for 10 min Figure legend: star=unspecific control; square=H8; diamond=051; circle=091; triangle=097.

Figure 15:
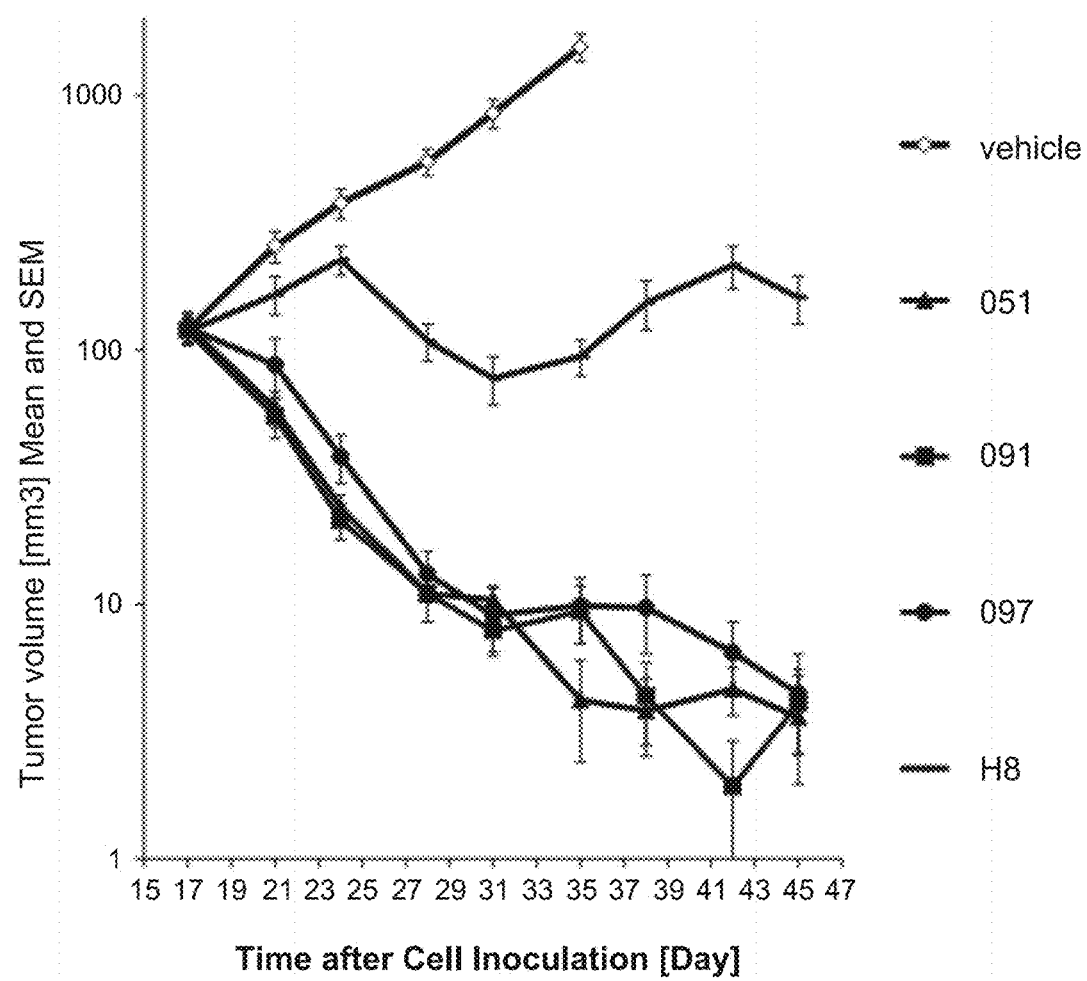

FIG. 15: In vivo anti-tumor efficacy of immunoconjugates comprising anti-TPBG antibodies (anti-TPBG Fab-PE fusion proteins) on human TPBG expressing human non-small cell lunger cancer H1975 cell xenografts (Example 30). Mean tumor growth is depicted on y-axis. Deviation is presented as standard error of the mean (SEM). Figure legend (anti-TPBG antibody): open diamonds=vehicle; dash=H8; triangle=051; square=091; circle=097.

Figure 16:
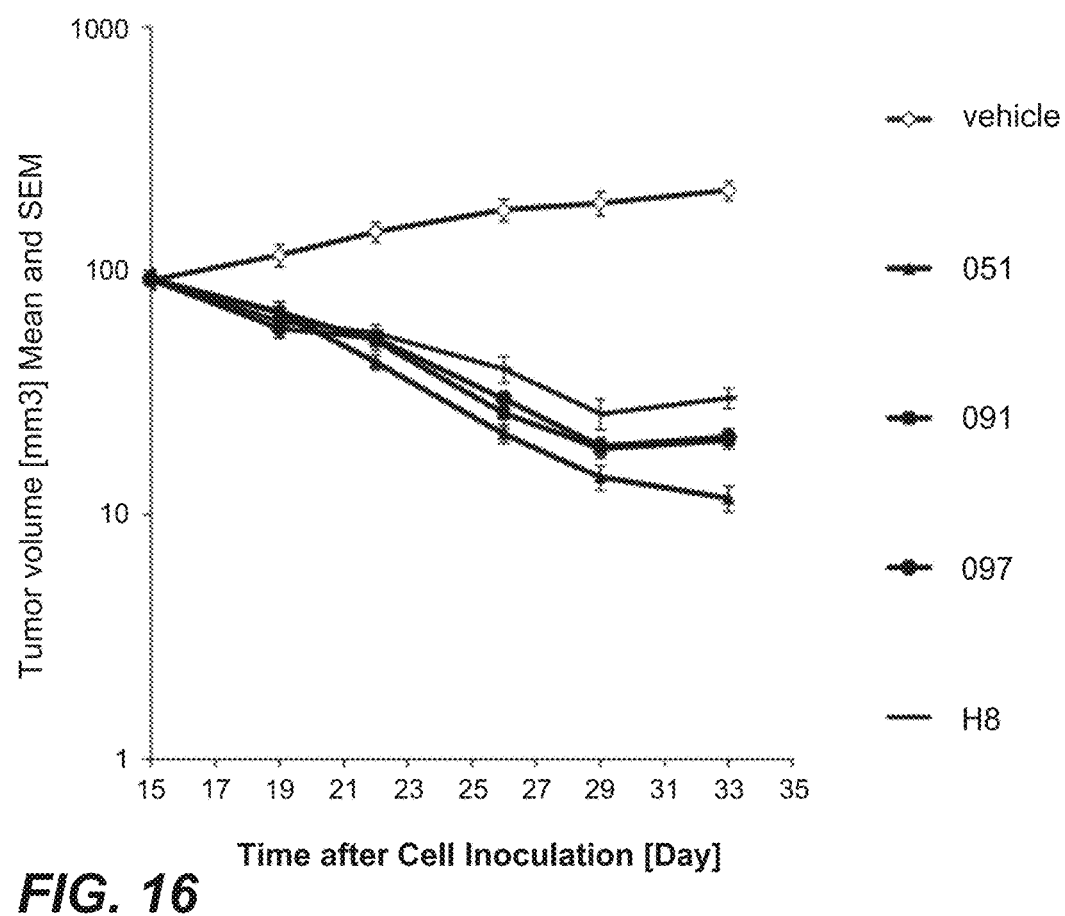

FIG. 16: In vivo anti-tumor efficacy of immunoconjugates comprising anti-TPBG antibodies (anti-TPBG Fab-PE fusion proteins) on human TPBG expressing human gastric cancer NCI-N87 cell xenografts (Example 31) Mean tumor growth is depicted on y-axis. Deviation is presented as standard error of the mean (SEM). Figure legend (anti-TPBG antibody): open diamonds=vehicle; dash=H8; triangle=051; square=091; circle=097.

Figure 17A:
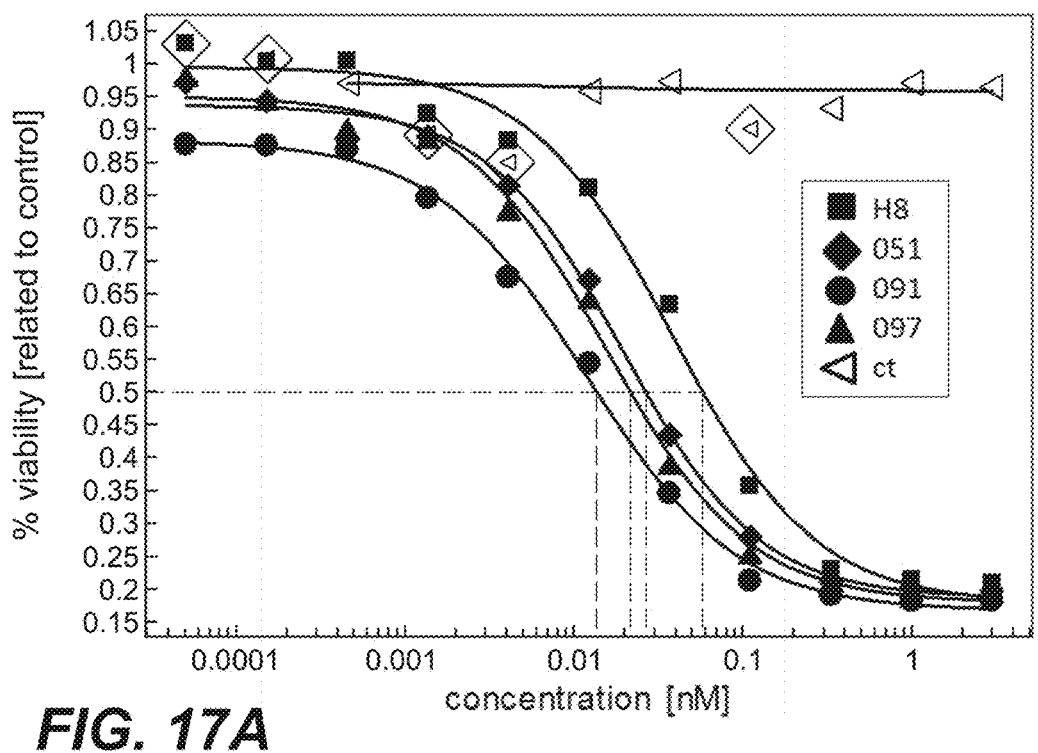
Figure 17B:
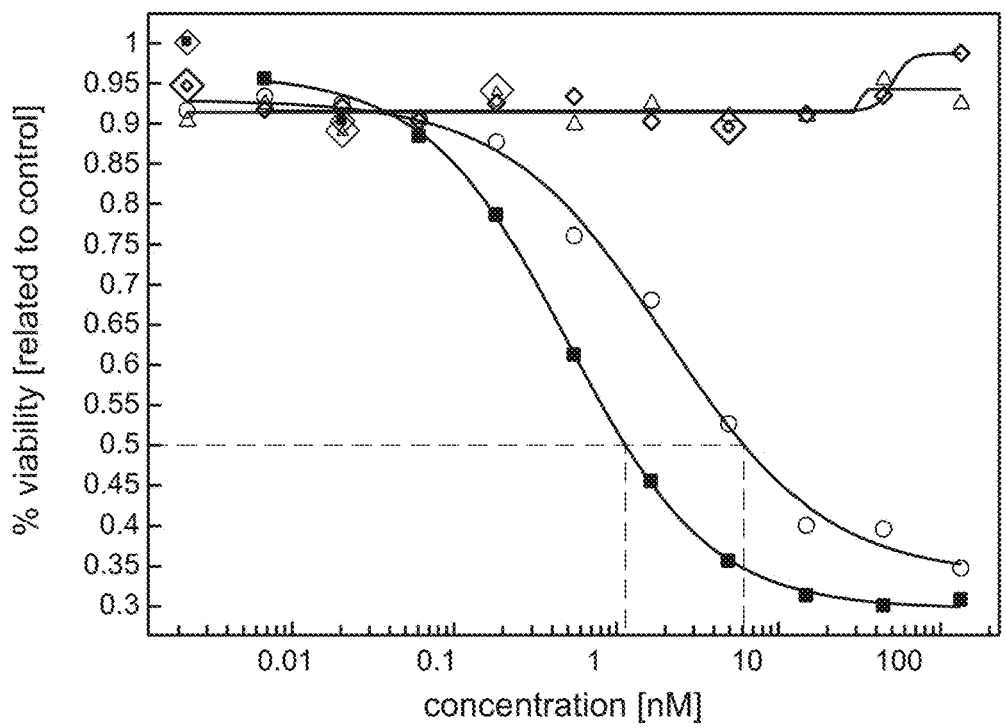

FIG. 17A-B: Protein synthesis assay using BxPC3/luc cells contacted with immunoconjugates comprising anti-TPBG antibodies (anti-TPBG Fab-PE fusion proteins) (Example 32). Viability was determined by luciferase assay and set in relation to buffer treated control cells. BxPC-3 stably transfected with a luciferase reporter were treated. FIG. 17A: Comparison of immunoconjugates comprising prior art antibody H8 with sandwich constructs comprising antibodies 051, 091 or 097 of the invention. FIG. 17B: Comparison of immunoconjugates comprising prior art antibodies. Figure legend: square=Fab(H8); triangle=Fab(A1); diamond=Fab(A2); circle=Fab(A3).

Figure 18:
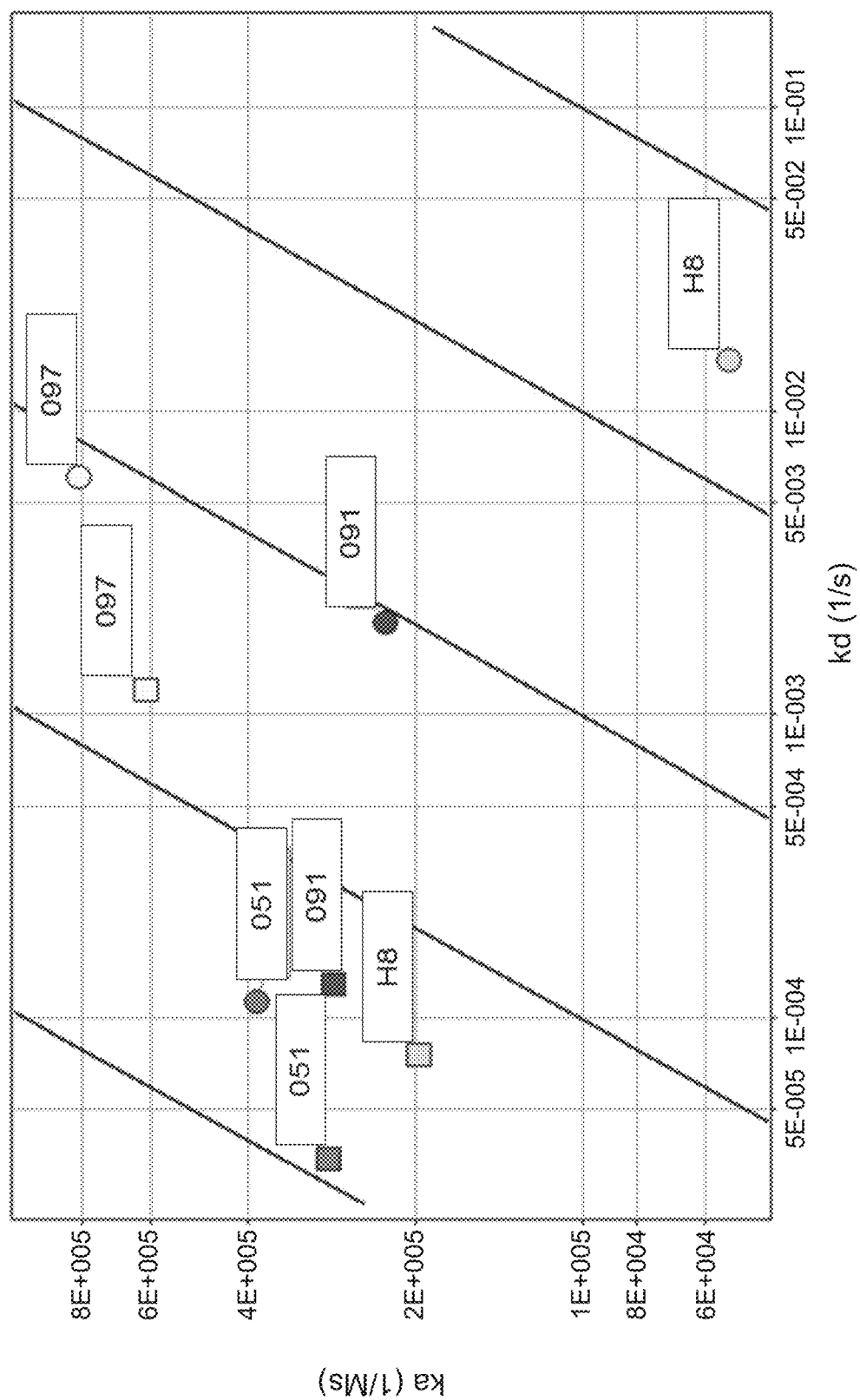

FIG. 18: Binding of immunoconjugates comprising anti-TPBG antibodies (anti-TPBG Fab-PE fusion proteins) to human TPBG at pH 5.5 and pH 7.4 (association-dissociation-plot, Example 35). Figure legend: Fab fragments comprised in immunoconjugates are indicated; circles indicate binding behaviour of respective immunoconjugate at pH 5.5, squares indicate binding behaviour of respective immunoconjugate at pH 7.4.

Figure 19:
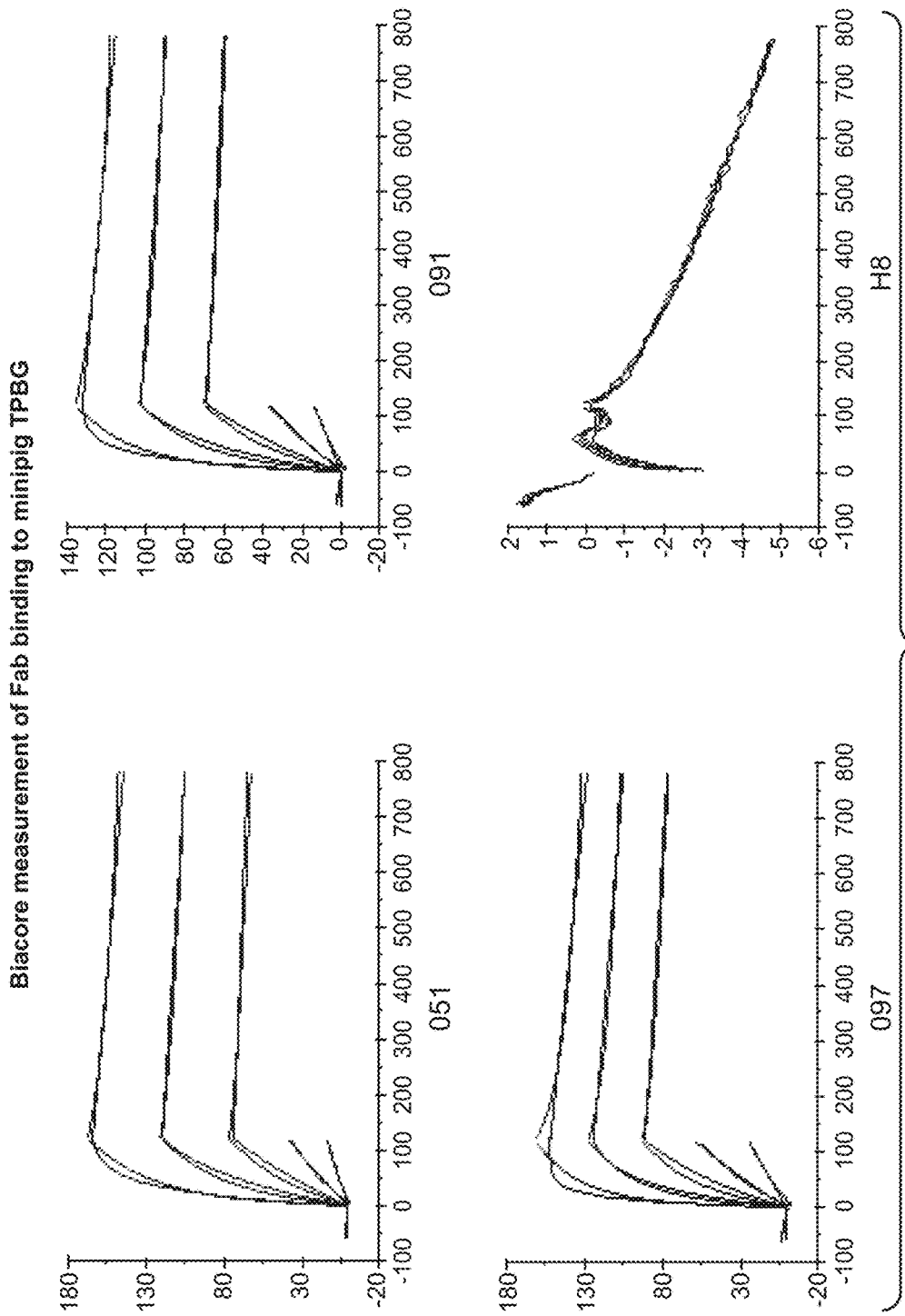

FIG. 19: Binding of anti-TPBG antibodies (Fab fragments) to minipig TPBG.

DETAILED DESCRIPTION OF EMBODIMENTS OF THE INVENTION

I. Definitions

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-TPBG antibody" and "an antibody that binds to TPBG" refer to an antibody that is capable of binding TPBG with sufficient affinity such that the antibody is useful as a diagnostic and/or therapeutic agent in targeting TPBG. In certain embodiments, an antibody that binds to TPBG has a dissociation constant (Kd) of $\leq 1$ μM, $\leq 100$ nM, $\leq 10$ nM, $\leq 1$ nM, $\leq 0.1$ nM, $\leq 0.01$ nM, or $\leq 0.001$ nM (e.g. $10^{-8}$ M or less, e.g. from $10^{-8}$ M to $10^{-13}$ M, e.g., from $10^{-9}$ M to $10^{-13}$ M). In certain embodiments, an anti-TPBG antibody binds to an epitope of TPBG that is conserved among TPBG from different species.

A "test antibody" refers to an antibody with unknown characteristics with respect to its binding properties to TPBG.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat, E. A. et al., Sequences of Proteins of Immunological Interest, 5th ed., Public Health Service, National Institutes of Health, Bethesda, Md. (1991), NIH Publication 91-3242.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat, E. A. et al., Sequences of Proteins of Immunological Interest, 5th ed., Bethesda Md. (1991), NIH Publication 91-3242, Vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the 1-Rs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest,* 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman, S. et al., J. Chromatogr. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-TPBG antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject, A pharmaceutically acceptable carrier includes, but is not limited to, a buffer, excipient, stabilizer, or preservative.

The term "TPBG," as used herein, refers to any native TPBG from any vertebrate source, including mammals such as primates (e.g. humans) and rodents (e.g., mice and rats), unless otherwise indicated. The term encompasses "full-length," unprocessed TPBG as well as any form of TPBG that results from processing in the cell. The term also encompasses naturally occurring variants of TPBG, e.g., splice variants or allelic variants. The amino acid sequence of an exemplary human TPBG is shown in SEQ ID NO: 1. The amino acid sequence of an exemplary minipig TPBG is shown in SEQ ID NO: 2.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt, T. J. et al. Kuby Immunology, 6th ed., W.H. Freeman and Co., N.Y. (2007), page 91) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano, S. et al., J. Immunol. 150 (1993) 880-887; Clackson, T. et al., Nature 352 (1991) 624-628).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

"Cancer" as used herein include both solid and haematologic cancers, such as lymphomas, lymphocytic leukemias, lung cancer, non-small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumours, brain stem glioma, glioblastoma multiforme, astrocytomas, schwanomas, ependymomas, medulloblastomas, meningiomas, squamous cell carcinomas, pituitary adenoma and Ewings sarcoma, including refractory versions of any of the above cancers, or a combination of one or more of the above cancers.

*Pseudomonas* Exotoxin A:

Native, wild-type *Pseudomonas* exotoxin A is a 66 kD bacterial toxin secreted by *Pseudomonas aeruginosa*, having the 613 amino acid sequence shown in SEQ ID NO:52 and also disclosed in U.S. Pat. No. 5,602,095. This sequence is shown without the native signal peptide, which is shown as the first 25 amino acids of UniProt accession number P11439.2 (gi: 12231043).

The native protein has three major structural domains. The N-terminal domain I comprises two subdomains Ia (amino acids 1-252) and Ib (amino acids 365-399) that are structurally adjacent but separated in the primary amino acid sequence.

Domain I and in particular domain Ia is the cell-binding domain. The function of domain Ib remains undefined. Domain I forms the major component of the B subunit. In the practice of the present invention, forms of PE in which the native domain Ia sequence is omitted or disrupted, and which consequently are unable to bind to LRP1 or LRP1B, are greatly preferred.

Domain II (amino acids 253-364) has been reported to mediate translocation into the cytosol, but this remains controversial (Weldon & Pastan 2011 FEBS J 278(23):4683-4700).

Domain III (amino acids 400-613) mediates ADP ribosylation of elongation factor 2. The structural boundary between domain Ib and domain III is not fully settled. According to WO2013/040141 it lies between residues 399 and 400, but Weldon and Pastan 2011 place it between residues 404 and 405. However, full catalytic activity requires a portion of domain Ib as well as domain III. Accordingly, the functional domain III of the native toxin is defined to start at residue 395. Amino acids 602-613 have been found to be inessential for NAD(+)-ribosyltransferase activity, but amino acids 609-613 of the native sequence are required for cytotoxic activity. These form an endoplasmic reticulum localisation sequence (WO 91/09948, Chaudhary et al 1991 Proc. Natl. Acad. Sci. USA 87: 308-312, Seetharam et al. 1991 J. Biol. Chem. 266: 17376-17381). Cytotoxicity can be maintained or enhanced by replacing the native ER localisation sequence with one or more other ER localisation sequences. Accordingly the functional domain III of native PE is considered to consist of residues 395-601.

An extensive body of work has been published disclosing variants and improvements of the native PE molecule for use in targeted cytotoxins. The terms "*Pseudomonas* exotoxin A", "*Pseudomonas* exotoxin", "exotoxin A chain (from *Pseudomonas aeruginosa*)" and "PE" as used herein are intended to encompass these and other variants and improvements of native PE that retain cytotoxic activity. In particular, the terms "*Pseudomonas* exotoxin A", "*Pseudomonas* exotoxin" and "PE" are specifically intended to include the variants and improvements disclosed in WO88/02401A1, WO90/12592A1, WO91/09949, WO91/09965, WO93/25690, WO97/13529, WO98/20135, WO2005/052006, WO2007/016150, WO2007/031741, WO2009/32954, WO2011/32022, WO2012/154530, WO2012/170617, WO2013/40141, Mazor R, et al PNAS 111 (2014) 8571-8576, and Alewine C, et al, Mol Cancer Ther. (2014) 2653-61 and WO2015/051199. All these publications are incorporated herein in their entirety for the purpose of exemplifying variants and improvements of *Pseudomonas* exotoxin A/PE that are suitable for use in the present invention and that are included, without limitation, within the terms "*Pseudomonas* exotoxin A", "*Pseudomonas* exotoxin" and "PE", with those variants and improvements disclosed in WO2005/052006, WO2007/016150, WO2007/031741, WO2009/32954, WO2011/32022, WO2012/154530, WO2012/170617, and WO2013/40141 being preferred and those disclosed in WO2009/32954, WO2011/32022, WO2012/154530, WO2012/170617, WO2013/40141, Mazor R, et al PNAS 111 (2014) 8571-8576, and Alewine C, et al, Mol Cancer Ther. (2014) 2653-61 and WO2015/051199 being particularly preferred.

It is anticipated that further variants and improvements of PE will be developed in future. Since the present invention relates to resistance against the cytotoxic effects of PE, it is anticipated that any such future variants and improvements of PE that retain cytotoxic activity may also be used in the practice of the invention and are therefore included within the terms "Pseudomonas exotoxin A" and "PE".

Generally, a PE toxin will have a polypeptide sequence comprising a PE functional domain III having at least 50% amino acid sequence identity over the full length of residues 395-601 of SEQ ID NO: 52, wherein the PE toxin has cytotoxic activity when introduced into a eukaryotic (preferably mammalian) cell. Preferred forms of PE comprise (1) a PE functional domain III having at least 50% amino acid sequence identity over the full length of residues 395-601 of SEQ ID NO: 52 and having NAD(+)-diphthamide ADP ribosyltransferase activity, and (2) at least one endoplasmic reticulum localisation sequence. In embodiments in which the PE is coupled to a cell-binding agent as a fusion polypeptide, the PE preferably also comprises (3) a cleavable linker sequence such as a furin-cleavable sequence (FCS) that permits cleavage of the PE functional domain III from the cell-binding agent following uptake into the target cell.

The cleavable linker (such as an FCS) will generally be on the N-terminal side of the PE functional domain III.

Other cleavable linkers may be used provided that they permit cleavage of the PE from the cell-binding agent following uptake into the target cell. Furthermore, other means of coupling the PE to the cell-binding agent are contemplated, provided again that they permit separation of the PE from the cell-binding agent following uptake into the target cell. For example, the cell-binding agent may be non-covalently linked to the PE, or linked by disulfide bonds which permit release of the PE moiety under reducing conditions, or linked by other conjugation chemistries that are known in the field of immunoconjugate production.

The PE for use in accordance with the present invention will generally lack a functional cell-binding domain I.

Much of the work on PE has focussed on eliminating portions of the native sequence that are unnecessary and/or disadvantageous for use in targeted therapies. For example, replacement of the B (receptor-binding) subunit with another cell-binding agent has reduced the non-specific toxicity of the molecule. Further removal of inessential sequences has reduced immunogenicity. This has led in particular to the development of the following truncated forms of PE: PE40, PE35, PE38, PE38QQR, PE-LR and PE24. PE40 is a truncated derivative of PE (Pai et al 1991 Proc. Natl. Acad. Sci. USA 88:3358-62 and Kondo et al. 1988 J. Biol. Chem. 263:9470-9475). PE35 is a 35 kD carboxyl-terminal fragment of PE in which amino acid residues 1-279 have been deleted and the molecule commences with a Met at position 280 followed by amino acids 281-364 and 381-613 of PE as defined by reference to SEQ ID NO: 52. PE35 and PE40 are disclosed, for example, in U.S. Pat. Nos. 5,602,095, 4,892,827, WO93/25690 and WO88/02401, each of which is incorporated herein by reference in its entirety.

PE38 contains the translocating and ADP ribosylating domains of PE but not the cell-binding portion (Hwang et al. 1987 Cell 48:129-136). PE38 (SEQ ID NO: 53) is a truncated PE pro-protein composed of amino acids 253-364 and 381-613 of SEQ ID NO: 52 which is activated to its cytotoxic form upon processing within a cell (see U.S. Pat. No. 5,608,039, which is incorporated by reference in its entirety herein, and Pastan et al. 1997 Biochim. Biophys. Acta, 1333:C1-C6). PE38QR is a variant of PE38 having mutations of the lysines at positions 590, 606 and 613 of domain III, to permit conjugation to antibodies.

PE-LR contains a deletion of domain II except for a furin-cleavable sequence (FCS) corresponding to amino acid residues 274-284 of SEQ ID NO: 52 (RHRQPRG-WEQL (SEQ ID NO: 54)) and a deletion of amino acid residues 365-394 of domain Ib. Thus, PE-LR contains amino acid residues 274-284 and 395-613 of SEQ ID NO: 52. PE-LR is described in WO 2009/032954 and Weldon et al 2009 Blood 113:3792-3800, which are each incorporated herein by reference in their entirety.

WO2012/154530 describes that the addition of a short, flexible linker of between 3 and 8 amino acids each independently selected from glycine and serine between the FCS and the PE functional domain III improves the cytotoxicity of the PE-LR molecule without disrupting binding by furin. Exemplary linkers are GGS and GGSGGS (SEQ ID NO: 55).

Other work has sought to further reduce the immunogenicity of PE.

WO2012/154530 reports that substitutions at the following amino acid residues within PE domain III reduce immunogenicity:

D403, D406, R412, R427, E431, R432, R458, D461, R467, R490, R505, R513, E522, R538, E548, R551, R576, K590, Q592 and L597.

Preferred substitutions are with a glycine, serine or alanine residue.

WO2012/170617 reports that substitutions at these residues may reduce immunogenicity of B cell epitopes, and that substitutions at one or more of residues R427, R458, R467, R490, R505 and F538 are preferred, particularly with alanine.

WO2013/040141 reports that substitutions at the following additional amino acid residues may reduce the immunogenicity of B cell epitopes within PE domain III:

E420, D463, Y481, L516, R563, D581, D589 and I(606.

Preferred substitutions are with a glycine, serine, alanine or glutamine residue.

WO2012/170617 reports that substitutions at the following residues can reduce the immunogenicity of T-cell epitopes within PE domain III:

R421, L422, L423, A425, R427, L429, Y439, H440, F443, L444, A446, A447, I450, 463-519, R551, L552, T554, I555, L556 and W558.

Preferred substitutions are at one or more of residues D463, Y481 and L516, which may also reduce the immunogenicity of B cell epitopes. Preferred substitutions are with a glycine, serine, alanine or glutamine residue.

WO2012/170617 also reports that substitutions at the following amino acid residues can reduce the immunogenicity of T cell epitopes within PE domain II:

L294, L297, Y298, L299 and R302.

Preferred substitutions are with a glycine, serine, alanine or glutamine residue.

WO2012/170617 also reports that substitutions at the following amino acid residues can reduce the immunogenicity of B cell epitopes within PE domain II:

E282, E285, P290, R313, N314, P319, D324, E327, E331 and Q332.

WO2012/170617 also reports that a particularly preferred combination of substitutions is D463A/R427A/R458A/R467A/R490A/R505A/R538A.

Alewine et al. 2014 Mol. Cancer Ther. 13(11): 2653-61 discloses a similar combination of 7 point mutations within PE domain III that reduce B-cell immunogenicity, namely R427A/R456A/D463A/R467A/R490A/R505A/R538A (that is, with R456A instead of R458A).

Mazor et al. Proc. Natl. Acad. Sci. USA 111(23): 8571-8576 discloses that a combination of 6 point mutations within PE domain III, together with deletion of most of PE domain II, reduced T cell responses by 93%. The mutations are R427A/F443A/L477H/R494A/R505A/L552E.

Accordingly, the PE functional domain III may comprise mutations at any one or any combination of more than one of the following sites:

D403, D406, R412, E420, R421, L422, L423, A425, R427, L429, E431, R432, Y439, H440, F443, L444, A446, A447, I450, R456, R458, D461, 463-519 (preferably D463, R467, L477, Y481, R490, R494, R505, R513 and/or L516), E522, R538, E548, R551, L552, T554, I555, L556, W558, R563, R576, D581, D589, K590, Q592, L597 and K606.

Preferably the mutation(s) reduce(s) the immunogenicity compared to the unmutated sequence of the amino acids 395-613 of SEQ ID NO: 52.

Insofar as the PE contains some or all of domain II, it may comprise mutations at any one or any combination of more than one of the following sites:

E282, E285, P290, L294, L297, Y298, L299, R302, R313, N314, P319, D324, E327, E331 and Q332.

Preferably the mutation(s) reduce(s) the immunogenicity compared to the unmutated sequence from domain II.

In particular, in embodiments in which the FCS is derived from the native furin-cleavable sequence of PE consisting of amino acids 274-284 (RHRQPRGWEQL, SEQ ID NO: 54) may comprise a substitution of the E282 residue, especially if the adjacent sequence from the native PE sequence is included downstream of the FCS.

In embodiments where the adjacent sequence from the native PE sequence is not included (such as PE-LR, in which the FCS is fused to domain III either directly or via a non-native linker sequence), the epitope from the native sequence may anyway be disrupted such that a mutation at the E282 residue may not be advantageous.

Mazor et al. 2014 Proc. Natl. Acad. Sci. USA 111(23): 8571-8576, Liu et al. 2012 Proc. Natl. Acad. Sci. USA 109(29): 11782-7, Kreitman et al. 2012 J. Clin. Oncol. 30(15): 1822-8, Pastan et al. 2011 Leukemia & Lymphoma 52 Suppl 2:87-90, Onda et al. 2011 Proc. Natl. Acad. Sci. USA 108(14): 5742-7, Hansen et al. 2010 Journal of Immunotherapy 33(3): 297-304, Kreitman et al. 2009 Clin Cancer Res. 15:5274-5279, Onda et al. 2008 Proc. Natl. Acad. Sci. USA 105(32): 11311-6, Ho et al. 2005 Clin. Cancer Res. 11(10): 3814-20, Kreitman et al. 2000 J Clin Oncol. 18:1622-1636 and Roscoe et al. 1994 Infection and Immunity 62(11): 5055-65 are all directed towards reducing the immunogenicity of PE.

Reduced immunogenicity in variant PE toxins may refer to a reduced ability of the variant sequence to induce a T cell response and/or a reduced ability of the variant sequence to induce a B cell (antibody) response, preferably both. Techniques for assessing the effect of mutations on T cell immunogenicity are well known in the art and described in the examples of WO 2012/170617. Techniques for assessing the effect of mutations on the B cell immunogenicity are likewise well known in the art and described in WO 2013/040141, for example. Human antibodies may be raised against the native PE sequence by phage display using a human antibody library. The ability of mutations in the PE sequence to disrupt binding of such antibodies to the variant PE molecule is indicative of reduced immunogenicity. Alternatively, the titre of PE-specific antibodies raised in transgenic mice carrying the human antibody repertoire may be compared for the native and mutated PE sequences.

The C-terminal end of the PE functional domain III may contain the native sequence of residues 609-613, namely REDLK (SEQ ID NO: 55). Additionally or alternatively to any other modifications of the native PE sequence, the PE functional domain III may contain a variant of the REDLK sequence, or other sequences, that function to maintain the PR protein in the endoplasmic reticulum or to recycle proteins into the endoplasmic reticulum. Such sequences are referred to here as "endoplasmic reticulum localisation sequences" or "ER localisation sequences". Preferred ER localisation sequences include such as KDEL (SEQ ID NO: 57), REDL (SEQ ID NO: 58), RDEL (SEQ ID NO: 59) or KEDLK (SEQ ID NO: 60). One or more additional ER localisation sequences, preferably independently selected from KDEL, REDL, REDLK, RDEL and KEDLK, may be added to the C-terminal end of the PE polypeptide sequence. The substitution of KDEL, or 2 or 3 tandem repeats of KDEL (KDELKDEL, SEQ ID NO 61; KDELKDELKDEL, SEQ ID NO: 62) for the native REDLK sequence, or the addition of KDEL after the native REDLK sequence is preferred. See for example WO91/099949, Chaudhary et al 1991 Seetharam et al 1991.

WO91/09949 discloses that the C-terminal end of the PE functional domain III may lack some or all of residues 602-608, which are not essential for the NAD(+)-diphthamide ADP ribosyltransferase activity.

Furin-Cleavable Sequence (FCS):

As described in WO2012/154530, the furin-cleavable sequence can be any polypeptide sequence cleavable by furin. Duckert et al. 2004, Protein Engineering, Design & Selection 17(1):107-112 (hereafter, "Duckert et al.") is incorporated herein by reference in its entirety and particularly with regard to the furin-cleavable sequences and motifs it discloses. Duckert et al. discloses that furin is an enzyme in a family of evolutionarily conserved dibasic- and monobasic-specific CA2+-dependent serine proteases called substilisin/kexin-like proprotein convertases. See page 107. Furin, also known as "paired basic amino acid cleaving enzyme", "PACE", or PCSK3, is one of several mammalian members of the PCSK family and is involved in processing several endogenous human proteins. See generally, Thomas 2002 Nat Rev Mol Cell Biol 10:753-66. It is a membrane-associated protein found mainly in the trans-Golgi network. The sequence of human furin has been known since the early 1990s. See for example Hatsuzawa et al. 1992 J Biol Chem 267: 16094-16099; and Molloy et al. 1992 J Biol Chem 267:16396-16402.

The minimal furin-cleavable sequence typically is, in the single letter code for amino acid residues, R-X-X-R (SEQ ID NO: 63), with cleavage occurring after the second "R". Duckert et al. summarizes the information available on the sequences of 38 proteins reported in the literature to have furin-cleavable sequences, including mammalian proteins, proteins of pathogenic bacteria, and viral proteins. It reports that 31, or 81%, of the cleavage motifs reviewed had the R-X-[R/K]-R (SEQ ID NO: 64, SEQ ID NO. 65) consensus sequence, of which 11, or 29%, had R-X-R-R (SEQ ID NO:

65), and 20, or 52%, were R-X-K-R (SEQ ID NO: 64). Three of the cleavage motifs contained only the minimal cleavage sequence. Duckert et al. further aligned the motifs and identified the residues found at each position in each furin both for the cleavage motif itself and in the surrounding residues. FIG. 1A of Duckert et al. shows by relative size the residues most commonly found at each position. By convention, the residues surrounding the furin cleavage site are numbered from the scissile bond (which is typically indicated by a downward arrow). Counting toward the N terminus, the substrate residues are designated P1, P2, and so on, while counting towards the C-terminus, the residues are designated P1', P2', and so on. See Rockwell and Thorner 2004 Trends Biochem. Sci. 29:80-87; and Thomas 2002 Nat. Rev. Mol. Cell Biol 3:753-766. Thus, following the convention, the following sequence can be used to align and number the residues of the minimal cleavage sequence and the surrounding residues:

P6-P5-P4-P3-P2-P1-P1'-P2'-P3'-P4'-P5', in which the minimal furin-cleavable sequence is numbered as P4-P1. Duckert et al.'s alignment of 38 sequences cleaved by furin identifies the variations permitted depending on the residues present at various positions. For example, if the residue at P4 is not an R, that can be compensated for by having arginine or lysine residues at P2 and P6. See page 109.

In native PE, furin cleavage occurs between arginine 279 and glycine 280 in an arginine-rich loop located in domain II of the toxin. The native furin-cleavable sequence in domain II of PE is set forth below (with numbers indicating the positions of the residues in the 613-amino acid native PE sequence), and aligned to show its numbering under the convention noted above:

274-R H R Q P R G W E Q L-284      (SEQ ID NO: 66)

P6-P5-P4-P3-P2-P1-P1'-P2'-P3'-P4'-P5'

In studies underlying WO2012/154530, substitutions were made at positions P3 and P2 to form the following sequence, with the substitutions underlined:

```
274- R H R S K R G W E Q L -284.   (SEQ ID NO: 67)
```

This sequence has shown a cleavage rate faster than that of the native sequence, and when used in an exemplary immunotoxin resulted in cytotoxicity to target cells approximately the same as that of the native sequence.

Figure 1:
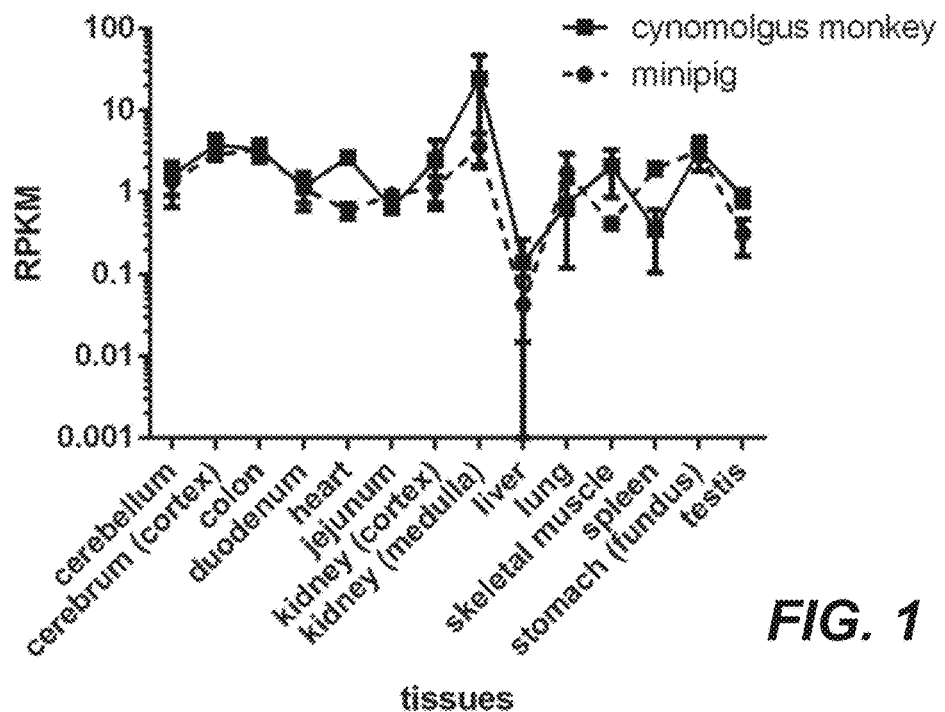
FIG. 1: mRNA expression profile of tissues from cynomolgus monkey and minipig (RPKM=reads assigned per kilobase of target per million mapped reads) (Example 1).

Based on this and previous studies, a furin-cleavable sequence used to attach the targeting molecule to PE domain III can be the minimal furin-cleavable sequence, R-X-X-R (wherein each X is independently any naturally occurring amino acid), preferably R-X4R/K1-R (wherein X is any naturally occurring amino acid and [R/K] denotes either arginine or lysine), or any of the other furin-cleavable sequences known in the art or permitted by FIG. 1 A of Duckert et al., with the proviso that, if there is a residue present at the position identified as P2', it should be tryptophan or, if not tryptophan, should not be valine or alanine. For example, in some embodiments, the sequence can be RKKR (SEQ ID NO: 68), RRRR (SEQ ID NO: 69), RKAR (SEQ ID NO: 70), SRVARS (SEQ ID NO: 71), TSSRKRRFW (SEQ ID NO: 72), or ASRRKARSW (SEQ ID NO: 73).

As noted in Duckert et al., a less favorable residue than R (primarily valine) can be used position P4 if compensated for by arginine or lysine residues at positions P2 and P6, so that at least two of the three residues at P2, P4 and P6 are basic. Thus, in some embodiments, the furin-cleavable sequence is RRVKKRFW (SEQ ID NO: 74), RNVVRRDW (SEQ ID NO: 75), or TRAVRRRSW (SEQ ID NO: 76). The residue at position PI can be the arginine present in the native sequence, or lysine. Thus, a lysine can be substituted for the arginine at position PI in, for example, any the sequences set forth above.

In some embodiments, the furin-cleavable sequence contains the native furin-cleavable sequence of PE: R—H-R-Q-P-R-G-W-E-Q-L (SEQ ID NO: 66) or a truncated version of the native sequence, so long as it contains the minimal furin-cleavable sequence and is cleavable by furin. Thus, in some embodiments, the furin-cleavable sequence can be RQPR (SEQ ID NO: 77), RHRQPRGW (SEQ ID NO: 78), RHRQPRGWE (SEQ ID NO: 79), HRQPRGWEQ (SEQ ID NO: 80), or RQPRGWE (SEQ ID NO: 81). In some embodiments, the sequence is RHRSKRGWEQL (SEQ ID NO: 67) or a truncated version of this sequence, so long as it contains the minimal furin-cleavable sequence and is cleavable by furin. Thus, in some embodiments, the furin-cleavable sequence can be RSKR (SEQ ID NO: 82), RHRSKRGW (SEQ ID NO: 83), HRSKRGWE (SEQ ID NO: 84), RSKRGWEQL (SEQ ID NO: 85), HRSKRGWEQL (SEQ ID NO: 86), or RHRSKR (SEQ ID NO: 87).

As mentioned above, the E282 residue at the P3' position of FCS sequences derived from PE may be replaced by another amino acid to reduce B cell immunogenicity. Where the sequence lacks native PE residues downstream of this residue, or where the FCS contains other mutations relative to the native PE sequence, such replacement may not be necessary.

Whether or not any particular sequence is cleavable by furin can be determined by methods known in the art. For example, whether or not a sequence is cleavable by furin can be tested by incubating the sequence with furin in furin buffer (0.2 M NaOAc (pH 5.5), 5 mM CaCl2) at a 1:10 enzyme:substrate molar ratio at 25° C. for 16 hours. These conditions have previously been established as optimal for furin cleavage of PE. Preferably, the furin used is human furin. Recombinant truncated human furin is commercially available, for example, from New England Biolabs (Beverly, Mass.). See also, Bravo et al. 1994 J Biol Chem 269(14): 25830-25837.

Alternatively, a furin-cleavable sequence can be tested by making it into an immunotoxin with an antibody against a cell surface protein and testing the resulting immunotoxin on a cell line expressing that cell surface protein. Suitable antibody sequences are disclosed in, for example, WO2012/154530 and WO2009/032954.

General Formula for Preferred PE Toxins

Preferred PE toxins for use in accordance with the present invention have the following structure:

$$FCS_l - R^1_m - R^2_n - R^3_p - \text{PE functional domain III-} R^4_q$$

wherein:

l, m, n, p and q are each, independently, 0 or 1;

FCS is a furin-cleavable sequence, preferably (i) R-H-R-Q-P-R-G-W-E-Q-L or a truncated version thereof containing R-Q-P-R, optionally R-Q-P-R, R-H-R-Q-P-R-G-W, R-H-R-Q-P-R-G-W-E, H-R-Q-P-R-G-W-E-Q, or R-Q-P-R-G-W-E; or (ii) R-H-R-S-K-R-G-W-E-Q-L or a truncated version thereof containing R-S-K-R, optionally R-S-K-R, R-H-R-S-K-R-G-W, H-R-S-K-R-G-W-E, R-S-K-R-G-W-E-Q-L, H-R-S-K-R-G-W-E-Q-L, or R-H-R-S-K-R, wherein the glutamic acid residue corresponding to position 282 of the native PE sequence (where present) is optionally replaced by another residue, preferably glycine, serine, alanine or glutamine;

$R_1$ is a linker sequence of 1 to 10 amino acids, preferably GGS or GGSGGS;

$R_2$ is one or more consecutive amino acid residues of residues 285-364 of SEQ ID NO:52, in which any one or more of residues E285, P290, L294, L297, Y298, L299, R302, R313, N314, P319, D324, E327, E331 and Q332, where present, is/are optionally independently replaced by another amino acid, preferably glycine, serine, alanine or glutamine;

$R_3$ is one or more consecutive amino acid residues of residues 365-394 of SEQ ID NO:52;

PE functional domain III comprises residues 395-613 of SEQ ID NO:52 in which:

(a) some or all of residues 602-608 are optionally deleted, and
(b) residues 609-613 are optionally replaced by another ER localisation sequence, preferably KDEL, REDL, RDEL or KEDLK, and
(c) any one or more of residues D403, D406, R412, E420, R421, L422, L423, A425, R427, L429, E431, R432, Y439, H440, F443, L444, A446, A447, I450, R456, R458, D461, 463-519 (preferably D463, R467, L477, Y481, R490, R494, R505, R513 and/or L516), E522, R538, E548, R551, L552, T554, I555, L556, W558, R563, R576, D581, D589, K590, Q592, L597 and (where present) K606 is/are optionally independently replaced by another amino acid, preferably glycine, serine, alanine or glutamine, or histidine in the case of L477;

R4 is one or more (preferably 1 or 2) additional ER localisation sequences, preferably REDLK, KDEL, REDL, RDEL or KEDLK.

Within the formula above:
l is preferably 1; that is, an FCS is preferably present;
m is preferably 1; that is, a linker is preferably present especially in the case that 1 is 1;
n is preferably 0; that is, residues 285-364 of SEQ ID NO:1 are preferably absent;
p is preferably 0; that is residues 365-394 of SEQ ID NO:1 are preferably absent;
PE functional domain III preferably includes the combination of mutations R427A/F443A/L477H/R494A/R505A/L552E, or the combination of mutations R427A/R456A/D463A/R467A/R490A/R505A/R538A, or the combination of mutations R427A/F443A/R456A/D463A/R467A/L477H/R490A/R494A/R505A/R538A/L552E.

Particularly preferred PE toxins for use in accordance with the present invention comprise the amino acid sequence corresponding to amino acid residues 395-613 of SEQ ID NO: 52 with Ala substitutions at positions 427, 456, 463, 467, 490, 505 and 538 (as disclosed in WO2015/51199 as L010R-456A and SEQ ID NO:37) or the amino acid sequence corresponding to amino acid residues 395-613 of SEQ ID NO: 52 with Ala substitutions at positions 427, 443, 477, 494, 505 and 552 (as is disclosed in WO2015/051199 as T18/T20 and SEQ ID NO:289).

II. Compositions and Methods

In one aspect, the invention is based, in part, on antibodies that are crossreactive with human and minipig TPGF. In certain embodiments, antibodies that bind to human TPBG at neutral as well as at slightly acidic pH are provided. Antibodies of the invention are useful, e.g., for the diagnosis or treatment of cancer.

A. Exemplary Anti-TPBG Antibodies

In one aspect, the invention provides isolated antibodies that bind to TPBG. In certain embodiments, an anti-TPBG antibody of the invention binds to human TPBG according to SEQ ID NO: 1 and binds to to minipig TPBG according to SEQ ID NO: 2. In certain embodiments, an anti-TPBG antibody of the invention binds to human TPBG at a pH of 5.5 and at a pH of 7.2.

In one aspect, the invention provides an anti-TPBG antibody comprising at least one, two, three, four, five, or six CDRs selected from (a) CDR1 of the heavy chain of SEQ ID NO: 3, (b) CDR2 of the heavy chain of SEQ ID NO: 4, (c) CDR3 of the heavy chain of SEQ ID NO: 5, (d) CDR1 of the light chain of SEQ ID NO: 6, (e) CDR2 of the light chain of SEQ ID NO: 7, and (f) CDR3 of the light chain of SEQ ID NO: 8 (corresponding to the aforementioned CDRs of the antibody "051" as disclosed herein).

In one aspect, the invention provides an antibody comprising at least one, at least two, or all three VH CDR sequences selected from (a) CDR1 of the heavy chain of SEQ ID NO: 3, (b) CDR2 of the heavy chain of SEQ ID NO: 4, (c) CDR3 of the heavy chain of SEQ ID NO: 5 (corresponding to the aforementioned CDRs of the antibody "051" as disclosed herein). In one embodiment, the antibody comprises CDR3 of the heavy chain comprising the amino acid sequence of SEQ ID NO: 5. In another embodiment, the antibody comprises CDR3 of the heavy chain comprising the amino acid sequence of SEQ ID NO: 5 and CDR3 of the light chain comprising the amino acid sequence of SEQ ID NO: 8. In a further embodiment, the antibody comprises CDR3 of the heavy chain comprising the amino acid sequence of SEQ ID NO: 5, CDR3 of the light chain comprising the amino acid sequence of SEQ ID NO: 5, and CDR2 of the heavy chain comprising the amino acid sequence of SEQ ID NO: 4. In a further embodiment, the antibody comprises (a) CDR3 of the heavy chain of SEQ ID NO: 5, (b) CDR3 of the light chain of SEQ ID NO: 8, and (c) CDR2 of the heavy chain of SEQ ID NO: 4.

In another aspect, the invention provides an antibody comprising at least one, at least two, or all three VL CDR sequences selected from (a) CDR1 of the light chain comprising the amino acid sequence of SEQ ID NO: 6; (b) CDR2 of the light chain comprising the amino acid sequence of SEQ ID NO: 7; and (c) CDR3 of the light chain comprising the amino acid sequence of SEQ ID NO: 8. In one embodiment, the antibody comprises (a) CDR1 of the light chain comprising the amino acid sequence of SEQ ID NO: 6; (b) CDR2 of the light chain comprising the amino acid sequence of SEQ ID NO: 7; and (c) CDR3 of the light chain comprising the amino acid sequence of SEQ ID NO: 8.

In another aspect, an antibody of the invention comprises (a) a VH domain comprising at least one, at least two, or all three VH CDR sequences selected from (i) CDR1 of the heavy chain comprising the amino acid sequence of SEQ ID NO: 3, (ii) CDR2 of the heavy chain comprising the amino acid sequence of SEQ ID NO: 4, and (iii) CDR3 of the heavy chain comprising an amino acid sequence selected from SEQ ID NO: 5; and (b) a VL domain comprising at least one, at least two, or all three VL HVR sequences selected from (i) CDR1 of the light chain comprising the amino acid sequence of SEQ ID NO: 6, (ii) CDR2 of the light chain comprising the amino acid sequence of SEQ ID NO: 7, and (c) CDR3 of the light chain comprising the amino acid sequence of SEQ ID NO: 8.

In another aspect, the invention provides an antibody comprising (a) CDR1 of the heavy chain comprising the amino acid sequence of SEQ ID NO: 3, (b) CDR2 of the heavy chain comprising the amino acid sequence of SEQ ID NO: 4, and (c) CDR3 of the heavy chain comprising an amino acid sequence selected from SEQ ID NO: 5, (d) CDR1 of the light chain comprising the amino acid sequence of SEQ ID NO: 6, (e) CDR2 of the light chain comprising the amino acid sequence of SEQ ID NO: 7, and (f) CDR3 of the light chain comprising the amino acid sequence of SEQ ID NO: 8. In one embodiment, the anti-TPBG antibody is a humanized antibody derived from an antibody comprising the aforementioned CDRs.

In one aspect, the invention provides an anti-TPBG antibody comprising at least one, two, three, four, five, or six CDRs selected from (a) CDR1 of the heavy chain of SEQ ID NO: 11, (b) CDR2 of the heavy chain of SEQ ID NO: 12, (c) CDR3 of the heavy chain of SEQ ID NO: 13, (d) CDR1 of the light chain of SEQ ID NO: 14, (e) CDR2 of the light chain of SEQ ID NO: 15, and (f) CDR3 of the light chain of SEQ ID NO: 16 (corresponding to the aforementioned CDRs of the antibody "091" as disclosed herein).

In one aspect, the invention provides an antibody comprising at least one, at least two, or all three VH CDR sequences selected from (a) CDR1 of the heavy chain of SEQ ID NO: 11, (b) CDR2 of the heavy chain of SEQ ID NO: 12, (c) CDR3 of the heavy chain of SEQ ID NO: 13 (corresponding to the aforementioned CDRs of the antibody "091" as disclosed herein). In one embodiment, the antibody comprises CDR3 of the heavy chain comprising the amino acid sequence of SEQ ID NO: 13. In another embodiment, the antibody comprises CDR3 of the heavy chain comprising the amino acid sequence of SEQ ID NO: 13 and CDR3 of the light chain comprising the amino acid sequence of SEQ ID NO: 16. In a further embodiment, the antibody comprises CDR3 of the heavy chain comprising the amino acid sequence of SEQ ID NO: 13, CDR3 of the light chain comprising the amino acid sequence of SEQ ID NO: 13, and CDR2 of the heavy chain comprising the amino acid sequence of SEQ ID NO: 12. In a further embodiment, the antibody comprises (a) CDR3 of the heavy chain of SEQ ID NO: 13, (b) CDR3 of the light chain of SEQ ID NO: 16, and (c) CDR2 of the heavy chain of SEQ ID NO: 12.

In another aspect, the invention provides an antibody comprising at least one, at least two, or all three VL CDR sequences selected from (a) CDR1 of the light chain comprising the amino acid sequence of SEQ ID NO: 14; (b) CDR2 of the light chain comprising the amino acid sequence of SEQ ID NO: 15; and (c) CDR3 of the light chain comprising the amino acid sequence of SEQ ID NO: 16. In one embodiment, the antibody comprises (a) CDR1 of the light chain comprising the amino acid sequence of SEQ ID NO: 14; (b) CDR2 of the light chain comprising the amino acid sequence of SEQ ID NO: 15; and (c) CDR3 of the light chain comprising the amino acid sequence of SEQ ID NO: 16.

In another aspect, an antibody of the invention comprises (a) a VH domain comprising at least one, at least two, or all three VH CDR sequences selected from (i) CDR1 of the heavy chain comprising the amino acid sequence of SEQ ID NO: 11, (ii) CDR2 of the heavy chain comprising the amino acid sequence of SEQ ID NO: 12, and (iii) CDR3 of the heavy chain comprising an amino acid sequence selected from SEQ ID NO: 13; and (b) a VL domain comprising at least one, at least two, or all three VL HVR sequences selected from (i) CDR1 of the light chain comprising the amino acid sequence of SEQ ID NO: 14, (ii) CDR2 of the light chain comprising the amino acid sequence of SEQ ID NO: 15, and (c) CDR3 of the light chain comprising the amino acid sequence of SEQ ID NO: 16.

In another aspect, the invention provides an antibody comprising (a) CDR1 of the heavy chain comprising the amino acid sequence of SEQ ID NO: 11, (b) CDR2 of the heavy chain comprising the amino acid sequence of SEQ ID NO: 12, and (c) CDR3 of the heavy chain comprising an amino acid sequence selected from SEQ ID NO: 13, (d) CDR1 of the light chain comprising the amino acid sequence of SEQ ID NO: 14, (e) CDR2 of the light chain comprising the amino acid sequence of SEQ ID NO: 15, and (f) CDR3 of the light chain comprising the amino acid sequence of SEQ ID NO: 16. In one embodiment, the anti-TPBG antibody is a humanized antibody derived from an antibody comprising the aforementioned CDRs.

In one aspect, the invention provides an anti-TPBG antibody comprising at least one, two, three, four, five, or six CDRs selected from (a) CDR1 of the heavy chain of SEQ ID NO: 19, (b) CDR2 of the heavy chain of SEQ ID NO: 20, (c) CDR3 of the heavy chain of SEQ ID NO: 21, (d) CDR1 of the light chain of SEQ ID NO: 22, (e) CDR2 of the light chain of SEQ ID NO: 23, and (f) CDR3 of the light chain of SEQ ID NO: 24 (corresponding to the aforementioned CDRs of the antibody "097" as disclosed herein).

In one aspect, the invention provides an antibody comprising at least one, at least two, or all three VH CDR sequences selected from (a) CDR1 of the heavy chain of SEQ ID NO: 19, (b) CDR2 of the heavy chain of SEQ ID NO: 20, (c) CDR3 of the heavy chain of SEQ ID NO: 21 (corresponding to the aforementioned CDRs of the antibody "097" as disclosed herein). In one embodiment, the antibody comprises CDR3 of the heavy chain comprising the amino acid sequence of SEQ ID NO: 21. In another embodiment, the antibody comprises CDR3 of the heavy chain comprising the amino acid sequence of SEQ ID NO: 21 and CDR3 of the light chain comprising the amino acid sequence of SEQ ID NO: 24. In a further embodiment, the antibody comprises CDR3 of the heavy chain comprising the amino acid sequence of SEQ ID NO: 21, CDR3 of the light chain comprising the amino acid sequence of SEQ ID NO: 21, and CDR2 of the heavy chain comprising the amino acid sequence of SEQ ID NO: 20. In a further embodiment, the antibody comprises (a) CDR3 of the heavy chain of SEQ ID NO: 21, (b) CDR3 of the light chain of SEQ ID NO: 24, and (c) CDR2 of the heavy chain of SEQ ID NO: 20.

In another aspect, the invention provides an antibody comprising at least one, at least two, or all three VL CDR sequences selected from (a) CDR1 of the light chain comprising the amino acid sequence of SEQ ID NO: 22; (b) CDR2 of the light chain comprising the amino acid sequence of SEQ ID NO: 23; and (c) CDR3 of the light chain comprising the amino acid sequence of SEQ ID NO: 24. In one embodiment, the antibody comprises (a) CDR1 of the light chain comprising the amino acid sequence of SEQ ID NO: 22; (b) CDR2 of the light chain comprising the amino acid sequence of SEQ ID NO: 23; and (c) CDR3 of the light chain comprising the amino acid sequence of SEQ ID NO: 24.

In another aspect, an antibody of the invention comprises (a) a VH domain comprising at least one, at least two, or all three VH CDR sequences selected from (i) CDR1 of the heavy chain comprising the amino acid sequence of SEQ ID NO: 19, (ii) CDR2 of the heavy chain comprising the amino acid sequence of SEQ ID NO: 20, and (iii) CDR3 of the heavy chain comprising an amino acid sequence selected from SEQ ID NO: 21; and (b) a VL domain comprising at least one, at least two, or all three VL HVR sequences selected from (i) CDR1 of the light chain comprising the amino acid sequence of SEQ ID NO: 22, (ii) CDR2 of the light chain comprising the amino acid sequence of SEQ ID NO: 23, and (c) CDR3 of the light chain comprising the amino acid sequence of SEQ ID NO: 24.

In another aspect, the invention provides an antibody comprising (a) CDR1 of the heavy chain comprising the amino acid sequence of SEQ ID NO: 19, (b) CDR2 of the heavy chain comprising the amino acid sequence of SEQ ID NO: 20, and (c) CDR3 of the heavy chain comprising an amino acid sequence selected from SEQ ID NO: 21, (d) CDR1 of the light chain comprising the amino acid sequence of SEQ ID NO: 22, (e) CDR2 of the light chain comprising the amino acid sequence of SEQ ID NO: 23, and (f) CDR3 of the light chain comprising the amino acid sequence of SEQ ID NO: 24. In one embodiment, the anti-TPBG antibody is a humanized antibody derived from an antibody comprising the aforementioned CDRs.

In any of the above embodiments, an anti-TPBG antibody is humanized. In one embodiment, an anti-TPBG antibody comprises CDRs as in any of the above embodiments, and further comprises an acceptor human framework, e.g. a human immunoglobulin framework or a human consensus framework.

In another aspect, an anti-TPBG antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 9 (corresponding to the variable heavy chain domain of the antibody "051" as disclosed herein). In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-TPBG antibody comprising that sequence retains the ability to bind to TPBG. In certain embodiments, a total of 1 to 10 amino acids have been substituted, inserted and/or deleted in SEQ ID NO: 9. In certain embodiments, substitutions, insertions, or deletions occur in regions outside the CDRs (i.e., in the FRs). Optionally, the anti-TPBG antibody comprises the VH sequence in SEQ ID NO: 9, including post-translational modifications of that sequence. In a particular embodiment, the VH comprises one, two or three CDRs selected from: (i) CDR1 of the heavy chain comprising the amino acid sequence of SEQ ID NO: 3, (ii) CDR2 of the heavy chain comprising the amino acid sequence of SEQ ID NO: 4, and (iii) CDR3 of the heavy chain comprising an amino acid sequence selected from SEQ ID NO: 5.

In another aspect, an anti-TPBG antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 10. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-TPBG antibody comprising that sequence retains the ability to bind to PRO. In certain embodiments, a total of 1 to 10 amino acids have been substituted, inserted and/or deleted in SEQ ID NO: 10. In certain embodiments, the substitutions, insertions, or deletions occur in regions outside the CDRs (i.e., in the FRs). Optionally, the anti-TPBG antibody comprises the VL sequence in SEQ ID NO: 10, including post-translational modifications of that sequence. In a particular embodiment, the VL comprises one, two or three HVRs selected from (i) CDR1 of the light chain comprising the amino acid sequence of SEQ ID NO: 6, (ii) CDR2 of the light chain comprising the amino acid sequence of SEQ ID NO: 7, and (c) CDR3 of the light chain comprising the amino acid sequence of SEQ ID NO: 8.

In another aspect, an anti-TPBG antibody is provided, wherein the antibody comprises a VH as in any of the embodiments provided above, and a VL as in any of the embodiments provided above. In one embodiment, the antibody comprises the VH and VL sequences in SEQ ID NO: 9 and SEQ ID NO: 10, respectively, including post-translational modifications of those sequences.

In a further aspect, the invention provides an antibody that binds to the same epitope as an anti-TPBG antibody provided herein. For example, in certain embodiments, an antibody is provided that binds to the same epitope as an anti-TPBG antibody comprising a VH sequence of SEQ ID NO: 9 and a VL sequence of SEQ ID NO: 10.

In another aspect, an anti-TPBG antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 17 (corresponding to the variable heavy chain domain of the antibody "091" as disclosed herein). In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-TPBG antibody comprising that sequence retains the ability to bind to TPBG. In certain embodiments, a total of 1 to 10 amino acids have been substituted, inserted and/or deleted in SEQ ID NO: 17. In certain embodiments, substitutions, insertions, or deletions occur in regions outside the CDRs (i.e., in the FRs). Optionally, the anti-TPBG antibody comprises the VH sequence in SEQ ID NO: 17, including post-translational modifications of that sequence. In a particular embodiment, the VH comprises one, two or three CDRs selected from: (i) CDR1 of the heavy chain comprising the amino acid sequence of SEQ ID NO: 11, (ii) CDR2 of the heavy chain comprising the amino acid sequence of SEQ ID NO: 12, and (iii) CDR3 of the heavy chain comprising an amino acid sequence selected from SEQ ID NO: 13.

In another aspect, an anti-TPBG antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 18. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-TPBG antibody comprising that sequence retains the ability to bind to PRO. In certain embodiments, a total of 1 to 10 amino acids have been substituted, inserted and/or deleted in SEQ ID NO: 10. In certain embodiments, the substitutions, insertions, or deletions occur in regions outside the CDRs (i.e., in the FRs). Optionally, the anti-TPBG antibody comprises the VL sequence in SEQ ID NO: 18, including post-translational modifications of that sequence. In a particular embodiment, the VL comprises one, two or three HVRs selected from (i) CDR1 of the light chain comprising the amino acid sequence of SEQ ID NO: 14, (ii)

CDR2 of the light chain comprising the amino acid sequence of SEQ ID NO: 15, and (c) CDR3 of the light chain comprising the amino acid sequence of SEQ ID NO: 16.

In another aspect, an anti-TPBG antibody is provided, wherein the antibody comprises a VH as in any of the embodiments provided above, and a VL as in any of the embodiments provided above. In one embodiment, the antibody comprises the VH and VL sequences in SEQ ID NO: 17 and SEQ ID NO: 18, respectively, including post-translational modifications of those sequences.

In a further aspect, the invention provides an antibody that binds to the same epitope as an anti-TPBG antibody provided herein. For example, in certain embodiments, an antibody is provided that binds to the same epitope as an anti-TPBG antibody comprising a VH sequence of SEQ ID NO: 17 and a VL sequence of SEQ ID NO: 18.

In another aspect, an anti-TPBG antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 25 (corresponding to the variable heavy chain domain of the antibody "097" as disclosed herein). In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-TPBG antibody comprising that sequence retains the ability to bind to TPBG. In certain embodiments, a total of 1 to 10 amino acids have been substituted, inserted and/or deleted in SEQ ID NO: 25. In certain embodiments, substitutions, insertions, or deletions occur in regions outside the CDRs (i.e., in the FRs). Optionally, the anti-TPBG antibody comprises the VH sequence in SEQ ID NO: 25, including post-translational modifications of that sequence. In a particular embodiment, the VH comprises one, two or three CDRs selected from: (i) CDR1 of the heavy chain comprising the amino acid sequence of SEQ ID NO: 19, (ii) CDR2 of the heavy chain comprising the amino acid sequence of SEQ ID NO: 20, and (iii) CDR3 of the heavy chain comprising an amino acid sequence selected from SEQ ID NO: 21.

In another aspect, an anti-TPBG antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 26. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-TPBG antibody comprising that sequence retains the ability to bind to PRO. In certain embodiments, a total of 1 to 10 amino acids have been substituted, inserted and/or deleted in SEQ ID NO: 10. In certain embodiments, the substitutions, insertions, or deletions occur in regions outside the CDRs (i.e., in the FRs). Optionally, the anti-TPBG antibody comprises the VL sequence in SEQ ID NO: 26, including post-translational modifications of that sequence. In a particular embodiment, the VL comprises one, two or three HVRs selected from (i) CDR1 of the light chain comprising the amino acid sequence of SEQ ID NO: 22, (ii) CDR2 of the light chain comprising the amino acid sequence of SEQ ID NO: 23, and (c) CDR3 of the light chain comprising the amino acid sequence of SEQ ID NO: 24.

In another aspect, an anti-TPBG antibody is provided, wherein the antibody comprises a VH as in any of the embodiments provided above, and a VL as in any of the embodiments provided above. In one embodiment, the antibody comprises the VH and VL sequences in SEQ ID NO: 25 and SEQ ID NO: 26, respectively, including post-translational modifications of those sequences.

In a further aspect, the invention provides an antibody that binds to the same epitope as an anti-TPBG antibody provided herein. For example, in certain embodiments, an antibody is provided that binds to the same epitope as an anti-TPBG antibody comprising a VH sequence of SEQ ID NO: 17 and a VL sequence of SEQ ID NO: 18.

In a further aspect of the invention, an anti-TPBG antibody according to any of the above embodiments is a monoclonal antibody, including a chimeric, humanized or human antibody. In one embodiment, an anti-TPBG antibody is an antibody fragment, e.g., a Fv, Fab, Fab', scFv, diabody, or F(ab')2 fragment. In another embodiment, the antibody is a full length antibody, e.g., an intact $IgG_1$ antibody or other antibody class or isotype as defined herein.

In one embodiment, the invention relates to an isolated antibody that binds to TPBG, wherein the antibody binds to human TPBG (SEQ ID NO: 1) and to minipig TPBG (SEQ ID NO: 2), and wherein the antibody specifically binds to human TPBG at a pH of 5.5 and a pH of 7.2.

In one embodiment of the invention, the antibody specifically binds to cell surface expressed human TPBG at a pH of 5.5 and a pH of 7.2.

In one embodiment of the invention, the antibody specifically binds to cell surface expressed TPBG on SW620 cells at a pH of 5.5 and a pH of 7.2.

The binding of human TPBG at those different pH values may be defined by a "binding ratio", which is herein defined as the ratio of the mean fluorescence intensity detected by flow cytometry in a cell surface binding assay (in one embodiment an assay as described in Example 18) at pH 7.2 to the mean fluorescence intensity detected by flow cytometry at pH 5.5 (in one embodiment an assay as described in Example 18).

In one embodiment of the invention, the antibody specifically binds to human TPBG at a pH of 5.5 and a pH of 7.2, wherein the binding ratio at pH 7.2 to pH 5.5 is less than 1.5, in one preferred embodiment between 0.8 and 1.5, in another preferred embodiment between 0.9 and 1.2. In one embodiment the binding is detected via flow cytometry and the binding ratio is determined by comparing mean fluorescence intensities as described in Example 18.

In one embodiment of the invention, the antibody specifically binds to cell surface expressed human TPBG at a pH of 5.5 and a pH of 7.2, wherein the binding ratio at pH 7.2 to pH 5.5 is less than 1.5, in one preferred embodiment between 0.8 and 1.5, in another preferred embodiment between 0.9 and 1.2. In one embodiment the binding is detected via flow cytometry and the binding ratio is determined by comparing mean fluorescence intensities as described in Example 18.

In one embodiment of the invention, the antibody specifically binds to cell surface expressed human TPBG at a pH of 5.5 and a pH of 7.2, wherein a binding ratio, which is defined as the ratio of the mean fluorescence intensity detected by flow cytometry in a cell surface binding assay (in one embodiment an assay as described in Example 18) at pH 7.2 to the mean fluorescence intensity detected by flow cytometry at pH 5.5 is less than 1.5, in one preferred embodiment between 0.8 and 1.5, in another preferred embodiment between 0.9 and 1.2.

In one embodiment of the invention, the antibody specifically binds to cell surface expressed TPBG on SW620 cells at a pH of 5.5 and a pH of 7.2, wherein binding ratio at pH 7.2 to pH 5.5 is less than 1.5, in one preferred embodiment between 0.8 and 1.5, in another preferred embodiment between 0.9 and 1.2. In one embodiment the binding is detected via flow cytometry and the binding ratio is determined by comparing mean fluorescence intensities as described in Example 18.

In one embodiment of the invention, the antibody specifically binds to cell surface expressed TPBG on SW620 cells at a pH of 5.5 and a pH of 7.2, wherein a binding ratio, which is defined as the ratio of the mean fluorescence intensity detected by flow cytometry in a cell surface binding assay (in one embodiment an assay as described in Example 18) at pH 7.2 to the mean fluorescence intensity detected by flow cytometry at pH 5.5 is less than 1.5, in one preferred embodiment between 0.8 and 1.5, in another preferred embodiment between 0.9 and 1.2.

In a further aspect, an anti-TPBG antibody according to any of the above embodiments may incorporate any of the features, singly or in combination, as described in Sections 1-7 below:

1. Antibody Affinity

In certain embodiments, an antibody provided herein has a dissociation constant (Kd) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$M to $10^{-13}$ M).

In one embodiment, Kd is measured by a radiolabeled antigen binding assay (RIA) performed with the Fab version of an antibody of interest and its antigen as described by the following assay. Solution binding affinity of FABs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen, Y. et al., J. Mol. Biol. 293 (1999) 865-881). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta, L. G. et al., Cancer Res. 57 (1997) 4593-4599). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CMS chips at ~10 response units (RU). Briefly, carboxymethylated dextran biosensor chips (CMS, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μl/min Association rates ($k_{on}$) and dissociation rates ($k_{off}$) are calculated using a simple one-to-one Langmuir binding model (BIACORE Evaluation Software version 3.2) by simultaneously fitting the association and dissociation sensorgrams. The equilibrium dissociation constant (Kd) is calculated as the ratio $k_{off}/k_{on}$. See, e.g., Chen, Y. et al., J. Mol. Biol. 293 (1999) 865-881. If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to Fab, Fab', Fab'-SH, F(ab')$_2$, Fv, and scFv fragments, and other fragments described below. For a review of certain antibody fragments, see Hudson, P. J. et al., Nat. Med. 9 (2003) 129-134. For a review of scFv fragments, see, e.g., Plueckthun, A., In; The Pharmacology of Monoclonal Antibodies, Vol. 113, Rosenburg and Moore (eds.), Springer-Verlag, New York (1994), pp. 269-315; see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 0 404 097; WO 1993/01161; Hudson, P. J. et al., Nat. Med. 9 (2003) 129-134; and Holliger, P. et al., Proc. Natl. Acad. Sci. USA 90 (1993) 6444-6448. Triabodies and tetrabodies are also described in Hudson, P. J. et al., Nat. Med. 9 (20039 129-134).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. E. coli or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison, S. L. et al., Proc. Natl. Acad. Sci. USA 81 (1984) 6851-6855). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro, J. C. and Fransson, J., Front. Biosci. 13 (2008) 1619-1633, and are further described, e.g., in Riechmann, I et al., Nature 332 (1988) 323-329; Queen, C. et al., Proc. Natl. Acad. Sci. USA 86 (1989) 10029-10033; U.S. Pat. Nos. 5,821,337, 7,527,791, 6,982,321, and 7,087,409; Kashmiri, S. V. et al., Methods 36 (2005) 25-34 (describing SDR (a-CDR) grafting); Padlan, E. A., Mol. Immunol. 28 (1991) 489-498 (describing "resurfacing"); Dall'Acqua, W. F. et al., Methods 36 (2005) 43-60 (describing "FR shuffling"); and Osbourn, J. et al., Methods 36 (2005) 61-68 and Klimka, A. et al., Br. J. Cancer 83 (2000) 252-260 (describing the "guided selection" approach to FR shuffling).

Human framework regions that may be used for humanization include but are not limited to: framework regions selected using the "best-fit" method (see, e.g., Sims, M. J. et al., J. Immunol. 151 (1993) 2296-2308; framework regions derived from the consensus sequence of human antibodies of a particular subgroup of light or heavy chain variable regions (see, e.g., Carter, P. et al., Proc. Natl. Acad. Sci. USA 89 (1992) 4285-4289; and Presta, L. G. et al., J. Immunol. 151 (1993) 2623-2632); human mature (somatically mutated) framework regions or human germline framework regions (see, e.g., Almagro, J. C. and Fransson, J., Front. Biosci. 13 (2008) 1619-1633); and framework regions derived from screening FR libraries (see, e.g., Baca, M. et al., J. Biol. Chem. 272 (1997) 10678-10684 and Rosok, M. J. et al., J. Biol. Chem. 271 (19969 22611-22618).

4. Human Antibodies

In certain embodiments, an antibody provided herein is a human antibody. Human antibodies can be produced using various techniques known in the art. Human antibodies are described generally in van Dijk, M. A. and van de Winkel, J. G., Curr. Opin. Pharmacol. 5 (2001) 368-374 and Lonberg, N., Curr. Opin. Immunol. 20 (2008) 450-459.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, N., Nat. Biotech. 23 (2005) 1117-1125. See also, e.g., U.S. Pat. Nos. 6,075,181 and 6,150,584 describing XENOMOUSE™ technology; U.S. Pat. No. 5,770,429 describing HuMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor, D., J. Immunol. 133 (1984) 3001-3005; Brodeur, B. R. et al., Monoclonal Antibody Production Techniques and Applications, Marcel Dekker, Inc., New York (1987), pp. 51-63; and Boerner, P. et al., J. Immunol. 147 (1991) 86-95) Human antibodies generated via human B-cell hybridoma technology are also described in Li, J. et al., Proc. Natl. Acad. Sci. USA 103 (2006) 3557-3562. Additional methods include those described, for example, in U.S. Pat. No. 7,189,826 (describing production of monoclonal human IgM antibodies from hybridoma cell lines) and Ni, J., Xiandai Mianyixue 26 (2006) 265-268 (describing human-human hybridomas). Human hybridoma technology (Trioma technology) is also described in Vollmers, H. P. and Brandlein, S., Histology and Histopathology 20 (2005) 927-937 and Vollmers, H. P. and Brandlein, S., Methods and Findings in Experimental and Clinical Pharmacology 27 (2005) 185-191.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom, H. R. et al., Methods in Molecular Biology 178 (2001) 1-37 and further described, e.g., in the McCafferty, J. et al., Nature 348 (1990) 552-554; Clackson, T. et al., Nature 352 (1991) 624-628; Marks, J. D. et al., J. Mol. Biol. 222 (1992) 581-597; Marks, J. D. and Bradbury, A., Methods in Molecular Biology 248 (2003) 161-175; Sidhu, S. S. et al., J. Mol. Biol. 338 (2004) 299-310; Lee, C. V. et al., J. Mol. Biol. 340 (2004) 1073-1093; Fellouse, F. A., Proc. Natl. Acad. Sci. USA 101 (2004) 12467-12472; and Lee, C. V. et al., J. Immunol. Methods 284 (2004) 119-132.

In certain phage display methods, repertoires of VH and VL genes are separately cloned by polymerase chain reaction (PCR) and recombined randomly in phage libraries, which can then be screened for antigen-binding phage as described in Winter, G. et al., Ann. Rev. Immunol. 12 (1994) 433-455. Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths, A. D. et al., EMBO J. 12 (1993) 725-734. Finally, naive libraries can also be made synthetically by cloning non-rearranged V-gene segments from stem cells, and using PCR primers containing random sequence to encode the highly variable CDR3 regions and to accomplish rearrangement in vitro, as described by Hoogenboom, H. R. and Winter, G., J. Mol. Biol. 227 (1992) 381-388. Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for TPBG and the other is for any other antigen. In certain embodiments, bispecific antibodies may bind to two different epitopes of TPBG. Bispecific antibodies may also be used to localize cytotoxic agents to cells which express TPBG. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A. et al., EMBO J. 10 (1991) 3655-3659), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan, M. et al., Science 229 (1985) 81-83); using leucine zippers to produce bi-specific antibodies (see, e.g., Kostelny, S. A. et al., J. Immunol. 148 (1992) 1547-1553; using "diabody" technology for making bispecific antibody fragments (see, e.g., Holliger, P. et al., Proc. Natl. Acad. Sci. USA 90 (1993) 6444-6448); and using single-chain Fv (sFv) dimers (see, e.g. Gruber, M et al., J. Immunol. 152 (1994) 5368-5374); and preparing trispecific antibodies as described, e.g., in Tutt, A. et al., J. Immunol. 147 (1991) 60-69).

Engineered antibodies with three or more functional antigen binding sites, including "Octopus antibodies," are also included herein (see, e.g. US 2006/0025576).

The antibody or fragment herein also includes a "Dual Acting Fab" or "DAF" comprising an antigen binding site that binds to TPBG as well as another, different antigen (see, US 2008/0069820, for example).

The antibody or fragment herein also includes multispecific antibodies described in WO 2009/080251, WO 2009/080252, WO 2009/080253, WO 2009/080254, WO 2010/112193, WO 2010/115589, WO 2010/136172, WO 2010/145792, and WO 2010/145793.

7. Antibody Variants

In certain embodiments, amino acid sequence variants of the antibodies provided herein are contemplated. For example, it may be desirable to improve the binding affinity and/or other biological properties of the antibody Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Exemplary changes are provided in the following Table under the heading of "exemplary substitutions", and as further described below in reference to amino acid side chain classes. Conservative substitutions are shown in Table 1 under the heading of "preferred substitutions" Amino acid substitutions may be introduced into an antibody of interest and the products screened for a desired activity, e.g., retained/improved antigen binding, decreased immunogenicity, or improved ADCC or CDC.

TABLE

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, P. S., Methods Mol. Biol. 207 (2008) 179-196), and/or SDRs (a-CDRs), with the resulting variant VH or VL being tested for binding affinity. Affinity maturation by constructing and reselecting from secondary libraries has been described, e.g., in Hoogenboom, H. R. et al. in Methods in Molecular Biology 178 (2002) 1-37. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham, B. C. and Wells, J. A., Science 244 (1989) 1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright, A. and Morrison, S. L., TIBTECH 15 (1997) 26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US 2003/0157108; US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2002/031140; Okazaki, A. et al., J. Mol. Biol. 336 (2004) 1239-1249; Yamane-Ohnuki, N. et al., Biotech. Bioeng. 87 (2004) 614-622. Examples of cell lines capable of producing defucosylated antibodies include Lec13 CHO cells deficient in protein fucosylation (Ripka, J. et al., Arch. Biochem. Biophys. 249 (1986) 533-545; US 2003/0157108; and WO 2004/056312, especially at Example 11), and knockout cell lines, such as alpha-1,6-fucosyltransferase gene, FUT8, knockout CHO cells (see, e.g., Yamane-Ohnuki, N. et al., Biotech. Bioeng. 87 (2004) 614-622; Kanda, Y. et al., Biotechnol. Bioeng. 94 (2006) 680-688; and WO 2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express FcγRI, FcγRII and FcγRIII. FcR expression on hematopoietic cells is summarized in Table 3 on page 464 of Ravetch, J. V. and Kinet, J. P., Annu. Rev. Immunol. 9 (1991) 457-492. Non-limiting examples of in vitro assays to assess ADCC activity of a molecule of interest is described in U.S. Pat. No. 5,500,362 (see, e.g. Hellstrom, I. et al., Proc. Natl. Acad. Sci. USA 83 (1986) 7059-7063; and Hellstrom, I. et al., Proc. Natl. Acad. Sci. USA 82 (1985) 1499-1502); U.S. Pat. No. 5,821,337 (see Bruggemann, M. et al., J. Exp. Med. 166 (1987) 1351-1361). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes, R. et al., Proc. Natl. Acad. Sci. USA 95 (1998) 652-656. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro, H. et al., J. Immunol. Methods 202 (1996) 163-171; Cragg, M. S. et al., Blood 101 (2003) 1045-1052; and Cragg, M. S. and M. J. Glennie, Blood 103 (2004) 2738-2743). FcRn binding and in vivo clearance/half life determinations can also be performed using methods known in the art (see, e.g., Petkova, S. B. et al., Int. Immunol. 18 (2006: 1759-1769).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields, R. L. et al., J. Biol. Chem. 276 (2001) 6591-6604)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie, E. E. et al., J. Immunol. 164 (2000) 4178-4184.

Antibodies with increased half lives and improved binding to the neonatal Fc receptor (FcRn), which is responsible for the transfer of maternal IgGs to the fetus (Guyer, R. L. et al., J. Immunol. 117 (1976) 587-593, and Kim, J K et al., J. Immunol. 24 (1994) 2429-2434), are described in US 2005/0014934. Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan, A. R. and Winter, G., Nature 322 (1988) 738-740; U.S. Pat. Nos. 5,648,260; 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and 5400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and non-proteinaceous moiety that may be selectively heated by exposure to radiation are provided. In one embodiment, the non-proteinaceous moiety is a carbon nanotube (Kam, N. W.

et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

B. Recombinant Methods and Compositions

Antibodies may be produced using recombinant methods and compositions, e.g., as described in U.S. Pat. No. 4,816, 567. In one embodiment, isolated nucleic acid encoding an anti-TPBG antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-TPBG antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-TPBG antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B. K. C. (ed.), Humana Press, Totowa, N.J. (2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P. et al., Annals N.Y. Acad. Sci. 383 (1982) 44-68; MRC 5 cells; and FS4 cells. Other useful mammalian host cell lines include Chinese hamster ovary (CHO) cells, including DHFR− CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

C. Assays

Anti-TPBG antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc.

In another aspect, competition assays may be used to identify an antibody that competes with an antibody selected from the group of antibodies 051, 091, or 097 as disclosed herein and defined by their respective amino acid sequences of VH and VL domains for binding to TPBG. In certain embodiments, such a competing antibody binds to the same epitope (e.g., a linear or a conformational epitope) that is bound by an antibody selected from the group of antibodies 051, 091, or 097 as disclosed herein and defined by their respective amino acid sequences of VH and VL domains. Detailed exemplary methods for mapping an epitope to which an antibody binds are provided in Morris, G. E. (ed.), Epitope Mapping Protocols, In: Methods in Molecular Biology, Vol. 66, Humana Press, Totowa, N.J. (1996).

In an exemplary competition assay, immobilized TPBG is incubated in a solution comprising a first labeled antibody that binds to TPBG (e.g., an antibody selected from the group of antibodies 051, 091, or 097 as disclosed herein and defined by their respective amino acid sequences of VH and VL domains) and a second unlabeled antibody that is being tested for its ability to compete with the first antibody for binding to TPBG. The second antibody may be present in a hybridoma supernatant. As a control, immobilized TPBG is incubated in a solution comprising the first labeled antibody but not the second unlabeled antibody. After incubation under conditions permissive for binding of the first antibody to TPBG, excess unbound antibody is removed, and the amount of label associated with immobilized TPBG is measured. If the amount of label associated with immobilized TPBG is substantially reduced in the test sample relative to the control sample, then that indicates that the second antibody is competing with the first antibody for binding to TPBG. See Harlow, E. and Lane, D., Antibodies: A Laboratory Manual, Chapter 14, Cold Spring Harbor Laboratory, Cold Spring Harbor, N.Y. (1988).

2. Activity Assays

In one aspect, assays are provided for identifying anti-TPBG antibodies thereof having biological activity. Biological activity may include, e.g., binding to TPBG-expressing tumor cells. Antibodies having such biological activity in vivo and/or in vitro are also provided.

In certain embodiments, an antibody of the invention is tested for such biological activity.

D. Immunoconjugates

The invention also provides immunoconjugates comprising an anti-TPBG antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020 5,416,064 and EP 0 425 235 B1); an auristatin such as monomethyl auristatin drug moieties DE and DF (MMAE and MMAF) (see U.S. Pat. Nos. 5,635,483, 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman, L M et al., Cancer Res. 53 (1993) 3336-3342; and Lode, H. N. et al., Cancer Res. 58 (1998) 2925-2928); an anthracycline such as daunomycin or doxorubicin (see Kratz, F. et al., Curr. Med. Chem. 13 (2006) 477-523; Jeffrey, S. C. et al., Bioorg. Med. Chem. Lett. 16 (2006) 358-362; Torgov, M. Y. et al., Bioconjug. Chem. 16 (2005) 717-721; Nagy, A. et al., Proc. Natl. Acad. Sci. USA 97 (2000) 829-834; Dubowchik, G. M. et al., Bioorg. & Med. Chem. Letters 12 (2002) 1529-1532; King, H. D. et al., J. Med. Chem. 45 (20029 4336-4343; and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of exotoxin A chain (from *Pseudomonas aeruginosa*), diphtheria toxin, ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. In one embodiment the enzymatically active toxin is *Pseudomonas* exotoxin A or a variant thereof.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example $TC^{99m}$ or $I^{123}$ or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta, E. S. et al., Science 238 (1987) 1098-1104. Carbon-14-labeled 1-isothiocyanatobenzyl-3-methyldiethylene triamine pentaacetic acid (MX-DTPA) is an exemplary chelating agent for conjugation of radionucleotide to the antibody. See WO 94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari, R. V. et al., Cancer Res. 52 (1992) 127-131; U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

Conjugates of the antibody and cytotoxic agents, which are polypeptides, may also be provided as recombinant fusion proteins, e.g. by direct expression of said fusion protein within a host cell, thereby not requiring an additional coupling step for provision.

E. Methods and Compositions for Diagnostics and Detection

In certain embodiments, any of the anti-TPBG antibodies provided herein is useful for detecting the presence of TPBG in a biological sample. The term "detecting" as used herein encompasses quantitative or qualitative detection. In certain embodiments, a biological sample comprises a cell or tissue, such as tumor cells.

In one embodiment, an anti-TPBG antibody for use in a method of diagnosis or detection is provided. In a further aspect, a method of detecting the presence of TPBG in a biological sample is provided. In certain embodiments, the method comprises contacting the biological sample with an anti-TPBG antibody as described herein under conditions permissive for binding of the anti-TPBG antibody to TPBG, and detecting whether a complex is formed between the anti-TPBG antibody and TPBG. Such method may be an in vitro or in vivo method. In one embodiment, an anti-TPBG antibody is used to select subjects eligible for therapy with an anti-TPBG antibody, e.g. where TPBG is a biomarker for selection of patients.

Exemplary disorders that may be diagnosed using an antibody of the invention include cancer, e.g. lymphomas, lymphocytic leukemias, lung cancer, non-small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumours, brain stem glioma, glioblastoma multiforme, astrocytomas, schwanomas, ependymomas, medulloblastomas, meningiomas, squamous cell carcinomas, pituitary adenoma and Ewings sarcoma, including refractory versions of any of the above cancers, or a combination of one or more of the above cancers.

In certain embodiments, labeled anti-TPBG antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-TPBG antibody as described herein are prepared by mixing such antibody having the desired degree of purity with one or more optional pharmaceutically acceptable carriers (Remington's Pharmaceutical Sciences, 16th edition, Osol, A. (ed.) (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as poly(vinylpyrrolidone); amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter International, Inc.). Certain exemplary sHASEGPs and methods of use, including rhuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide a chemotherapeutic agent, preferably a chemotherapeutic agent listed below. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. (ed.) (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-TPBG antibodies provided herein, or the recombinant fusion proteins or immunoconjugates comprising the anti-TPBG antibodies provided herein, may be used in therapeutic methods.

In one aspect, an anti-TPBG antibody for use as a medicament is provided. In further aspects, an anti-TPBG antibody for use in treating cancer is provided. In certain embodiments, an anti-TPBG antibody for use in a method of treatment is provided. In certain embodiments, the invention provides an anti-TPBG antibody for use in a method of treating an individual having cancer comprising administering to the individual an effective amount of the anti-TPBG antibody. In one such embodiment, the method further comprises administering to the individual an effective amount of at least one additional therapeutic agent, e.g., as described below. An "individual" according to any of the above embodiments is preferably a human.

In a further aspect, the invention provides for the use of an anti-TPBG antibody in the manufacture or preparation of a medicament. In one embodiment, the medicament is for treatment of cancer. In a further embodiment, the medicament is for use in a method of treating cancer comprising administering to an individual having cancer an effective amount of the medicament. In one such embodiment, the method further comprises administering to the individual an effective amount of at least one additional therapeutic agent, e.g., as described below. An "individual" according to any of the above embodiments may be a human.

In a further aspect, the invention provides a method for treating cancer. In one embodiment, the method comprises administering to an individual having cancer an effective amount of an anti-TPBG antibody. In one such embodiment, the method further comprises administering to the individual an effective amount of at least one additional therapeutic agent, as described below. An "individual" according to any of the above embodiments may be a human.

In a further aspect, the invention provides pharmaceutical formulations comprising any of the anti-TPBG antibodies provided herein, e.g., for use in any of the above therapeutic methods. In one embodiment, a pharmaceutical formulation comprises any of the anti-TPBG antibodies provided herein and a pharmaceutically acceptable carrier. In another embodiment, a pharmaceutical formulation comprises any of the anti-TPBG antibodies provided herein and at least one additional therapeutic agent, e.g., as described below.

Antibodies of the invention can be used either alone or in combination with other agents in a therapy. For instance, an antibody of the invention may be co-administered with at least one additional therapeutic agent. In certain embodiments, an additional therapeutic agent is a chemotherapeutic agent.

In one embodiment such chemotherapeutic agents include, but are not limited to, anti-neoplastic agents including alkylating agents including: nitrogen mustards, such as mechlorethamine, cyclophosphamide, ifosfamide, melphalan and chlorambucil; nitrosoureas, such as carmustine (BCNU), lomustine (CCNU), and semustine (methyl-CCNU); Temodal™ (temozolamide), ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil (5FU), fluorodeoxyuridine, gemcitabine, cytosine arabinoside (AraC, cytarabine), 5-azacytidine, 2,2'-difluorodeoxycytidine, purine analogs such as 6-merca.rho.topurine, 6-thioguamne, azathioprine, T-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; pipodophylotoxins such as etoposide and teniposide; antibiotics such as actinomycin D, daunomycin (rubidomycin), doxorubicin, mitoxantrone, idarubicin, bleomycins, plicamycin (mithramycin), mitomycin C, and actinomycin; enzymes such as L-asparaginase; biological response modifiers such as interferon-alpha, IL-2, G-CSF and GM-CSF; miscellaneous agents including platinum coordination complexes such as oxaliplatin, cisplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o, p-DDD) and aminoglutethimide; hormones and antagonists including adrenocorticosteroid antagonists such as prednisone and equivalents, dexamethasone and aminoglutethimide; Gemzar™ (gemcitabine), progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and nonsteroidal antiandrogens such as flutamide. Therapies targeting epigenetic mechanism including, but not limited to, histone deacetylase inhibitors, demethylating agents (e.g., Vidaza) and release of transcriptional repression (ATRA) therapies can also be combined with antibodies of the invention.

In one embodiment the chemotherapeutic agent is selected from the group consisting of taxanes (like e.g. paclitaxel (Taxol), docetaxel (Taxotere), modified paclitaxel (e.g., Abraxane and Opaxio), doxorubicin, sunitinib (Sutent), sorafenib (Nexavar), and other multikinase inhibitors, oxaliplatin, cisplatin and carboplatin, etoposide, gemcitabine, and vinblastine. In one embodiment the chemotherapeutic agent is selected from the group consisting of taxanes (like e.g. taxol (paclitaxel), docetaxel (Taxotere), modified paclitaxel (e.g. Abraxane and Opaxio)). In one embodiment, the additional chemotherapeutic agent is selected from 5-fluorouracil (5-FU), leucovorin, irinotecan, or oxaliplatin. In one embodiment the chemotherapeutic agent is 5-fluorouracil, leucovorin and irinotecan (FOLFIRI). In one embodiment the chemotherapeutic agent is 5-fluorouracil, and oxaliplatin (FOLFOX).

Specific examples of therapeutic applications of antibodies of the invention with additional chemotherapeutic agents include, for instance,

- therapies with taxanes (e.g., docetaxel or paclitaxel) or a modified paclitaxel (e.g., Abraxane or Opaxio), doxorubicin), capecitabine and/or bevacizumab (Avastin) for the treatment of breast cancer;
- therapies with carboplatin, oxaliplatin, cisplatin, paclitaxel, doxorubicin (or modified doxorubicin (Caelyx or Doxil)), or topotecan (Hycamtin) for the treatment of ovarian cancer,
- therapies with a multi-kinase inhibitor, MKI, (Sutent, Nexavar, or 706) and/or doxorubicin for the treatment of kidney cancer;
- therapies with oxaliplatin, cisplatin and/or radiation for the treatment of squamous cell carcinoma; and
- therapies with taxol and/or carboplatin for the treatment of lung cancer.

Therefore, in one embodiment the additional chemotherapeutic agent is selected from the group of taxanes (docetaxel or paclitaxel or a modified paclitaxel (Abraxane or Opaxio), doxorubicin, capecitabine and/or bevacizumab for the treatment of breast cancer.

In one embodiment the antibodies of the invention are administered in absence of an additional chemotherapeutic agent.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant. Antibodies of the invention can also be used in combination with radiation therapy.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 μg/kg to 15 mg/kg (e.g. 0.5 mg/kg-10 mg/kg) of antibody can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). However, other dosage regimens may be useful. The progress of this therapy is easily monitored by conventional techniques and assays.

It is understood that any of the above formulations or therapeutic methods may be carried out using an immunoconjugate of the invention or a recombinant fusion protein of the invention in place of or in addition to an anti-TPBG antibody.

III. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention or a recombinant fusion protein of the invention in place of or in addition to an anti-TPBG antibody.

IV. Specific Embodiments of the Invention

In the following specific embodiments of the invention are listed.

1. An isolated antibody that binds to trophoblast glycoprotein (TPBG), wherein the antibody binds to human TPBG (SEQ ID NO: 1) and to minipig TPBG (SEQ ID NO: 2).
2. An isolated antibody that binds to trophoblast glycoprotein (TPBG), wherein the antibody binds to human TPBG (SEQ ID NO: 1) and to cell surface expressed minipig TPBG (SEQ ID NO: 2).
3. An isolated antibody that binds to trophoblast glycoprotein (TPBG), wherein the antibody binds to human TPBG (SEQ ID NO: 1) and to minipig TPBG (SEQ ID NO: 2), and wherein the antibody specifically binds to human TPBG at a pH of 5.5 and a pH of 7.4.
4. An isolated antibody that binds to trophoblast glycoprotein (TPBG), wherein the antibody binds to human TPBG (SEQ ID NO: 1) and to minipig TPBG (SEQ ID NO: 2), and wherein the antibody specifically binds to human TPBG at a pH of 5.5 and a pH of 7.2.
5. The antibody of any one of embodiments 1 to 4, wherein the antibody specifically binds to human and minipig TPBG with a $K_D$ of $10^{-8}$ M or less, respectively.
6. The antibody of any one of embodiments 1 to 4, wherein the antibody specifically binds to human and minipig TPBG with a $K_D$ of $10^{-8}$ M to $10^{-13}$ M, respectively.
7. The antibody of any one of embodiments 4 to 6, wherein the antibody specifically binds to cell surface expressed human TPBG at a pH of 5.5 and a pH of 7.2.

8. The antibody of any one of embodiments 4 to 6, wherein the antibody specifically binds to cell surface expressed human TPBG on SW620 cells at a pH of 5.5 and a pH of 7.2.
9. The antibody of any one of embodiments 3 to 8, wherein the antibody specifically binds to human TPBG at a pH of 5.5 and a pH of 7.4 with a $K_D$ of $10^{-8}$ M or less.
10. The antibody of any one of embodiments 3 to 9, wherein the antibody specifically binds to human TPBG at a pH of 5.5 and a pH of 7.4 with a $K_D$ of $10^{-8}$ M to $10^{-13}$ M.
11. The antibody according to any one of embodiments 1 to 10, wherein the antibody is internalized into a TPBG-expressing cell upon binding.
12. The antibody of any one of embodiments 1 to 11, wherein the antibody comprises
    (a) a CDR3 of the heavy chain of SEQ ID NO: 5, a CDR3 of the light chain of SEQ ID NO: 8, and a CDR2 of the heavy chain of SEQ ID NO: 4; or [antibody 051]
    (b) a CDR3 of the heavy chain of SEQ ID NO: 13, a CDR3 of the light chain of SEQ ID NO: 16, and a CDR2 of the heavy chain of SEQ ID NO: 12; or [antibody 091]
    (c) a CDR3 of the heavy chain of SEQ ID NO: 21, a CDR3 of the light chain of SEQ ID NO: 24, and a CDR2 of the heavy chain of SEQ ID NO: 20, [antibody 097]
    or wherein the antibody is a humanized antibody derived from the antibody indicated in (a), (b) or (c).
13. The antibody of embodiment of any one of embodiments 1 to 11, wherein the antibody comprises a CDR3 of the heavy chain of SEQ ID NO: 5, a CDR3 of the light chain of SEQ ID NO: 8, and a CDR2 of the heavy chain of SEQ ID NO: 4. [antibody 051]
14. The antibody of embodiment of any one of embodiments 1 to 11, wherein the antibody comprises a CDR3 of the heavy chain of SEQ ID NO: 13, a CDR3 of the light chain of SEQ ID NO: 16, and a CDR2 of the heavy chain of SEQ ID NO: 12. [antibody 091]
15. The antibody of embodiment of any one of embodiments 1 to 11, wherein the antibody comprises a CDR3 of the heavy chain of SEQ ID NO: 21, a CDR3 of the light chain of SEQ ID NO: 24, and a CDR2 of the heavy chain of SEQ ID NO: 20. [antibody 097]
16. A humanized antibody derived from the antibody of any one of embodiments 13 to 15.
17. The antibody of any one of embodiments 1 to 11, wherein the antibody comprises
    (a) a CDR1 of the heavy chain of SEQ ID NO: 3, a CDR2 of the heavy chain of SEQ ID NO: 4, a CDR3 of the heavy chain of SEQ ID NO: 5, a CDR1 of the light chain of SEQ ID NO: 6, a CDR2 of the light chain of SEQ ID NO: 7, and a CDR3 of the light chain of SEQ ID NO: 8; or [antibody 051]
    (b) a CDR1 of the heavy chain of SEQ ID NO: 11, a CDR2 of the heavy chain of SEQ ID NO: 12, and a CDR3 of the heavy chain of SEQ ID NO: 13, a CDR1 of the light chain of SEQ ID NO: 14, a CDR2 of the light chain of SEQ ID NO: 15, and a CDR3 of the light chain of SEQ ID NO: 16; or [antibody 091]
    (c) a CDR1 of the heavy chain of SEQ ID NO: 19, a CDR2 of the heavy chain of SEQ ID NO: 20, and a CDR3 of the heavy chain of SEQ ID NO: 21, a CDR1 of the light chain of SEQ ID NO: 22, a CDR2 of the light chain of SEQ ID NO: 23, and a CDR3 of the light chain of SEQ ID NO: 24; [antibody 097]
    or wherein the antibody is a humanized antibody derived from the antibody indicated in (a), (b) or (c).
18. The antibody of embodiment of any one of embodiments 1 to 11, wherein the antibody comprises a CDR1 of the heavy chain of SEQ ID NO: 3, a CDR2 of the heavy chain of SEQ ID NO: 4, a CDR3 of the heavy chain of SEQ ID NO: 5, a CDR1 of the light chain of SEQ ID NO: 6, a CDR2 of the light chain of SEQ ID NO: 7, and a CDR3 of the light chain of SEQ ID NO: 8. [antibody 051]
19. The antibody of embodiment of any one of embodiments 1 to 11, wherein the antibody comprises a CDR1 of the heavy chain of SEQ ID NO: 11, a CDR2 of the heavy chain of SEQ ID NO: 12, and a CDR3 of the heavy chain of SEQ ID NO: 13, a CDR1 of the light chain of SEQ ID NO: 14, a CDR2 of the light chain of SEQ ID NO: 15, and a CDR3 of the light chain of SEQ ID NO: 16. [antibody 091]
20. The antibody of embodiment of any one of embodiments 1 to 11, wherein the antibody comprises a CDR1 of the heavy chain of SEQ ID NO: 19, a CDR2 of the heavy chain of SEQ ID NO: 20, and a CDR3 of the heavy chain of SEQ ID NO: 21, a CDR1 of the light chain of SEQ ID NO: 22, a CDR2 of the light chain of SEQ ID NO: 23, and a CDR3 of the light chain of SEQ ID NO: 24. [antibody 097]
21. A humanized antibody derived from the antibody of any one of embodiments 18 to 20.
22. The antibody of any one of embodiments 1 to 11, comprising
    (a) a VH sequence having at least 95% sequence identity to the amino acid sequence of SEQ ID NO: 9;
    (b) a VL sequence having at least 95% sequence identity to the amino acid sequence of SEQ ID NO: 10; or
    (c) a VH sequence as in (a) and a VL sequence as in (b). [antibody 051]
23. The antibody of embodiment 22, comprising a VH sequence of SEQ ID NO: 9. [antibody 051]
24. The antibody of embodiment 22 or 23, comprising a VL sequence of SEQ ID NO: 10. [antibody 051]
25. An antibody comprising a VH sequence of SEQ ID NO: 9 and a VL sequence of SEQ ID NO: 10. [antibody 051]
26. A humanized antibody that binds to TPBG derived from the antibody of embodiment 25.
27. The antibody of any one of embodiments 1 to 11, comprising
    (a) a VH sequence having at least 95% sequence identity to the amino acid sequence of SEQ ID NO: 17;
    (b) a VL sequence having at least 95% sequence identity to the amino acid sequence of SEQ ID NO: 18; or
    (c) a VH sequence as in (a) and a VL sequence as in (b). [antibody 091]
28. The antibody of embodiment 27, comprising a VH sequence of SEQ ID NO: 17. [antibody 091]
29. The antibody of embodiment 27 or 28, comprising a VL sequence of SEQ ID NO: 18. [antibody 091]
30. An antibody comprising a VH sequence of SEQ ID NO: 17 and a VL sequence of SEQ ID NO: 18. [antibody 091]
31. A humanized antibody that binds to TPBG derived from the antibody of embodiment 30.
32. The antibody of any one of embodiments 1 to 11, comprising
    (a) a VH sequence having at least 95% sequence identity to the amino acid sequence of SEQ ID NO: 25;
    (b) a VL sequence having at least 95% sequence identity to the amino acid sequence of SEQ ID NO: 26; or
    (c) a VH sequence as in (a) and a VL sequence as in (b). [antibody 097]
33. The antibody of embodiment 32, comprising a VH sequence of SEQ ID NO: 25. [antibody 097]

34. The antibody of embodiment 32 or 33, comprising a VL sequence of SEQ ID NO: 26. [antibody 097]
35. An antibody comprising a VH sequence of SEQ ID NO: 25 and a VL sequence of SEQ ID NO: 26. [antibody 097]
36. A humanized antibody that binds to TPBG derived from the antibody of embodiment 35.
37. The antibody of any one of embodiments 1 to 36, which is a monoclonal antibody.
38. The antibody of any one of embodiments 1 to 37, which is a human, humanized, or chimeric antibody.
39. The antibody of any one of embodiments 1 to 38, which is an antibody fragment that binds TPBG.
40. The antibody of any one of embodiments 1 to 39, which is a Fab fragment that binds TPBG.
41. The antibody of any one of embodiments 1 to 38, which is of IgG isotype.
42. The antibody of any one of embodiments 1 to 38, which is a full length IgG antibody.
43. The antibody of any one of embodiments 1 to 38, which is of $IgG_1$ isotype.
44. The antibody of any one of embodiments 1 to 38, which is a full length $IgG_1$ antibody.
45. An isolated nucleic acid encoding the antibody of any one of embodiments 1 to 44.
46. A host cell comprising the nucleic acid of embodiment 45.
47. A method of producing an antibody comprising culturing the host cell of embodiment 46 so that the antibody is produced.
48. The method of embodiment 47, further comprising recovering the antibody from the host cell.
49. An immunoconjugate comprising the antibody of any one of embodiments 1 to 44 and a cytotoxic agent.
50. The immunoconjugate of embodiment 49, wherein the cytotoxic agent is an enzymatically active toxin or fragment thereof.
51. The immunoconjugate of embodiment 50, wherein the cytotoxic agent is selected from the group consisting of exotoxin A chain (from *Pseudomonas aeruginosa*), diphtheria toxin, ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.
52. An immunoconjugate of any one of embodiments 49 to 51, wherein the cytotoxic agent is *Pseudomonas* exotoxin A or a variant thereof.
53. A method of producing an immunoconjugate according to any one of embodiments 49 to 52, including the step of coupling the antibody to the cytotoxic agent.
54. The method of embodiment 53, wherein the antibody is coupled to the cytotoxic agent via sortase mediated coupling.
55. The method of any one of embodiments 53 to 54, including the step of providing the antibody before the step of coupling.
56. The method of embodiment 55, wherein the antibody is provided by culturing the host cell of embodiment 46 so that the antibody is produced.
57. The method of embodiment 56, further including the step of recovering the antibody from the host cell before the step of coupling.
58. A recombinant fusion protein comprising an antibody of any one of embodiments 1 to 44 and any other polypeptide.
59. The recombinant fusion protein of embodiment 58, wherein the other polypeptide is fused to at least one of the heavy chains of the antibody.
60. The recombinant fusion protein of embodiment 59, wherein the other polypeptide is fused to the C-terminus of at least one of the heavy chains of the antibody.
61. The recombinant fusion protein of any one of embodiments 58 to 60, wherein the polypeptide is a cytotoxic agent.
62. The recombinant fusion protein of any one of embodiments 58 to 61, wherein the polypeptide is an enzymatically active toxin or fragment thereof.
63. The recombinant fusion protein of any one of embodiments 58 to 62, wherein the cytotoxic agent is selected from the group of exotoxin A chain (from *Pseudomonas aeruginosa*), diphtheria toxin, ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.
64. The recombinant fusion protein of any one of embodiments 58 to 63, wherein the cytotoxic agent is *Pseudomonas* exotoxin A or a variant thereof.
65. An isolated nucleic acid encoding the recombinant fusion protein of any one of the embodiments 58 to 64.
66. A host cell comprising the nucleic acid of embodiment 65.
67. A method of producing a recombinant fusion protein comprising culturing the host cell of embodiment 66 so that the recombinant fusion protein is produced.
68. The method of embodiment 67, further comprising recovering the recombinant fusion protein from the host cell.
69. The method of embodiment 67 or 68, wherein the recombinant fusion protein is an immunoconjugate comprising the antibody of any one of embodiments 1 to 44 and a cytotoxic agent.
70. The method of any of embodiments 67 to 69, comprising isolating inclusion bodies of the host cell and solubilizing the inclusion bodies.
71. The method of embodiment 70, further comprising the step of renaturation of the material from the solubilized inclusion bodies.
72. The method of any of embodiments 67 to 71, wherein the host cell is a bacterial cell.
73. The method of any of embodiments 67 to 72, wherein the host cell is *E. coli*.
74. A pharmaceutical formulation comprising the antibody of any one of embodiments 1 to 44 and a pharmaceutically acceptable carrier.
75. The pharmaceutical formulation of embodiment 74, further comprising an additional therapeutic agent.
76. The pharmaceutical formulation of embodiment 75, wherein the additional therapeutic agent is a chemotherapeutic agent.
77. A pharmaceutical formulation comprising the immunoconjugate of any one of embodiments 49 to 52 and a pharmaceutically acceptable carrier.
78. The pharmaceutical formulation of embodiment 77, further comprising an additional therapeutic agent.
79. The pharmaceutical formulation of embodiment 78, wherein the additional therapeutic agent is a chemotherapeutic agent.

80. A pharmaceutical formulation comprising the recombinant fusion protein of any one of embodiments 58 to 64 and a pharmaceutically acceptable carrier.
81. The pharmaceutical formulation of embodiment 80 further comprising an additional therapeutic agent.
82. The pharmaceutical formulation of embodiment 81, wherein the additional therapeutic agent is a chemotherapeutic agent.
83. The pharmaceutical formulation of embodiment 80 for administration in combination with radiation therapy.
84. The antibody of any one of embodiments 1 to 44 for use as a medicament.
85. The antibody of any one of embodiments 1 to 44 for use in the treatment of cancer.
86. The antibody for use of embodiment 85, wherein the cancer is selected from lymphomas, lymphocytic leukemias, lung cancer, non-small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumours, brain stem glioma, glioblastoma multiforme, astrocytomas, schwanomas, ependymomas, medulloblastomas, meningiomas, squamous cell carcinomas, pituitary adenoma and Ewings sarcoma, including refractory versions of any of the above cancers, or a combination of one or more of said cancers.
87. The antibody for use of embodiment 85 or 86, wherein the cancer is non-small cell lung cancer.
88. Use of the antibody of any one of embodiments 1 to 44 in the manufacture of a medicament.
89. The use of embodiment 88, wherein the medicament is for treatment of cancer.
90. The use of embodiment 89, wherein the cancer is selected from lymphomas, lymphocytic leukemias, lung cancer, non-small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumours, brain stem glioma, glioblastoma multiforme, astrocytomas, schwanomas, ependymomas, medulloblastomas, meningiomas, squamous cell carcinomas, pituitary adenoma and Ewings sarcoma, including refractory versions of any of the above cancers, or a combination of one or more of said cancers.
91. The use of embodiment 89 or 90, wherein the cancer is non-small cell lung cancer.
92. The use of one of embodiments 89 to 91, wherein the medicament is for administration in combination with one or more chemotherapeutic agents and/or radiotherapy.
93. A method of treating an individual having cancer comprising administering to the individual an effective amount of the antibody of any of embodiments 1 to 44.
94. The method of embodiment 93, further comprising administering an additional therapeutic agent to the individual.
95. The method of embodiment 94, wherein the additional therapeutic agent is a chemotherapeutic agent.
96. The method of embodiment 93, further comprising administering radiation therapy to the individual.
97. The immunoconjugate of any one of embodiments 49 to 52 for use as a medicament.
98. The immunoconjugate of any one of embodiments 49 to 52 for use in treating cancer.
99. The immunoconjugate for use of embodiment 98, wherein the cancer is selected from lymphomas, lymphocytic leukemias, lung cancer, non-small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumours, brain stem glioma, glioblastoma multiforme, astrocytomas, schwanomas, ependymomas, medulloblastomas, meningiomas, squamous cell carcinomas, pituitary adenoma and Ewings sarcoma, including refractory versions of any of the above cancers, or a combination of one or more of said cancers.
100. The immunoconjugate for use of embodiment 98 or 99, wherein the cancer is non-small cell lung cancer.
101. The immunoconjugate for use of one of embodiments 98 to 100, wherein the immunoconjugate is for administration in combination with a chemotherapeutic agent and/or radiotherapy.
102. Use of the immunoconjugate of any one of embodiments 49 to 52 in the manufacture of a medicament.
103. The use of embodiment 102, wherein the medicament is for treatment of cancer.
104. The use of embodiment 103, wherein the cancer is selected from lymphomas, lymphocytic leukemias, lung cancer, non-small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumours, brain stem glioma, glioblastoma multiforme, astrocytomas, schwanomas, ependymomas, medulloblastomas, meningiomas, squamous cell carcinomas, pituitary adenoma and Ewings sarcoma, including refractory versions of any of the above cancers, or a combination of one or more of said cancers.

105. The use of embodiment 103 or 104, wherein the cancer is non-small cell lung cancer.

106. The use of one of embodiments 102 to 105, wherein the immunoconjugate is for administration in combination with one or more chemotherapeutic agents and/or radiotherapy.

107. A method of treating an individual having cancer comprising administering to the individual an effective amount of the immunoconjugate of any one of embodiments 49 to 52.

108. The method of embodiment 107, further comprising administering an additional therapeutic agent to the individual.

109. The method of embodiment 108, wherein the additional therapeutic agent is a chemotherapeutic agent.

110. The method of one of embodiments 107 to 109, further comprising administering radiation therapy.

111. The recombinant fusion protein of any one of embodiments 58 to 64 for use as a medicament.

112. The recombinant fusion protein of any one of embodiments 58 to 64 for use in treating cancer.

113. The recombinant fusion protein for use of embodiment 112, wherein the cancer is selected from lymphomas, lymphocytic leukemias, lung cancer, non-small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumours, brain stem glioma, glioblastoma multiforme, astrocytomas, schwanomas, ependymomas, medulloblastomas, meningiomas, squamous cell carcinomas, pituitary adenoma and Ewings sarcoma, including refractory versions of any of the above cancers, or a combination of one or more of said cancers.

114. The recombinant fusion protein for use of embodiment 112 or 113, wherein the cancer is non-small cell lung cancer.

115. The recombinant fusion protein for use of one of embodiments 112 to 114, wherein the recombinant fusion protein is for administration in combination with a chemotherapeutic agent and/or radiotherapy.

116. Use of the recombinant fusion protein of any one of embodiments 58 to 64 in the manufacture of a medicament.

117. The use of embodiment 116, wherein the medicament is for treatment of cancer.

118. The use of embodiment 117, wherein the cancer is selected from lymphomas, lymphocytic leukemias, lung cancer, non-small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumours, brain stem glioma, glioblastoma multiforme, astrocytomas, schwanomas, ependymomas, medulloblastomas, meningiomas, squamous cell carcinomas, pituitary adenoma and Ewings sarcoma, including refractory versions of any of the above cancers, or a combination of one or more of said cancers.

119. The use of embodiment 117 or 118, wherein the cancer is non-small cell lung cancer.

120. The use of one of embodiments 117 to 119, wherein the recombinant fusion protein is for administration in combination with one or more chemotherapeutic agents and/or radiotherapy.

121. A method of treating an individual having cancer comprising administering to the individual an effective amount of the recombinant fusion protein of any one of embodiments 58 to 64.

122. The method of embodiment 121, further comprising administering an additional therapeutic agent to the individual.

123. The method of embodiment 122, wherein the additional therapeutic agent is a chemotherapeutic agent.

124. The method of one of embodiments 121 to 123, further comprising administering radiation therapy.

125. A method of screening for an antibody that binds to TPBG, wherein the antibody binds to human and to minipig TPBG, the method comprising the steps of testing the binding of a test antibody to human TPBG and to minipig TPBG, and selecting the antibody that binds to human TPBG and to minipig TPBG.

126. The method of embodiment 125, including the step of selecting the antibody that binds to human TPBG and to minipig TPBG with a $K_D$ of $10^{-8}$ M or less.

127. The method of embodiment 125 or 126, wherein the method is for screening of an antibody for therapeutic application.

128. The method of any one of embodiments 125 to 127, wherein the method is for screening of an antibody of embodiments 1 to 44.

129. The method of any one of embodiments 125 to 128, wherein the method comprises the step of testing the binding of a test antibody in monovalent form.
130. The method of any one of embodiments 125 to 129, wherein the method comprises the steps of testing the binding of a test antibody to human TPBG at pH 5.5 and at pH 7.2, and selecting the antibody that binds to human TPBG at pH 5.5 and at pH 7.2.
131. The method of any one of embodiments 125 to 130, wherein the method comprises the steps of testing the binding of a test antibody to human TPBG at pH 5.5 and at pH 7.4, and selecting the antibody that binds to human TPBG at pH 5.5 and at pH 7.4.
132. The method of embodiment 131, including the step of selecting the antibody that binds to human TPBG at pH 5.5 and at pH 7.4 with a $K_D$ of $10^{-8}$ M or less.
133. An antibody obtained by the method according to any one of embodiments 125 to 132.
134. A method of generating an antibody that binds to TPBG, wherein the antibody binds to human and to minipig TPBG, the method comprising the steps of (a) immunizing an animal with human TPBG or with human TBPG extracellular domain (ECD), (b) isolating B cells specific for human TPBG from the blood of the animal, (c) identifying the amino acid sequence of the variable domains (VH and VL) of the antibodies produced by the isolated B cells, (d) providing an antibody comprising the variable domains identified, (e) testing the binding of a the provided antibody to human TPBG and to minipig TPBG, and (f) selecting the antibody that binds to human TPBG and to minipig TPBG.
135. The method of embodiment 134, including the step of selecting the antibody that binds to human TPBG and to minipig TPBG with a $K_D$ of $10^{-8}$ M or less.
136. The method of embodiment 134 or 135, wherein the method is for generating an antibody for therapeutic application.
137. The method of any one of embodiments 134 to 136, wherein the method is for screening of an antibody of embodiments 1 to 44.
138. The method of any one of embodiments 134 to 137, wherein the animal is a rodent.
139. The method of any one of embodiments 134 to 138, wherein the animal is a rabbit.
140. The method of any one of embodiments 134 to 139, wherein the method comprises the step of testing the binding of the provided antibody in monovalent form.
141. The method of any one of embodiments 134 to 140, wherein the method comprises the steps of testing the binding of the provided antibody to human TPBG at pH 5.5 and at pH 7.2, and selecting the antibody that binds to human TPBG at pH 5.5 and at pH 7.2.
142. The method of any one of embodiments 134 to 141, wherein the method comprises the steps of testing the binding of a test antibody to human TPBG at pH 5.5 and at pH 7.4, and selecting the antibody that binds to human TPBG at pH 5.5 and at pH 7.4.
143. The method of embodiment 142, including the step of selecting the antibody that binds to human TPBG at pH 5.5 and at pH 7.4 with a $K_D$ of $10^{-8}$ M or less.
144. An antibody obtained by the method according to any one of embodiments 134 to 143.

V. Description of the Amino Acid Sequences

```
SEQ ID NO: 1  human TPBG (mature form, without signal peptide)
              SSPTSSASSFSSSAPFLASAVSAQPPLPDQCPALCECSEAARTVKCVNR
              NLTEVPTDLPAYVRNLFLTGNQLAVLPAGAFARRPPLAELAALNLSGSR
              LDEVRAGAFEHLPSLRQLDLSHNPLADLSPFAFSGSNASVSAPSPLVEL
              ILNHIVPPEDERQNRSFEGMVVAALLAGRALQGLRRLELASNHFLYLPR
              DVLAQLPSLRHLDLSNNSLVSLTYVSFRNLTHLESLHLEDNALKVLHNG
              TLAELQGLPHIRVFLDNNPWVCDCHMADMVTWLKETEVVQGKDRLTCAY
              PEKMRNRVLLELNSADLDCDPILPPSLQTSYVFLGIVLALIGAIFLLVL
              YLNRKGIKKWMHNIRDACRDHMEGYHYRYEINADPRLTNLSSNSDV SEQ ID NO: 2  minipig TPBG (mature form, without signal peptide)
              SSLTSSASSTSSASFPASAASALPPLPGRCPQPCECSEAARTVKCVGRN
              LTEVPADLPPYVRTLFLTGNQLAVLPTGAFARRPPLAELSALNLSGSRL
              TEVQAGAFEHLPSLRLLDLSHNPLANLSAFAFSGSNASVAAPSPLVDLI
              LNHIVTSAAQRQNRSFEGMVAAALRAGHALRGLRRLELASNHLLYLPLD
              VLAQLPDLRHLDLRNNSLVSLTYVFFRNLTHLESFHLEDNALKVLHNGT
              LAELQSLPHVRVFLDDNPWVCDCHLADMVAWLKETEVVQDKARLTCAFP
              EKMRHRVLLELNSSDLDCDPDLPPSLQTSYVFLGIVLALIGAIFLLVLY
              LNRKGIKKWMHNIRDACRDHMEGYHYRYEINADPRLTNLSSNSDV SEQ ID NO: 3  heavy chain CDR1 of antibody 051
              IYWMT SEQ ID NO: 4  heavy chain CDR2 of antibody 051
              AISGSGGSTYYADSVKG SEQ ID NO: 5  heavy chain CDR3 of antibody 051
              DYYSNVY SEQ ID NO: 6  light chain CDR1 of antibody 051
              RASQGIYSWLA SEQ ID NO: 7  light chain CDR2 of antibody 051
              AASSLQS SEQ ID NO: 8  light chain CDR3 of antibody 051
              QQSDSPPYT SEQ ID NO: 9  variable heavy chain domain VH of
              antibody 051
```

```
                    EVQLLESGGGLLQPGGSLRLSCAASGFTFSIYWMTWVRQAPGKG
                    LEWVSAISGSGGSTYYADSVKGRFTISRDNSKNTLYLQMNSLRA
                    EDTAVYYCAKDYYSNVYWGQGTLVTVSS

SEQ ID NO: 10  variable light chain domain VL of
               antibody 051
               DIQMTQSPSSVSASVGDRVTITCRASQGIYSWLAWYQQKPGKAP
               KLLIYAASSLQSGVPSRFSGSGSGTDFTLTISSLQPEDFATYYC
               QQSDSPPYTFGQGTKLEIK SEQ ID NO: 11  heavy chain CDR1 of antibody 091
               SDAMH SEQ ID NO: 12  heavy chain CDR2 of antibody 091
               GVSGSGGSPYYADSVKG SEQ ID NO: 13  heavy chain CDR3 of antibody 091
               GGSIAGSYYYYPMDV SEQ ID NO: 14  light chain CDR1 of antibody 091
               QASQDISNYLN SEQ ID NO: 15  light chain CDR2 of antibody 091
               AASTLQI SEQ ID NO: 16  light chain CDR3 of antibody 091
               QQANSFPLT SEQ ID NO: 17  variable heavy chain domain VH of
               antibody 091
               EVHLLESGGGLVHPGGSLRLSCAASGFTFRSDAMHWVRQAPGKG
               LEWVSGVSGSGGSPYYADSVKGRFTISRDDSKTTLYLQMNSLRA
               EDTAVYYCATGGSIAGSYYYYPMDVWGQGTTVTVSS SEQ ID NO: 18  variable light chain domain VL of
               antibody 091
               DIQMTQSPSSLSASVGDRVTITCQASQDISNYLNWYQQKPGKAP
               KLLIYAASTLQIGVPSRFSGSGSGTDFTFTISSLQPEDFATYYC
               QQANSFPLTFGGGTKVEIK SEQ ID NO: 19  heavy chain CDR1 of antibody 097
               NDAMT SEQ ID NO: 20  heavy chain CDR2 of antibody 097
               AISGSGGSTYYADSVKG SEQ ID NO: 21  heavy chain CDR3 of antibody 097
               GGSWGDWYYYFYPMDV SEQ ID NO: 22  light chain CDR1 of antibody 097
               RASQSISSYLN SEQ ID NO: 23  light chain CDR2 of antibody 097
               AASSLQS SEQ ID NO: 24  light chain CDR3 of antibody 097
               QQSDSFPLT SEQ ID NO: 25  variable heavy chain domain VH of
               antibody 097
               EVQLLESGGGLAQPGGSLRLSCAASGFTFNNDAMTWVRQAPGKG
               LEWVSAISGSGGSTYYADSVKGRFTISRDNSKNTLYLQMNSLRA
               EDTAVYYCAKGGSWGDWYYYFYPMDVWGQGTTVTVSS SEQ ID NO: 26  variable light chain domain VL of
               antibody 097
               DIQMTQSPSSLSASVGDRVTITCRASQSISSYLNWYQQKPGKAP
               KLLIYAASSLQSGVPSRFSGSGSGTDFTLTISSLQPEDFATYYC
               QQSDSFPLTFGGGTKVEIK SEQ ID NO: 27  human TPBG extracellular domain, His6Avi
               MPGGCSRGPAAGDGRLRLARLALVLLGWVSSSSPTSSASSFSSS
               APFLASAVSAQPPLPDQCPALCECSEAARTVKCVNRNLTEVPTD
               LPAYVRNLFLTGNQLAVLPAGAFARRPPLAELAALNLSGSRLDE
               VRAGAFEHLPSLRQLDLSHNPLADLSPFAFSGSNASVSAPSPLV
               ELILNHIVPPEDERQNRSFEGMVVAALLAGRALQGLRRELASN
               HFLYLPRDVLAQLPSLRHLDLSNNSLVSLTYVSFRNLTHLESLH
               LEDNALKVLHNGTLAELQGLPHIRVFLDNNPWVCDCHMADMVTW
```

```
                   LKETEVVQGKDRLTCAYPEKMRNRVLLELNSADLDCDPILPPSL
                   QTSAAALEVLFQGPGTHHHHHHHHHIGLNDIFEAQKIEWHE

SEQ ID NO: 28 human TPBG extracellular domain,
              huIgG1-Fc-His6
                   MPGGCSRGPAAGDGRLRLARLALVLLGWVSSSSPTSSASSFSSS
                   APFLASAVSAQPPLPDQCPALCECSEAARTVKCVNRNLTEVPTD
                   LPAYVRNLFLTGNQLAVLPAGAFARRPPLAELAALNLSGSRLDE
                   VRAGAFEHLPSLRQLDLSHNPLADLSPFAFSGSNASVSAPSPLV
                   ELILNHIVPPEDERQNRSFEGMVVAALLAGRALQGLRRLELASN
                   HFLYLPRDVLAQLPSLRHDLSNNSLVSLTYVSFRNLTHLESLH
                   LEDNALKVLHNGTLAELQGLPHIRVFLDNNPWVCDCHMADMVTW
                   LKETEVVQGKDRLTCAYPEKMRNRVLLELNSADLDCDPILPPSL
                   QTSAAALEVLFQGPGTIEGRMDPKSCDKTHTCPPCPAPELLGGP
                   SVFLFPPKPKDTLMISRTPEVTCVVVDVSHEDPEVKFNWYVDGV
                   EVHNAKTKPREEQYNSTYRVVSVLTVLHQDWLNGKEYKCKVSNK
                   ALPAPIEKTISKAKGQPREPQVYTLPPSREEMTKNQVSLTCLVK
                   GFYPSDIAVEWESNGQPENNYKTTPPVLDSDGSFFLYSKLTVDK
                   SRWQQGNVFSCSVMHEALHNHYTQKSLSLSPGKSGHHHHHH SEQ ID NO: 29 minipig TPBG extracellular domain, His6Avi
                   MPGGCSRGPAAGDGRLRLARLALVLLGWVSSSSLTSSASSTSSA
                   SFPASAASALPPLPGRCPQPCECSEAARTVKCVGRNLTEVPADL
                   PPYVRTLFLTGNQLAVLPTGAFARRPPLAELSALNLSGSRLTEV
                   QAGAFEHLPSLRLLDLSHNPLANLSAFAFSGSNASVAAPSPLVD
                   LILNHIVTSAAQRQNRSFEGMVAAALRAGHALRGLRRLELASNH
                   LLYLPLDVLAQLPDLRHLDLRNNSLVSLTYVFFRNLTHLESFHL
                   EDNALKVLHNGTLAELQSLPHVRVFLDDNPWVCDCHLADMVAWL
                   KETEVVQDKARLTCAFPEKMRHRVLLELNSSDLDCDPDLPPSLQ
                   TSAAALEVLFQGPGTHHHHHHHHHIGLNDIFEAQKIEWHE SEQ ID NO: 30 minipig TPBG extracellular domain,
              huIgG1-Fc-His
                   MPGGCSRGPAAGDGRLRLARLALVLLGWVSSSSLTSSASSTSSA
                   SFPASAASALPPLPGRCPQPCECSEAARTVKCVGRNLTEVPADL
                   PPYVRTLFLTGNQLAVLPTGAFARRPPLAELSALNLSGSRLTEV
                   QAGAFEHLPSLRLLDLSHNPLANLSAFAFSGSNASVAAPSPLVD
                   LILNHIVTSAAQRQNRSFEGMVAAALRAGHALRGLRRLELASNH
                   LLYLPLDVLAQLPDLRHLDLRNNSLVSLTYVFFRNLTHLESFHL
                   EDNALKVLHNGTLAELQSLPHVRVFLDDNPWVCDCHLADMVAWL
                   KETEVVQDKARLTCAFPEKMRHRVLLELNSSDLDCDPDLPPSLQ
                   TSAAALEVLFQGPGTIEGRMDPKSCDKTHTCPPCPAPELLGGPS
                   VFLFPPKPKDTLMISRTPEVTCVVVDVSHEDPEVKFNWYVDGVE
                   VHNAKTKPREEQYNSTYRVVSVLTVLHQDWLNGKEYKCKVSNKA
                   LPAPIEKTISKAKGQPREPQVYTLPPSREEMTKNQVSLTCLVKG
                   FYPSDIAVEWESNGQPENNYKTTPPVLDSDGSFFLYSKLTVDKS
                   RWQQGNVFSCSVMHEALHNHYTQKSLSLSPGKSGHHHHHH SEQ ID NO: 31 cynomolgus TPBG extracellular domain,
              His6Avi
                   MPGGCSRGPAAGDGRLRLARLALVLLGWVSSSSPTSSASSFSSS
                   APFLASAASAQPPLPDQCPALCECSEAARTVKCVNRNLTEVPTD
                   LPLYVRNLFLTGNQLAVLPAGAFARRPPLAELAALNLSGSRLDE
                   VRAGAFEHLPSLRQLDLSHNPLAYLSPFAFSGSNASISAPSPLV
                   ELILNHIVPPDDKRQNRSFEGMVAAALVAGRALQGLHLLELASN
                   HFLYLPRDVLAQLPSLRYLDLSNNSLVSLTYVSFRNLTHLESLH
                   LEDNALKVLHNGTLAELQGLPHVRVFLDNNPWVCDCHMADMVTW
                   LKQTEVVQGKDRLTCAFPEKMRNRVLLELNSADLDCDPILPPSL
                   QTSAAALEVLFQGPGTHHHHHHHHHIGLNDIFEAQKIEWHE SEQ ID NO: 32 cynomolgus TPBG extracellular domain,
              huIgG1-Fc-His6
                   MPGGCSRGPAAGDGRLRLARLALVLLGWVSSSSPTSSASSFSSS
                   APFLASAASAQPPLPDQCPALCECSEAARTVKCVNRNLTEVPTD
                   LPLYVRNLFLTGNQLAVLPAGAFARRPPLAELAALNLSGSRLDE
                   VRAGAFEHLPSLRQLDLSHNPLAYLSPFAFSGSNASISAPSPLV
                   ELILNHIVPPDDKRQNRSFEGMVAAALVAGRALQGLHLLELASN
                   HFLYLPRDVLAQLPSLRYLDLSNNSLVSLTYVSFRNLTHLESLH
                   LEDNALKVLHNGTLAELQGLPHVRVFLDNNPWVCDCHMADMVTW
                   LKQTEVVQGKDRLTCAFPEKMRNRVLLELNSADLDCDPILPPSL
                   QTSAAALEVLFQGPGTIEGRMDPKSCDKTHTCPPCPAPELLGGP
                   SVFLFPPKPKDTLMISRTPEVTCVVVDVSHEDPEVKFNWYVDGV
                   EVHNAKTKPREEQYNSTYRVVSVLTVLHQDWLNGKEYKCKVSNK
                   ALPAPIEKTISKAKGQPREPQVYTLPPSREEMTKNQVSLTCLVK
                   GFYPSDIAVEWESNGQPENNYKTTPPVLDSDGSFFLYSKLTVDK
                   SRWQQGNVFSCSVMHEALHNHYTQKSLSLSPGKSGHHHHHH SEQ ID NO: 33 murine TPBG extracellular domain, His6Avi
                   MPGAGSRGPSAGDGRLRLARLALVLLGWVSASAPSSSVPSSSTS
```

```
                    PAAFLASGSAQPPPAERCPAACECSEAARTVKCVNRNLLEVPAD
                    LPPYVRNLFLTGNQMTVLPAGAFARQPPLADLEALNLSGNHLKE
                    VCAGAFEHLPGLRRLDLSHNPLTNLSAFAFAGSNASVSAPSPLE
                    ELILNHIVPPEDQRQNGSFEGMVAFEGMVAAALRSGLALRGLTR
                    LELASNHFLFLPRDLLAQLPSLRYLDLRNNSLVSLTYASFRNLT
                    HLESLHLEDNALKVLHNSTLAEWHGLAHVKVFLDNNPWVCDCYM
                    ADMVAWLKETEVVPDKARLTCAFPEKMRNRGLLDLNSSDLDCDA
                    VLPQSLQTSAAALEVLFQGPGTHHHHHHHHHIGLNDIFEAQKI
                    EWHE

SEQ ID NO: 34      murine TPBG extracellular domain,
                    huIgG1-Fc-His6
                    MPGAGSRGPSAGDGRLRLARLALVLLGWVSASAPSSSVPSSSTS
                    PAAFLASGSAQPPPAERCPAACECSEAARTVKCVNRNLLEVPAD
                    LPPYVRNLFLTGNQMTVLPAGAFARQPPLADLEALNLSGNHLKE
                    VCAGAFEHLPGLRRLDLSHNPLTNLSAFAFAGSNASVSAPSPLE
                    ELILNHIVPPEDQRQNGSFEGMVAFEGMVAAALRSGLALRGLTR
                    LELASNHFLFLPRDLLAQLPSLRYLDLRNNSLVSLTYASFRNLT
                    HLESLHLEDNALKVLHNSTLAEWHGLAHVKVFLDNNPWVCDCYM
                    ADMVAWLKETEVVPDKARLTCAFPEKMRNRGLLDLNSSDLDCDA
                    VLPQSLQTSAAALEVLFQGPGTIEGRMDPKSCDKTHTCPPCPAP
                    ELLGGPSVFLFPPKPKDTLMISRTPEVTCVVVDVSHEDPEVKFN
                    WYVDGVEVHNAKTKPREEQYNSTYRVVSVLTVLHQDWLNGKEYK
                    CKVSNKALPAPIEKTISKAKGQPREPQVYTLPPSREEMTKNQVS
                    LTCLVKGFYPSDIAVEWESNGQPENNYKTTPPVLDSDGSFFLYS
                    KLTVDKSRWQQGNVFSCSVMHEALHNHYTQKSLSLSPGKSGHHH
                    HHH SEQ ID NO: 35      rat TPBG extracellular domain, His6Avi
                    MPGAGSRGPSAGDGRLRLARLALVLLGWVSASAPSSSLPSSSTS
                    PAAFLASGSAQPPPAERCPAACECSEAARTVKCVNRNLLEVPAD
                    LPPYVRNLFLTGNQMTVLPAGAFARQPPLADLAVLNLSGNHLKE
                    VGAGAFEHLPGLRRLDLSHNPLTNLSAFTFAGSNVSVSTPSPLL
                    ELILNHIVPPEDQRQNGSFEGMVAFEGMVAAALRSGLALRGLTR
                    LELASNHFLYLPRDLLDQLPSLKHLDLRNNSLVSLTYASFRNLT
                    HLESLHLEDNALKVLHNSTLAEWQGLAHVRVFLDNNPWVCDCYM
                    ADMVSWLKETEVVPDKARLTCAFPEKMRNRGLLDLTSSDLDCDA
                    TLPQSLQTSAAALEVLFQGPGTHHHHHHHHHIGLNDIFEAQKI
                    EWHE SEQ ID NO: 36      rat TPBG extracellular domain,
                    huIgG1-Fc-His6
                    MPGAGSRGPSAGDGRLRLARLALVLLGWVSASAPSSSLPSSSTS
                    PAAFLASGSAQPPPAERCPAACECSEAARTVKCVNRNLLEVPAD
                    LPPYVRNLFLTGNQMTVLPAGAFARQPPLADLAVLNLSGNHLKE
                    VGAGAFEHLPGLRRLDLSHNPLTNLSAFTFAGSNVSVSTPSPLL
                    ELILNHIVPPEDQRQNGSFEGMVAFEGMVAAALRSGLALRGLTR
                    LELASNHFLYLPRDLLDQLPSLKHLDLRNNSLVSLTYASFRNLT
                    HLESLHLEDNALKVLHNSTLAEWQGLAHVRVFLDNNPWVCDCYM
                    ADMVSWLKETEVVPDKARLTCAFPEKMRNRGLLDLTSSDLDCDA
                    TLPQSLQTSAAALEVLFQGPGTIEGRMDPKSCDKTHTCPPCPAP
                    ELLGGPSVFLFPPKPKDTLMISRTPEVTCVVVDVSHEDPEVKFN
                    WYVDGVEVHNAKTKPREEQYNSTYRVVSVLTVLHQDWLNGKEYK
                    CKVSNKALPAPIEKTISKAKGQPREPQVYTLPPSREEMTKNQVS
                    LTCLVKGFYPSDIAVEWESNGQPENNYKTTPPVLDSDGSFFLYS
                    KLTVDKSRWQQGNVFSCSVMHEALHNHYTQKSLSLSPGKSGHHH
                    HHH SEQ ID NO: 37      H8 heavy chain for sortase coupling
                    without signal peptide
                    EVQLQQSGPDLVKPGASVKISCKASGYSFTGYYMHWVKQSHGKS
                    LEWIGRINPNNGVTLYNQKFKDKAILTVDKSSTTAYMELRSLTS
                    EDSAVYYCARSTMITNYVMDYWGQVTSVTVSSASTKGPSVFPLA
                    PSSKSTSGGTAALGCLVKDYFPEPVTVSWNSGALTSGVHTFPAV
                    LQSSGLYSLSSVVTVPSSSLGTQTYICNVNHKPSNTKVDKKVEP
                    KSCGGGSLPETGGSGSHHHHHH SEQ ID NO: 38      H8 light chain for sortase coupling
                    without signal peptide
                    SIVMTQTPTFLLVSAGDRVTITCKASQSVSNDVAWYQQKPGQSP
                    TLLISYTSSRYAGVPDRFIGSGYGTDFTFTISTLQAEDLAVYFC
                    QQDYNSPPTFGGGTKLEIKRTVAAPSVFIFPPSDEQLKSGTASV
                    VCLLNNFYPREAKVQWKVDNALQSGNSQESVTEQDSKDSTYSLS
                    STLTLSKADYEKHKVYACEVTHQGLSSPVTKSFNRGEC SEQ ID NO: 39      O51 heavy chain for sortase coupling
                    without signal peptide
                    EVQLLESGGGLLQPGGSLRLSCAASGFTFSIYWMTWVRQAPGKG
                    LEWVSAISGSGGSTYYADSVKGRFTISRDNSKNTLYLQMNSLRA
```

```
                    EDTAVYYCAKDYYSNVYWGQGTLVTVSSASTKGPSVFPLAPSSK
                    STSGGTAALGCLVKDYFPEPVTVSWNSGALTSGVHTFPAVLQSS
                    GLYSLSSVVTVPSSSLGTQTYICNVNHKPSNTKVDKKVEPKSCG
                    GGSLPETGGSSEQKLISEEDLHHHHHHGAAEPEA

SEQ ID NO: 40 051 light chain for sortase coupling
                    without signal peptide
                    DIQMTQSPSSVSASVGDRVTITCRASQGIYSWLAWYQQKPGKAP
                    KLLIYAASSLQSGVPSRFSGSGSGTDFTLTISSLQPEDFATYYC
                    QQSDSPPYTFGQGTKLEIKRTVAAPSVFIFPPSDEQLKSGTASV
                    VCLLNNFYPREAKVQWKVDNALQSGNSQESVTEQDSKDSTYSLS
                    STLTLSKADYEKHKVYACEVTHQGLSSPVTKSFNRGEC SEQ ID NO: 41 091 heavy chain for sortase coupling
                    without signal peptide
                    EVHLLESGGGLVHPGGSLRLSCAASGFTFRSDAMHWVRQAPGKG
                    LEWVSGVSGSGGSPYYADSVKGRFTISRDDSKTTLYLQMNSLRA
                    EDTAVYYCATGGSIAGSYYYYPMDVWGQGTTVTVSSASTKGPSV
                    FPLAPSSKSTSGGTAALGCLVKDYFPEPVTVSWNSGALTSGVHT
                    FPAVLQSSGLYSLSSVVTVPSSSLGTQTYICNVNHKPSNTKVDK
                    KVEPKSCGGGSLPETGGSSEQKLISEEDLHHHHHHGAAEPEA SEQ ID NO: 42 091 light chain for sortase coupling
                    without signal peptide
                    DIQMTQSPSSLSASVGDRVTITCQASQDISNYLNWYQQKPGKAP
                    KLLIYAASTLQIGVPSRFSGSGSGTDFTFTISSLQPEDFATYYC
                    QQANSFPLTFGGGTKVEIKRTVAAPSVFIFPPSDEQLKSGTASV
                    VCLLNNFYPREAKVQWKVDNALQSGNSQESVTEQDSKDSTYSLS
                    STLTLSKADYEKHKVYACEVTHQGLSSPVTKSFNRGEC SEQ ID NO: 43 097 heavy chain for sortase coupling
                    without signal peptide
                    EVQLLESGGGLAQPGGSLRLSCAASGFTFNNDAMTWVRQAPGKG
                    LEWVSAISGSGGSTYYADSVKGRFTISRDNSKNTLYLQMNSLRA
                    EDTAVYYCAKGGSWGDWYYYFYPMDVWGQGTTVTVSSASTKGPS
                    VFPLAPSSKSTSGGTAALGCLVKDYFPEPVTVSWNSGALTSGVH
                    TFPAVLQSSGLYSLSSVVTVPSSSLGTQTYICNVNHKPSNTKVD
                    KKVEPKSCGGGSLPETGGSSEQKLISEEDLHHHHHHGAAEPEA SEQ ID NO: 44 097 light chain for sortase coupling
                    without signal peptide
                    DIQMTQSPSSLSASVGDRVTITCRASQSISSYLNWYQQKPGKAP
                    KLLIYAASSLQSGVPSRFSGSGSGTDFTLTISSLQPEDFATYYC
                    QQSDSFPLTFGGGTKVEIKGTVAAPSVFIFPPSDEQLKSGTASV
                    VCLLNNFYPREAKVQWKVDNALQSGNSQESVTEQDSKDSTYSLS
                    STLTLSKADYEKHKVYACEVTHQGLSSPVTKSFNRGEC SEQ ID NO: 45 Pseudomonas exotoxin for sortase coupling
                    GGGGRHRQPRGWEQLYPTGAEFLGDGGAVSFSTRGTQNWTVERLL
                    QAHRQLEEGGYVFVGYHGTFLEAAQSIVFGGVRARSQDLDAIWA
                    GFYIAGDPALAYGYAQDQEPDAAGRIRNGALLRVYVPRSSLPGF
                    YATSLTLAAPEAAGEVERLIGHPLPLRLDAITGPEESGGRLETI
                    LGWPLAERTVVIPSAIPTDPRNVGGDLDPSSIPDSEAAISALPD
                    YASQPGKPPREDL SEQ ID NO: 46 heavy chain of anti-TPBG 051 Fab-PE
                    fusion protein
                    MEVQLLESGGGLLQPGGSLRLSCAASGFTFSIYWMTWVRQAPGK
                    GLEWVSAISGSGGSTYYADSVKGRFTISRDNSKNTLYLQMNSLR
                    AEDTAVYYCAKDYYSNVYWGQGTLVTVSSASTKGPSVFPLAPSS
                    KSTSGGTAALGCLVKDYFPEPVTVSWNSGALTSGVHTFPAVLQS
                    SGLYSLSSVVTVPSSSLGTQTYICNVNHKPSNTKVDKKVEPKSC
                    DKTHKASGGRHRQPRGWEQLGGGGGSPTGAEFLGDGGDVSFSTR
                    GTQNWTVERLLQAHAQLEERGYVFVGYHGTFLEAAQSIVFGGVA
                    ARSQDLAAIWAGFYIAGDPALAYGYAQDQEPDAAGRIRNGALLR
                    VYVPASSLPGFYRTSLTLAAPEAAGEVERLIGHPLPLALDAITG
                    PEEEGGRLETILGWPLAERTVVIPSAIPTDPRNVGGDLDPSSIP
                    DKEQAISALPDYASQPGKPPREDLK SEQ ID NO: 47 light chain of anti-TPBG 051 Fab-PE
                    fusion protein
                    MDIQMTQSPSSVSASVGDRVTITCRASQGIYSWLAWYQQKPGKA
                    PKLLIYAASSLQSGVPSRFSGSGSGTDFTLTISSLQPEDFATYY
                    CQQSDSPPYTFGQGTKLEIKRTVAAPSVFIFPPSDEQLKSGTAS
                    VVCLLNNFYPREAKVQWKVDNALQSGNSQESVTEQDSKDSTYSL
                    SSTLTLSKADYEKHKVYACEVTHQGLSSPVTKSFNRGEC
```

SEQ ID NO: 48 heavy chain of anti-TPBG 091 Fab-PE
fusion protein
MEVHLLESGGGLVHPGGSLRLSCAASGFTFRSDAMHWVRQAPGK
GLEWVSGVSGSGGSPYYADSVKGRFTISRDDSKTTLYLQMNSLR
AEDTAVYYCATGGSIAGSYYYYPMDVWGQGTTVTVSSASTKGPS
VFPLAPSSKSTSGGTAALGCLVKDYFPEPVTVSWNSGALTSGVH
TFPAVLQSSGLYSLSSVVTVPSSSLGTQTYICNVNHKPSNTKVD
KKVEPKSCDKTHKASGGRHRQPRGWEQLGGGGGSPTGAEFLGDG
GDVSFSTRGTQNWTVERLLQAHAQLEERGYVFVGYHGTFLEAAQ
SIVFGGVAARSQDLAAIWAGFYIAGDPALAYGYAQDQEPDAAGR
IRNGALLRVYVPASSLPGFYRTSLTLAAPEAAGEVERLIGHPLP
LALDAITGPEEEGGRLETILGWPLAERTVVIPSAIPTDPRNVGG
DLDPSSIPDKEQAISALPDYASQPGKPPREDLK SEQ ID NO: 49 light chain of anti-TPBG 091 Fab-PE
fusion protein
MDIQMTQSPSSLSASVGDRVTITCQASQDISNYLNWYQQKPGKA
PKLLIYAASTLQIGVPSRFSGSGSGTDFTFTISSLQPEDFATYY
CQQANSFPLTFGGGTKVEIKRTVAAPSVFIFPPSDEQLKSGTAS
VVCLLNNFYPREAKVQWKVDNALQSGNSQESVTEQDSKDSTYSL
SSTLTLSKADYEKHKVYACEVTHQGLSSPVTKSFNRGEC SEQ ID NO: 50 heavy chain of anti-TPBG 097 Fab-PE
fusion protein
MEVQLLESGGGLAQPGGSLRLSCAASGFTFNNDAMTWVRQAPGK
GLEWVSAISGSGGSTYYADSVKGRFTISRDNSKNTLYLQMNSLR
AEDTAVYYCAKGGSWGDWYYYFYPMDVWGQGTTVTVSSASTKGP
SVFPLAPSSKSTSGGTAALGCLVKDYFPEPVTVSWNSGALTSGV
HTFPAVLQSSGLYSLSSVVTVPSSSLGTQTYICNVNHKPSNTKV
DKKVEPKSCDKTHKASGGRHRQPRGWEQLGGGGGSPTGAEFLGD
GGDVSFSTRGTQNWTVERLLQAHAQLEERGYVFVGYHGTFLEAA
QSIVFGGVAARSQDLAAIWAGFYIAGDPALAYGYAQDQEPDAAG
RIRNGALLRVYVPASSLPGFYRTSLTLAAPEAAGEVERLIGHPL
PLALDAITGPEEEGGRLETILGWPLAERTVVIPSAIPTDPRNVG
GDLDPSSIPDKEQAISALPDYASQPGKPPREDLK SEQ ID NO: 51 light chain of anti-TPBG 097 Fab-PE
fusion protein
MDIQMTQSPSSLSASVGDRVTITCRASQSISSYLNWYQQKPGKA
PKLLIYAASSLQSGVPSRFSGSGSGTDFTLTISSLQPEDFATYY
CQQSDSFPLTFGGGTKVEIKGTVAAPSVFIFPPSDEQLKSGTAS
VVCLLNNFYPREAKVQWKVDNALQSGNSQESVTEQDSKDSTYSL
SSTLTLSKADYEKHKVYACEVTHQGLSSPVTKSFNRGEC SEQ ID NO: 52 Pseudomonas exotoxin A wild type
AEEAAFDLWNECAKACVLDLKDGVRSSRMSVDPAIADTNGQGVLH
YSMVLEGGNDALKLAIDNALSITDGLTIRLEGGVEPNKPVRYS
YTRQARGSWSLNWLVPIGHEKPSNIKVFIHELNAGNQLSHMSPI
YTIEMGDELLAKLARDATFFVRAHESNEMQPTLAISHAGVSVVA
AQTQPRREKRWSEWASGKVLCLLDPLDGVYNYLAQQRCNLDDTW
EGKIYRVLAGNPAKHDLDIKPTVISHRLHFPEGGSLAALTAHQA
CHLPLETFTRHRQPRGWEQLEQCGYPVQRLVALYLAARLSWNQV
DQVIRNALASPGSGGDLGEAIREQPEQARLALTLAAAESERFVR
QGTGNDEAGAANADVVSLTCPVAAGECAGPADSGDALLERNYPT
GAEFLGDGGDVSFSTRGTQNWTVERLLQAHRQLEERGYVFVGYH
GTFLEAAQSIVFGGVRARSQDLDAIWRGFYIAGDPALAYGYAQD
QEPDARGRIRNGALLRVYVPRSSLPGFYRTSLTLAAPEAAGEVE
RLIGHPLPLRLDAITGPEEEGGRLETILGWPLAERTVVIPSAIP
TDPRNVGGDLDPSSIPDKEQAISALPDYASQPGKPPREDLK SEQ ID NO: 53 Pseudomonas exotoxin A synthetic variant
PE38
GGSLAALTAHQACHLPLETFTRHRQPRGWEQLEQCGYPVQRLVA
LYLAARLSWNQVDQVIRNALASPGSGGDLGEAIREQPEQARLAL
TLAAAESERFVRQGTGNDEAGAANGPADSGDALLERNYPTGAEF
LGDGGDVSFSTRGTQNWTVERLLQAHRQLEERGYVFVGYHGTFL
EAAQSIVFGGVRARSQDLDAIWRGFYIAGDPALAYGYAQDQEPD
ARGRIRNGALLRVYVPRSSLPGFYRTSLTLAAPEAAGEVERLIG
HPLPLRLDAITGPEEEGGRLETILGWPLAERTVVIPSAIPTDPR
NVGGDLDPSSIPDKEQAISALPDYASQPGKPPREDLK SEQ ID NO: 54 Pseudomonas exotoxin A variant PE-LR
RHRQPRGWEQL SEQ ID NO: 55 flexible glycin serine linker
GGSGGS -continued SEQ ID NO: 56 C-terminal end of the PE functional
             domain III native
             REDLK SEQ ID NO: 57 C-terminal end of the PE functional
             domain III with endoplasmic reticulum
             localisation sequences
             KDEL SEQ ID NO: 58 C-terminal end of the PE functional
             domain III with endoplasmic reticulum
             localisation sequences
             REDL SEQ ID NO: 59 C-terminal end of the PE functional
             domain III with endoplasmic reticulum
             localisation sequences
             RDEL SEQ ID NO: 60 C-terminal end of the PE functional
             domain III with endoplasmic reticulum
             localisation sequences
             KEDLK SEQ ID NO: 61 C-terminal end of the PE functional
             domain III with endoplasmic reticulum
             localisation sequences
             KDELKDEL SEQ ID NO: 62 C-terminal end of the PE functional
             domain III with endoplasmic reticulum
             localisation sequences
             KDELKDELKDEL SEQ ID NO: 63 furin cleavage site
             RXXR SEQ ID NO: 64 furin cleavage site
             RXKR SEQ ID NO: 65 furin cleavage site
             RXRR SEQ ID NO: 66 native furin-cleavable sequence in
             domain II of Pseudomonas exotoxin A
             RHRQPRGWEQL SEQ ID NO: 67 furin-cleavable sequence in domain II of modified Pseudomonas exotoxin A
RHRSKRGWEQL SEQ ID NO: 68 furin-cleavable sequence
RKKR SEQ ID NO: 69 furin-cleavable sequence
RRRR SEQ ID NO: 70 furin-cleavable sequence
RKAR SEQ ID NO: 71 furin-cleavable sequence
SRVARS SEQ ID NO: 72 furin-cleavable sequence
TSSRKRRFW SEQ ID NO: 73 furin-cleavable sequence
ASRRKARSW SEQ ID NO: 74 furin-cleavable sequence
RRVKKRFW SEQ ID NO: 75 furin-cleavable sequence
RNVVRRDW SEQ ID NO: 76 furin-cleavable sequence
TRAVRRRSW

```
SEQ ID NO: 77 truncated version of native
              furin-cleavable sequence in
              domain II of Pseudomonas
              exotoxin A
              RQPR SEQ ID NO: 78 truncated version of native
              furin-cleavable sequence in
              domain II of Pseudomonas
              exotoxin A
              RHRQPRGW SEQ ID NO: 79 truncated version of native
              furin-cleavable sequence in
              domain II of Pseudomonas
              exotoxin A
              RHRQPRGWE SEQ ID NO: 80 truncated version of native
              furin-cleavable sequence in
              domain II of Pseudomonas
              exotoxin A
              HRQPRGWEQ SEQ ID NO: 81 truncated version of native
              furin-cleavable sequence in
              domain II of Pseudomonas
              exotoxin A
              RQPRGWE SEQ ID NO: 82 truncated version of furin-
              cleavable sequence in domain
              II of modified Pseudomonas
              exotoxin A
              RSKR SEQ ID NO: 83 truncated version of furin-
              cleavable sequence in domain
              II of modified Pseudomonas
              exotoxin A
              RHRSKRGW SEQ ID NO: 84 truncated version of furin-
              cleavable sequence in domain
              II of modified Pseudomonas
              exotoxin A
              HRSKRGWE SEQ ID NO: 85 truncated version of furin-
              cleavable sequence in domain
              II of modified Pseudomonas
              exotoxin A
              RSKRGWEQL SEQ ID NO: 86 truncated version of furin-
              cleavable sequence in domain
              II of modified Pseudomonas
              exotoxin A
              HRSKRGWEQL SEQ ID NO: 87 truncated version of furin-
              cleavable sequence in domain
              II of modified Pseudomonas
              exotoxin A
              RHRSKR
```

VI. Examples

The following are examples of methods and compositions of the invention. It is understood that various other embodiments may be practiced, given the general description provided above.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

Materials & General Methods

Recombinant DNA Techniques

Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions.

DNA and Protein Sequence Analysis and Sequence Data Management

General information regarding the nucleotide sequences of human immunoglobulins light and heavy chains is given in: Kabat, E. A. et al., (1991) Sequences of Proteins of Immunological Interest, Fifth Ed., NIH Publication No 91-3242. Amino acids of antibody chains are numbered according to EU numbering (Edelman, G. M., et al., PNAS 63 (1969) 78-85; Kabat, E. A., et al., (1991) Sequences of Proteins of Immunological Interest, Fifth Ed., NIH Publication No 91-3242). Vector NTI Advance suite version 11.5 (Invitrogen) was used for sequence creation, mapping, analysis, annotation and illustration.

DNA Sequencing

DNA sequences were determined by double strand sequencing performed at SequiServe (Vaterstetten, Germany) and Geneart AG (Regensburg, Germany).

Gene Synthesis

Desired gene segments were prepared by Geneart AG (Regensburg, Germany) from synthetic oligonucleotides and PCR products by automated gene synthesis. The gene segments which are flanked by singular restriction endonuclease cleavage sites were cloned into pGA18 (ampR) plasmids. The plasmid DNA was purified from transformed bacteria and concentration determined by UV spectroscopy. The DNA sequence of the sub-cloned gene fragments was confirmed by DNA sequencing.

Example 1

Expression of TPBG-RNA in Minipig and Cynomolgus

Cynomolgus monkey was previously used to evaluate TPBG-specific antibodies or conjugates thereof for their tolerability (Sapra et al. (2013) Mol Canc Ther 12: 38-47). 14 different tissues of cynomolgus monkey and minipig were prepared and the mRNA expression profile evaluated. Transcription profiling by sequencing of tissue RNAs coming from Roche cynomolgus monkey and minipig RNAseq-projects was evaluated on Illumina NextSeq500 as indexed, 75 bp, paired-end run with an average depth of 30 million reads pairs. Gene expression signals are indicated as unique reads per kilobase exon model per million reads (rpkm) in log scale indicating median expression levels and standard deviation.

Obtained signals were compared to each other. The results imply that the RNA expression profile of minipig and cynomolgus monkey are largely comparable. Thus, minipig is a suitable toxicology species to evaluate novel minipig cross-reactive anti-TPBG antibodies and Fab-PE constructs (FIG. 1).

Example 2

Cloning and Transient Expression of Extracellular Domains of TPBG

The cDNA of either full length TPBG, thus comprising extracellular domain, transmembrane domain and intracellular domain or fragments thereof was cloned in eukaryotic expression vectors. Cloning was performed by standard restriction digest. For plasmids containing a C-terminal PreScission site followed by a $HIS_6$-Avi epitope tag or a C-terminal PreScission site followed by a $huIgG_1$-Fc-$HIS_6$ epitope tag, site-directed cloning was performed with BamHI and NotI restriction enzymes. Plasmids were sequence verified and amplified according to standard molecular biology techniques.

Plasmids containing the extracellular domain of TPBG or fragments thereof were transiently transfected in HEK293F (Life Technologies) cells. Briefly, cells were cultured in FreeStyle 293-F (Life Technologies) expression medium. The day before transfection cells were seeded at a density of $1 \times 10^6$/ml culture medium. The following day 1 µg of plasmid DNA was used per ml culture medium. 293Free (Life Technologies) transfection reagent was used for transient transfection. Transfected cells were incubated at 37° C. and 8% $CO_2$ for 7 d while shaking at 125-130 rpm in Erlenmeyer flasks. Supernatant was harvested and either frozen at −80° C. or directly processed for protein purification.

Example 3

Purification of Recombinant TPBG

Recombinant TPBG containing a $huIgG_1$-Fc-$HIS_6$ epitope tag (human TPBG: SEQ ID NO: 28; minipig TPGB: SEQ ID NO: 30; cynomolgus TPBG: SEQ ID NO: 32; murine TPBG: SEQ ID NO: 34, rat TPBG: SEQ ID NO: 36; the listed sequences all include signal peptides) was purified from cell culture supernatant using a HiTrap MabSelect Xtra protein A column (GE Healthcare). Elution occurred under acidic conditions (100 mM citrate buffer, pH3.0). Eluates were pH neutralized by addition of small amounts of Tris-Cl, pH9.0. Recombinant TPBG containing a $HIS_6$-Avi epitope tag (human TPBG: SEQ ID NO: 27; minipig TPGB: SEQ ID NO: 29; cynomolgus TPBG: SEQ ID NO: 31; murine TPBG: SEQ ID NO: 33, rat TPBG: SEQ ID NO: 35, the listed sequences all include signal peptides) was purified from cell culture supernatant using a HisTrap HP (GE Healthcare) column Elution occurred with an imidazole step gradient. Affinity purified protein was subsequently loaded on a HiLoad 16/60 Superdex 200 prep grade (GE Healthcare) size exclusion column. The product peak was collected and volume adjusted by ultracentrifugation with Amicon Ultra Filters (Merck Millipore). The final storage buffer consisted of 20 mM Histidine, 140 mM NaCl, pH 5.5.

Example 4

Immunization of Rabbits Against TPBG

Roche proprietary transgenic rabbits expressing a humanized antibody repertoire were immunized either with recombinant TPBG protein or genetically.

One set of 3 rabbits was immunized with 400 µg of recombinant human TPBG extracellular domain (ECD) coupled to huFc, emulsified with complete Freund's adjuvant, at day 0 by intradermal application, and with 200 µg each of TPBG-huFc, emulsified with complete Freund's adjuvant, at days 7, 14, 28, 56 and 84, by alternating intramuscular and subcutaneous applications. Blood (10% of estimated total blood volume) was taken at days 20, 34, 62 and 90. Serum was prepared, which was used for titer determination by ELISA (see below), and peripheral mononuclear cells were isolated, which were used as a source of antigen-specific B cells in the B cell cloning process.

Another set of 3 rabbits was immunized genetically, using a plasmid expression vector coding for full-length human TPBG, by intradermal application of 400 µg vector DNA, followed by electroporation (5 square pulses of 750 V/cm, duration 10 ms, interval 1 s). Rabbits received 7 consecutive immunizations at days 0, 14, 28, 49, 70, 98 and 126. Blood (10% of estimated total blood volume) was taken at days 35, 77, 105 and 133. Serum was prepared, which was used for titer determination by ELISA (see below), and peripheral mononuclear cells were isolated, which were used as a source of antigen-specific B cells in the B cell cloning process.

Example 5

Determination of Serum Titers (ELISA) from Immunized Rabbits

Human recombinant soluble TPBG extracellular domain was immobilized on a 96-well NUNC Maxisorp plate at 2 µg/ml, 100 µl/well, in PBS, followed by: blocking of the plate with 2% Crotein C in PBS, 200 µl/well; application of serial dilutions of antisera, in duplicates, in 0.5% Crotein C in PBS, 100 µl/well; detection with either (1) HRP-conjugated donkey anti-rabbit IgG antibody (Jackson Immunoresearch/Dianova), or (2) HRP-conjugated rabbit anti-human IgG antibody (Pierce/Thermo Scientific; 1/5000), or (3) biotinylated goat anti-human kappa antibody (Southern Biotech/Biozol; 1/5000) and streptavidin-HRP; each diluted in 0.5% Crotein C in PBS, 100 µl/well. For all steps, plates were incubated for 1 h at 37° C. Between all steps plates were washed 3 times with 0.05% Tween 20 in PBS. Signal was developed by addition of BM Blue POD Substrate soluble (Roche), 100 µl/well; and stopped by addition of 1 M HCl, 100 µl/well. Absorbance was read out at 450 nm, against 690 nm as reference. Titer was defined as dilution of antisera resulting in half-maximal signal.

Example 6

Isolation of TPBG-Specific B Cells

Blood samples were taken of immunized rabbits. EDTA-containing whole blood was diluted twofold with 1×PBS (PAA, Pasching, Austria) before density centrifugation using lympholyte mammal (Cedarlane Laboratories, Burlington, Ontario, Canada) according to the specifications of the manufacturer. PBMCs were washed twice with 1×PBS. Sterile streptavidin coated 6-well plates (Microcoat, Bernried, Germany) were coated with 2 µg/ml of the biotinylated extracellular domain of human TPBG protein in PBS for 3 h at room temperature. Prior to the panning step these 6-well plates were washed three times with sterile PBS. The PBMCs were seeded on sterile 6-well plates (cell culture grade) to deplete macrophages and monocytes through unspecific adhesion. Each well was filled at maximum with 4 ml medium and up to 6×10e6 PBMCs from the immunized rabbit and were allowed to bind for 1 h at 37° C. and 5% $CO_2$. The cells in the supernatant (peripheral blood lymphocytes (PBLs)) were used for the antigen panning step. 6-well plates coated with TPBG protein were seeded with up to 6×10e6 PBLs per 4 ml medium and allowed to bind for 1 h at 37° C. and 5% $CO_2$ to enrich TPBG-specific B cells. Non-adherent cells were removed by carefully washing the wells 1-2 times with 1×PBS. The remaining sticky cells were detached by trypsin for 10 min at 37° C. and 5% $CO_2$. Trypsination was stopped with EL-4 B5 medium (EL-4 B5: RPMI 1640 (Pan Biotech, Aidenbach, Germany) supplemented with 10% fetal calf serum (Hyclone, Logan, Utah, USA), 2 mM Glutamin, 1% penicillin/streptomycin solution (PAA, Pasching, Austria), 2 mM sodium pyruvate, 10 mM HEPES (PAN Biotech, Aidenbach, Germany) and 0.05 mM b-mercaptoethanole (Gibco, Paisley, Scotland). The cells were kept on ice until the immune fluorescence staining. Anti-IgG FITC (AbD Serotec, Düsseldorf, Germany) was used for single cell sorting. For surface staining, cells from the depletion and enrichment step were incubated with anti-IgG FITC antibody in PBS and incubated for 45 min in the dark at 4° C. After staining the PBLs were washed two times with ice cold PBS. Finally the PBLs were resuspended in ice cold PBS and immediately subjected to the FACS analyses. Propidium iodide at a concentration of 5 µg/ml (BD Pharmingen, San Diego, Calif., USA) was added prior to FACS analyses to discriminate between dead and live cells. A Becton Dickinson FACSAria equipped with a computer and the FACSDiva software (BD Biosciences, USA) was used for single cell sort. The cultivation of the rabbit B cells was done by a method described by Seeber S. et al., PLoS One. 2014 Feb. 4; 9(2):e86184. Briefly, single sorted rabbit B cells were incubated in 96-well plates with 200 µl/well EL-4 B5 medium containing Pansorbin cells (1:100000) (Calbiochem (Merck), Darmstadt, Deutschland), 5% rabbit thymocyte supernatant (MicroCoat, Bernried, Germany) and gamma-irradiated murine EL-4 B5 thymoma cells (2.5×10e4 cells/well) for 7 days at 37° C. in the incubator. The supernatants of the B-cell cultivation were removed for screening and the remaining cells were harvested immediately and were frozen at −80° C. in 100 µl RLT buffer (Qiagen, Hilden, Germany).

Example 7

B Cell PCR

Total RNA was prepared from B cells lysate (resuspended in RLT buffer—Qiagen) using the NucleoSpin 8/96 RNA kit (Macherey&Nagel) according to manufacturer's protocol. RNA was eluted with 60 µl RNase free water. 6 µl of RNA was used to generate cDNA by reverse transcriptase reaction using the Superscript III First-Strand Synthesis SuperMix (Invitrogen) and an oligo dT-primer according to the manufactures's instructions. All steps were performed on a Hamilton ML Star System. 4 µl of cDNA were used to amplify the immunoglobulin heavy and light chain variable regions (VH and VL) with the AccuPrime Supermix (Invitrogen) in a final volume of 50 µl using the primers rbHC.up and rbHC.do for the heavy chain and BcPCR_FHLC_leader.fw and BcPCR_huCkappa.rev for the light chain. All forward primers were specific for the signal peptide (of respectively VH and VL) whereas the reverse primers were specific for the constant regions (of respectively VH and VL). The PCR conditions for the RbVH+RbVL were as follows: Hot start at 94° C. for 5 min; 35 cycles of 20 s at 94° C., 20 s at 70° C., 45 s at 68° C., and a final extension at 68° C. for 7 min. The PCR conditions for the HuVL were as follows: Hot start at 94° C. for 5 min; 40 cycles of 20 s at 94° C., 20 s at 52° C., 45 s at 68° C., and a final extension at 68° C. for 7 min.

Primer Sequences:

```
rbHC.up
AAGCTTGCCACCATGGAGACTGGGCTGCGCTGGCTTC rbHCf.do
CCATTGGTGAGGGTGCCCGAG

BcPCR_FHLC_leader.fw
ATGGACATGAGGGTCCCCGC

BcPCR_huCkappa.rev
GATTTCAACTGCTCATCAGATGGC
```

8 µl of 50 µl PCR solution were loaded on a 48 E-Gel 2% (Invitrogen G8008-02). Positive PCR reactions were cleaned using the NucleoSpin Extract II kit (Macherey&Nagel; 740609250) according to manufacturer's protocol and eluted in 50 µl elution buffer. All cleaning steps were performed on a Hamilton ML Starlet System.

Example 8

Binding of TPBG-Specific Fab Fragments to TPBG of Different Species

To assess binding of recombinant TPBG of different species, Nunc maxisorp streptavidin coated plates (MicroCoat #11974998001) were coated with 25 µl/well biotinylated TPBG-AviHis of the relevant species (hu=human; mu=murine; rt=rat; cy=cynomolgus; mp=minipig) at a concentration of 100 ng/ml for human, cyno, and minipig TPBG and at a concentration of 500 ng/ml for mouse and rat TPBG. Plates were incubated at 4° C. over night. After washing (3×90 µl/well with PBST-buffer) anti-TPBG samples were added in a 1:2 dilution series starting at 2 µg/ml and incubated 1 h at RT. After washing (3×90 µl/well with PBST-buffer) 25 µl/well goat anti c-myc HRP (Bethyl, # A190-104P) or goat anti hu kappa HRP (Millipore, # AP502P) was added in a 1:7000 or 1:4000 dilution, respectively and incubated at RT for 1 h on a shaker. After washing (3×90 µl/well with PBST-buffer) 25 TMB substrate (Calbiochem, #CL07) was added and incubated 2 min for human and minipig TPBG, 3 min for cyno TPBG and 4 min for mouse and rat TPBG. Measurement took place at 370/492 nm on a Safire2 reader (Tecan).

To assess cellular binding of human TPBG, the human breast cancer tumor cell line MFC7 endogenously expressing TPBG was seeded at a concentration of 21000 cells/well in 384-well cellcoat Poly-D-Lysine plates (Greiner, #781940). Cells were allowed to attach over night at 37° C. After removing the supernatant, 25 µl/well of supernatant containing anti-TPBG antibodies were added in a 1:2 dilution series starting at 5 µg/ml and incubated 1 h at 4° C. Upon washing (2×50 µl/well PBST) cells were fixed by adding 50 µl/well 0.05% Glutaraldehyde (Sigma, 25%) diluted in 1×PBS-buffer and incubated for 10 min at RT. After washing (3 times; 90 PBS-T), 25 µl/well secondary antibody was added for detection: goat anti c-myc HRP (1:5000, Bethyl) followed by 1 h incubation at room temperature on a shaker. After washing (3 times; 90 µl/well PBS-T) 25 TMB substrate solution (Calbiochem) was added. After 10 min at room temperature, measurement took place at 370/492 nm on a Safire2 reader (Tecan).

TABLE 1

Binding of anti-TPBG Fab fragments to TPBG of different species

| EC50 [ng/ml] | recombinant TPBG | | | | | MCF7 |
|---|---|---|---|---|---|---|
| | sample: | | | | | |
| | huTPBG | muTPBG | rtTPBG | cyTPBG | mpTPBG | huTPBG |
| 051 | 18.1 | — | — | >2000 | 175.0 | 57.5 |
| 091 | 27.7 | — | — | 1229.8 | 61.8 | 14.0 |
| 097 | 15.2 | — | — | — | 43.6 | 451.3 |

Fab fragments of 051, 091, and 097 were found to be crossreactive between human and minipig TPBG. Cell binding of human TPBG expressed on cells of a human breast cancer cell line was confirmed.

Example 9

Binding of Purified Antibodies (mAbs) to TPBG of Different Species [Comparison with Prior Art]

Nunc maxisorp plates (Nunc, 464718) were coated with 25 Fc-TPBG at a concentration of 1 µg/ml for rat, minipig, mouse, cyno and at a concentration of 500 ng/ml for human TPBG. Plates were incubated at 4° C. overnight. After washing (3×90 µl/well; PBS-T buffer) plates were blocked with 90 µl blocking buffer (PBS with 2% BSA and 0.05% Tween-20) for 1 h at room temperature. After washing (3×90 µl/well with PBST-buffer) anti-TPBG antibodies were added in a 1:2 dilution series starting at 1 µg/ml and incubated 1 h at RT. After washing (3×90 µl/well with PBST-buffer) 25 µl/well, goat anti kappa antibody-POD conjugate (Millipore, AP502P) or donkey anti rabbit Fc antibody-POD conjugate (Amersham, NA9310V) was added in a 1:4000 dilution or a 1:1000 dilution, respectively and incubated at RT for 1 h on a shaker. After washing (3×90 with PBST-buffer) 25 TMB substrate (Roche Diagnostics GmbH, Cat. No.: 11835033001) was added and incubated for 5 min Measurement took place at 370/492 nm on a Safire2 reader (Tecan).

For comparison, prior art antibodies as disclosed in WO 2006/031653 (antibody H8, as defined by its VH and VL domain amino acid sequences as indicated in SEQ ID NO: 2 and 1 of WO 2006/031653) and WO 2007/106744 A2 (antibodies A1, A2, A3; as defined by their VH and VL domain amino acid sequences as indicated in table 2 of WO 2007/106744) were assessed in parallel.

TABLE 2

Binding of anti-TPBG antibodies (mAbs) to TPBG of different species

| | antibody | | | | | | |
|---|---|---|---|---|---|---|---|
| TPBG*: | 051 | 091 | 097 | A1 | A2 | A3 | H8 |
| hu | + | + | + | + | + | + | + |
| rt | − | + | − | +/− | − | − | − |
| mp | + | + | + | − | − | − | + |
| mo | +/− | − | − | − | − | − | − |
| cy | + | + | − | + | + | + | +/− |

(+) . . . binding,
(−) . . . no binding,
(+/−) partial binding;
hu . . . human,
mp . . . minipig,
rt . . . rat,
mo . . . mouse,
cy . . . cynomolgus

Example 10

Binding Competition of Antibodies (mAbs) 051, 091, and 097 with Prior Art Antibodies A1, A2, and A3

384-well TRSA-SA Maxisorp (MicroCoat) plates were coated with 25 µl/well biotinylated human TPBG-AviHis at a concentration of 200 ng/ml followed by an incubation at 4° C. overnight. After washing 3 times with 90 µl/well PBS-T, antibodies A1, A2, A3 were added at a concentration of 4 µg/ml followed by an incubation for 1 h at room temperature. Wells were washed 3 times with 90 µl/well PBS-T.

Anti-TPBG antibodies were added at a concentration of 0.1 µg/ml and incubated for 1 h at room temperature on a shaker. After washing 3 times with 90 PBST, 25 µl/well goat anti c-myc HRP (1:6000, Bethyl) was added followed by 1 h incubation at room temperature on a shaker. After washing (3 times; 90 µl/well PBST) 25 TMB substrate solution (Calbiochem) was added. After 10 min at room temperature, measurement took place at 370/492 nm on a Safire2 reader (Tecan).

TABLE 3

Binding competition between anti-TPBG antibodies (mAbs) 051, 097, and 097 and antibodies (mAbs) A1, A2, and A3 as disclosed in WO 2007/106744

|     | A1 | A2 | A3  |
|-----|----|----|-----|
| 051 | –  | –  | –   |
| 091 | –  | –  | +/– |
| 097 | –  | –  | +/– |

+/– = very weak competition (was confirmed to be equal or less than 15% in a BiaCore assay)

The results indicate that anti-TPBG antibodies 051, 091 and 097 bind to different epitopes on TPBG as the indicated prior art antibodies.

Example 11

Cloning and Expression of TPBG-Specific Fabs

Recombinant Expression of Rabbit Monoclonal Bivalent Antibodies

For recombinant expression of rabbit monoclonal bivalent antibodies, PCR-products coding for VH or VL were cloned as cDNA into expression vectors by the overhang cloning method (R S Haun et al., Biotechniques (1992) 13, 515-518; MZ Li et al., Nature Methods (2007) 4, 251-256). The expression vectors contained an expression cassette consisting of a 5' CMV promoter including intron A, and a 3' BGH poly adenylation sequence. In addition to the expression cassette, the plasmids contained a pUC18-derived origin of replication and a beta-lactamase gene conferring ampicillin resistance for plasmid amplification in E. coli. Three variants of the basic plasmid were used: one plasmid containing the rabbit IgG constant region designed to accept the VH regions while two additional plasmids containing rabbit or human kappa LC constant region to accept the VL regions.

Linearized expression plasmids coding for the kappa or gamma constant region and VL/VH inserts were amplified by PCR using overlapping primers.

Purified PCR products were incubated with T4 DNA-polymerase which generated single-strand overhangs. The reaction was stopped by dCTP addition.

In the next step, plasmid and insert were combined and incubated with recA which induced site specific recombination. The recombined plasmids were transformed into E. coli. The next day the grown colonies were picked and tested for correct recombined plasmid by plasmid preparation, restriction analysis and DNA-sequencing.

For antibody expression, the isolated HC and LC plasmids were transiently co-transfected into HEK293 cells and the supernatants were harvested after 1 week.

Recombinant Expression of Rabbit Monoclonal Monovalent Antibodies

For recombinant expression of selected candidates as monoclonal monovalent antibodies rabbit constant regions of all VH chains were converted into human constant regions enclosing the Knob-mutation in the CH3 segment.

For VL chains derived from rabbit wild type B cells, rabbit C kappa constant regions were converted into human. 4 µl of cDNA of the selected candidates were used to amplify the immunoglobulin heavy and light chain variable regions with the AccuPrime Supermix (Invitrogen 12344-040) in a final volume of 50 µl with forward primers specific for the signal peptide and reverse primers specific for the CDR3-J region with (at the 3' end) overlap sequence (20 bp) homologous to the human constant regions (respectively of VH and VL). The PCR conditions for the VH and VL chain amplification were as follows: Hot start at 94° C. for 5 min; 35 cycles of 20 s at 94° C., 20 s at 68° C., 45 s at 68° C., and a final extension at 68° C. for 7 min.

PCR-products coding for VH or VL were cloned as cDNA into expression vectors by the overhang cloning method (R S Haun et al., Biotechniques (1992) 13, 515-518; MZ Li et al., Nature Methods (2007) 4, 251-256). The expression vectors contained an expression cassette consisting of a 5' CMV promoter including intron A, and a 3' BGH poly adenylation sequence. In addition to the expression cassette, the plasmids contained a pUC18-derived origin of replication and a beta-lactamase gene conferring ampicillin resistance for plasmid amplification in E. coli. Two variants of the basic plasmid were used: one plasmid containing the human IgG constant region designed to accept the new amplified VH chain and a second plasmid containing the human kappa LC constant region to accept the VL chain.

Linearized expression plasmids coding for the kappa or gamma constant region and VL/VH inserts were amplified by PCR using overlapping primers.

Purified PCR products were incubated with T4 DNA-polymerase which generated single-strand overhangs. The reaction was stopped by dCTP addition.

In the next step, plasmid and insert were combined and incubated with recA which induced site specific recombination. The recombined plasmids were transformed into E. coli. The next day the grown colonies were picked and tested for correct recombined plasmid by plasmid preparation, restriction analysis and DNA-sequencing.

The following polypeptides were generated:

TABLE 4

Amino acid sequences of Fabs and PE for sortase coupling

| | Amino acid sequences | SEQ ID NO: |
|---|---|---|
| 051 VH ok | EVQLLESGGGLLQPGGSLRLSCAASGFTFSIYWMTWVRQAP GKGLEWVSAISGSGGSTYYADSVKGRFTISRDNSKNTLYLQ MNSLRAEDTAVYYCAKDYYSNVYWGQGTLVTVSS | 9 |
| ok VL | DIQMTQSPSSVSASVGDRVTITCRASQGIYSWLAWYQQKPG KAPKLLIYAASSLQSGVPSRFSGSGSGTDFTLTISSLQPED FATYYCQQSDSPPYTFGQGTKLEIK | 10 |
| 091 VH ok | EVHLLESGGGLVHPGGSLRLSCAASGFTFRSDAMHWVRQAP GKGLEWVSGVSGSGGSPYYADSVKGRFTISRDDSKTTLYLQ MNSLRAEDTAVYYCATGGSIAGSYYYPMDVWGQGTTVTVS S | 17 |
| ok VL | DIQMTQSPSSLSASVGDRVTITCQASQDISNYLNWYQQKPG KAPKLLIYAASTLQIGVPSRFSGSGSGTDFTFTISSLQPED FATYYCQQANSFPLTFGGGTKVEIK | 18 |
| 097 VH ok | EVQLLESGGGLAQPGGSLRLSCAASGFTFNNDAMTWVRQAP GKGLEWVSAISGSGGSTYYADSVKGRFTISRDNSKNTLYLQ MNSLRAEDTAVYYCAKGGSWGDWYYYFYPMDVWGQGTTVTV SS | 25 |

TABLE 4-continued

Amino acid sequences of Fabs and PE for sortase coupling

| | Amino acid sequences | SEQ ID NO: |
|---|---|---|
| ok VL | DIQMTQSPSSLSASVGDRVTITCRASQSISSYLNWYQQKPGKAPKLLIYAASSLQSGVPSRFSGSGSGTDFTLTISSLQPEDFATYYCQQSDSFPLTFGGGTKVEIK | 26 |

TABLE 5

CDRs according to Kabat of anti-TPBG antibodies (HC . . . heavy chain, LC . . . light chain)

| | | Amino acid sequences | SEQ ID NO: |
|---|---|---|---|
| 051 ok | HC-CDR1 | IYWMT | 3 |
| | HC-CDR2 | AISGSGGSTYYADSVKG | 4 |
| | HC-CDR3 | DYYSNVY | 5 |
| | LC-CDR1 | RASQGIYSWLA | 6 |
| | LC-CDR2 | AASSLQS | 7 |
| | LC-CDR3 | QQSDSPPYT | 8 |
| 091 ok | HC-CDR1 | SDAMH | 11 |
| | HC-CDR2 | GVSGSGGSPYYADSVKG | 12 |
| | HC-CDR3 | GGSIAGSYYYYPMDV | 13 |
| | LC-CDR1 | QASQDISNYLN | 14 |
| | LC-CDR2 | AASTLQI | 15 |
| | LC-CDR3 | QQANSFPLT | 16 |
| 097 ok | HC-CDR1 | NDAMT | 19 |
| | HC-CDR2 | AISGSGGSTYYADSVKG | 20 |
| | HC-CDR3 | GGSWGDWYYYFYPMDV | 21 |
| | LC-CDR1 | RASQSISSYLN | 22 |
| | LC-CDR2 | AASSLQS | 23 |
| | LC-CDR3 | QQSDSFPLT | 24 |

Example 12

Sortase Coupling of Fab Fragment to a Truncated GGG-PE24 Variant (LR8M)

An immunoconjugate of an anti-TPBG antibody Fab fragment and a truncated variant of exotoxin A chain of *P. aeruginosa* was generated via enzymatic coupling with sortase.

The following polypeptides were used:

TABLE 6

Amino acid sequences of Fabs and PE for sortase coupling (HC . . . heavy chain, LC . . . light chain)

| | Amino acid sequences | SEQ ID NO: |
|---|---|---|
| H8 HC ok | EVQLQQSGPDLVKPGASVKISCKASGYSFTGYYMHWVKQSHGKSLEWIGRINPNNGVTLYNQKFKDKAILTVDKSSTTAYMELRSLTSEDSAVYYCARSTMITNYVMDYWGQVTSVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCGGGSLPETGGSGSHHHHHH | 37 |
| ok LC | SIVMTQTPTFLLVSAGDRVTITCKASQSVSNDVAWYQQKPGQSPTLLISYTSSRYAGVPDRFIGSGYGTDFTFTISTLQAEDLAVYFCQQDYNSPPTFGGGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 38 |
| 051 HC ok | EVQLLESGGGLLQPGGSLRLSCAASGFTFSIYWMTWVRQAPGEGLEWVSAISGSGGSTYYADSVKGRFTISRDNSKNTLYLQMNSLRAEDTAVYYCAKDYYSNVYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDEKVEPESCGGGSLPETGGSGSEQKLISEEDLHHHHHHGAAEPEA | 39 |
| ok LC | DIQMTQSPSSVSASVGDRVTITCRASQGIYSWLAWYQQKPGKAPKLLIYAASSLQSGVPSRFSGSGSGTDFTLTISSLQPEDFATYYCQQSDSPPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 40 |
| 091 HC ok | EVHLLESGGGLVHPGGSLRLSCAASGFTFRSDAMHWVRQAPGEGLEWVSGVSGSGGSPYYADSVEGRFTISRDDSKTTLYLQMNSLRAEDTAVYYCATGGSIAGSYYYYPMDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDEKVEPESCGGGSLPETGGSGSEQKLISEEDLHHHHHHGAAEPEA | 41 |
| ok LC | DIQMTQSPSSLSASVGDRVTITCQASQDISNYLNWYQQKPGKAPKLLIYAASTLQIGVPSRFSGSGSGTDFTFTISSLQPEDFATYYCQQANSFPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 42 |
| 097 HC ok | EVQLLESGGGLAQPGGSLRLSCAASGFTFNNDAMTWVRQAPGKGLEWVSAISGSGGSTYYADSVKGRFTISRDNSKNTLYLQMNSLRAEDTAVYYCAKGGSWGDWYYYFYPMDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCGGGSLPETGGSGSEQKLISEEDLHHHHHHGAAEPEA | 43 |
| ok LC | DIQMTQSPSSLSASVGDRVTITCRASQSISSYLNWYQQKPGKAPKLLIYAASSLQSGVPSRFSGSGSGTDFTLTISSLQPEDFATYYCQQSDSFPLTFGGGTKVEIKGTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 44 |
| PE (LR8M) | GGGRHRQPRGWEQLYPTGAEFLGDGGAVSFSTRGTQNWTVERLLQAHRQLEEGGYVFVGYHGTFLEAAQSIVFGGVRARSQDLDAIWAGFYIAGDPALAYGYAQDQEPDAAGRIRNGALLRVYVPRSSLPGFYATSLTLAAPEAAGEVERLIGHPLPLRLDAITGPEESGGRLETILGWPLAERTVVIPSAIPTDPRNVGGDLDPSSIPDSEAAISALPDYASQPGKPPREDL | 45 |

Purified Fab fragments transiently expressed in HEK293-F (with LPETG-HIS$_6$ motif at the C-terminus) and GGG-PE24 LR8M (purified from *E. coli* extract as published in the literature) were concentrated to 7-8 mg/ml in 20 mM Tris, 150 mM NaCl, 5 mM CaCl$_2$), pH 7.5. Both proteins were combined in a 1:1 molar ratio. Coupling reaction was started by adding HIS-tagged Sortase (0.8 molar equivalent). After incubation for 1 h at 37° C. the reaction mixture was chromatographed on a Ni HiTrap column (GE Healthcare) to remove uncoupled Fab and Sortase. Coupled Fab-PE24 eluted in the flow through and was further purified on a Superdex200 gel filtration column in 20 mM His, 140 mM NaCl, pH 6.0. The final product was concentrated to 1 mg/ml and frozen in aliquots at −80° C.

Example 13

Expression of Fab-PE and Inclusion Body Isolation

An immunoconjugate of an anti-TPBG antibody Fab fragment and a truncated variant of exotoxin A chain of *P. aeruginosa* was generated via expression of the immunoconjugate as recombinant fusion protein in *E. coli* cells. The toxin was fused to the C-terminus of the heavy chain of the anti-TPBG antibody.

The following polypeptides were used:

TABLE 7

Amino acid sequences of anti-TPBG Fab-PE fusion proteins

| | Amino acid sequences | SEQ ID NO: |
|---|---|---|
| 051 HC-PE | MEVQLLESGGGLLQPGGSLRLSCAASGFTFSIYWMTWVRQA PGKGLEWVSAISGSGGSTYYADSVKGRFTISRDNSKNTLYL QMNSLRAEDTAVYYCAKDYYSNVYWGQGTLVTVSSASTKGP SVFPLAPSSKSTSGGTAALGCLVKDYFPEPVTVSWNSGALT SGVHTFPAVLQSSGLYSLSSVVTVPSSSLGTQTYICNVNHK PSNTKVDKKVEPKSCDKTHKASGGRHRQPRGWEQLGGGGGS PTGAEFLGDGGDVSFSTRGTQNWTVERLLQAHAQLEERGYV FVGYHGTFLEAAQSIVFGGVAARSQDLAAIWAGFYIAGDPA LAYGYAQDQEPDAAGRIRNGALLRVYVPASSLPGFYRTSLT LAAPEAAGEVERLIGHPLPLALDAITGPEEEGGRLETILGW PLAERTVVIPSAIPTDPRNVGGDLDPSSIPDKEQAISALPD YASQPGKPPREDLK | 46 |
| 051 LC | MDIQMTQSPSSVSASVGDRVTITCRASQGIYSWLAWYQQKP GKAPKLLIYAASSLQSGVPSRFSGSGSGTDFTLTISSLQPE DFATYYCQQSDSPPYTFGQGTKLEIKRTVAAPSVFIFPPSD EQLKSGTASVVCLLNNFYPREAKVQWKVDNALQSGNSQESV TEQDSKDSTYSLSSTLTLSKADYEKHKVYACEVTHQGLSSP VTKSFNRGEC | 47 |
| 091 HC-PE | MEVHLLESGGGLVHPGGSLRLSCAASGFTFRSDAMHWVRQA PGKGLEWVSGVSGSGGSPYYADSVKGRFTISRDNSKNTLYL QMNSLRAEDTAVYYCATGGSIAGSYYYYPMDVWGQGTTVTV SSASTKGPSVFPLAPSSKSTSGGTAALGCLVKDYFPEPVTV SWNSGALTSGVHTFPAVLQSSGLYSLSSVVTVPSSSLGTQT YICNVNHKPSNTKVDKKVEPKSCDKTHKASGGRHRQPRGWE QLGGGGGSPTGAEFLGDGGDVSFSTRGTQNWTVERLLQAHA QLEERGYVFVGYHGTFLEAAQSIVFGGVAARSQDLAAIWAG FYIAGDPALAYGYAQDQEPDAAGRIRNGALLRVYVPASSLP GFYRTSLTLAAPEAAGEVERLIGHPLPLALDAITGPEEEGG RLETILGWPLAERTVVIPSAIPTDPRNVGGDLDPSSIPDKE QAISALPDYASQPGKPPREDLK | 48 |
| 091 LC | MDIQMTQSPSSLSASVGDRVTITCQASQDISNYLNWYQQKP GKAPKLLIYAASTLQIGVPSRFSGSGSGTDFTFTISSLQPE DFATYYCQQANSFPLTFGGGTKVEIKRTVAAPSVFIFPPSD EQLKSGTASVVCLLNNFYPREAKVQWKVDNALQSGNSQESV TEQDSKDSTYSLSSTLTLSKADYEKHKVYACEVTHQGLSSP VTKSFNRGEC | 49 |
| 097 HC-PE | MEVQLLESGGGLAQPGGSLRLSCAASGFTFNNDAMTWVRQA PGKGLEWVSAISGSGGSTYYADSVKGRFTISRDNSKNTLYL QMNSLRAEDTAVYYCAKGGSWGDWYYYFYPMDVWGQGTTVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHKASGGRHRQPRGW EQLGGGGGSPTGAEFLGDGGDVSFSTRGTQNWTVERLLQAH AQLEERGYVFVGYHGTFLEAAQSIVFGGVAARSQDLAAIWA GFYIAGDPALAYGYAQDQEPDAAGRIRNGALLRVYVPASSL PGFYRTSLTLAAPEAAGEVERLIGHPLPLALDAITGPEEEG GRLETILGWPLAERTVVIPSAIPTDPRNVGGDLDPSSIPDK EQAISALPDYASQPGKPPREDLK | 50 |
| 097 LC | MDIQMTQSPSSLSASVGDRVTITCRASQSISSYLNWYQQKP GKAPKLLIYAASSLQSGVPSRFSGSGSGTDFTLTISSLQPE DFATYYCQQSDSFPLTFGGGTKVEIKNTVAAPSVFIFPPSD EQLKSGTASVVCLLNNFYPREAKVQWKVDNALQSGNSQESV TEQDSKDSTYSLSSTLTLSKADYEKHKVYACEVTHQGLSSP VTKSFNRGEC | 51 |

The variable light chain constructs (LC) and the variable heavy chain constructs (HC-PE) were produced in *E. coli* cells applying the Roche in-house antibiotic free expression system (EP 0 972 838 and U.S. Pat. No. 6,291,245) and a fermentation process on chemical defined medium with alkaline feeding (WO2012/028522). In all fermentations the product was located in the insoluble fraction of the cytoplasm as inclusion bodies which were isolated and solubilized. The solubilized IB material was then combined during the renaturation process with its respective partner to form the TPBG binding Fab-PE fusion molecules. In brief, the *E. coli* K12 strain CSPZ-25 (thi-1, ΔompT, ΔpyrF, Δlon, ΔgalE) was transformed by electroporation with the relevant expression plasmids. The transformed *E. coli* cells were first grown at 37° C. on agar plates. For each transformation a colony picked from this plate was transferred to a 3 mL roller culture and grown at 37° C. to an optical density of 1-2 (measured at 578 nm). Then 1000 µl culture were mixed with 1000 µl sterile 86%-glycerol and immediately frozen at −80° C. for long time storage. The correct product expression of these clones was verified in small scale shake flask experiments and analyzed with SDS-Page.

For pre-cultivation one 1000 mL shake-flask with four baffles was inoculated with 1.0 mL out of a research seed bank ampoule. The cultivation was performed on a rotary shaker for 8-11 hours at 37° C. and 170 rpm until an optical density (578 nm) of 4 to 8 was obtained. 100 ml of the pre cultivation was used to inoculate a 10 L bioreactor. After 24 hours of cultivation the whole broth is cooled down to 4-8° C. and stored overnight in the fermenter vessel. The bacteria were harvested via centrifugation with a flow-through centrifuge (13,000 rpm, 13 l/h) and the obtained biomass was immediately processed in an inclusion body isolation process or stored at −20° C. until further processing.

Inclusion body preparations (IBP) of the 10 L fermentations were routinely started directly after the harvest of the bacteria with the re-suspension of the cell pellet in buffer containing 12.1 g/l Tris, 0.246 g/l MgSO4*7H2O and 12 ml/l 25%-HCl. The buffer volume was calculated in dependence of the dry matter content of the biomass. Lysozyme (100 kU/mg) and a small amount of Benzonase™ were added. Then the suspension was homogenized at 900 bar (APV Rannie 5, 1 pass) to disrupt the bacteria cells followed by further addition of Benzonase and an incubation for 30 min at 30-37° C. Then the first wash buffer (60 g/l Brij, 87.6 g/l NaCl, 22.5 g/l EDTA, 6 ml/l 10N NaOH) was added and again the suspension was incubated for 30 minutes. The following centrifugation step (BP12, Sorvall) lead to the inclusion body slurry which was re-suspended in the second wash buffer (12.1 g/l Tris, 7.4 g/l EDTA, 11 ml/l 25%-HCl) and incubated for 20 min. A further separation step yielded the inclusion bodies which are stored frozen at −20° C. or immediately transferred to the DSP department.

Example 14

Renaturation and Purification of Anti-TPBG Fab-PE Fusion Proteins

Inclusion bodies of HC-PE and LC (HC=heavy chain; LC=light chain) were solubilized separately in 6.7 M Guanidinium-Hydrochloride, 100 mM Tris/HCl, 5 mM acetate, 1 mM EDTA pH 8.0+100 mM Dithiothreitol (DTT) 2 h at room temperature. Solubilized material was adjusted to pH 5 and microfiltrated (6.7 M Guanidinium-HCl, 100 mM Tris, 1 mM EDTA, 5 mM acetate, 100 mM DTT pH 5.0) using a 1000 kDa membrane. After diafiltration against 6.7 M Guanidinium-HCl, 100 mM Tris, 10 mM EDTA, 5 mM acetate, pH 5.0 in order to remove DTT and for concentration, the total protein concentration was determined using Biuret method. The purity of HC and LC content was estimated using a Bioanalyzer (Agilent Technologies). Solubilisates were diluted at a 1:1 molar ratio in renaturation buffer containing 0.5 M arginine, 2 mM EDTA, pH 10+1 mM GSH/GSSG, respectively, at 2-10° C. The target protein concentration was increased in four steps to 0.5 g/L, with an incubation time of 2 h between the two doses. Afterwards the renaturation solution was kept at 2-10° C. overnight. The renaturate was diafiltrated against 20 mM Tris/HCl, 40 mM NaCl pH7.4 (pH 8.0 for TPBG-0199) and pumped onto an anion exchange column (AIEX) equilibrated in 20 mM Tris/HCl, 40 mM NaCl pH 7.4 (pH 8.0 for TPBG-0199). After washing the column with equilibration buffer the protein was eluted with a gradient up to 20 mM Tris/HCl, 320 mM NaCl, pH 7.4 (pH 8.0 for TPBG-0199). Peak fractions containing Fab-PE were pooled, concentrated and applied onto a preparative Size Exclusion Column (SEC) in 20 mM Tris, 150 mM NaCl, pH 7.4 to remove aggregates, fragments and *E. coli* proteins. The final protein pool was adjusted to the required protein concentration and analyzed via Bioanalyzer (Agilent Technologies), analytical SEC and $UV_{280}$, identity was confirmed by mass spectrometry Example 15

MS Analysis and Identity Confirmation of Proteins

The correct molecular mass (identity) and integrity of the amino acid backbones of the Fab fragments were verified by Electrospray ionization (ESI) mass spectrometry with and without prior reduction. Reduction was performed using TCEP (Thermo Scientific). Desalting was performed on self-packed G25-Sephadex-Superfine (GE Healthcare) columns using an isocratic formic acid gradient. ESI mass spectra (+ve) were recorded on a Q-TOF instrument (maXis, Bruker) equipped with a nano ESI source (TriVersa NanoMate, Advion). MS parameter settings were as follows: Transfer: Funnel RF, 400 Vpp; ISCID Energy, 0 or 85 eV; Multipole RF, 400 Vpp; Quadrupole: Ion Energy, 3.0 eV; Low Mass, 850 m/z; Source: Dry Gas, 8 L/min; Dry Gas Temperature, 160° C.; Collision Cell: Collision Energy, 8 eV; Collision RF: 3800 Vpp; Ion Cooler: Ion Cooler RF, 800 Vpp; Transfer Time: 140 µs; Pre Puls Storage, 20 µs; scan ranges m/z 600 to 2000 and m/z 1000 to 4000. The MassAnalyzer software (developed in-house) was used for data evaluation.

Example 16

Generation of Stable TPBG Expressing CHO Cell Lines

CHO-K1 cells were stably transfected with full length TPBG from different species, namely human, or minipig, to evaluate cellular binding properties and potency of novel TPBG-specific antibodies. CHO-K1 cells (ATCC) were cultivated in DMEM/F12 medium (no phenol red) supplemented with 10% fetal calf serum and 2 mM L-Glutamine. Upon reaching 80-90% confluency lipid/DNA complexes were prepared with TPBG expression vectors using Roche's XtremeGeneHP transfection reagent. After pre-incubation, lipid/DNA complexes were added to $2\times10^5$ CHO-K1 cells in suspension at a total volume of 2 ml of selection medium (DMEM/F12, 10% fetal calf serum, 400 µg/ml G418). Cells were cultivated for 14 days under selection pressure and then stained with in-house TPBG antibodies. Briefly, $2\times10^5$ cells were stained with 2 µg/ml primary anti-TPBG antibody for 30 min on ice, washed and counterstained with PE-labelled anti-human kappa antibody (1:50 in PBS containing 2% fetal calf serum, 30 min on ice). Single cell sorting of high or medium to low expressing clones was performed on a FacsARIA (BD) and single cells were deposited into 96-well flat bottom cell culture plates. After 12 days a variety of clones for each species (human, cynomolgus, minipig TPBG) were transferred to 24-well plates and cultivated for three more days. Clones were stained with above mentioned internal reference TPBG antibodies as formerly described and analyzed on a FacsCanto (BD). Selected clones were cultivated for one more week and stored in FCS containing 7.5% DMSO liquid nitrogen. For stability testing, cells were further cultivated for two more weeks, then stained and analyzed on a FacsCanto (BD) resulting in the final selection of TPBG-expressing CHO cells that were stable over the observed time period.

Example 17 pH Dependent Binding of Anti-TPBG Antibodies to Cell Surface Expressed Human TPBG pH-dependent binding of anti-TPBG Fabs as expressed in Example 11 to human TPBG was assessed. To this end, a SW620 clone (clone 4), stably expressing high level of TPBG, was chosen as cellular model. Cells growing in the logarithmic growth phase were detached using Accutase (Sigma) and a cell suspension was prepared in a PBS buffer (bufferA) containing 1% fetal calf serum and pH adjusted to pH 7.2, 6.0, and 5.5. Respective Fabs were added to cell suspension and binding occurred for 30 min on ice. Cells were subsequently washed twice with buffer of the same pH (buffer A). Cells were then resuspended in PBS containing 2% fetal calf serum, pH 7.4 (buffer B) and a secondary anti-kappa mouse anti-human mAb coupled to PE (phycoerythrin) (Life Technologies) was added for 30 min on ice. Cells were then again washed twice with buffer B and finally resuspended in onetime CellFix buffer (BD). To discriminate life from dead cells Hoechst 33258 stain was applied. Signals were detected on a FACS Canto II (BD). Data evaluation was done with FACS Diva software and Microsoft Excel. Experiments were done in biological replicates.

Figure 2:
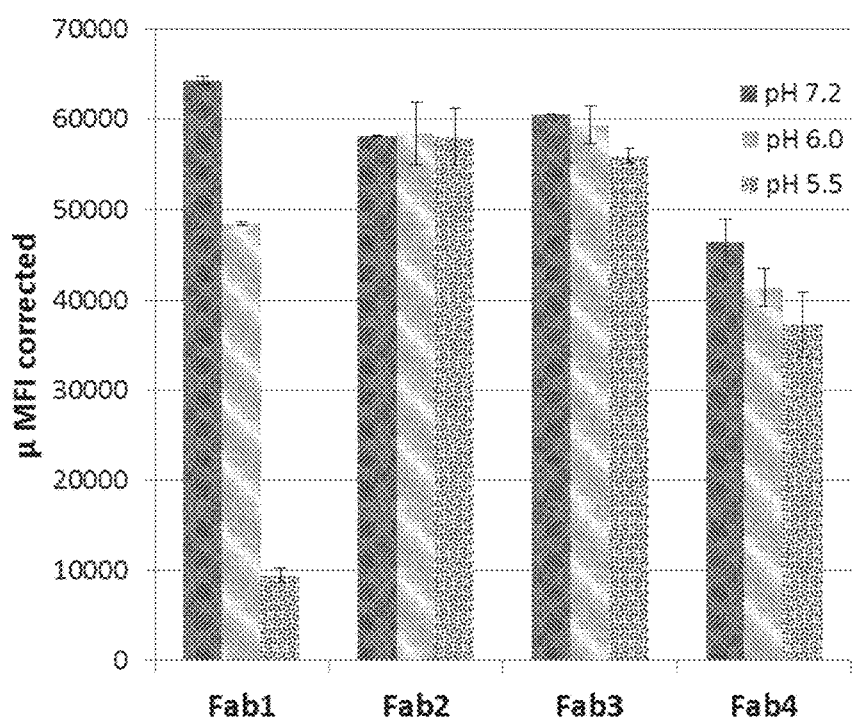
FIG. 2: Binding of different anti-TPBG antibodies (Fab fragments: Fab1=H8; Fab2=091; Fab3=051; Fab4=097) to cell surface expressed human TPBG at different pH values (Example 17). The human cell line SW620 clone 4, stably expressing TPBG, was incubated with different Fabs at varying pH. Upon incubation with a secondary antibody coupled to a fluorescent dye, signals were detected by flow cytometry. Baseline corrected mean fluorescent intensities (MFI) are shown.

While the applied pH range does not closely reflect physiological values it was used to evaluate the pH-dependent binding of different Fabs using a maximal window. From the analysis it is obvious that the Fab(H8) prior art antibody displays a much higher pH-dependent binding than the antibodies of the invention (FIG. 2). This would indicate that the binding of Fab(H8) in comparison to the antibodies of the invention has likely a much higher contribution of hydrogen-bonds. In biological replicates, comparing pH 5.5 and pH 7.2 this factor was between 4.2 and 6.8 calculated from the mean fluorescence intensity (MFI) while it was for the Fabs of the invention in the range of 0.9-1.2 (Table 8).

TABLE 8

Comparison of anti-TPBG Fab binding to cell surface TPBG at different pH values

| | SW620 cl.4 Fold change pH 7.2 vs pH 5.5 | |
|---|---|---|
| Fab | replicate 1 | replicate 2 |
| H8 | 4.2 | 6.8 |
| 051 | 1.1 | 1.1 |
| 091 | 0.9 | 1.0 |
| 097 | 1.2 | 1.2 |

Example 18

Internalization of Anti-TPBG Antibodies (Fab Fragments) in Human TPBG-Expressing MCF7 Cells Internalization upon target binding of TPBG-specific Fabs as expressed in Example 11 was evaluated in MCF7 cells.

Cells in the logarithmic growth phase were detached using Accutase (Sigma). 2.5×10e5 cells per sample were resuspended in ice-cold buffer (PBS containing 2% fetal calf serum) and 10 µg/mL of the respective Fabs and kept for 15 min on ice. Cells were spun down at 300 g for 5 min at 4° C. and washed twice with 150 µL ice-cold buffer. Cells were resuspended in 100 µL buffer and incubated for 30, 60 or 180 min at 37° C. Samples for time point zero remained on ice. Plates for time course at 37° C. were pre-warmed prior sample addition. Cells were resuspended in 50 µL ice-cold buffer containing 10 µg/mL anti-kappa light chain RE-PE (phycoerythrin) labeled secondary antibody (Life Technologies). The suspension was incubated for 45 min on ice. Cells were then washed twice as described and resuspended in 200 µL ice-cold fixation buffer (BD CellFix). Samples were measured on a FACSCanto II (BD). Data processing was done using the FlowJo Software. Data analysis was performed with Excel (Microsoft) and XLfit 5.3.1 (IDBS) add-in. The GeoMean fluorescence signal of each Fab sample was corrected by the mean fluorescence intensity (MFI) of the corresponding isotype control. The MFI for each time point was set in relation to time point zero and calculated as percentage value. The percentage of internalization was calculated by subtracting the percentage of detected antibody from 100%.

Figure 3:
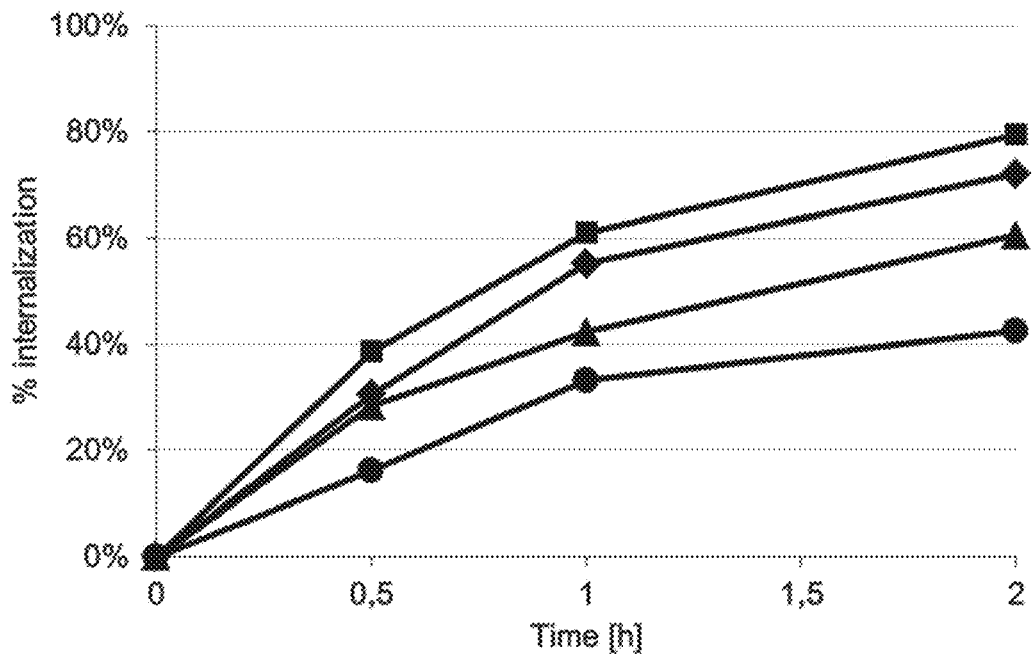
FIG. 3: Internalization of anti-TPBG antibodies (Fab fragments: square=H8; triangle=097; diamond=051; circle=091) evaluated in the tumor cell line MCF7 (Example 18). The y-axis displays the loss of signal for cell surface bound Fabs as function of time.

All Fabs did internalize within the given time frame (FIG. 3).

TABLE 9

Internalization of anti-TPBG antibodies (Fab fragments) in human TPBG-expressing MCF7 cells

| Fab | time [h] | | |
|-----|------|------|------|
|     | 0.5  | 1.0  | 2.0  |
| H8  | 39%  | 61%  | 79%  |
| 051 | 31%  | 55%  | 72%  |
| 091 | 16%  | 33%  | 42%  |
| 097 | 28%  | 42%  | 61%  |

Example 19

Cellular Binding of Anti-TPBG Antibodies (Fab Fragments) to Minipig-TPBG Expressing CHO Cells Binding of TPBG-specific Fabs as expressed in Example 11 to cell surface expressed minipig TPBG was assessed using stably transfected CHO cells (Example 16) and a flow cytometry based assay.

Stable transfectants expressing cell surface levels of TPBG in a similar range were used for the flow cytometry based analysis of cellular binding. Dilution series of antibodies were prepared spanning a concentration range from 0.01-20 µg/ml. In brief, cell suspensions were prepared in ice cold PBS (Gibco) containing 2% fetal calf serum (PAN Biotech). 2.5×10e5 cells were dispensed per well in a v-shaped 96well-MTP. Antibody dilution series prepared in the same buffer were added as twofold concentrated solution. Samples were incubated on ice for 45 min upon which they were washed twice with 150 µL ice cold PBS containing 2% fetal calf serum. In between, cells were spun down at 300 g for 5 min at 4° C. Cells were resuspended in 50 µL ice-cold buffer containing 10 µg/mL anti-kappa light chain RE-PE (phycoerythrin) labeled secondary antibody (Life Technologies). The suspension was incubated for 45 min on ice. Cells were washed twice as described and resuspended in 50 µL ice-cold buffer containing 1 µg/mL Hoechst 33258. After 10 min cells were washed once more and finally resuspended in 200 µL ice-cold fixation buffer (BD CellFix). Samples were measured on a FACSCanto II (BD). Data processing was done using the FlowJo Software. Data analysis was performed with Excel (Microsoft) and XLfit 5.3.1 (IDBS) add-in.

Figure 4A:
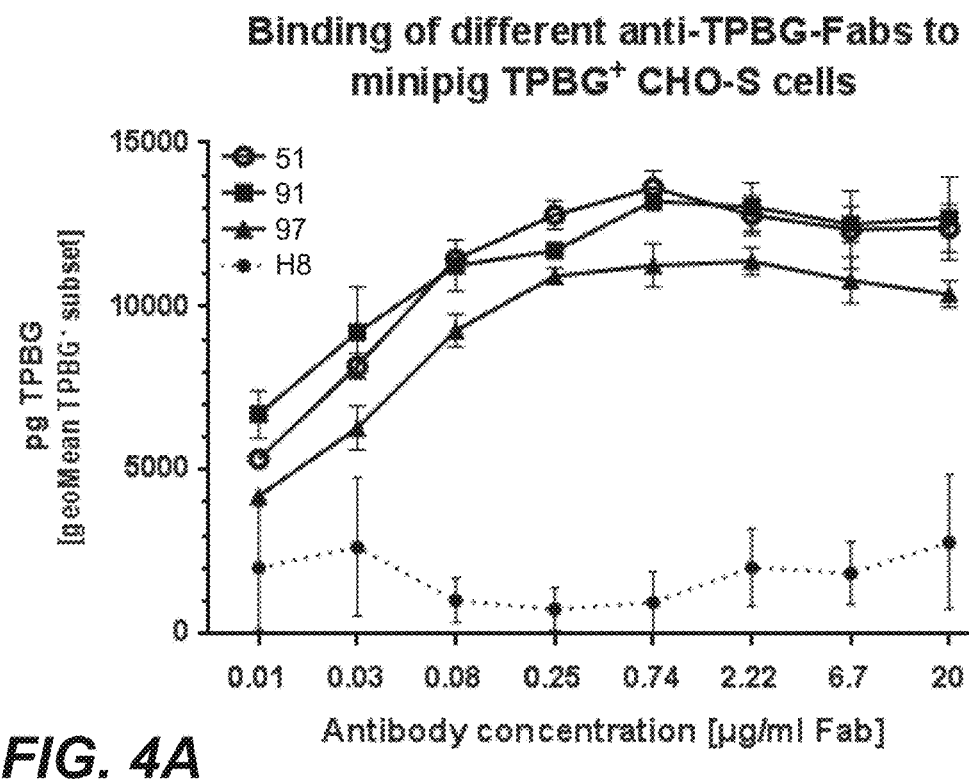
FIG. 4A: Cellular binding of anti-TPBG antibodies (Fab fragments: open circle=051; square=91; triangle=97; circle=H8) to minipig-TPBG expressing CHO cells (Example 19). Baseline corrected mean fluorescent intensities (MFI) are shown.

Antibodies 051, 091 and 097 of the invention bound to cell surface expressed TPBG to a similar degree, while prior art antibody H8 did not bind to cell surface expressed TPBG in sufficient extent (FIG. 4A).

Example 20

Cellular Binding of Immunoconjugates Comprising Anti-TPBG Antibodies (Fab-PE Fragments) to Human and Minipig-TPBG Expressing CHO Cells Binding of TPBG-specific antibodies to either human (hu) or minipig (pg) TPBG was evaluated using CHO-K1 cells stably transfected with the respective full length antigen (Example 16). Stable transfectants expressing cell surface levels of TPBG in a similar range were used for flow cytometry based analysis of cellular binding. Dilution series of Fab-PEs (anti-TPBG Fab-PE fusion proteins as expressed in Examples 13 and 14) were prepared spanning a concentration range from 400-0.002 nM. In brief, cell suspensions were prepared in ice cold PBS (Gibco) containing 2% fetal calf serum (PAN Biotech). 2.5×10e5 cells were dispensed per well in a v-shaped 96well-MTP. Fab-PE dilution series prepared in the same buffer were added as twofold concentrated solution. Samples were incubated on ice for 45 min upon which they were washed twice with 150 µL ice cold PBS containing 2% fetal calf serum. In between, cells were spun down at 300 g for 5 min at 4° C. Cells were resuspended in 50 µL ice-cold buffer containing 10 µg/mL anti-kappa light chain RE-PE (phycoerythrin) labeled secondary antibody (Life Technologies). The suspension was incubated for 45 min on ice. Cells were washed twice as described and resuspended in 50 µL ice-cold buffer containing 1 µg/mL Hoechst 33258. After 10 min cells were washed once more and finally resuspended in 200 µL ice-cold fixation buffer (BD CellFix). Samples were measured on a FACSCanto II (BD). Data processing was done using the FlowJo Software. Data analysis was performed with Excel (Microsoft) and XLfit 5.3.1 (IDBS) add-in.

Figure 4B:
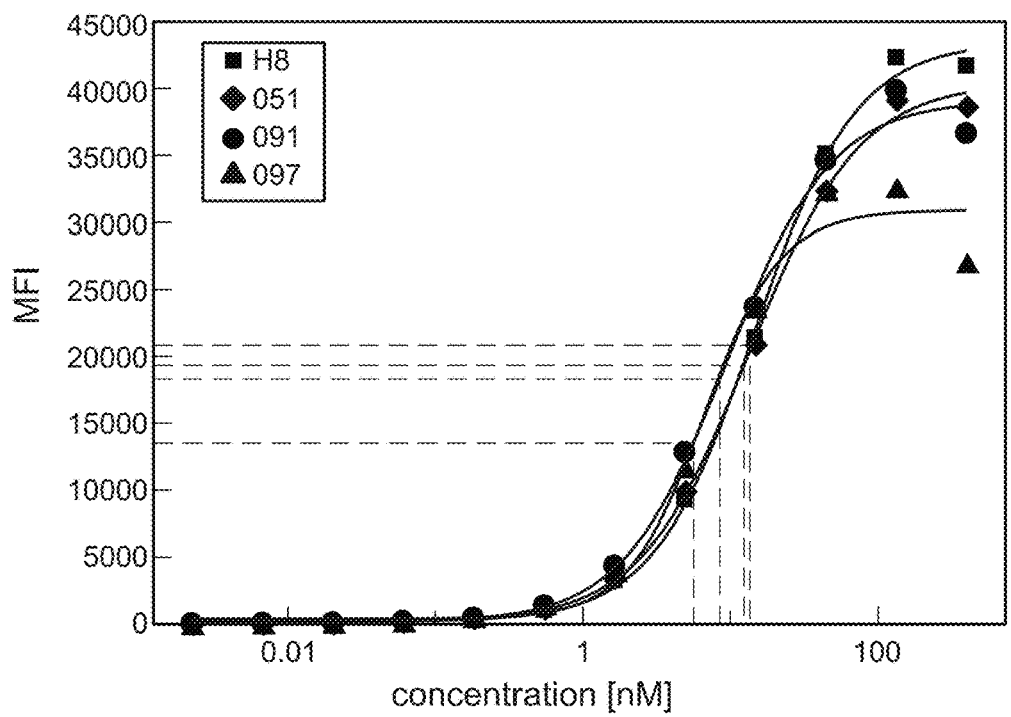
FIG. 4B: Cellular binding of anti-TPBG antibodies (Fab-PE fusion proteins; Fab fragments: square=H8; triangle=097; diamond=051; circle=091) to human TPBG stably displayed on the cell surface of CHO-K1 (Example 20). A dilution series of Fab-PE was added to cells. Cellular binding was visualized with a secondary fluorescence labeled antibody and analysis in flow cytometry. Baseline corrected mean fluorescent intensities (MFI) are shown.

All Fab-PE bound to a similar degree to CHO-K1 expressing human TPBG with at most a twofold difference in the EC50 (FIG. 4B).

Figure 4C:
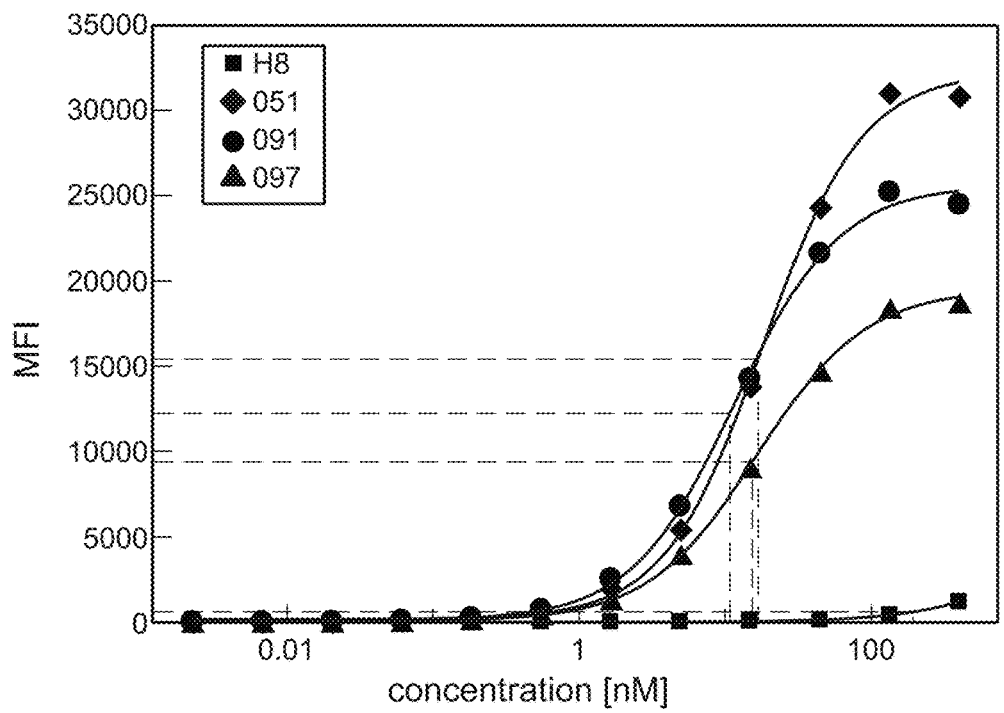
FIG. 4C: Cellular binding of immunoconjugates comprising anti-TPBG antibodies (Fab-PE fusion proteins; Fab fragments derived from antibodies: square=H8; triangle=097; diamond=051; circle=091) to minipig TPBG stably displayed on the cell surface of CHO-K1 (Example 20). A dilution series of Fab-PE was added to cells. Cellular binding was visualized with a secondary fluorescence labeled antibody and analysis in flow cytometry.

Only Fab-PEs comprising antibodies 051, 091 and 097 of the invention were found to bind to cell surface expressed minipig TPBG while Fab-PEs comprising prior art antibody H8 did not bind to cell surface expressed minipig TPB (FIG. 4C).

TABLE 10

Cellular binding to human and minipig TPBG EC50 [nM]

| Fab-PE comprising antibody | stable CHO-K1 transfectants | |
|---|---|---|
| | huTPBG | pgTPBG |
| H8 | 13.6 | — |
| 051 | 12.4 | 16.9 |
| 091 | 8.5 | 10.8 |
| 097 | 5.6 | 15.4 |

Example 21

Cytotoxicity of Immunoconjugates Comprising Anti-TPBG Antibodies (Fabs Coupled to PE Fragment Via Sortase Coupling) on Human and Minipig-TPBG Expressing CHO Cells A surrogate assay to evaluate the potency of Fab-PE constructs (Fabs coupled to PE fragment via sortase coupling as provided in Example 12) on cells expressing human (hu) or minipig (pg) TPBG was established. To this end, CHO-K1 cells were transiently transfected with full length TPBG from the respective species. In addition a luciferase reporter plasmid was co-transfected. Upon treatment with test compound potency was determined by measuring luciferase activity.

CHO-K1 cells were transiently transfected with TPBG and luciferase containing plasmids in a ratio of 2:1 in suspension using Lipofectamine 3000 at a ratio of 3:1 and 3 µg total DNA per 1×10e6 cells. 30.000 cells per well were then seeded in a 98well-MTP in 100 µL medium (Gibco) containing 10% fetal calf serum (PAN Biotech). Cells were allowed to attach for 21 h prior addition of compounds. Dilution series of Fab-PEs were prepared in medium spanning a concentration range from 15 to 0.0003 nM. Individual data points were measured as triplicates. 24 h after compound addition luciferase reporter activity as a surrogate marker for cellular protein synthesis capacity was quantified using Steady Glo (Promega). Luminescence was recorded in a microplate reader (Tecan). Data analysis was performed with Excel (Microsoft) and XLfit 5.3.1 (IDBS) add-in. Experiments were performed as biological replicates.

Figure 5A:
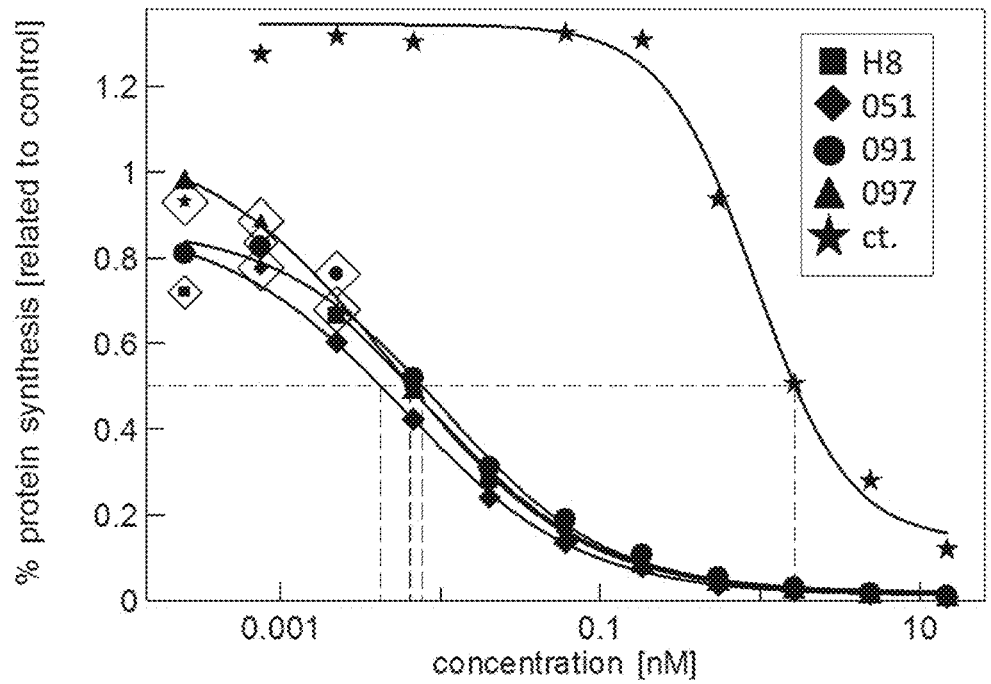
FIG. 5A: Cytotoxicity of immunoconjugates comprising anti-TPBG antibodies (Fabs coupled to PE via sortase coupling: square=H8; triangle=097; diamond=051; circle=091) on CHO-K1 cells transiently expressing human TPBG (Example 21).
Figure 5B:
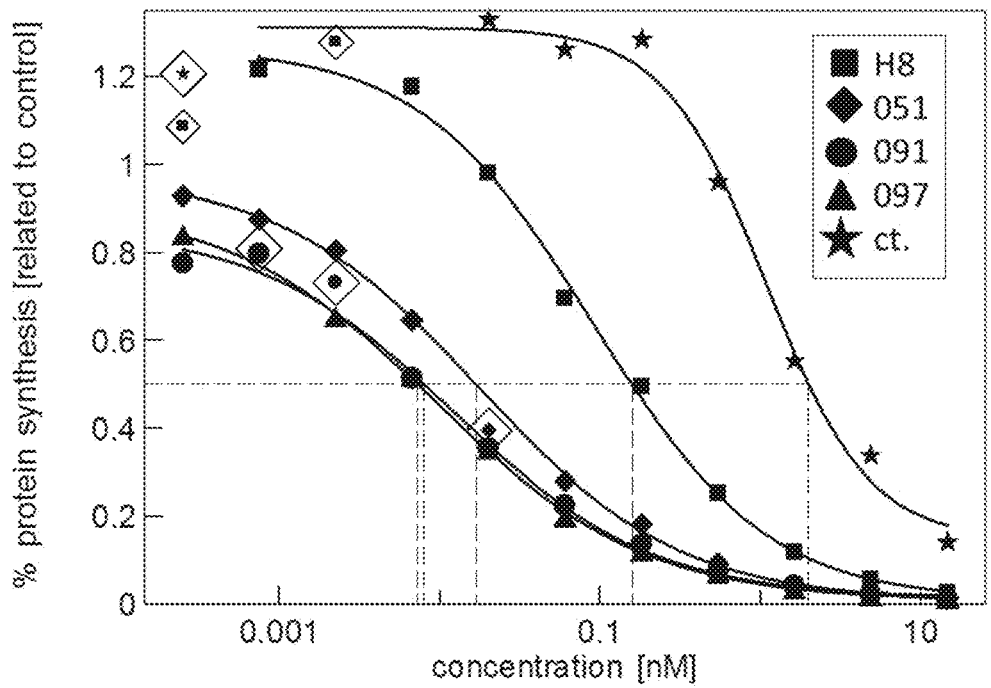
FIG. 5B: Cytotoxicity of immunoconjugates comprising anti-TPBG antibodies (Fabs coupled to PE via sortase coupling: square=H8; triangle=097; diamond=051; circle=091) on CHO-K1 cells transiently expressing minipig TPBG (Example 21).
Figure 6A:
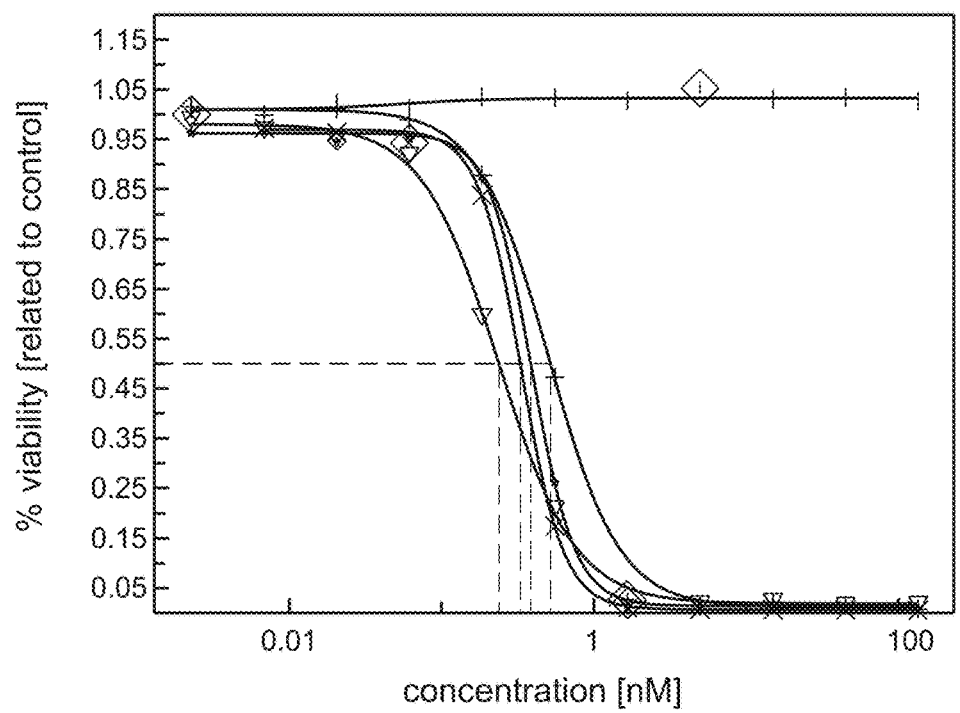
FIG. 6A-D: Cytotoxicity mediated by anti-TPBG antibodies (anti-TPBG Fab antibodies bound by anti-kappa chain antibody-PE fusion protein, prior art antibodies H8, A1, A2, A3 as well as antibodies 051, 091 and 097 of the invention) on human and minipig-TPBG expressing CHO cells (Example 22). Viability was determined by ATP-release assay (CellTiter-Glo) and set in relation to buffer treated control cells.
Figure 6B:
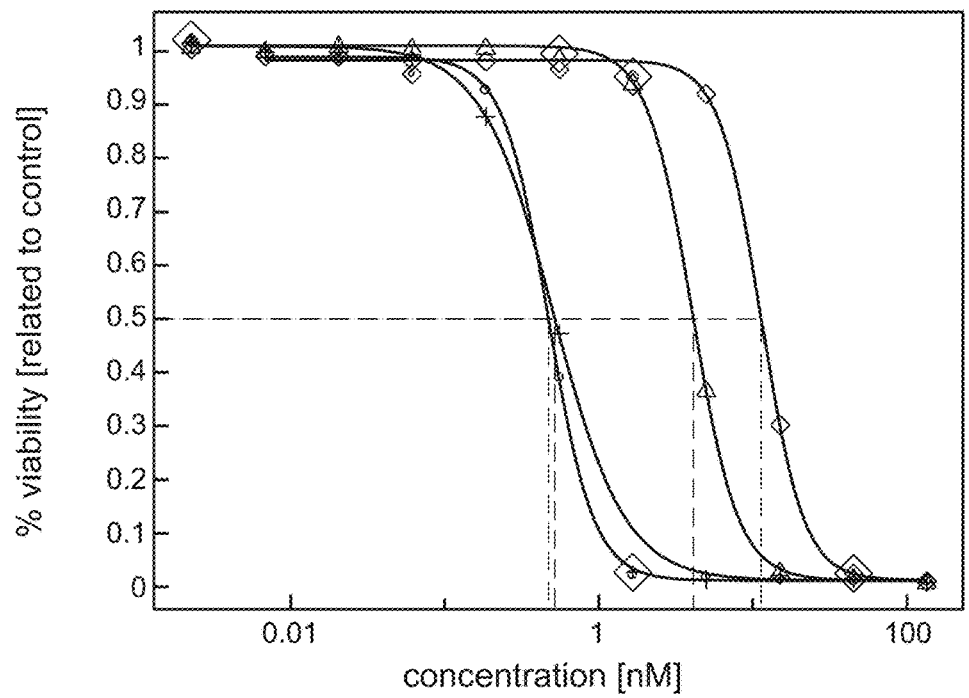
Figure 6C:
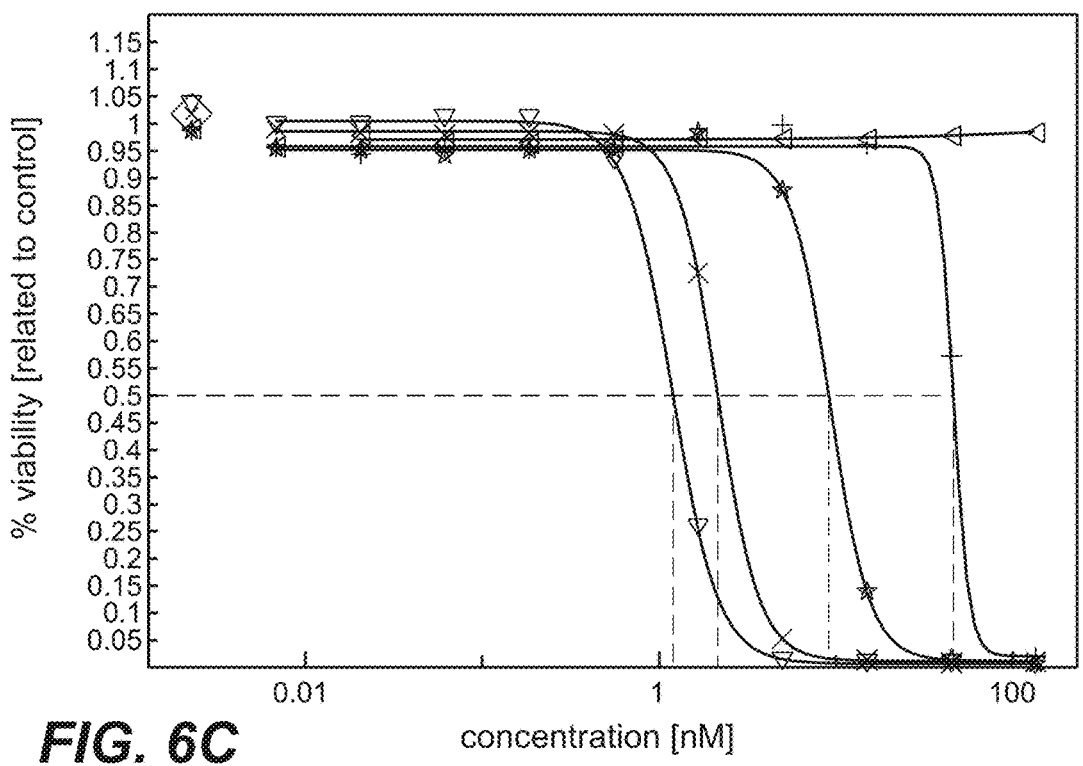
Figure 6D:
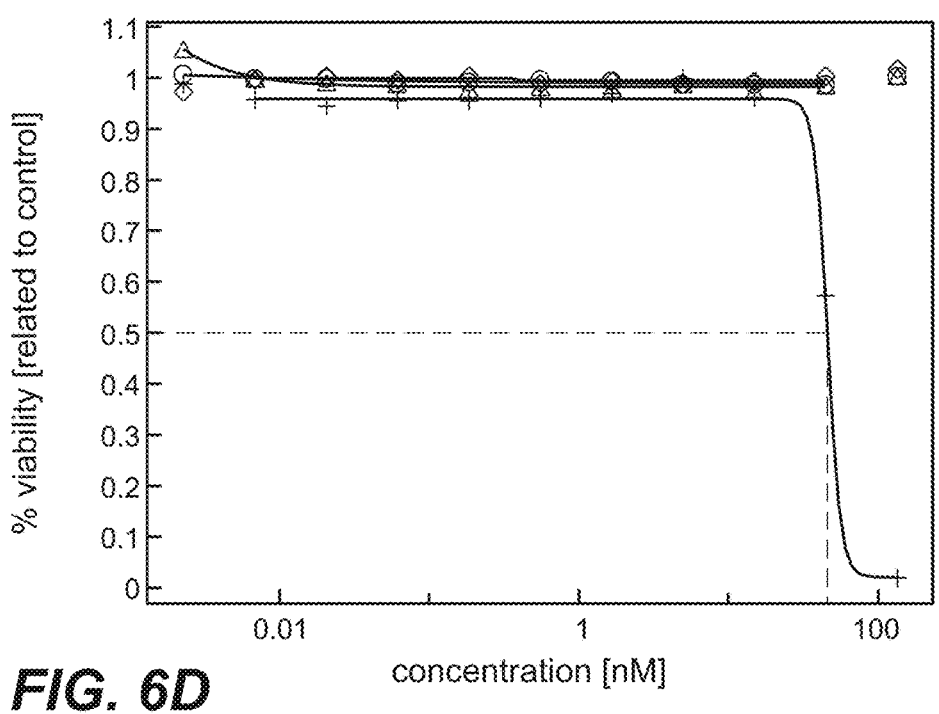

All immunoconjugates comprising antibodies of the invention (i.e. antibodies 051, 091, and 097) as well as immunoconjugates comprising prior art antibody H8 displayed potent and similar activity on cells expressing human TPBG (FIG. 5 A). On the other hand, activity on minipig expressing CHO cells was clearly better for the antibodies of the invention while prior art antibody H8 displayed much lower activity (FIG. 5 B). It is noteworthy that also the negative control, an immunoconjugate which does not bind to a cell surface target, displays potency between 1-10 nM. This is due to the transient transfection procedure which exerts additional stress on the cells. For this reason CHO-K1 clones stably expressing the respective TPBG antigens were generated (cf. example 16 and 21).

Example 22

Cytotoxicity Mediated by Anti-TPBG Antibodies (Anti-TPBG Fab Antibodies Bound by Anti-Kappa Chain Antibody-PE Fusion Protein) on Human and Minipig-TPBG Expressing CHO Cells To evaluate the suitability of anti-TPBG Fab fragments for payload delivery a surrogate assay was performed. In this assay, TPBG-specific Fabs were co-incubated in a 1:3 molar ratio for 30 min prior addition to cells with a second Fab binding to the kappa-light chain of the TPBG-specific Fab. The kappa binding Fab carried in addition a *pseudomonas* exotoxin (PE) moiety. The so formed complex was added to CHO-K1 cells stably expressing either human or minipig TPBG. CHO-K1 cells were stably transfected with full length TPBG from the respective species (Example 16). Single clones were selected and expanded. Clones expressing cell surface TPBG in a similar range were selected for subsequent proliferation assays. While the clones were maintained under selection pressure, the actual proliferation assays were performed in medium without selection pressure.

10.000 cells were seeded per well in a 98well-MTP in 100 µL medium (Gibco) containing 10% fetal calf serum (PAN Biotech). Cells were allowed to attach for 24 h prior addition of compounds. Dilution series of Fab-PE sandwich constructs were prepared in medium spanning a concentration range from 133 to 0.002 nM. Individual data points were measured as triplicates. 72 h after compound addition Cell-TiterGlo (Promega) assay was performed. Luminescence was recorded in a microplate reader (Tecan). Data analysis was performed with Excel (Microsoft) and XLfit 5.3.1 (IDBS) add-in. Experiments were performed as biological replicates.

On CHO-K1 stably transfected with human TPBG all candidates showed potency to some degree.

Fabs derived from antibodies A1, A2, and A3 do not display significant potency on CHO-K1 stably transfected with minipig TPBG. Also, the Fab fragment derived from antibody H8 displays a significantly lower potency in this assay and has an about 100× lower potency on cells expressing minipig than on cell expressing human TPBG (FIG. 6 A-D).

TABLE 11

Cytotoxic activity of anti-TPBG Fab-PE sandwich constructs on human and minipig TPBG expressing CHO cells (EC50 in [nM])

| Fab + anti-kappa-Fab-PE | CHO-K1/human TPBG | | CHO-K1/minipig TPBG | |
|---|---|---|---|---|
| | replicate 1 | replicate 2 | replicate 1 | replicate 2 |
| Unspecific Fab | — | — | — | — |
| H8 | 0.41 | 0.52 | 47.97 | 45.86 |
| A1 | 3.63 | 4.12 | — | — |
| A2 | 9.81 | 11.33 | — | — |
| A3 | 0.26 | 0.47 | — | — |
| 051 | 0.28 | 0.38 | 6.18 | 5.04 |
| 091 | 0.23 | 0.24 | 1.05 | 1.20 |
| 097 | 0.30 | 0.33 | 2.08 | 2.15 |

Example 23

Cytotoxicity of Immunoconjugates Comprising Anti-TPBG Antibodies (Anti-TPBG Fab-PE Fusion Proteins) on Human and Minipig-TPBG Expressing CHO Cells A surrogate assay to evaluate the potency of Fab-PE constructs (anti-TPBG Fab-PE fusion proteins as expressed in Examples 13 and 14) on cells expressing human (hu) or minipig (pg) TPBG was established. To this end, CHO-K1 cells were stably transfected with full length TPBG from the respective species. Single clones were selected and expanded. Clones expressing cell surface TPBG in a similar range were selected for subsequent proliferation assays.

While the clones were maintained under selection pressure, the actual proliferation assays were performed in medium without selection pressure.

10.000 cells were seeded per well in a 98well-MTP in 100 μL medium (Gibco) containing 10% fetal calf serum (PAN Biotech). Cells were allowed to attach for 24 h prior addition of compounds. Dilution series of Fab-PEs were prepared in medium spanning a concentration range from 133 to 0.002 nM. Individual data points were measured as triplicates. 72 h after compound addition CellTiter-Glo (Promega) assay was performed. Luminescence was recorded in a microplate reader (Tecan). Data analysis was performed with Excel (Microsoft) and XLfit 5.3.1 (IDBS) add-in. Experiments were performed as biological replicates.

Figure 7A:
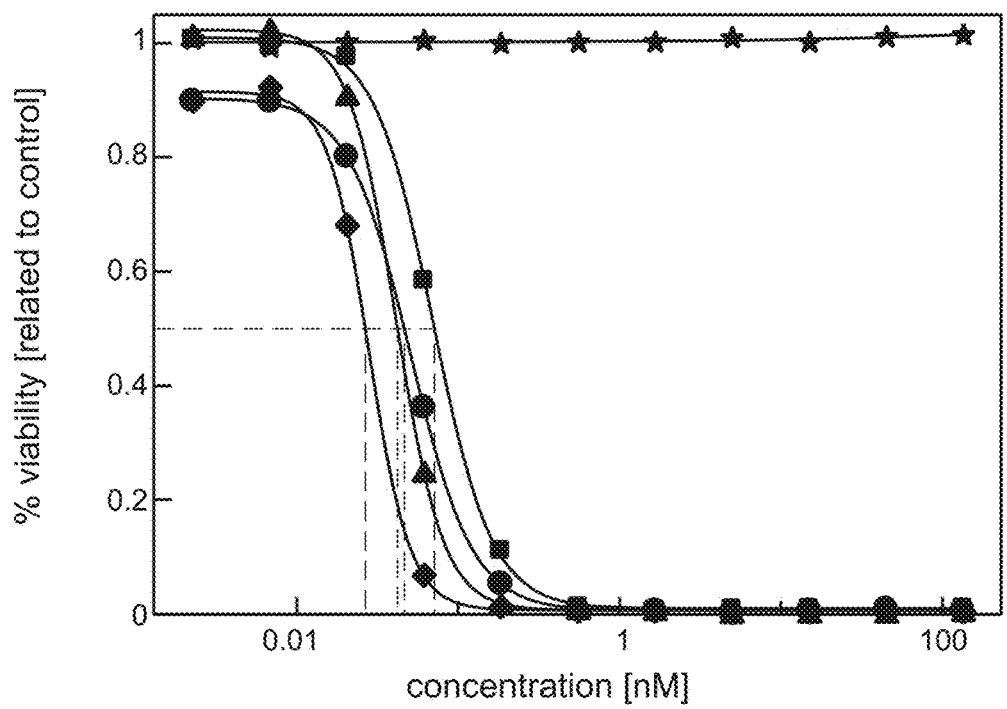
FIG. 7A-C: Cytotoxicity of immunoconjugates comprising anti-TPBG antibodies (Fab-PE fusion proteins: star=unspecific control; square=H8; diamond=051; circle=091; triangle=097) on human and minipig-TPBG expressing CHO-K1 cells (Example 23). Viability was determined by ATP-release assay (CellTiter-Glo).
Figure 7B:
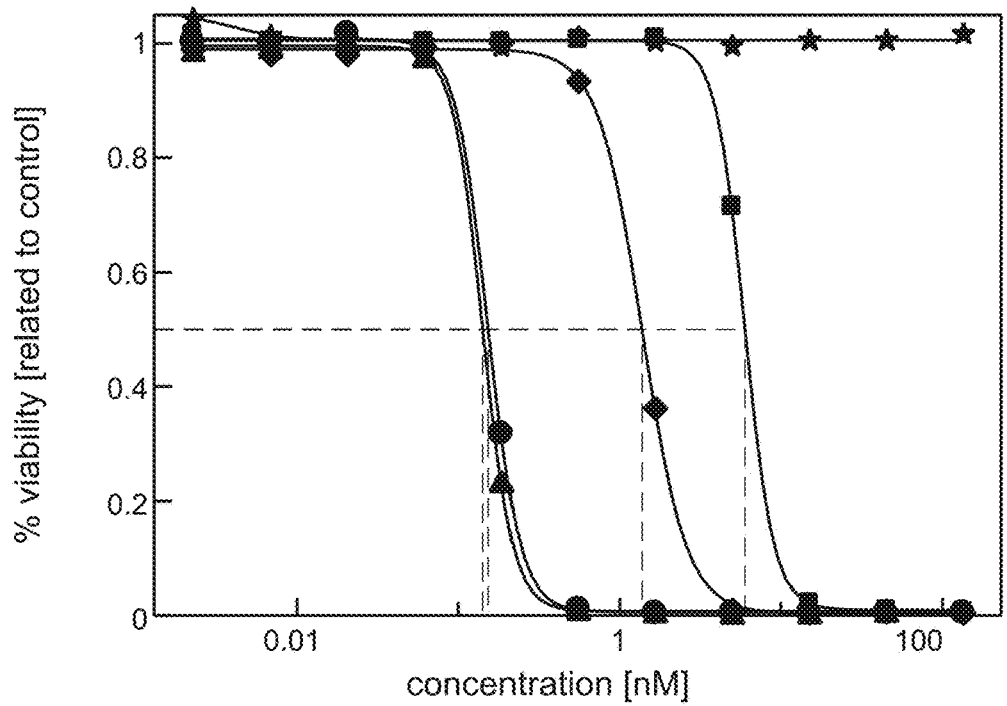
Figure 7C:
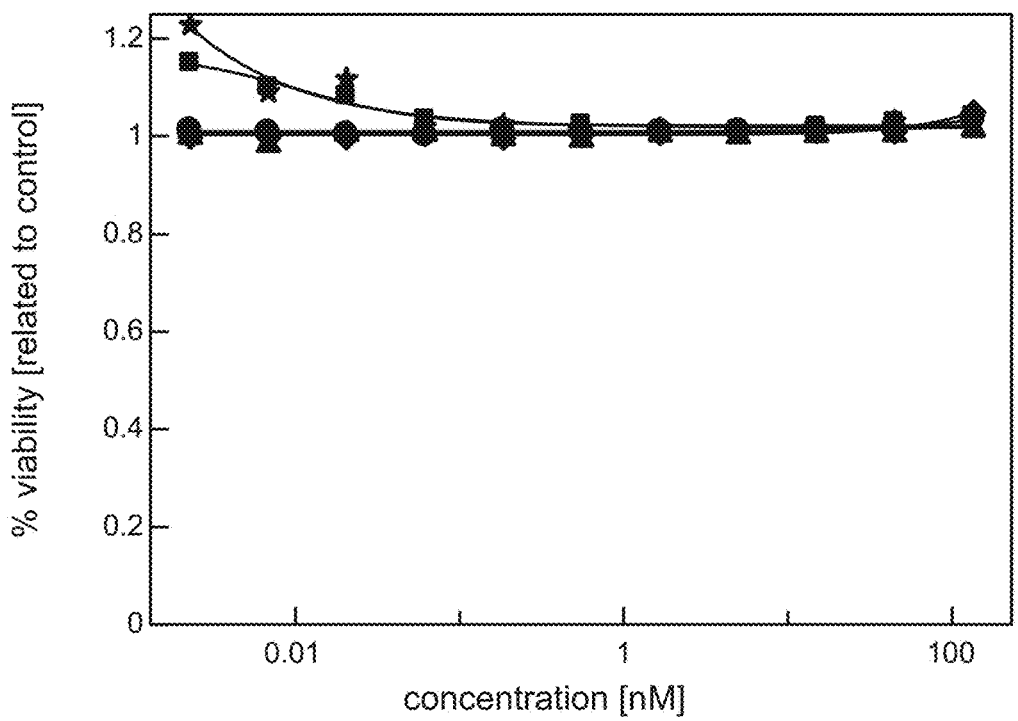

All immunoconjugates comprising antibodies of the invention (i.e. antibodies 051, 091, and 097) displayed potent activity on cells expressing either human or minipig TPBG. An unspecific Fab-PE which does not bind to transfected CHO-K1 cells has no activity in the measured concentration range (FIG. 7 A).

For comparison a Fab-PE version of the prior art antibody H8 was used. For this immunoconjugate only a low cytotoxic activity on cells expressing minipig TPBG was observed. On parental CHO-K1 none of the Fab-PEs displayed activity (FIG. 7 C).

TABLE 12

Cytotoxic activity of anti-TPBG Fab-PE fusion proteins on CHO cells stably expressing either human or minipig TPBG (EC50 in [nM])

| Fab-PE comprising antibody | stable CHO-K1 transfectants | | X-fold lower potency pgTPBG versus huTPBG |
|---|---|---|---|
| | huTPBG | pgTPBG | |
| Unspecific Fab | — | — | |
| H8 | 0.07 | 5.98 | 83.9 |
| 051 | 0.03 | 1.37 | 51.7 |
| 091 | 0.05 | 0.15 | 3.3 |
| 097 | 0.04 | 0.14 | 3.4 |

Example 24

Cellular Binding of Immunoconjugates Comprising Anti-TPBG Antibodies (Anti-TPBG Fab-PE Fusion Proteins) on Human TPBG Expressing MCF7 Cells Binding of anti-TPBG Fab-PE fusion proteins as provided in Example 13 and 14, as well as binding of Fabs coupled to PE fragment via sortase coupling as provided in Example 12 to human tumor cells was studied using the breast cancer tumor cell line MCF7. Cells growing in the logarithmic growth pase were detached using Accutase (Sigma). In brief, cell suspensions were prepared in ice cold PBS (Gibco) containing 2% fetal calf serum (PAN Biotech).

2.5×10e5 cells were dispensed per well in a v-shaped 96well-MTP. Fab-PE dilution series ranging from 133-0.001 nM prepared in the same buffer were added as twofold concentrated solution. Samples were incubated on ice for 45 min upon which they were washed twice with 150 μL ice cold PBS containing 2% fetal calf serum. In between, cells were spun down at 300 g for 5 min at 4° C. Cells were resuspended in 50 μL ice-cold buffer containing 10 μg/mL anti-kappa light chain RE-PE (phycoerythrin) labeled secondary antibody (Life Technologies). The suspension was incubated for 45 min on ice. Cells were washed twice as described and resuspended in 50 μL ice-cold buffer containing 1 μg/mL Hoechst 33258. After 10 min cells were washed once more and finally resuspended in 200 μL ice-cold fixation buffer (BD CellFix). Samples were measured on a FACSCanto II (BD). Data processing was done using the FlowJo Software. Data analysis was performed with Excel (Microsoft) and XLfit 5.3.1 (IDBS) add-in.

Figure 8:
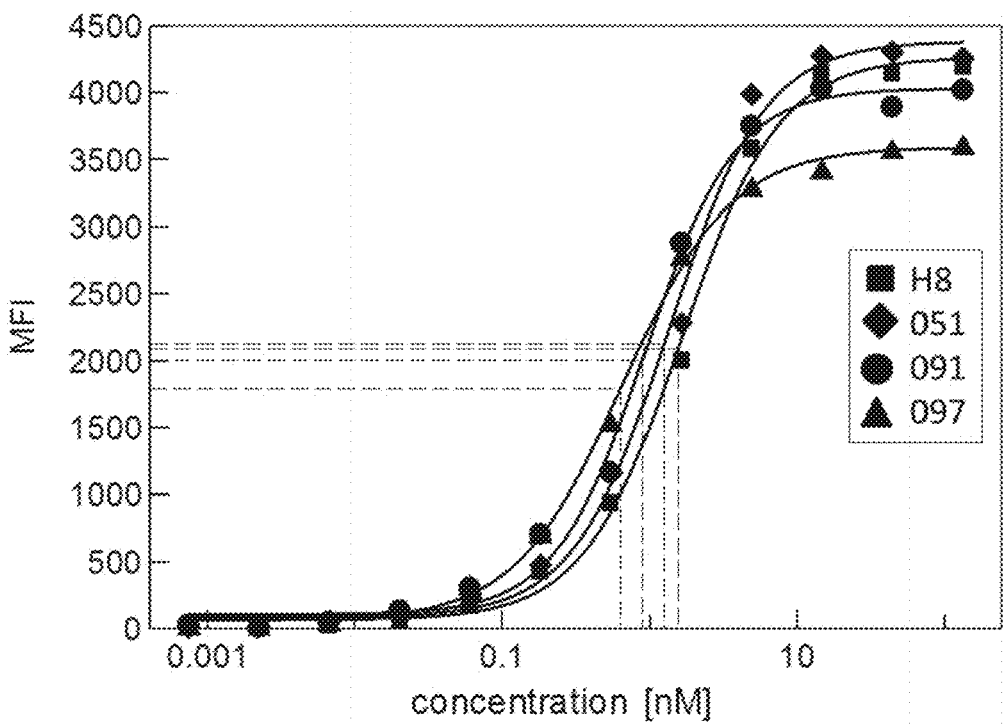
FIG. 8: Cellular binding of immunoconjugates comprising anti-TPBG antibodies (anti-TPBG Fab-PE fusion proteins) on human TPBG expressing MCF7 cells (Example 24). Binding was determined by flow cytometry (y-axis: mean fluorescence intensity=MFI). Baseline corrected mean fluorescent intensities (MFI) are shown.

All anti-TPBG Fab-PE fusion proteins display low nM or sub-nM EC50 values in their binding to the human breast tumor cell line MCF7 (FIG. 8).

TABLE 13

Cellular binding of anti-TPBG Fab-PE fusion proteins on human TPBG expressing MCF7 cells (EC50 in [nM])

| Fab comprised in immunoconjugate | type of immunoconjugate | EC50 [nM] |
|---|---|---|
| H8 | sortase-coupled | 1.56 |
| 051 | sortase-coupled | 0.67 |
| | refolded | 1.25 |
| 091 | sortase-coupled | 0.61 |
| | refolded | 0.89 |
| 097 | sortase-coupled | 0.63 |
| | refolded | 0.64 |

Example 25

Cytotoxicity Mediated by Anti-TPBG Antibodies (Anti-TPBG Fab Antibodies Bound by Anti-Kappa Chain Antibody-PE Fusion Protein) on Human TPBG Expressing MCF7 Cells The ideal properties of antibodies or antibody fragments suitable for delivery of payloads, specifically *pseudomonas* exotoxin, are not well defined. Theoretically, one could assume that every internalizing antibody would fulfill this purpose.

To evaluate the suitability of anti-TPBG antibodies of the invention for payload delivery a surrogate assay was performed. In this assay, TPBG-specific Fabs were co-incubated in a 1:3 molar ratio for 30 min prior addition to cells with a second Fab binding to the kappa-light chain of the TPBG-specific Fab. The kappa binding Fab carried in addition a *pseudomonas* exotoxin (PE) moiety. The so formed complex ("Fab-PE sandwich construct") was added to human MCF7 breast cancer cells.

In brief, 20.000 cells were seeded per well in a 98well-MTP in 100 μL medium (Gibco) containing 10% fetal calf serum (PAN Biotech). Cells were allowed to attach for 24 h prior addition of compounds. Dilution series were prepared in medium spanning a concentration range from 133 to 0.002 nM as calculated for the respective TPBG-specific Fab. Individual data points were measured as triplicates. 72 h after compound addition CellTiter-Glo (Promega) assay was performed. Luminescence was recorded in a microplate reader (Tecan). Data analysis was performed with Excel (Microsoft) and XLfit 5.3.1 (IDBS) add-in. Experiments were performed as biological replicates.

Figure 9:
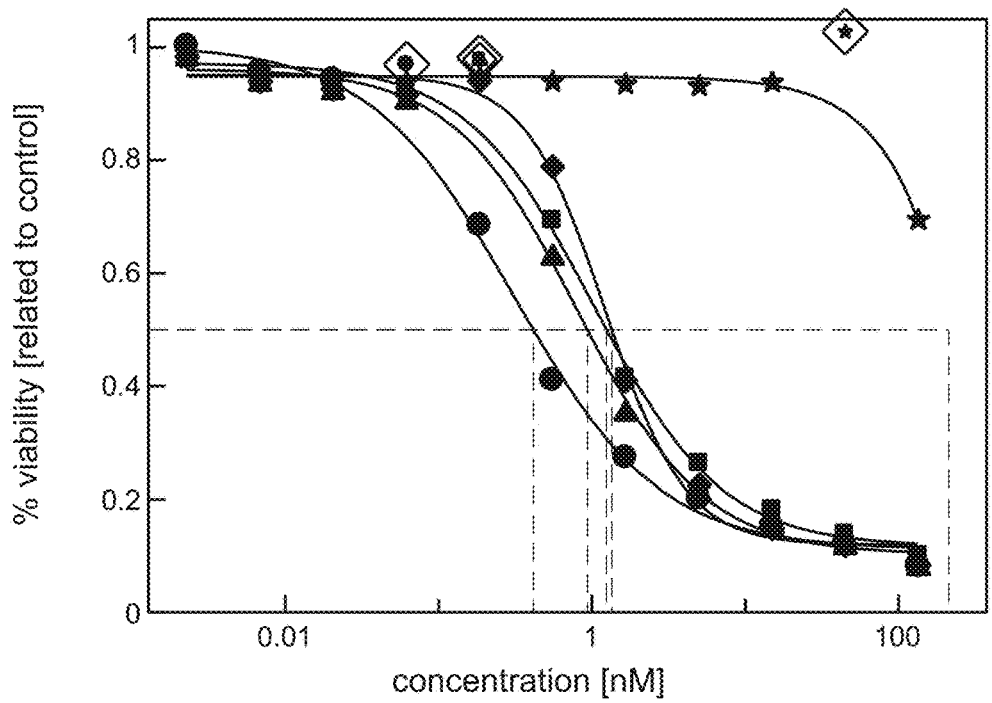
FIG. 9: Cytotoxicity mediated by anti-TPBG antibodies of the invention (anti-TPBG Fab antibodies bound by anti-kappa chain antibody-PE fusion protein) on human TPBG expressing MCF7 cells (Example 25). Fab fragments were co-incubated with an anti-kappa-binding Fab-PE (*pseudomonas* exotoxin). The human breast cancer cell line MCF7 was incubated with the complex of Fab:Fab-PE constructs. Viability was determined by ATP-release assay (CellTiter-Glo) after 72 h. Figure legend: star=unspecific control; square=H8; diamond=051; circle=091; triangle=097.

The complex consisting of TPBG-specific Fab and anti-kappa-Fab-PE elicited a strong cytotoxic response on MCF7 cells (FIG. 9). All Fab-PE sandwich constructs displayed low nM to sub-nM activity while an unrelated Fab co-incubated with an anti-kappa-Fab-PE had no toxicity in this dose range. All Fab-PE sandwich constructs comprising antibodies 051, 091 and 097 of the invention were slightly more portent to induce cytotoxicity in MCF7 cells than Fab-PE sandwich constructs comprising prior art antibody H8.

This observation could be reproduced in an independent experiment as shown in the last column of (Table 14) for the calculated potency difference. This assay setup differs in the absolute nM values obtained for biological replicates by a factor of about 2-3 fold. All generated values were therefore referenced to the H8-comprising construct.

TABLE 14

Cytotoxic activity of anti-TPBG Fab-PE sandwich constructs on human TPBG expressing MCF7 cells (EC50 in [nM])

| Fab | MCF7 | X-fold higher potency compared to TPBG(H8)PE |
|---|---|---|
| Unspecific Fab | — | |
| H8 | 1.248 | — |
| 051 | 1.354 | 1.1/— |
| 091 | 0.414 | 3.0/2.7 |
| 097 | 0.935 | 1.3/2.4 |

As an additional comparative experiment, further prior art antibodies A1, A2 and A3 (U.S. Pat. No. 8,044,178) were assessed with respect to their suitability for payload delivery in an assay as outlined above, and compared with reference to prior art antibody H8.

Functionality of antibodies A1, A2 and A3 was confirmed in surface plasmon resonance and cellular binding experiments (data not shown). To evaluate the suitability of these Fabs derived from antibodies A1, A2 and A3 for payload delivery a surrogate assay was performed. In this assay, TPBG-specific Fabs were co-incubated in a 1:3 molar ratio for 30 min prior addition to cells with a second Fab binding to the kappa-light chain of the TPBG-specific Fab. The kappa binding Fab carried in addition a *pseudomonas* exotoxin (PE) moiety. The so formed complex was added to human MCF7 breast cancer cells. In brief, 20.000 cells were seeded per well in a 98well-MTP in 100 µL medium (Gibco) containing 10% fetal calf serum (PAN Biotech). Cells were allowed to attach for 24 h prior addition of compounds. Dilution series were prepared in medium spanning a concentration range from 133 to 0.002 nM as calculated for the respective TPBG-specific Fab. Individual data points were measured as triplicates. 72 h after compound addition CellTiter-Glo (Promega) assay was performed. Luminescence was recorded in a microplate reader (Tecan). Data analysis was performed with Excel (Microsoft) and XLfit 5.3.1 (IDBS) add-in. Experiments were performed as biological replicates.

Figure 10:
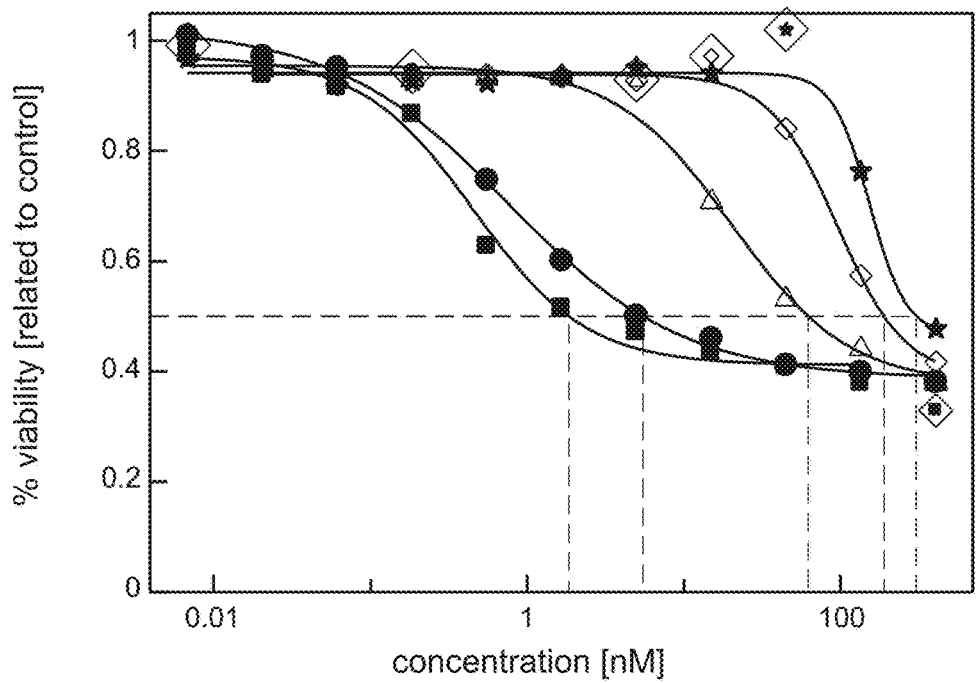
FIG. 10: Cytotoxicity mediated by prior art anti-TPBG antibodies H8, A1, A2 and A3 (anti-TPBG Fab antibodies bound by anti-kappa chain antibody-PE fusion protein) on human TPBG expressing MCF7 cells (Example 25). Fab fragments were co-incubated with an anti-kappa-binding Fab-PE (*pseudomonas* exotoxin). The human breast cancer cell line MCF7 was incubated with the complex of Fab:Fab-PE constructs. Viability was determined by ATP-release assay (CellTiter-Glo) after 72 h. Figure legend: star=unspecific control; square=H8; triangle=A1; diamond=A2; circle=A3.

Compared to the Fab fragment of prior art antibody H8, which has a potency of 1.85 nM on MCF7 in this experiment, the Fabs derived from antibodies A1, A2 and A3 displaced a significantly lower potency (FIG. 10).

TABLE 15

Cytotoxic activity of anti-TPBG Fab-PE sandwich constructs on human TPBG expressing MCF7 cells (EC50 in [nM])

| Fab | MCF7 | X-fold lower potency compared to TPBG(H8)PE |
|---|---|---|
| H8 | 1.85 | — |
| A1 | 62.08 | 33.5 |
| A2 | 189.65 | 102.5 |
| A3 | 5.45 | 2.9 |

Example 26

Cytotoxicity of Immunoconjugates Comprising Anti-TPBG Antibodies (Fabs Coupled to PE Fragment Via Sortase Coupling) on Human TPBG Expressing MCF7 Cells To evaluate potency of Fab-PE constructs (Fabs coupled to PE fragment via sortase coupling as provided in Example 12) on tumor cell lines the breast cancer cell line MCF7 was selected. 20.000 cells were seeded per well in a 98well-MTP in 100 µL medium (Gibco) containing 10% fetal calf serum (PAN Biotech). Cells were allowed to attach for 24 h prior addition of compounds. Dilution series of sortase-coupled Fab-PEs were prepared in medium spanning a concentration range from 133 to 0.002 nM. Individual data points were measured as triplicates. 72 h after compound addition CellTiter-Glo (Promega) assay was performed. Luminescence was recorded in a microplate reader (Tecan). Data analysis was performed with Excel (Microsoft) and XLfit 5.3.1 (IDBS) add-in. Experiments were performed as biological replicates.

Figure 11:
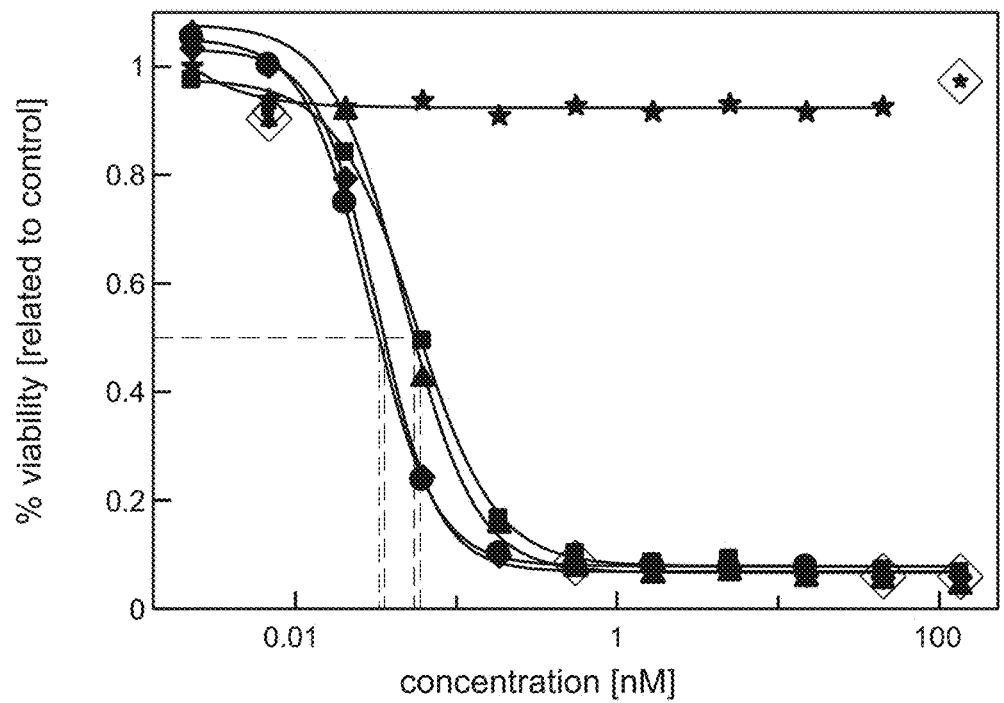
FIG. 11: Cytotoxicity of immunoconjugates comprising anti-TPBG antibodies (Fabs coupled to PE fragment via sortase coupling) on human TPBG expressing MCF7 cells (Example 26). The human breast cancer cell line MCF7 was incubated with sortase coupled Fab-PE constructs. Viability was determined by ATP-release assay (CellTiter-Glo) after 72 h. Figure legend: star=unspecific control; square=H8; diamond=051; circle=091; triangle=097.

All evaluated sortase-coupled Fab-PE constructs displayed potent sub-nM activity on MCF7 cells (FIG. 11). An unspecific Fab-PE not binding to the cell surface had no activity in this assay. For sortase-coupled Fab-PE constructs comprising antibodies 051, 091 and 097 of the invention a similar to slightly higher activity compared to a similar construct comprising prior art antibody H8 was observed (Table 16).

TABLE 16

Cytotoxic activity of sortase coupled anti-TPBG Fab-PE constructs on human TPBG expressing MCF7 cells (EC50 in [nM])

| Fab-PE comprising antibody | MCF7 | X-fold higher potency compared to TPBG(H8)PE |
|---|---|---|
| Unspecific Fab | — | |
| H8 | 0.059 | — |
| 051 | 0.036 | 1.7 |
| 091 | 0.033 | 1.8 |
| 097 | 0.054 | 1.1 |

Example 27

Cytotoxicity Mediated by Anti-TPBG Antibodies (Anti-TPBG Fab Antibodies Bound by Anti-Kappa Chain Antibody-PE Fusion Protein) on Human TPBG Expressing H1975 Non-Small Cell Lung Cancer Cells To evaluate the suitability of Fabs for payload delivery to non-small cell lung cancer cells a surrogate assay was performed.

In this assay, TPBG-specific Fabs expressed as described in Example 11 were co-incubated in a 1:3 molar ratio for 30 min prior addition to cells with a second Fab binding to the kappa-light chain of the TPBG-specific Fab. The kappa binding Fab carried in addition a *pseudomonas* exotoxin (PE) moiety. The so formed complex was added to human H1975 lung cancer cells. In brief, 10.000 cells were seeded per well in a 98well-MTP in 100 µL medium (Gibco) containing 10% fetal calf serum (PAN Biotech) and penicillin/streptomycin (Gibco). Cells were allowed to attach for 24 h prior addition of compounds. Dilution series were prepared in medium spanning a concentration range from 133 to 0.002 nM as calculated for the respective TPBG-specific Fab. Individual data points were measured as triplicates. 72 h after compound addition CellTiter-Glo (Promega) assay was performed. Luminescence was recorded in a microplate reader (Tecan). Data analysis was performed with Excel (Microsoft) and XLfit 5.3.1 (IDBS) add-in. Experiments were performed as biological replicates.

Sandwich constructs comprising Fab fragments of prior art antibody H8, as well as of antibodies of the invention 051, 091, and 097 elicited a strong cytotoxic response with EC50 in the sub-nM range. In three biological replicates the Fab fragment of antibody 091 of the invention was consistently performing as the best candidate (Table 17).

Figure 12:
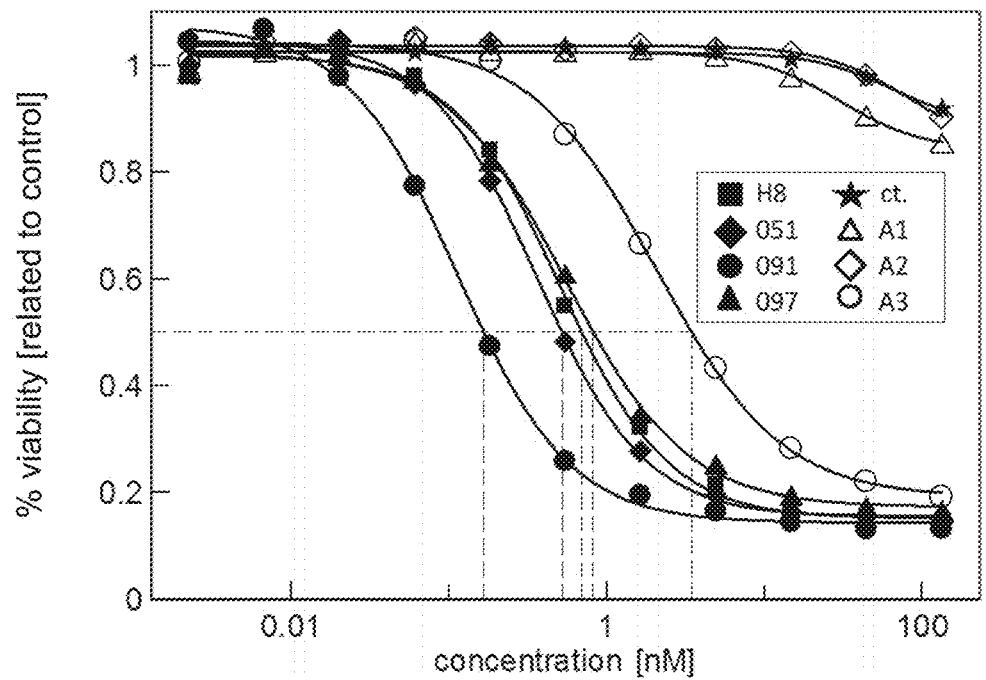
FIG. 12: Cytotoxicity mediated by anti-TPBG antibodies (anti-TPBG Fab antibodies bound by anti-kappa chain antibody-PE fusion protein) on human TPBG expressing H1975 non-small cell lung cancer cells (Example 27). H1975 cells were incubated with the complex of Fab:Fab-PE constructs. Viability was determined by ATP-release assay (CellTiter-Glo) after 72 h.

Sandwich constructs comprising Fab fragments of prior art antibodies A1, A2 and A3 displayed no (for A1 and A2) or significantly lower cytotoxicity than the other tested constructs (FIG. 12).

TABLE 17

Cytotoxic activity mediated by anti-TPBG Fab-PE sandwich constructs on human TPBG expressing H1975 cells (EC50 in [nM])

| Fab of antibody | H1975 | | |
|---|---|---|---|
| | replicate 1 | replicate 2 | replicate 3 |
| H8 | 0.698 | 0.451 | 0.656 |
| 051 | 0.522 | 0.397 | 0.527 |
| 091 | 0.166 | 0.129 | 0.182 |
| 097 | 0.826 | 0.656 | 0.706 |
| A1 | — | — | — |
| A2 | — | — | — |
| A3 | 3.444 | 2.765 | >3 |

Example 28

Cytotoxicity of Immunoconjugates Comprising Anti-TPBG Antibodies (Anti-TPBG Fab-PE Fusion Proteins) on Human TPBG Expressing H1975 Non-Small Cell Lung Cancer Cells To evaluate potency of anti-TPBG Fab-PE fusion proteins as expressed in Example 13 and 14 on tumor cell lines the non-small cell lung cancer cell line H1975 was selected. The number of cell surface TPBG molecules was approximately 30.000/cell as determined by flow cytometry based receptor quantitation. 10.000 cells were seeded per well in a 98well-MTP in 100 µL medium (Gibco) containing 10% fetal calf serum (PAN Biotech). Cells were allowed to attach for 24 h prior addition of compounds. Dilution series of Fab-PEs were prepared in medium spanning a concentration range from 3 to 0.00005 nM. Individual data points were measured as triplicates. 72 h after compound addition CellTiter-Glo (Promega) assay was performed. Luminescence was recorded in a microplate reader (Tecan). Data analysis was performed with Excel (Microsoft) and XLfit 5.3.1 (IDBS) add-in. Experiments were performed as biological replicates.

Figure 13:
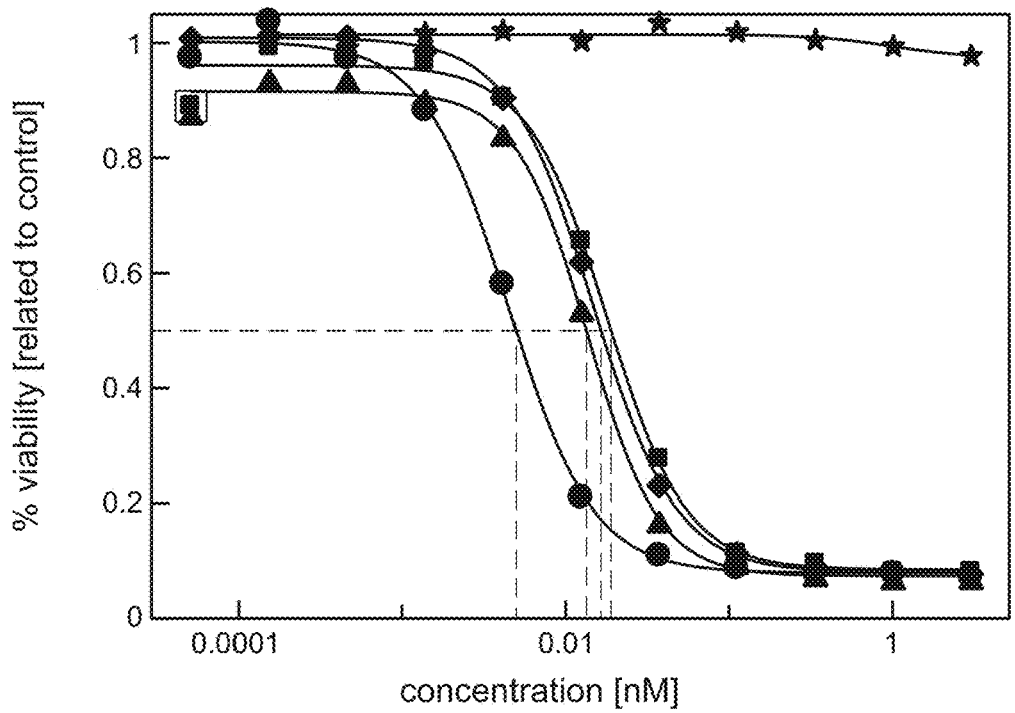
FIG. 13: Cytotoxicity of immunoconjugates comprising anti-TPBG antibodies (anti-TPBG Fab-PE fusion proteins)

Potency of all anti-TPBG Fab-PE constructs was dose-dependent (FIG. 13). An unspecific Fab-PE not binding to H1975 did not show significant activity in the measured dose range. All tested anti-TPBG Fab-PEs displayed sub-nM potency. The Fab-PE fusion protein comprising antibody 091 of the invention was consistently about 3-4 fold more potent in this cell line than the fusion protein derived from prior art antibody H8 (Table 18).

TABLE 18

Cytotoxic activity mediated by anti-TPBG Fab-PE fusion proteins on human TPBG expressing H1975 cells (EC50 in [nM])

| Fab of antibody | H1975 | | X-fold higher potency compared to Fab-PE fusion protein of H8 |
|---|---|---|---|
| | replicate 1 | replicate 2 | |
| Unspecific Fab | — | — | |
| H8 | 0.019 | 0.013 | — |
| 051 | 0.016 | 0.014 | 1.2/1.1 |
| 091 | 0.005 | 0.003 | 3.8/3.7 |
| 097 | 0.013 | 0.013 | 1.4/1.1 |

Example 29

Time Course Proliferation Assay of Immunoconjugates Comprising Anti-TPBG Antibodies (Anti-TPBG Fab-PE Fusion Proteins) Applied to Human TPBG Expressing H1975 Non-Small Cell Lung Cancer Cells In a different experimental setup the exposure time of anti-TPBG Fab-PE fusion proteins as expressed in Example 13 and 14 to tumor cells was varied. The non-small cell lung cancer cell line H1975 was used to evaluate, if shorter incubation time with Fab-PE constructs has an impact on potency in a proliferation assay.

10.000 cells were seeded per well in a 98well-MTP in 100 µL medium (Gibco) containing 10% fetal calf serum (PAN Biotech). Cells were allowed to attach for 24 h prior addition of compounds. Dilution series of Fab-PEs were prepared in medium spanning a concentration range from 3 to 0.00005 nM. After 10, 30 and 60 min of incubation medium was replaced with fresh medium without Fab-PE and cells were further maintained for a total of 72 h. In addition, cells with continuous exposure to Fab-PE were cultivated. Individual data points were measured as triplicates. 72 h after compound addition CellTiter-Glo (Promega) assay was performed. Luminescence was recorded in a microplate reader (Tecan). Data analysis was performed with Excel (Microsoft) and XLfit 5.3.1 (IDBS) add-in.

All tested Fab-PE fusion proteins displayed potent sub-nM potency on this human tumor cell line (FIG. 14 A-D). Shorter incubation periods with Fab-PE fusion proteins resulted in a slight decrease of potency. Anti-TPBG Fab-PE fusion protein comprising the Fab fragment of antibody 091 of the invention was more potent than the other tested molecules, which is consistent with the observation of Example 30 (Tables 19 and 20).

TABLE 19

Time course proliferation experiment of human TPBG expressing H1975 cells contacted with anti-TPBG Fab-PE fusion proteins (EC50 in [nM])

| Fab comprised in immunoconjugate | H1975 | | | |
|---|---|---|---|---|
| | continuous | 60 min | 30 min | 10 min |
| H8 | 0.013 | 0.180 | 0.201 | 0.229 |
| 051 | 0.014 | 0.180 | 0.204 | 0.241 |
| 091 | 0.003 | 0.043 | 0.062 | 0.057 |
| 097 | 0.013 | 0.203 | 0.189 | 0.211 |

TABLE 20

Time course proliferation experiment of human TPBG expressing
H1975 cells contacted with anti-TPBG Fab-PE fusion proteins
(X-fold hihger potency than anti-TPBG Fab-PE fusion
protein of prior art antibody H8)

| Fab comprised in immunoconjugate | H1975 | | | |
|---|---|---|---|---|
| | continuous | 60 min | 30 min | 10 min |
| H8 | 1.0 | 1.0 | 1.0 | 1.0 |
| 051 | 1.1 | 1.0 | 1.0 | 1.1 |
| 091 | 3.7 | 4.2 | 3.3 | 4.0 |
| 097 | 1.1 | 1.1 | 0.9 | 0.9 |

Example 30

In Vivo Anti-Tumor Efficacy of Immunoconjugates Comprising Anti-TPBG Antibodies (Anti-TPBG Fab-PE Fusion Proteins) on Human TPBG Expressing Human Non-Small Cell Lunger Cancer H1975 Cell Xenografts The in vivo antitumor efficacy of anti-TPBG Fab-PE fusion proteins as expressed in Examples 13 and 14 was monitored in a human tumor cell line based model of transplanted nude mice. The non-small cell lung cancer (NSCLC) NCI-H1975 cell line was chosen as xenograft model. NCI-H1975 displays cell surface TPBG as was independently confirmed.

NCI-H1975 were cultured in RPMI high glucose medium with 1.0 mM sodium pyruvate supplemented with 10% fetal calf serum, 2.0 mM L-glutamine, and 10 mM HEPES at 37° C. in a water-saturated atmosphere at 5% $CO_2$. Culture passages were performed with trypsin/EDTA (Life Technologies) splitting every third day. Nude mice were purchased from breeder (e.g. Charles River, Sulzfeld, Germany) and maintained under specific-pathogen-free condition with daily cycles of 12 h light/12 h darkness according to committed guidelines (GV-Solas; Felasa; TierschG). Experimental study protocol was reviewed and approved by local government. After arrival animals were maintained in the quarantine part of the animal facility for one week to get accustomed to new environment and for observation. Continuous health monitoring was carried out on regular basis. Diet food (Provimi Kliba 3337) and water (acidified pH 2.5-3) were provided ad libitum. Animals were controlled daily for clinical symptoms and detection of adverse effects. For monitoring throughout the experiment body weight of animals was documented.

Animal treatment started after animal randomisation after cell transplantation when mean tumor size was about 100-200 mm³. Fab-PE fusion proteins were administered as single agent at 1 mg/kg i.v. once daily every second day for several times. The corresponding vehicle was administered on the same days. Fab-PE proteins were provided as stock solution from Roche, Penzberg, Germany. Buffer included histidine and injection solution was diluted appropriately in buffer from stock prior injections.

NCI-H1975 NSCLC xenograft bearing mice were treated with the Fab-PE fusion proteins from study day 17 to 44 at dose of 1.0 mg/kg for a total of 8 times (days 17, 19, 21, 24, 26, 28, 42 and 44). Each treatment group consisted of 10 animals. As a result, treatments with the Fab-PE fusion proteins comprising antibodies of the invention showed significant anti-tumor efficacy with strong tumor regression of s.c. NCI-H1975 xenografts. Notably, a majority of complete tumor remissions were achieved.

The strong efficacy of the immunoconjugated of the invention was statistically different from the immunoconjugated comprising prior art antibody H8 (FIG. 15).

Example 31

In Vivo Anti-Tumor Efficacy of Immunoconjugates Comprising Anti-TPBG Antibodies (Anti-TPBG Fab-PE Fusion Proteins) on Human TPBG Expressing Human Gastric Cancer NCI-N87 Cell Xenografts The in vivo antitumor efficacy of anti-TPBG Fab-PE fusion proteins as expressed in Examples 13 and 14 was monitored in a human tumor cell line based model of transplanted nude mice. The gastric cancer NCI-N87 cell line was chosen as xenograft model. NCI-N87 displays cell surface TPBG as was independently confirmed.

NCI-N87 were cultured in RPMI high glucose medium with 1.0 mM sodium pyruvate supplemented with 10% fetal calf serum, 2.0 mM L-glutamine, and 10 mM HEPES at 37° C. in a water-saturated atmosphere at 5% $CO_2$. Culture passages were performed with trypsin/EDTA (Life Technologies) splitting every third day. Nude mice were purchased from breeder (e.g. Charles River, Sulzfeld, Germany) and maintained under specific-pathogen-free condition with daily cycles of 12 h light/12 h darkness according to committed guidelines (GV-Solas; Felasa; TierschG). Experimental study protocol was reviewed and approved by local government. After arrival animals were maintained in the quarantine part of the animal facility for one week to get accustomed to new environment and for observation. Continuous health monitoring was carried out on regular basis. Diet food (Provimi Kliba 3337) and water (acidified pH 2.5-3) were provided ad libitum. Animals were controlled daily for clinical symptoms and detection of adverse effects. For monitoring throughout the experiment body weight of animals was documented.

Animal treatment started after animal randomisation after cell transplantation when mean tumor size was about 100-200 mm³. Fab-PE fusion proteins were administered as single agent at 1 mg/kg i.v. once daily every second day for several times. The corresponding vehicle was administered on the same days. Fab-PE fusion proteins were provided as stock solution from Roche, Penzberg, Germany Buffer included histidine and injection solution was diluted appropriately in buffer from stock prior injections.

In the NCI-N87 gastic cancer xenograft model tumor mice were treated with Fab-PE fusion proteins from study day 15 to 33 at dose of 1.0 mg/kg for a total of 7 times (days 15, 17, 19, 22, 24, 26 and 33). Each treatment group consisted of 10 animals. As a result, treatments with the Fab-PE fusion proteins as well as the reference (H8 antibody) showed anti-tumor efficacy with distinct tumor regression of s.c. N87 xenografts (FIG. 16).

Example 32

Protein Synthesis Assay Using BxPC3/Luc Cells Contacted with Immunoconjugates Comprising Anti-TPBG Antibodies (Anti-TPBG Fab-PE Fusion Proteins)

Inhibition of protein synthesis was measured by exposing BxPC/luc cells to anti-TPBG Fab-PE fusion proteins as expressed in Examples 13 and 14.

In brief, BxPC3 cells were stably transfected with a plasmid encoding for a luciferase which contains cellular degradation signals (Promega) and has a half-life of about 0.4 h. Single clones were derived and re-assessed for stable plasmid incorporation. Inhibition of protein synthesis by ADP-ribosylation conferred by the *pseudomonas* exotoxin results in a rapid loss of luciferase and can thus be measured upon cell lysis and incubation with luciferin as loss of signal in comparison to controls.

BxPC3/luc in the logarithmic growth phase were detached with Accutase (Sigma) and counted. 40.000 BxPC3/luc cells were seeded per well in 96well-MTP in 100 μl medium containing 10% fetal calf serum and were incubated 24 h prior compound addition. TPBG-specific immunoconjugates were added in a concentration range from 3-0.0001 nM. All samples were measured in triplicates.

An unspecific immunoconjugate has no effect on the luciferase signal (ct). All TPBG-specific immunoconjugates display sub-nM potency. Antibodies of this invention display higher potency than the prior art antibody H8 (FIG. 17A and Table 21).

TABLE 21

Cytotoxic activity mediated by anti-TPBG Fab-PE fusion proteins on human TPBG expressing BxPC-3 cells (EC50 in [nM])

| Fab of antibody | BxPC-3 | | X-fold higher potency compared to Fab-PE fusion protein of H8 |
|---|---|---|---|
| | replicate 1 | replicate 2 | |
| Unspecific Fab | — | — | |
| H8 | 0.058 | 0.020 | |
| 051 | 0.027 | 0.015 | 2.2/1.4 |
| 091 | 0.014 | 0.007 | 4.3/2.8 |
| 097 | 0.022 | 0.008 | 2.7/2.6 |

In addition, inhibition of protein synthesis by anti-TPBG Fab-PE sandwich constructs comprised of antibodies A1, A2, A3 and H8 was determined in BxPC3/luc. TPBG-specific Fabs were mixed with anti-human kappa Fab-PE (*pseudomonas* exotoxin) in a 1:3 molar ratio and kept at room temperature for 15 min to allow for sandwich construct formation. Dilution series of this mixture were prepared in medium. Final concentrations on cells ranged from 133 nM to 0.002 nM as calculated for the TPBG-specific Fab. 24 h post-addition Steady-Glo luciferase assay (Promega) was performed. All samples were measured in triplicates. Comparing Fabs co-incubated with anti-human kappa Fab-PE revealed that A1 and A2 did not display activity in the given concentration range, while A3 exhibited an about 5-fold lower potency than H8 (FIG. 17B).

Example 33

Affinity of Anti-TPBG Fab Fragments to Human TPBG

Affinity of Fab fragments of antibodies 051, 091, and 097 of the invention (as expressed in Example 11) to human TPBG was assessed by Biacore™. Fab fragments of prior art antibody H8 were assessed as a control.

Affinity to Human TPBG was Assessed as Follows:

A CMS sensor chip was mounted into a Biacore T200 System. Flow cell one was prepared as reference flow cell, by blank immobilization. On flow cell two, about 500 RU of 1.5 μg/ml huTPBG in pH 4.5 acetate buffer were immobilized (120 s at 10 μl/min). The amine-coupling was done as described by the manufacturer.

The samples were injected in a concentration series of 4.9 nM, 14.8 nM, 44.4 nM, 133.3 nM, 400 nM and 0 nM for 150 s at a flow speed of 50 μl/min, followed by a dissociation phase of 660 seconds.

The sample-antigen-complex was regenerated after every sample injection by one 40 s pulse of Glycine-HCl pH 1.5 at 30 μl/min and one 40 s long injection of a regeneration solution containing 0.31 M KSCN, 1.22 M MgCl$_2$, 0.61 M urea, 1.22 M Gua-HCl and 6.7 mM EDTA at 30 μl/min followed by an extra wash after injection with buffer.

Relevant kinetic data was calculated using the Biacore T200 evaluation software.

TABLE 22

Affinity constants of anti-TPBG Fab fragments to human TPBG

| Sample | $k_a$ (1/MS) | $K_d$ (1/S) | $K_D$ (M) |
|---|---|---|---|
| 051 | 4.89E+05 | 7.83E−05 | 1.60E−10 |
| 091 | 4.87E+05 | 2.72E−05 | 5.58E−11 |
| 097 | 9.93E+05 | 8.14E−04 | 8.20E−10 |
| H8 | 1.37E+05 | 2.17E−07 | 1.58E−12 |

Example 34

Affinity of Anti-TPBG Fab Fragments to Minipig TPBG

Affinity of Fab fragments of antibodies 051, 091, and 097 of the invention (as expressed in Example 11) to minipig TPBG was assessed by Biacore™. Fab fragments of prior art antibody H8 were assessed as a control.

Affinity to Human TPBG was Assessed as Follows:

A CMS sensor chip was mounted into a Biacore T200 System. Flow cell one was prepared as reference flow cell by blank immobilization. An <huFab> capture antibody (#28958325, GE-HC) was immobilized via amine coupling onto the flow cells 2, 3 and 4 with an injection time of 1200 s at a concentration of 20 μg/ml (diluted in the buffer, also provided in the capturing-kit #28958325, GE-HC) and a flow speed of 5 μl/min.

The samples were successively captured on flow cells 2, 3 and 4 with an injection time of 60 s and a flow speed of 20 μl/min, followed by a 120 seconds long injection of one minipig TPBG dilution out of a dilution series (4.9 nM, 14.8 nM, 44.4 nM, 133.3 nM, 400 nM and 2×0 nM). After a dissociation phase of 660 s (except the 14.8 nM, 4.9 nM and one 0 nM dilution, for which the diss. time was set to 0 s), the <huFab> surface was regenerated according to the manufacturer's instructions with the regeneration solution provided in the Fab-capture-kit and the next cycle was carried out.

Relevant kinetic data was calculated using the Biacore T200 evaluation software. The data indicates no stable binding of antibody H8 to recombinant extracellular domain of minipig TPBG (FIG. 19 and Table 23).

TABLE 23

Affinity constants of anti-TPBG Fab fragments to minipig TPBG

| Sample | $k_a$ (1/Ms) | $k_d$ (1/S) | $K_D$ (M) |
|---|---|---|---|
| 051 | 9.40E+04 | 1.93E−04 | 2.05E−09 |
| 091 | 1.18E+05 | 2.05E−04 | 1.74E−09 |
| 097 | 1.89E+05 | 2.54E−04 | 1.35E−09 |
| Fab(H8) | No binding | No binding | No binding |

Example 35 pH Dependent Binding of Anti-TPBG Antibodies to Human TPBG Antigen

A CMS sensor chip was mounted into a Biacore T200 System. Flow cell one was prepared as reference flow cell, by blank immobilization. On flow cell two, 80 RU were the aim for the immobilization with 1.5 µg/ml huTPBG in pH 4.5 acetate buffer. The amine-coupling was done as described by the manufacturer.

In one embodiment of the assay HBS-EP+pH 5.5 was used as running and sample buffer, in a second embodiment HBS-EP+pH 7.4 was used.

The samples were injected in a concentration series of 1.9 nM, 5.6 nM, 2×16.7 nM, 50 nM, 150 nM and 2×0 nM for 300 s at a flow speed of 50 µl/min. The 50 nM, one 0 nM and one 16.7 nM sample were allowed to dissociate for 1200 s, all other dissociation phases were only 10 s long.

The sample-antigen-complex was regenerated after every sample injection by one 40 s pulse of Glycine-HCl pH 1.5 at 30 µl/min and one 40 s long injection of a regeneration solution containing 0.31 M KSCN, 1.22 M $MgCl_2$, 0.61 M urea, 1.22 M Gua-HCl and 6.7 mM EDTA at 30 µ/min followed by an extra wash after injection with buffer.

Relevant kinetic data was calculated using the Biacore T200 evaluation software.

Experimental results for Fab-PE fusions proteins clearly indicate that prior art antibody H8 binds in a pH dependent manner A pH shift from 7.4 to 5.5 results in a significant decrease of $K_D$ while huTPBG-binding of antibodies 051, 091, and 097 of the invention is largely unaffected. This can also be visualized in an association-dissociation blot highlighting the pH dependent binding of prior art antibody H8 (FIG. 18).

TABLE 24

Affinity constants of anti-TPBG Fab-PE fusion proteins to human TPBG at different pH values

| pH | Fab comprised in immunoconjugate | $k_a$ (1/Ms) | $k_d$ (1/S) | $K_D$ (M) |
|---|---|---|---|---|
| 5.5 | H8 | 5.43E+04 | 1.47E−02 | 2.70E−07 |
| | 051 | 3.86E+05 | 1.13E−04 | 2.92E−10 |
| | 091 | 2.26E+05 | 2.01E−03 | 8.89E−09 |
| | 097 | 8.08E+05 | 6.05E−03 | 7.49E−09 |
| 7.4 | H8 | 1.97E+05 | 7.61E−05 | 3.85E−10 |
| | 051 | 2.86E+05 | 3.46E−05 | 1.21E−10 |
| | 091 | 2.80E+05 | 1.29E−04 | 4.61E−10 |
| | 097 | 6.14E+05 | 1.21E−03 | 1.97E−09 |

---

The invention claimed is:

1. An isolated antibody that binds to trophoblast glycoprotein (TPBG) comprising a heavy chain CDR1 comprising the amino acid sequence of SEQ ID NO: 3, a heavy chain CDR2 comprising the amino acid sequence of SEQ ID NO: 4, a heavy chain CDR3 comprising the amino acid sequence of SEQ ID NO: 5, a light chain CDR1 comprising the amino acid sequence of SEQ ID NO: 6, a light chain CDR2 comprising the amino acid sequence of SEQ ID NO: 7, and a light chain CDR3 comprising the amino acid sequence of SEQ ID NO: 8.

2. The antibody of claim 1 comprising a variable heavy chain domain (VH) having at least 95% amino acid sequence identity to the amino acid sequence of SEQ ID NO: 9 and a variable light chain domain (VL) having at least 95% amino acid sequence identity to the amino acid sequence of SEQ ID NO: 10.

3. The antibody of claim 1 comprising a variable heavy chain domain (VH) with the amino acid sequence of SEQ ID NO: 9 and a variable light chain domain (VL) with the amino acid sequence of SEQ ID NO: 10.

4. An isolated antibody that binds to trophoblast glycoprotein (TPBG) comprising a heavy chain CDR1 comprising the amino acid sequence of SEQ ID NO: 11, a heavy chain CDR2 comprising the amino acid sequence of SEQ ID NO: 12, a heavy chain CDR3 comprising the amino acid sequence of SEQ ID NO: 13, a light chain CDR1 comprising the amino acid sequence of SEQ ID NO: 14, a light chain CDR2 comprising the amino acid sequence of SEQ ID NO: 15, and a light chain CDR3 comprising the amino acid sequence of SEQ ID NO: 16.

5. The antibody of claim 4 comprising a variable heavy chain domain (VH) having at least 95% amino acid sequence identity to the amino acid sequence of SEQ ID NO: 17 and a variable light chain domain (VL) having at least 95% amino acid sequence identity to the amino acid sequence of SEQ ID NO: 18.

6. The antibody of claim 4 comprising a variable heavy chain domain (VH) with the amino acid sequence of SEQ ID NO: 17 and a variable light chain domain (VL) with the amino acid sequence of SEQ ID NO: 18.

7. An isolated antibody that binds to trophoblast glycoprotein (TPBG) comprising a heavy chain CDR1 comprising the amino acid sequence of SEQ ID NO: 19, a heavy chain CDR2 comprising the amino acid sequence of SEQ ID NO: 20, a heavy chain CDR3 comprising the amino acid sequence of SEQ ID NO: 21, a light chain CDR1 comprising the amino acid sequence of SEQ ID NO: 22, a light chain CDR2 comprising the amino acid sequence of SEQ ID NO: 23, and a light chain CDR3 comprising the amino acid sequence of SEQ ID NO: 24.

8. The antibody of claim 7 comprising a variable heavy chain domain (VH) having at least 95% amino acid sequence identity to the amino acid sequence of SEQ ID NO: 25 and a variable light chain domain (VL) having at least 95% amino acid sequence identity to the amino acid sequence of SEQ ID NO: 26.

9. The antibody of claim 7 comprising a variable heavy chain domain (VH) with the amino acid sequence of SEQ ID NO: 25 and a variable light chain domain (VL) with the amino acid sequence of SEQ ID NO: 26.

10. The antibody of any one of claim 1, 4 or 7, wherein the antibody is a Fab fragment that binds to TPBG.

11. An isolated nucleic acid encoding the antibody of any one of claim 1, 4 or 7.

12. A host cell comprising the nucleic acid of claim 11.

13. A method of producing an antibody comprising culturing the host cell of claim 12 so that the antibody is produced.

14. An immunoconjugate comprising the antibody of any one of claim 1, 4 or 7, and a cytotoxic agent.

15. The immunoconjugate of claim 14, wherein the cytotoxic agent is *Pseudomonas* exotoxin A or a variant thereof.

16. The immunoconjugate of claim 14, wherein the antibody is a Fab fragment that binds to TPBG.

17. A pharmaceutical formulation comprising the antibody of any one of claim 1, 4 or 7, and a pharmaceutically acceptable carrier.

18. A pharmaceutical formulation comprising the immunoconjugate of claim 14 and a pharmaceutically acceptable carrier.

19. A method of treating cancer in a patient, comprising administering the antibody of any one of claim 1, 4 or 7 to a patient in need thereof.

20. The method of claim 19, wherein the cancer is non-small cell lung cancer.

21. A method of treating cancer in a patient, comprising administering the immunoconjugate of claim 14 to a patient in need thereof.

22. The method of claim 21, wherein the cancer is non-small cell lung cancer.

* * * * *